United States Patent
Fan et al.

(10) Patent No.: US 11,827,713 B2
(45) Date of Patent: Nov. 28, 2023

(54) CHIMERIC ANTIBODY IMMUNE EFFECTOR CELL ENGAGERS AND METHODS OF USE THEREOF

(71) Applicant: NANJING LEGEND BIOTECH CO., LTD., Jiangsu (CN)

(72) Inventors: Xiaohu Fan, Edmonton (CA); Qiuchuan Zhuang, Nanjing (CN); Lei Yang, Huainan (CN); Pingyan Wang, Fengyang (CN); Qingyan Li, Nanjing (CN)

(73) Assignee: Nanjing Legend Biotech Co., Ltd., Nanjing (CN)

( * ) Notice: Subject to any disclaimer, the term of this patent is extended or adjusted under 35 U.S.C. 154(b) by 510 days.

(21) Appl. No.: 16/626,721

(22) PCT Filed: Jun. 27, 2018

(86) PCT No.: PCT/CN2018/093135
§ 371 (c)(1),
(2) Date: Dec. 26, 2019

(87) PCT Pub. No.: WO2019/001474
PCT Pub. Date: Jan. 3, 2019

(65) Prior Publication Data
US 2020/0123269 A1    Apr. 23, 2020

(30) Foreign Application Priority Data
Jun. 27, 2017    (WO) ................ PCT/CN2017/090343

(51) Int. Cl.
| | |
|---|---|
| C07K 16/28 | (2006.01) |
| A61P 35/00 | (2006.01) |
| A61K 39/00 | (2006.01) |
| C07K 14/765 | (2006.01) |

(52) U.S. Cl.
CPC .......... *C07K 16/2896* (2013.01); *A61P 35/00* (2018.01); *C07K 14/765* (2013.01); *C07K 16/2809* (2013.01); *C07K 16/2878* (2013.01); *A61K 2039/505* (2013.01); *C07K 2317/24* (2013.01); *C07K 2317/31* (2013.01); *C07K 2317/565* (2013.01); *C07K 2317/569* (2013.01); *C07K 2317/622* (2013.01); *C07K 2317/73* (2013.01); *C07K 2317/92* (2013.01); *C07K 2319/02* (2013.01); *C07K 2319/30* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell |
| 4,816,567 A | 3/1989 | Cabilly |
| 5,545,806 A | 8/1996 | Lonberg |
| 5,545,807 A | 8/1996 | Surani et al. |
| 5,569,825 A | 10/1996 | Lonberg |
| 5,571,894 A | 11/1996 | Wels |
| 5,587,458 A | 12/1996 | King |
| 5,625,126 A | 4/1997 | Lonberg |
| 5,633,425 A | 5/1997 | Lonberg |
| 5,641,870 A | 6/1997 | Rinderknecht |
| 5,661,016 A | 8/1997 | Lonberg |
| 5,869,046 A | 2/1999 | Presta et al. |
| 6,075,181 A | 6/2000 | Kucherlapati |
| 6,150,584 A | 11/2000 | Kucherlapati |
| 6,982,321 B2 | 1/2006 | Winter |
| 7,087,409 B2 | 8/2006 | Barbas, III |
| 8,754,287 B2 | 6/2014 | Macdonald |
| 10,934,363 B2* | 3/2021 | Fan ........ C12N 15/63 |
| 2006/0270045 A1 | 11/2006 | Cregg |
| 2009/0307787 A1 | 12/2009 | Grosveld |
| 2010/0122358 A1 | 5/2010 | Brueggemann |
| 2013/0273055 A1* | 10/2013 | Borges ........ A61P 35/00 |
| | | 530/387.3 |
| 2014/0302064 A1 | 10/2014 | Moore |
| 2015/0289489 A1 | 10/2015 | Macdonald |
| 2018/0230225 A1* | 8/2018 | Fan ........ C12N 15/62 |

FOREIGN PATENT DOCUMENTS

| | | |
|---|---|---|
| CN | 101490085 | 7/2009 |
| CN | 103842383 | 6/2014 |
| CN | 104487457 | 4/2015 |
| EP | 0368684 A1 | 5/1990 |
| EP | 0404097 A2 | 12/1990 |
| JP | 2014500879 A | 1/2014 |
| JP | 2016511277 | 4/2016 |
| WO | 1991010741 A1 | 7/1991 |
| WO | 1993001161 A1 | 1/1993 |

(Continued)

OTHER PUBLICATIONS

Hipp et al, Leukemia (2017), vol. 31, 1743-1751. (Year: 2017).*
Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*
Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*

(Continued)

*Primary Examiner* — Meera Natarajan
*Assistant Examiner* — Cheom-Gil Cheong
(74) *Attorney, Agent, or Firm* — Fish & Richardson P.C.

(57) ABSTRACT

Provided is a chimeric antibody immune cell engager comprising a target cell binding domain that specifically binds to an antigen on a target cell, and an immune effector cell binding domain comprising an antigen-binding fragment that specifically binds to an antigen on an immune effector cell. Also provided are pharmaceutical compositions, kits and methods of treatment.

28 Claims, 9 Drawing Sheets

Specification includes a Sequence Listing.

(56) References Cited

FOREIGN PATENT DOCUMENTS

| WO | 1993016185 A2 | 8/1993 | |
| WO | 1994004678 A1 | 3/1994 | |
| WO | 1996033735 A1 | 10/1996 | |
| WO | 1996034096 A1 | 10/1996 | |
| WO | 1996034103 A1 | 10/1996 | |
| WO | 1997049805 A2 | 12/1997 | |
| WO | 199824893 A2 | 6/1998 | |
| WO | 1999037681 A2 | 7/1999 | |
| WO | 2000043507 A1 | 7/2000 | |
| WO | 2001090190 A2 | 11/2001 | |
| WO | 2003014161 A2 | 2/2003 | |
| WO | 2003025020 A1 | 3/2003 | |
| WO | 2003035694 A2 | 5/2003 | |
| WO | 2004049794 A2 | 6/2004 | |
| WO | 2004106380 A2 | 12/2004 | |
| WO | 2004106381 A1 | 12/2004 | |
| WO | 2006003388 A2 | 1/2006 | |
| WO | 2006030220 A1 | 3/2006 | |
| WO | 2007042261 A2 | 4/2007 | |
| WO | 2008119567 A2 | 10/2008 | |
| WO | 2010037838 A2 | 4/2010 | |
| WO | 2010104949 A2 | 9/2010 | |
| WO | 2010150918 A1 | 12/2010 | |
| WO | 2012066058 A1 | 5/2012 | |
| WO | WO 2013072406 | 5/2013 | |
| WO | 2013154760 A1 | 10/2013 | |
| WO | 2015149077 A1 | 10/2015 | |
| WO | 2016014789 A2 | 1/2016 | |
| WO | WO 2016086196 | 6/2016 | |
| WO | WO 2016087531 | 6/2016 | |
| WO | 2016180982 A1 | 11/2016 | |
| WO | WO 2017010874 | 1/2017 | |
| WO | 2017025038 A1 | 2/2017 | |
| WO | 2017031104 A1 | 2/2017 | |
| WO | 2017133633 A1 | 8/2017 | |
| WO | 2018028647 A1 | 2/2018 | |
| WO | WO-2018102795 A2 * | 6/2018 | ............. A61K 35/17 |
| WO | 2019000223 A1 | 1/2019 | |
| WO | 2019001474 A1 | 1/2019 | |

OTHER PUBLICATIONS

Klimka et al., British Journal of Cancer, 2000, 83:252-260. (Year: 2000).*

Ward et al., Nature, 1989, 341:544-546. (Year: 1989).*

Shah et al, Leukemia (2020) 34:985-1005. (Year: 2020).*

Alarcon, B. (1991). "The CD3-γ and CD3-δ Subunits of the T Cell Antigen Receptor Can be Expressed Within Distinct Functional TCR/CD3 Complexes," EMBO J. 10(4):903-912.

Anasetti, C. et al. (Dec. 1990). "Induction of Specific Nonresponsiveness in Unprimed Human T Cells by Anti-CD3 Antibody and Alloantigen," J. Exp. Med. 172:1691-1700.

Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," Proc Nat. Acad. Sci. USA 91:3809-3813.

Beverley, P. C. et al. (Apr. 1981). "Distinctive Functional Characteristics of Human "T" Lymphocytes Defined by E Rosetting or a Monoclonal Anti-T Cell Antibody," Eur. J. Immunol. 11(4):329-334.

Boerner, P. et al. (Jul. 1, 1991). "Production of a Antigen-Specific Human Monoclonal Antibodies from In Vitro-Primed Human Splenocytes," J. Immunol. 147(1):86-95.

Brüggemann, M. et al. (1993). "Designer Mice: The Production of Human Antibody Repertoires in Transgenic Animals," Year in Immuno. 7:33-40.

Carpenter, P.A. et al. (Apr. 15, 2002). "A Humanized Non-FcR-Binding Anti-CD3 Antibody, Visilizumab, For Treatment of Steroid-Refractory Acute Graft-Versus-Host Disease," Blood 99(8):2712-2719.

Chekmasova, A. et al. (Dec. 3, 2015). "Paper: A Novel and Highly Potent CART Cell Drug Product for Treatment of BCMA-Expressing Hematological Malignances," Blood 126(23):3094, 2 pages.

Chothia, C. et al. (Aug. 20, 1987). "Canonical Structures for the Hypervariable Regions of Immunoglobulins," J. Mol. Biol. 196(4):901-917.

Chowdhury, P.S. (2008). "Engineering Hot Spots for Affinity Enhancement of Antibodies," Methods Mol. Biol. 207:179-196.

Clackson, T. et al. (Aug. 15, 1991). "Making Antibody Fragments Using Phage Display Libraries," Nature 352:624-628.

Cole et al. (1985). "The EBV-Hybridoma Technique and Its Application to Human Lung Cancer," Monolclonal Antibodies and Cancer Therapy 27:77-96.

Conrad, M.L. et al. (2007, e-pub. Jul. 25, 2007). "TCR and CD3 Antibody Cross-Reactivity in 44 Species," Cytometry Part A 71A:925-933.

Cunningham, B.C. et al. (Jun. 2, 1989). "High-Resolution Epitope Mapping of hGH-Receptor Interactions by Alanine-Scanning Mutagenesis," Science 244:1081-1085.

Davies, J. et al. (1996). "Single Antibody Domains as Small Recognition Units: Design and In Vitro Antigen Selection of Camelized, Human VH Domains with Improved Protein Stability," Protein Engineering 9(6):531-537.

Davies, J. et al. (Feb. 21, 1994). "'Camelising' Human Antibody Fragments: NMR Studies on VH Domains," FEBS Letters 339(3):285-290.

Deaglio, S. et al. (Jun. 15, 2007, e-pub. Feb. 27, 2007). "CD38/CD19: A Lipid Raft-Dependent Signaling Complex in Human B Cells," Blood 109(12):5390-5398.

Endo, Y. et al. (2003). "High-Throughput, Genome-Scale Protein Production Method Based on the Wheat Germ Cell-Free Expression System," Biotechnol. Adv. 21:695-713.

Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.

Fishwild, D.M. et al. (Jul. 1996). "High-Avidity Human IgGκ Monoclonal Antibodies from a Novel Strain of Minilocus Transgenic Mice," Nature Biotechnol. 14:845-851.

Greenberg, A.S. et al. (Mar. 9, 1995). "A New Antigen Receptor Gene Family That Undergoes Rearrangement and Extensive Somatic Diversification in Sharks" Nature 374(6518):168-173.

Hamers-Casterman, C. et al. (Jun. 3, 1993). "Naturally Occurring Antibodies Devoid of Light Chains," Nature 363:446-448.

Hammerling, G. et al. (1981). "Monoclonal Antibodies and T-Cell Hybridomas," in Monoclonal Antibodies and T-Cell Hybridomas, Elsevier/North Holland Biomedical Press, New York, pp. 563-586.

Harris, W.J. (1995). "Production of Humanized Monoclonal and Antibodies for in vivo Imaging and Therapy," Biochem. Soc. Transactions 23:1035-1038.

Hassanzadeh-Ghassabeh, G. et al. (2013, e-pub. Jun. 4, 2013). "Nanobodies and their Potential Applications," Nanomedicine (Lond) 8(6):1013-1026.

Hawkins, R.E. et al. (1992). "Selection of Phage Antibodies by Binding Affinity: Mimicking Affinity Maturations," J. Mol. Biol. 226:889-896.

Herold, K. C. et al. (Feb. 1, 2003). "Activation of Human T Cells by FcR Nonbinding Anti-CD3 mAb, hOKT3γ1 (Ala-Ala)," J. Clin. Invest. 111(3):409-418.

Hirsch, R. et al. (Jun. 1, 1988). "Effects of In Vivo Administration of Anti-T3 Monoclonal Antibody on T Cell Function in Mice. I. Immunosuppression of Transplantation Responses," J. Immunol. 140(11):3766-3772.

Holliger, P. et al. (Jul. 1993). "Diabodies: Small Bivalent and Bispecific Antibody Fragments," Proc. Natl. Acad. Sci. USA 90:6444-6448.

Holt, L.J. et al. (Nov. 2003) "Domain Antibodies: Proteins for Therapy," Trends in Biotechnology 21(11):484-490.

Hongo, J.A.S. et al. (1995). "Development and Characterization of Murine Monoclonal Antibodies to the Latency-Associated Peptide of Transforming Growth Factor Beta1," Hybridoma, 14(3):253-260.

(56) References Cited

OTHER PUBLICATIONS

Hoogenboom, H.R. (2002). "Overview of Antibody Phage-Display Technology and its Applications," in Chapter 1 of Methods in Molecular Biology, O'Brien, P.M. (ed.) et al., Humana Press Inc., Totowa, NJ, 178:1-37.

Hoogenboom, H.R. et al. (Sep. 1992). "By-Passing Immunisation: Human Antibodies from Synthetic Repertoires of Germline VH Gene Segments Rearranged in vitro," Journal of Molecular Biology 227(2):381-388.

Hudson, P.J. et al. (Jan. 2003). "Engineered Antibodies," Nat. Med. 9(1):129-134.

Hurle, M.R. et al. (1994). "Protein Engineering Techniques for Antibody Humanization," Curr. Op. Biotech. 5(4):428-433.

International Preliminary Report on Patentability dated Dec. 31, 2019 for PCT Application No. PCT/CN2017/090343, filed Jun. 27, 2017, 7 pages.

International Preliminary Report on Patentability dated Dec. 31, 2019 for PCT Application No. PCT/CN2018/093135, filed Jun. 27, 2018, 6 pages.

International Search Report and Written Opinion of the Searching Authority dated Mar. 27, 2018, for Patent Application No. PCT/CN2017/090343, 11 pages.

International Search Report and Written Opinion of the Searching Authority dated Sep. 20, 2018, for Patent Application No. PCT/CN2018/093135, 13 pages.

Jackson, J.R. et al. (Apr. 1, 1995). "In Vitro Antibody Maturation. Improvement of a High Affinity, Neutralizing Antibody Against IL-1 Beta," J. Immunol. 154(7):3310-3319.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90(6):2551-2555.

Jones, P. et al. (May 29, 1986). "Replacing the Complementarity-Determining Regions in a Human Antibody With Those From a Mouse," Nature 321:522-525.

Kalled, S. L. (Apr. 2005). "The Role of BAFF in Immune Function and Implications for Autoimmunity," Immunological Review 204:43-54.

Kober, L. et al. (Apr. 2013). "Optimized Signal Peptides for the Development of High Expressing CHO Cell Lines," Biotechnol Bioeng. 110(4):1164-1173.

Kohler, G. et al. (Aug. 7, 1975). "Continuous Culture of Fused Cells Secreting Antibody of Predefined Specificity," Nature 256:495-497.

Konopleva, M. et al. (1998). "Ligation of Cell Surface CD38 Protein with Agonistic Monoclonal Antibody Induces a Cell Growth Signal in Myeloid Leukemia Cells," J Immunol 161:4702-4708.

Lee, C.V. et al. (2004). "Bivalent Antibody Phage Display Mimics Natural Immunoglobulin," J. Immunol. Methods 284(1-2):119-132.

Lee, C.V. et al. (2004). "High-Affinity Human Antibodies From Phage-Displayed Synthetic Fab Libraries With a Single Framework Scaffold," J. Mol. Biol. 340:1073-1093.

Li, J. et al. (Mar. 7, 2006). "Human Antibodies for Immunotherapy Development Generated via a Human B Cell Hybridoma Technology," Proc. Natl. Acad. Sci. USA 103(10):3557-3562.

Lin, J et al. (Jan. 2001). "T Cell Receptor Signaling," Journal of Cell Science 114(Pt. 2):243-244.

Lin, P. et al. (Apr. 2004). "Flow Cytometric Immunophenotypic Analysis of 306 Cases of Multiple Myeloma," Am J Clin Pathol. 121(4):482-488.

Lokhorst, H.M. et al. (Sep. 24, 2015). "Targeting CD38 with Daratumumab Monotherapy in Multiple Myeloma," The New England Journal of Medicine 373(13):1207-1219.

Lonberg, N. et al. (1995), "Human Antibodies from Transgenic Mice," Int Rev Immunol. 13(1):65-93.

Lonberg, N. et al. (Apr. 28, 1994). "Antigen-Specific Human Antibodies From Mice Comprising Four Distinct Genetic Modifications," Nature 368(6474):856-859.

Marks, J.D. et al. (1991). "By-Passing Immunization Human Antibodies from V-gene Libraries Displayed on Phage," J. Mol. Biol. 222:581-597.

Marks, J.D. et al. (Jul. 1992). "By-Passing Immunization: Building High Affinity Human Antibodies by Chain Shuffling," Bio/Technology 10:779-783.

Mordenti, J. et al. (1989). "The Use of Interspecies Scaling in Toxicokinetics," Chapter 4 in Toxicokinetics and New Drug Development, Yacobi A. ed. et al.; Pergamon Press, New York, pp. 42-96.

Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.

Morrison, S.L. (Apr. 28, 1994). "Success in Specification," Nature 368:812-813.

Neri, P. et al. (Oct. 1, 2007). "Neutralizing B-Cell Activating Factor Antibody Improves Survival and Inhibits Osteoclastogenesis in a Severe Combined Immunodeficient Human Multiple Myeloma Model," Clinical Cancer Research 73(19):5903-5909.

Neuberger, M. (Jul. 1996) "Generating High-Avidity Human Mabs in Mice," Nature Biotechnology 14:826, 1 page.

Novak, A.N. et al. (Jan. 15, 2004). "Expression of BCMA, TACI, and BAFF-R in Multiple Myeloma: A Mechanism for Growth and Survival," Blood 103(2):689-694.

Oden, F. et al. (Aug. 2015, e-pub. Mar. 31, 2015). "Potent Anti-Tumor Response by Targeting B Cell Maturation Antigen (BCMA) in a Mouse Model of Multiple Myeloma," Mol. Oncology 9(7):1348-1358.

Ortho Multicenter Transplant Study Group. (Aug. 8, 1985). "A Randomized Clinical Trial of OKT3 Monoclonal Antibody for Acute Rejection of Cadaveric Renal Transplants," N. Engl. J. Med. 313(6):337-342.

Pessano, S. et al. (1985). "The T3/T Cell Receptor Complex: Antigenic Distinction Between the Two 20-kd T3 (T3-δ and T3-ε) Subunits," The EMBO Journal 4(2):337-344.

Plückthun, A. (1994) "Antibodies from *Escherichia coli*," Chapter 11 in Handbook of Experimental Pharmacology 113:269-315.

Presta, L.G. (1992). "Antibody Engineering," Current Opinion in Structural Biology 2:593-596.

Riechmann, L. (Jun. 28, 1996). "Rearrangement of the Former VL Interface in the Solution Structure of a Camelised, Single Antibody VH Domain," Journal of Molecular Biology 259(5):957-969.

Riechmann, L. et al. (Dec. 10, 1999). "Single Domain Antibodies: Comparison of Camel VH and Camelised Human VH Domains," Journal of Immunological Methods 231(1-2):25-38.

Riechmann, L. et al. (Mar. 24, 1988). "Reshaping Human Antibodies for Therapy," Nature 332:323-329.

Rosenberg, S.A. et al. (Dec. 22, 1988). "Use of Tumor-Infiltrating Lymphocytes and Interleukin-2 in the Immunotherapy of Patients With Metastatic Melanoma. A Preliminary Report," N Engl J Med. 319(25):1676-1680.

Running Deer, J. et al. (May-Jun. 2004, e-pub. Mar. 10, 2004). "High-Level Expression of Proteins in Mammalian Cells Using Transcription Regulatory Sequences From the Chinese Hamster EF-1Alpha Gene," Biotechnol. Prog. 20(3):880-889.

Salmeron, A. et al. (Nov. 1, 1991). "A Conformational Epitope Expressed Upon Association of CD3-Epsilon With Either CD3-Delta or CD3-Gamma is the Main Target for Recognition by Anti-CD3 Monoclonal Antibodies," J. Immunol. 147(9):3047-3052.

Schier, R. et al. (1995). "Identification of Functional and Structural Amino-Acid Residues by Parsimonious Mutagenesis," Gene 169:147-155.

Seckinger, A. et al. (Mar. 12, 2017). "Target Expression, Generation, Preclinical Activity, and Pharmacokinetics of the BCMA-T Cell Bispecific Antibody EM801 for Multiple Myeloma Treatment," Cancer cell 31(3):396-410.

Sheriff, S. et al. (Sep. 1996). "Redefining the Minimal Antigen-Binding Fragment," Nature Struct. Biol. 3(9):733-736.

Sidhu, S.S. et al. (2004). "Phage-Displayed Antibody Libraries of Synthetic Heavy Chain Complementarity Determining Regions," J. Mol. Biol. 338(2):299-310.

Sitaraman, K. et al. (2009). "High-Throughput Protein Expression Using Cell-Free System," Methods Mol. Biol. 498:229-244.

(56) References Cited

OTHER PUBLICATIONS

Spirin, A.S. (Oct. 2004). "High-Throughput Cell-Free Systems for Synthesis of Functionally Active Proteins," Trends Biotechnol. 22(10):538-545.

Streltsov, V.A. (Nov. 2005). "Structure of a Shark Ignar Antibody Variable Domain and Modeling of an Early-Developmental Isotype," Protein Sci. 14:2901-2909.

Thompson, J.S. et al. (Jul. 3, 2000). "Baff Binds to the Tumor Necrosis Factor Receptor-Like Molecule B Cell Maturation Antigen and is Important for Maintaining the Peripheral B Cell Population," J. Exp. Medicine 192(1):129-135.

Van Der Linden, R. (Jun. 23, 2000, e-pub. Jun. 13, 2000). "Induction of Immune Responses and Molecular Cloning of the Heavy Chain Antibody Repertoire of Lama Glama," J. Immunol. Methods 240(1-2):185-195.

Van Dijk, M.A. et al. (Aug. 2001). "Human Antibodies as Next Generation Therapeutics," Curr. Opin. Che. Biology 5(4):368-374.

Vaswani, S.K. et al. (Aug. 1998) "Humanized Antibodies as Potential Therapeutic Drugs," Annals of Allergy, Asthma, & Immunology 81:105-115.

Vu, M.D. et al. (Dec. 5, 2015). "A New Class of T-Cell Bispecific Antibodies for the Treatment of Multiple Myeloma, Binding to B Cell Maturation Antigen and CD3 and Showing Potent, Specific Antitumor Activity in Myeloma Cells and Long Duration of Action in Cynomolgus Monkeys," Blood 126(23):2998, 3 pages.

Ward, E.S. et al. (Oct. 12, 1989). "Binding Activities of a Repertoire of Single Immunoglobulin Variable Domains Secreted From *Escherichia coli*," Nature 341(6242): 544-546.

Yang, S.Y. et al. (Aug. 1986). "A Common Pathway for T Lymphocyte Activation Involving Both the CD3-Ti Complex and CD2 Sheep Erythrocyte Receptor Determinants," J. Immunol. 137(4):1097-1100.

Yelton, D.E. et al. (1995). "Affinity Maturation of the BR96 Anti-Carcinoma Antibody by Codon-Based Mutagenesis," J. Immunol. 155:1994-2004.

Yoshino, N. et al. (2000). "Upgrading of Flow Cytometric Analysis for Absolute Counts, Cytokines and OtherAntigenic Molecules of Cynomolgus Monkeys (Macaca Fascicularis) by Using Anti-Human Cross-ReactiveAntibodies," Exp. Anim. 49(2):97-100.

Zapata, G. et al. (1995). "Engineering Linear F(ab')2 Fragments for Efficient Production in *Escherichia coli* and Enhanced Antiproliferative Activity," Protein Engineering 8(10):1057-1062.

Dong, B. et al. (2016, e-pub. Mar. 1, 2016). "A Novel Bispecific Antibody BiSS, With Potent Anti-Cancer Activities," Cancer Bil. Ther. 17:364-370.

Li, L. et al. (Nov./Dec. 2015). "A Novel Bispecific Antibody, S-Fab, Induces Potent Cancer Cell Killing", J. of Immunotherapy 38(9):350-356.

Thakur et al., "Bispecific antibody based therapeutics: Strengths and challenges," Blood Reviews, Feb. 20, 2018, 32(4):339-347.

\* cited by examiner

US 11,827,713 B2

CHIMERIC ANTIBODY IMMUNE EFFECTOR CELL ENGAGERS AND METHODS OF USE THEREOF

CROSS REFERENCE TO RELATED APPLICATIONS

This application is a national stage application under 35 U.S.C. § 371 of International Application No. PCT/CN2018/093135, filed internationally on Jun. 27, 2018, which claims priority benefit of International Patent Application No. PCT/CN2017/090343 filed on Jun. 27, 2017, the contents of each of which are incorporated herein by reference in their entirety.

SUBMISSION OF SEQUENCE LISTING ON ASCII TEXT FILE

The contents of the following submission on ASCII text file are incorporated herein by reference in their entirety: a computer readable form (CRF) of the Sequence Listing (file name: 761422000400SUBSEQLIST.TXT, date recorded: Jun. 7, 2022, size: 397,948 bytes).

FIELD OF THE PRESENT APPLICATION

The present invention relates to chimeric antibody immune effector cell engagers, and methods of preparation and use thereof. The present application further provides compositions and methods useful for human therapy, such as cancer therapy.

BACKGROUND OF THE PRESENT APPLICATION

Immunotherapy is a rapidly growing area of cancer research. Antibody therapy is an important medicinal approach to treat human diseases, especially cancer. With high specificity, bispecific antibodies can bring together two distinct antigens, and therefore have great potential as therapeutic agents. Bispecific antibodies have found wide applications in cancer immunotherapy. For example, bispecific antibodies have been engineered to simultaneously bind to a cytotoxic cell (e.g., via the CD3 receptor on a T cell) and a target cell such as a tumor cell for destruction.

As part of the T cell receptor complex, the CD3 complex is an antigen expressed on mature human T cells, thymocytes and a subset of natural killer cells. In human, the T cell receptor (TCR) complex comprises TCRα and β chains as the central components. Accessory components of the TCR complex include the CD3 complex consisting of a γ chain, a δ chain, two ε chains, and two ξ chains. The intracellular tails of the CD3 molecules and the ξ chain contain immunoreceptor tyrosine-based activation motifs (ITAM), which are essential for signal transduction of the TCR complex. For example, activation of the TCR complex by binding to MHC-presented specific antigen epitopes results in phosphorylation of the ITAMs by Src family kinases, triggering recruitment of downstream kinases which results in T cell activation including $Ca^{2+}$ release. See, Lin and Weiss, *Journal of Cell Science* 114, 243-244 (2001). Clustering of CD3 on T cells, e.g., by immobilized anti-CD3 antibodies, leads to similar T cell activation response as by MHC engagement of the TCR, but independent from its clonal typical specificity to MHC epitopes.

Due to TCR's central role in modulating T cell activity, there have been attempts to develop molecules capable of specific binding to TCR with much focus on the generation of antibodies specific to the human CD3 antigen. Although T cell engaging bispecific antibodies developed to date have great therapeutic potential for the treatment of malignant diseases, most of these known bispecific molecules have limited usage. For example, some are species specific, and others lack desirable safety profile, or high efficacy in targeting certain cancer antigens.

The disclosures of all publications, patents, patent applications and published patent applications referred to herein are hereby incorporated herein by reference in their entirety.

BRIEF SUMMARY OF THE PRESENT APPLICATION

The present application provides chimeric antibody immune effector cell engagers, including chimeric antibody T cell engagers (CATE) and chimeric antibody Natural Killer cell engagers (CANKE). Also provides are pharmaceutical compositions, and methods of treating diseases (such as cancer or autoimmune disease) using the chimeric antibody immune effector cell engagers.

One aspect of the present application provides a chimeric antibody immune effector cell engager comprising: (a) a target cell binding domain comprising a single-domain antibody (sdAb) that specifically binds to an antigen on a target cell; and (b) an immune effector cell binding domain comprising an antigen-binding fragment that specifically binds to an antigen on an immune effector cell. In some embodiments, the sdAb is camelid, chimeric, human or humanized. In some embodiments, the sdAb is a $V_HH$ fragment. In some embodiments, the target cell is a tumor cell. In some embodiments, the target cell is a B cell.

In some embodiments according to any one of the chimeric antibody immune effector cell engagers described above, the target cell binding domain comprises an anti-BCMA sdAb. In some embodiments, the anti-BCMA sdAb is any one of the anti-BCMA sdAbs listed in Table 2. In some embodiments, the anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the anti-BCMA sdAb comprises an amino acid sequence selected from the group consisting of SEQ ID NOs: 78-88 and 290-316.

In some embodiments according to any one of the chimeric antibody immune effector cell engagers described above, the target cell binding domain comprises an anti-CD38 sdAb. In some embodiments, the anti-CD38 sdAb comprises any one of the following: (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58; (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59; (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60; (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61; (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62; (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63; (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64; (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65; (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66; (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; or (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68. In some embodiments, the anti-CD38 sdAb comprises an amino acid sequence selected from the group consisting of SEQ ID NOs: 89-100.

In some embodiments according to any one of the chimeric antibody immune effector cell engagers described above, the target cell binding domain comprises a first sdAb that specifically binds to a first antigen on a first target cell and a second sdAb that specifically binds to a second antigen on a second target cell. In some embodiments, the first sdAb is fused to the second sdAb via a peptide linker. In some embodiments, the first target cell and the second target cell are the same cell. In some embodiments, the first target cell and the second target cell are different cells. In some embodiments, the first antigen and the second antigen are the same. In some embodiments, the target cell binding domain comprises two, three or more anti-BCMA sdAbs. In some embodiments, the target cell binding domain comprises two, three or more anti-CD38 sdAbs. In some embodiments, the first sdAb and the second sdAb specifically bind to the same epitope. In some embodiments, the first sdAb and the second sdAb specifically bind to different epitopes. In some embodiments, the target cell binding domain comprises a first anti-BCMA sdAb and a second anti-BCMA sdAb. In some embodiments, the first antigen and the second antigen are different. In some embodiments, the target cell binding domain comprises an anti-BCMA sdAb and an anti-CD38 sdAb. In some embodiments, the anti-BCMA sdAb is fused to the N-terminus of the anti-CD38 sdAb. In some embodiments, the anti-BCMA sdAb is fused to the C-terminus of the anti-CD38 sdAb.

Another aspect of the present application provides a chimeric antibody immune effector cell engager, comprising: (a) a target cell binding domain comprising an anti-BCMA scFv; and (b) an immune effector cell binding domain comprising an antigen-binding fragment that specifically binds to an antigen on an immune effector cell. In some embodiments, the anti-BCMA scFv comprises the amino acid sequence of SEQ ID NO: 101 or SEQ ID NO: 102.

In some embodiments according to any one of the chimeric antibody immune effector cell engagers described above, the target cell binding domain is fused to the N-terminus of the immune effector cell binding domain. In some embodiments, the target cell binding domain is fused to the C-terminus of the immune effector cell binding domain.

In some embodiments according to any one of the chimeric antibody immune effector cell engagers described above, the target cell binding domain is fused to the immune effector cell binding domain via a peptide linker.

In some embodiments according to any one of the chimeric antibody immune effector cell engagers described above, the immune effector cell is a T cell. In some embodiments, the immune effector cell is an NK cell.

In some embodiments according to any one of the chimeric antibody immune effector cell engagers described above, the antigen-binding fragment in the immune effector cell binding domain is a Fab, scFv, or sdAb. In some embodiments, the antigen-binding fragment in the immune effector cell binding domain is murine, camelid, chimeric, human or humanized.

In some embodiments according to any one of the chimeric antibody immune effector cell engagers described above, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183.

Further provided by the present application are pharmaceutical compositions, comprising any one of the chimeric antibody immune effector cell engagers described above, and a pharmaceutically acceptable carrier.

Another aspect of the present application provides a method of treating a disease in an individual, comprising administering to the individual an effective amount of any one of the pharmaceutical compositions described above. In some embodiments, the disease is a B cell-related disorder. In some embodiments, the disease is cancer, such as multiple myeloma. In some embodiments, the disease is an autoimmune disease, such as systemic lupus erythematosus.

Also provided are methods of use, kits, and articles of manufacture comprising any one of the chimeric antibody immune effector cell engagers, isolated nucleic acids, or vectors described above.

DETAILED DESCRIPTION OF THE PRESENT APPLICATION

Figure 1:
FIG. 1 shows expression of exemplary CATEs (#001-#012 and #019-#030) by 293-6E cells. Antibody expression levels in the supernatants from the cells were determined using an anti-6×His tag-HRP based ELISA. A recombinant protein, CD123-His, was used to generate a standard curve. On average, the expression levels of the exemplary CATEs were about 1-2 µg/mL.

The present application provides chimeric antibody immune effector cell engagers comprising a target cell binding domain comprising an antigen binding domain such as a single-domain antibody (e.g., a $V_HH$) that specifically binds to an antigen on a target cell, and an immune effector cell binding domain that specifically binds to an antigen on an immune effector cell. In some embodiments, the target cell binding domain comprises two or more single-domain antibodies each specifically binding to an antigen on a target cell, thereby allowing multivalent or multispecific targeting of one or more target cells. Exemplary chimeric antibody immune effector cell engagers that target tumor cells via specific binding to BCMA and/or CD38 and engage T cells and/or NK cells via specific binding to CD3 epsilon are provided herein. The chimeric antibody immune effector cell engagers can be useful for treating a variety of diseases, including plasma cell disorders, B cell disorders, and autoimmune diseases.

Accordingly, one aspect of the present application provides a chimeric antibody immune effector cell engager comprising: (a) a target cell binding domain comprising a single-domain antibody (sdAb) that specifically binds to an antigen on a target cell; and (b) an immune effector cell binding domain that specifically binds to an antigen on an immune effector cell. In some embodiments, the target cell binding domain comprises an anti-BCMA sdAb (such as $V_HH$). In some embodiments, the target cell binding domain comprises an anti-CD38 sdAb (such as $V_HH$). In some embodiments, the immune effector cell binding domain comprises an anti-CD3 antigen-binding fragment.

In some embodiments, there is provided a chimeric antibody immune effector cell engager comprising: (a) a first sdAb that specifically binds to a first antigen on a first target cell and a second sdAb that specifically binds to a second antigen on a second target cell, and (b) an immune effector cell binding domain that specifically binds to an antigen on an immune effector cell. In some embodiments, the first antigen and the second antigen are the same. In some embodiments, the target cell binding domain comprises a first anti-BCMA sdAb and a second anti-BCMA sdAb. In some embodiments, the first antigen and the second antigen are different. In some embodiments, the target cell binding domain comprises an anti-BCMA sdAb and an anti-CD3 sdAb.

Another aspect of the present application provides chimeric antibody immune effector cell engager comprising: (a) a target cell binding domain comprising an anti-BCMA scFv; and (b) an immune effector cell binding domain that specifically binds to an antigen on an immune effector cell. In some embodiments, the immune effector cell binding domain comprises an anti-CD3 antigen-binding fragment.

Further provided are pharmaceutical compositions, kits, articles of manufacture and methods of treating a disease (such as cancer or autoimmune disease) using the chimeric antibody immune effector cell engagers described herein.

I. Definitions

The practice of the present invention will employ, unless indicated specifically to the contrary, conventional methods of virology, immunology, microbiology, molecular biology and recombinant DNA techniques within the skill of the art, many of which are described below for the purpose of illustration. Such techniques are explained fully in the literature. See, e.g., Current Protocols in Molecular Biology or Current Protocols in Immunology, John Wiley & Sons, New York, N.Y. (2009); Ausubel et al, Short Protocols in Molecular Biology, 3$^{rd}$ ed., Wiley & Sons, 1995; Sambrook and Russell, Molecular Cloning: A Laboratory Manual (3rd Edition, 2001); Maniatis et al. Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R. Freshney, ed., 1986); Perbal, A Practical Guide to Molecular Cloning (1984) and other like references.

The term "chimeric antibody immune effector cell engager" as used herein refers to a multispecific antibody (such as bispecific antibody) that can specifically bind to both an immune effector cell (such as T cell or NK cell) and a target cell (such as tumor cell).

The term "antibody" includes monoclonal antibodies (including full length 4-chain antibodies or full length heavy-chain only antibodies which have an immunoglobulin Fc region), antibody compositions with polyepitopic specificity, multispecific antibodies (e.g., bispecific antibodies, diabodies, and single-chain molecules), as well as antibody fragments (e.g., Fab, F(ab')$_2$, and Fv). The term "immunoglobulin" (Ig) is used interchangeably with "antibody" herein. Antibodies contemplated herein include single-domain antibodies, such as heavy chain only antibodies.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the $C_H$ sequence and function, e.g., humans express the following subclasses: IgG1, IgG2A, IgG2B, IgG3, IgG4, IgA1 and IgA2.

The term "heavy chain-only antibody" or "HCAb" refers to a functional antibody, which comprises heavy chains, but lacks the light chains usually found in 4-chain antibodies. Camelid animals (such as camels, llamas, or alpacas) are known to produce HCAbs.

The term "single-domain antibody" or "sdAb" refers to a single antigen-binding polypeptide having three complementary determining regions (CDRs). The sdAb alone is capable of binding to the antigen without pairing with a corresponding CDR-containing polypeptide. In some cases, single-domain antibodies are engineered from camelid HCAbs, and their heavy chain variable domains are referred herein as "$V_H$Hs". Some $V_H$Hs may also be known as Nanobodies. Camelid sdAb is one of the smallest known antigen-binding antibody fragments (see, e.g., Hamers-Casterman et al., Nature 363:446-8 (1993); Greenberg et al., Nature 374:168-73 (1995); Hassanzadeh-Ghassabeh et al., Nanomedicine (Lond), 8:1013-26 (2013)). A basic $V_H$H has the following structure from the N-terminus to the C-terminus: FR1-CDR1-FR2-CDR2-FR3-CDR3-FR4, in which FR1 to FR4 refer to framework regions 1 to 4, respectively, and in which CDR1 to CDR3 refer to the complementarity determining regions 1 to 3.

An "isolated" antibody is one that has been identified, separated and/or recovered from a component of its production environment (e.g., natural or recombinant). Preferably, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

The "variable region" or "variable domain" of an antibody refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites. Heavy-chain only antibodies from the Camelid species have a single heavy chain variable region, which is referred to as "$V_HH$". $V_HH$ is thus a special type of $V_H$.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture or recombinantly, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present application may be made by a variety of techniques, including, for example, the hybridoma method (e.g., Kohler and Milstein., *Nature*, 256: 495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, Intern. *Rev. Immunol.* 13: 65-93 (1995).

The terms "full-length antibody," "intact antibody" or "whole antibody" are used interchangeably to refer to an antibody in its substantially intact form, as opposed to an antibody fragment. Specifically, full-length 4-chain antibodies include those with heavy and light chains including an Fc region. Full-length heavy-chain only antibodies include the heavy chain (such as $V_HH$) and an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules; single-domain antibodies (such as $V_HH$), and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies described herein comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATTZFD® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., camelid) antibodies are chimeric antibodies that contain minimal sequence derived from non-human immunoglobulin. In some embodiments, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, single-domain antibodies comprise three HVRs (or CDRs): HVR1 (or CDR1), HVR2 (or CDR2), and HVR3 (or CDR3). HVR3 displays the most diversity of the three HVRs, and is believed to play a unique role in conferring fine specificity to antibodies. See, e.g., Hamers-Casterman et al., *Nature* 363:446-448 (1993); Sheriff et al., *Nature Struct. Biol.* 3:733-736 (1996).

The term "Complementarity Determining Region" or "CDR" are used to refer to hypervariable regions as defined by the Kabat system. See Kabat et al., *Sequences of Proteins of Immunological Interest*, 5th Ed. Public Health Service, National Institutes of Health, Bethesda, Md. (1991)

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below in Table 1.

TABLE 1

HVR delineations.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the $V_L$ and 26-35 (H1), 50-65 or 49-65 (H2) and 93-102, 94-102, or 95-102 (H3) in the $V_H$. The variable domain residues are numbered according to Kabat et al., supra, for each of these definitions.

The amino acid residues of a single-domain antibody (such as $V_HH$) are numbered according to the general numbering for $V_H$ domains given by Kabat et al. ("Sequence of proteins of immunological interest", US Public Health Services, NIH Bethesda, Md., Publication No. 91), as applied to $V_HH$ domains from Camelids in the article of Riechmann and Muyldermans, J. Immunol. Methods 2000 Jun. 23; 240 (1-2): 185-195. According to this numbering, FR1 of a $V_HH$ comprises the amino acid residues at positions 1-30, CDR1 of a $V_HH$ comprises the amino acid residues at positions 31-35, FR2 of a $V_HH$ comprises the amino acids at positions 36-49, CDR2 of a $V_HH$ comprises the amino acid residues at positions 50-65, FR3 of a $V_HH$ comprises the amino acid residues at positions 66-94, CDR3 of a $V_HH$ comprises the amino acid residues at positions 95-102, and FR4 of a $V_HH$ comprises the amino acid residues at positions 103-113. In this respect, it should be noted that—as is well known in the art for $V_H$ domains and for $V_HH$ domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering).

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin $V_L$ or $V_H$ framework sequences. Generally, the selection of human immunoglobulin $V_L$ or $V_H$ sequences is from a subgroup of variable domain sequences. Generally, the subgroup of sequences is a subgroup as in Kabat et al., *Sequences of Proteins of Immunological Interest*, 5th Ed. Public Health Service, National Institutes of Health, Bethesda, Md. (1991). Examples include for the $V_L$, the subgroup may be subgroup kappa I, kappa II, kappa III or kappa IV as in Kabat et al., supra. Additionally, for the $V_H$, the subgroup may be subgroup I, subgroup II, or subgroup III as in Kabat et al. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In some embodiments, an affinity-matured antibody has nanomolar or even picomolar affinities for the target antigen. Affinity-matured antibodies are produced by procedures known in the art. For example, Marks et al., *Bio/Technology* 10:779-783 (1992) describes affinity maturation by $V_H$- and $V_L$-domain shuffling. Random mutagenesis of HVR and/or framework residues is described by, for example: Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

As use herein, the term "specifically binds," "specifically recognizes," or is "specific for" refers to measurable and reproducible interactions such as binding between a target and an antigen binding protein, which is determinative of the presence of the target in the presence of a heterogeneous population of molecules including biological molecules. For example, an antigen binding protein that specifically binds a target (which can be an epitope) is an antigen binding protein that binds this target with greater affinity, avidity, more readily, and/or with greater duration than it binds other targets. In some embodiments, the extent of binding of an antigen binding protein to an unrelated target is less than about 10% of the binding of the antigen binding protein to the target as measured, e.g., by a radioimmunoassay (RIA). In some embodiments, an antigen binding protein that specifically binds a target has a dissociation constant (Kd) of ≤1 µM, ≤100 nM, ≤10 nM, ≤1 nM, or ≤0.1 nM. In some embodiments, an antigen binding protein specifically binds an epitope on a protein that is conserved among the protein from different species. In some embodiments, specific binding can include, but does not require exclusive binding.

The term "specificity" refers to selective recognition of an antigen binding protein for a particular epitope of an antigen. Natural antibodies, for example, are monospecific. The term "multispecific" as used herein denotes that an antigen binding protein has two or more antigen-binding sites of which at least two bind a different antigen or a different epitope of the same antigen. "Bispecific" as used herein denotes that an antigen binding protein has two different antigen-binding specificities. The term "monospecific" as used herein denotes an antigen binding protein that has one or more binding sites each of which bind the same epitope of the same antigen.

The term "valent" as used herein denotes the presence of a specified number of binding sites in an antigen binding protein. A natural antibody for example or a full length antibody has two binding sites and is bivalent. As such, the terms "trivalent", "tetravalent", "pentavalent" and "hexavalent" denote the presence of two binding site, three binding sites, four binding sites, five binding sites, and six binding sites, respectively, in an antigen binding protein.

"Binding affinity" generally refers to the strength of the sum total of non-covalent interactions between a single binding site of a molecule (e.g., an antibody or a chimeric antibody immune effector cell engager) and its binding partner (e.g., an antigen). Unless indicated otherwise, as used herein, "binding affinity" refers to intrinsic binding affinity that reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present application. Specific illustrative and exemplary embodiments for measuring binding affinity are described in the following.

"Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNAS TAR) software. Those skilled in the art can determine appropriate parameters for measuring alignment, including any algorithms needed to achieve maximal alignment over the full length of the sequences being compared.

An "isolated" nucleic acid molecule described herein is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous Linking is accomplished by ligation at convenient restriction sites. If such sites do not exist, the synthetic oligonucleotide adaptors or linkers are used in accordance with conventional practice.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells.

As used herein, "treatment" or "treating" is an approach for obtaining beneficial or desired results including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread (e.g., metastasis) of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing the quality of life, and/or prolonging survival. Also encompassed by "treatment" is a reduction of pathological consequence of the disease. The methods of the present application contemplate any one or more of these aspects of treatment.

As used herein, an "individual" or a "subject" refers to a mammal, including, but not limited to, human, bovine, horse, feline, canine, rodent, or primate. In some embodiments, the individual is a human.

The term "effective amount" used herein refers to an amount of an agent, such as a chimeric antibody immune effector cell engager, or a pharmaceutical composition thereof, sufficient to treat a specified disorder, condition or disease such as ameliorate, palliate, lessen, and/or delay one or more of its symptoms. In reference to cancer, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay recurrence. An effective amount can be administered in one or more administrations. The effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

As used herein, "delaying" the development of cancer means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. A method that "delays" development of cancer is a method that reduces probability of disease development in a given time frame and/or reduces the extent of the disease in a given time frame, when compared to not using the method. Such comparisons are typically based on clinical studies, using a statistically significant number of individuals. Cancer development can be detectable using standard methods, including, but not limited to, computerized axial tomography (CAT Scan), Magnetic Resonance Imaging (MRI), abdominal ultrasound, clotting tests, arteriography, or biopsy. Development may also refer to cancer progression that may be initially undetectable and includes occurrence, recurrence, and onset.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile. A "sterile" formulation is aseptic or free from all living microorganisms and their spores.

It is understood that embodiments of the present application described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Chimeric Antibody Immune Effector Cell Engagers

The present application provides a chimeric antibody immune effector cell engager comprising a target cell binding domain that specifically binds to an antigen on a target cell, and an immune effector cell that specifically binds to an antigen of an immune effector cell. In some embodiments, the target cell binding domain comprises one or more antigen-binding domains derived from single-domain antibodies (sdAb), such as $V_HH$. In some embodiments, the target cell binding domain comprises one or more antigen-binding fragments derived from four-chain antibodies, such as scFv. In some embodiments, the target cell binding domain comprises an anti-BCMA scFv.

Thus, in some embodiments, there is provided a chimeric antibody immune effector cell engager comprising: (a) a target cell binding domain comprising a sdAb (such as $V_HH$) that specifically binds to an antigen on a target cell; and (b) an immune effector cell binding domain comprising an antigen-binding fragment that specifically binds to an antigen on an immune effector cell. In some embodiments, the target cell is a tumor cell or a B cell. In some embodiments, the antigen-binding fragment in the immune effector cell binding domain is a Fab, scFv, or sdAb. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, the immune effector cell is a T cell, and the chimeric antibody T cell engager is also referred herein as CATE. In some embodiments, the immune effector cell is a T cell, and the chimeric antibody NK cell engager is also referred herein as CANKE. In some embodiments, the immune effector cell binding domain comprises an antigen-binding fragment that specifically binds to CD3, such as CD3ε.

In some embodiments, there is provided a chimeric antibody T cell engager comprising: (a) a target cell binding domain comprising a sdAb (such as $V_HH$) that specifically binds to an antigen on a target cell; and (b) a T cell binding domain comprising an antigen-binding fragment that specifically binds to an antigen on a T cell. In some embodiments, the target cell is a tumor cell or a B cell. In some embodiments, the antigen-binding fragment in the immune effector cell binding domain is a Fab, scFv, or sdAb. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody NK cell engager comprising: (a) a target cell binding domain comprising a sdAb (such as $V_HH$) that specifically binds to an antigen on a target cell; and (b) an NK cell binding domain comprising an antigen-binding fragment that specifically binds to an antigen on an NK cell. In some embodiments, the target cell is a tumor cell or a B cell. In some embodiments, the antigen-binding fragment in the immune effector cell binding domain is a Fab, scFv, or sdAb. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as comprising an amino acid sequence selected from the group consisting of SEQ ID NOs: 72-77.

In some embodiments, there is provided a chimeric antibody immune effector cell engager comprising: (a) a target cell binding domain comprising an sdAb (such as $V_HH$) that specifically binds to an antigen on a target cell; and (b) an immune effector cell binding domain comprising an anti-CD3 antigen-binding fragment. In some embodiments, the target cell is a tumor cell or a B cell. In some embodiments, the anti-CD3 antigen-binding fragment is a Fab, scFv, or sdAb. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a VL comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, the target cell binding domain comprises an sdAb that specifically binds to BCMA (also referred herein as "anti-BCMA sdAb"), such as human BCMA. In some embodiments the target cell binding domain comprises an anti-BCMA $V_HH$. The anti-BCMA sdAb can be derived from any single-domain antibodies, such as heavy chain only antibodies, that specifically bind to BCMA. In some embodiments, the anti-BCMA sdAb is camelid, chimeric, human or humanized. In some embodiments, the target cell binding domain comprises an anti-BCMA scFv. In some embodiments, the anti-BCMA scFv is derived from C11D5.3 or J22.9-xi.

B cell mature antigen (BCMA), also known as CD269, is a member of the tumor necrosis factor receptor superfamily, namely TNFRSF17 (Thompson et al., J. Exp. Medicine, 192 (1):129-135, 2000). Human BCMA is almost exclusively expressed in plasma cells and multiple myeloma cells (see e.g. Novak et al., Blood, 103(2): 689-694, 2004; Neri et al., Clinical Cancer Research, 73(19):5903-5909; Felix et al., Mol. Oncology, 9(7):1348-58, 2015). BCMA can bind B-cell activating factor (BAFF) and a proliferation including ligand (APRIL) (e.g. Mackay et al., 2003 and Kalled et al., Immunological Review, 204: 43-54, 2005). BCMA can be a suitable tumor antigen target for immunotherapeutic agents against multiple myeloma. Antibodies of high affinity can block the binding between BCMA and its native ligands BAFF and APRIL.

Thus, in some embodiments, there is provided a chimeric antibody immune effector cell engager comprising: (a) a target cell binding domain comprising an anti-BCMA sdAb (such as anti-BCMA $V_HH$); and (b) an immune effector cell binding domain comprising an antigen-binding fragment that specifically binds to an antigen on an immune effector cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-BCMA sdAb is any one of the anti-BCMA sdAbs listed in Table 2. In some embodiments, the anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the anti-BCMA sdAb comprises an amino acid sequence selected from the group consisting of SEQ ID NOs: 78-88 and 290-316. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising an anti-BCMA sdAb (such as anti-BCMA $V_H$H); and (b) an immune effector cell binding domain comprising an anti-CD3 antigen-binding fragment. In some embodiments, the target cell is a tumor cell or a B cell. In some embodiments, the anti-CD3 antigen-binding fragment is a Fab, scFv, or sdAb. In some embodiments, the anti-CD3 antigen-binding fragment is derived from OKT3, L2K, UCHT1, 60E11, or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_H$H comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_H$H comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-BCMA sdAb is any one of the anti-BCMA sdAbs listed in Table 2. In some embodiments, the anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the anti-BCMA sdAb comprises an amino acid sequence selected from the group consisting of SEQ ID NOs: 78-88 and 290-316. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising an anti-BCMA scFv; and (b) an immune effector cell binding domain comprising an antigen-binding fragment that specifically binds to an antigen on an immune effector cell. In some embodiments, the antigen-binding fragment in the immune effector cell binding domain is a Fab, scFv, or sdAb. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-BCMA scFv is derived from C11D5.3. In some embodiments, the anti-BCMA scFv is derived from J22.9-xi. In some embodiments, the anti-BCMA scFv has the format N-terminus-$V_H$-$V_L$-C terminus. In some embodiments, the anti-BCMA scFv has the format N-terminus-$V_L$-$V_H$-C terminus. In some embodiments, the anti-BCMA scFv comprises the amino acid sequence of SEQ ID NO: 101 or SEQ ID NO: 102. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, the target cell binding domain comprises an sdAb that specifically binds to CD38 (also referred herein as "anti-CD38 sdAb"), such as human CD38. In some embodiments, the target cell binding domain comprises an anti-CD38 $V_H$H. The anti-CD38 sdAb can be derived from any single-domain antibodies, such as heavy chain only antibodies, that specifically bind to CD38. In some embodiments, the anti-CD38 sdAb is camelid, chimeric, human or humanized.

CD38 is a type II transmembrane glycoprotein that associates with cell-surface receptors, regulates cytoplasmic $Ca^{2+}$ flux, and mediates signal transduction in lymphoid and myeloid (Konopleva et al., J Immunol, 161:4702-8, 1998; Deaglio et al., Blood, 109:5390-8, 2007). Human CD38 is highly and uniformly expressed on myeloma cells and is expressed at relatively low levels on normal lymphoid and myeloid cells and in some tissues of non-hematopoietic origin, which makes it a potential target in the treatment of myeloma (See, for example, Lin et al., *Am J Clin Pathol*, 2004, 121:482; H. M. Lokhorst et al., *New Eng. J. Med.*, 2015, 373:13).

Thus, in some embodiments, there is provided a chimeric antibody immune effector cell engager comprising: (a) a target cell binding domain comprising an anti-CD38 sdAb (such as anti-CD38 $V_H$H); and (b) an immune effector cell binding domain comprising an antigen-binding fragment that specifically binds to an antigen on an immune effector cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-CD38 sdAb comprises any one of the following: (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58; (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59; (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60; (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61; (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62; (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63; (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64; (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65; (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66; (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68; or (12) a CDR1 comprising the amino acid sequence of SEQ ID NO:45; a CDR2 comprising the amino acid sequence of SEQ ID NO:57; and a CDR3 comprising the amino acid sequence of SEQ ID NO:69. In some embodiments, the anti-CD38 sdAb comprises an amino acid sequence selected from the group consisting of SEQ ID NOs: 89-100. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising an anti-CD38 sdAb (such as anti-CD38 $V_H$H); and (b) an immune effector cell binding domain comprising an anti-CD3 antigen-binding fragment. In some embodiments, the target cell is a tumor cell or a B cell. In some embodiments, the anti-CD3 antigen-binding fragment is a Fab, scFv, or sdAb. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-CD38 sdAb comprises any one of the following: (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58; (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59; (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60; (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61; (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62; (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63; (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64; (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65; (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66; (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68; or (12) a CDR1 comprising the amino acid sequence of SEQ ID NO:45; a CDR2 comprising the amino acid sequence of SEQ ID NO:57; and a CDR3 comprising the amino acid sequence of SEQ ID NO:69. In some embodiments, the anti-CD38 sdAb comprises an amino acid sequence selected from the group consisting of SEQ ID NOs: 89-100. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, the target cell binding domain is monospecific. In some embodiments, the target cell binding domain is monovalent. In some embodiments, the target cell binding domain is multivalent, such as bivalent or trivalent. In some embodiments, the target cell binding domain is multispecific, such as bispecific or trispecific.

In some embodiments, there is provided a chimeric antibody immune effector cell engager comprising: (a) a target cell binding domain comprising a first sdAb (such as $V_HH$) that specifically binds to a first antigen on a first target cell and a second sdAb (such as $V_HH$) that specifically binds to a second antigen on a second target cell; and (b) an immune effector cell binding domain comprising an antigen-binding fragment that specifically binds to an antigen on an immune effector cell. In some embodiments, the first target cell and the second target cell are the same cell. In some embodiments, the first target cell and the second target cell are different cells. In some embodiments, the first cell and the second cell are tumor cells. In some embodiments, the first sdAb is fused to the second sdAb via a peptide linker. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising a first sdAb (such as $V_HH$) that specifically binds to a first antigen on a target cell and a second sdAb (such as $V_HH$) that specifically binds to a second antigen on the target cell; and (b) an immune effector cell binding domain comprising an antigen-binding fragment that specifically binds to an antigen on an immune effector cell. In some embodiments, the first antigen and the second antigen are the same. In some embodiments, the first sdAb and the second sdAb specifically bind to the same epitope. In some embodiments, the first sdAb and the second sdAb specifically bind to different epitopes. In some embodiments, the first antigen and the second antigen are different. In some embodiments, the first sdAb is fused to the second sdAb via a peptide linker. In some embodiments, the target cell is a tumor cell or a B cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, the target cell binding domain comprises a first anti-BCMA sdAb and a second anti-BCMA sdAb. In some embodiments, the first anti-BCMA sdAb and the second anti-BCMA sdAb recognizes different epitopes on BCMA. In some embodiments, the target cell binding domain comprises a first anti-CD38 sdAb and a second anti-CD38 sdAb. In some embodiments, the first anti-CD38 sdAb and the second anti-CD38 sdAb recognizes different epitopes on CD38. In some embodiments, the target cell binding domain comprises an anti-BCMA sdAb and an anti-CD38 sdAb. In some embodiments, the anti-BCMA sdAb is fused to the N-terminus of the anti-CD38 sdAb. In some embodiments, the anti-BCMA sdAb is fused to the C-terminus of the anti-CD38 sdAb.

Thus, in some embodiments, there is provided a chimeric antibody immune effector cell engager comprising: (a) a target cell binding domain comprising a first anti-BCMA sdAb (such as anti-BCMA $V_HH$) and a second anti-BCMA sdAb (such as anti-BCMA $V_HH$); and (b) an immune effector cell binding domain comprising an antigen-binding fragment that specifically binds to an antigen on an immune effector cell. In some embodiments, the first anti-BCMA sdAb is fused to the second anti-BCMA sdAb via a peptide linker. In some embodiments, the first anti-BCMA sdAb and the second anti-BCMA sdAb recognizes different epitopes on BCMA. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-BCMA sdAb is any one of the anti-BCMA sdAbs listed in Table 2. In some embodiments, the first anti-BCMA sdAb and/or the second anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the first anti-BCMA sdAb and/or the second anti-BCMA sdAb comprises an amino acid sequence selected from the group consisting of SEQ ID NOs: 78-88 and 290-316. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising a first anti-BCMA sdAb (such as anti-BCMA $V_HH$) and a second anti-BCMA sdAb (such as anti-BCMA $V_HH$); and (b) an immune effector cell binding domain comprising an anti-CD3 antigen-binding fragment (such as anti-CD3 $V_HH$ or anti-CD3 scFv). In some embodiments, the first anti-BCMA sdAb is fused to the second anti-BCMA sdAb via a peptide linker. In some embodiments, the first anti-BCMA sdAb and the second anti-BCMA sdAb recognizes different epitopes on BCMA. In some embodiments, the anti-CD3 antigen-binding fragment is an anti-CD3 sdAb such as an anti-CD3 $V_HH$. In some embodiments, the anti-CD3 $V_HH$ is derived from 60E11 or 117G03. In some embodiments, the anti-CD3 antigen-binding fragment is an anti-CD3 scFv. In some embodiments, the anti-CD3 scFv is derived from OKT3, L2K, or UCHT1. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-BCMA sdAb is any one of the anti-BCMA sdAbs listed in Table 2. In some embodiments, the first anti-BCMA sdAb and/or the second anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the first anti-BCMA sdAb and/or the second anti-BCMA sdAb comprises an amino acid sequence selected from the group consisting of SEQ ID NOs: 78-88 and 290-316. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising an anti-BCMA sdAb (such as anti-BCMA $V_HH$) and an anti-CD38 sdAb (such as anti-CD38 $V_HH$); and (b) an immune effector cell binding domain comprising an antigen-binding fragment that specifically binds to an antigen on an immune effector cell. In some embodiments, the anti-BCMA sdAb is fused to the anti-CD38 sdAb via a peptide linker. In some embodiments, the anti-BCMA sdAb is fused to the N-terminus of the anti-CD38 sdAb. In some embodiments, the anti-BCMA sdAb is fused to the C-terminus of the anti-CD38 sdAb. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-BCMA sdAb is any one of the anti-BCMA sdAbs listed in Table 2. In some embodiments, the anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the anti-BCMA sdAb comprises an amino acid sequence selected from the group consisting of SEQ ID NOs: 78-88. In some embodiments, the anti-CD38 sdAb comprises any one of the following: (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58; (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59; (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60; (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61; (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62; (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63; (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64; (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65; (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66; (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68; or (12) a CDR1 comprising the amino acid sequence of SEQ ID NO:45; a CDR2 comprising the amino acid sequence of SEQ ID NO:57; and a CDR3 comprising the amino acid sequence of SEQ ID NO:69. In some embodiments, the anti-CD38 sdAb comprises an amino acid sequence selected from the group consisting of SEQ ID NOs: 89-100. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a chimeric antibody immune effector cell engager comprising: (a) a target cell binding domain comprising an anti-BCMA sdAb (such as anti-BCMA $V_HH$) and an anti-CD38 sdAb (such as anti-CD38 $V_HH$); and (b) an immune effector cell binding domain comprising an anti-CD3 sdAb (such as anti-CD3 $V_HH$). In some embodiments, the anti-BCMA sdAb is fused to the anti-CD38 sdAb via a peptide linker. In some embodiments, the anti-BCMA sdAb is fused to the C-terminus of the anti-CD38 sdAb. In some embodiments, the anti-CD3 antigen-binding fragment is derived from 60E11 or 117G03. In some embodiments, the anti-CD3 antigen-binding fragment comprises: (1) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (2) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises the amino acid sequence of SEQ ID NO: 182 or 183. In some embodiments, the anti-BCMA sdAb comprises a CDR1 comprising the amino acid sequence of SEQ ID NO:1; a CDR2 comprising the amino acid sequence of SEQ ID NO:12; and a CDR3 comprising the amino acid sequence of SEQ ID NO:23. In some embodiments, the anti-BCMA sdAb comprises the amino acid sequence of SEQ ID NO: 78. In some embodiments, the anti-CD38 sdAb comprises a CDR1 comprising the amino acid sequence of SEQ ID NO:38; a CDR2 comprising the amino acid sequence of SEQ ID NO:50; and a CDR3 comprising the amino acid sequence of SEQ ID NO:62. In some embodiments, the anti-CD38 sdAb comprises the amino acid sequence of SEQ ID NO: 93. In some embodiments, the target cell binding domain is fused to the N-terminus of the immune effector cell binding domain. In some embodiments, the target cell binding domain is fused to the immune effector cell binding domain via a peptide linker, such as a peptide linker comprising the amino acid sequence of SEQ ID NO: 206 or 207.

In some embodiments, there is provided a chimeric antibody immune effector cell engager comprising the amino acid sequence of any one of SEQ ID NOs: 106-163 and 184-207. In some embodiments, there is provided a polypeptide comprising the amino acid of any one of SEQ ID NOs: 106-163 and 184-207.

Target Cell Binding Domain

The chimeric antibody immune effector cell engagers described herein comprise a target cell binding domain. The target cell binding domain comprises one or more antigen-binding fragments derived from single-domain antibodies or four-chain antibodies.

1. Single-Domain Antibodies

In some embodiments, the target cell binding domain comprises one or more (such as any one of 1, 2, 3, 4, or more) single-domain antibodies. The sdAbs may be of the same or different origins, and of the same or different sizes. Exemplary sdAbs include, but are not limited to, heavy chain variable domains from heavy-chain only antibodies (e.g., $V_HH$ or $V_{NAR}$), binding molecules naturally devoid of light chains, single domains (such as $V_H$ or $V_L$) derived from conventional 4-chain antibodies, humanized heavy-chain only antibodies, human single-domain antibodies produced by transgenic mice or rats expressing human heavy chain segments, and engineered domains and single domain scaffolds other than those derived from antibodies. Any sdAbs known in the art or described herein that target an antigen on a target cell (such as tumor cell) may be used to construct the chimeric antibody immune effector cell engagers described herein. The sdAbs may be derived from any species including, but not limited to mouse, rat, human, camel, llama, lamprey, fish, shark, goat, rabbit, and bovine. Single-domain antibodies contemplated herein also include naturally occurring single-domain antibody molecules from species other than Camelidae and sharks.

In some embodiments, the sdAb is derived from a naturally occurring single-domain antigen binding molecule known as heavy chain antibody devoid of light chains (also referred herein as "heavy chain only antibodies"). Such single domain molecules are disclosed in WO 94/04678 and Hamers-Casterman, C. et al. (1993) Nature 363:446-448, for example. For clarity reasons, the variable domain derived from a heavy chain molecule naturally devoid of light chain is known herein as a $V_HH$ to distinguish it from the conventional $V_H$ of four chain immunoglobulins. Such a $V_HH$ molecule can be derived from antibodies raised in Camelidae species, for example, camel, llama, vicuna, dromedary, alpaca and guanaco. Other species besides Camelidae may produce heavy chain molecules naturally devoid of light chain, and such $V_HH$s are within the scope of the present application.

$V_HH$ molecules from Camelids are about 10 times smaller than IgG molecules. They are single polypeptides and can be very stable, resisting extreme pH and temperature conditions. Moreover, they can be resistant to the action of proteases which is not the case for conventional 4-chain antibodies. Furthermore, in vitro expression of $V_HH$s produces high yield, properly folded functional $V_HH$s. In addition, antibodies generated in Camelids can recognize epitopes other than those recognized by antibodies generated in vitro through the use of antibody libraries or via immunization of mammals other than Camelids (see, for example, WO9749805). As such, multispecific or multivalent chimeric antibody immune effector cell engagers comprising one or more $V_HH$ domains may interact more efficiently with targets than multispecific or multivalent chimeric antibody immune effector cell engagers comprising antigen binding fragments derived from conventional 4-chain antibodies. Since $V_HH$s are known to bind into 'unusual' epitopes such as cavities or grooves, the affinity of chimeric antibody immune effector cell engagers comprising such $V_HH$s may be more suitable for therapeutic treatment than conventional multispecific polypeptides.

In some embodiments, the sdAb is derived from a variable region of the immunoglobulin found in cartilaginous fish. For example, the sdAb can be derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) Protein Sci. 14:2901-2909.

In some embodiments, the sdAb is recombinant, CDR-grafted, humanized, camelized, de-immunized and/or in vitro generated (e.g., selected by phage display). In some embodiments, the amino acid sequence of the framework regions may be altered by "camelization" of specific amino acid residues in the framework regions. Camelization refers to the replacing or substitution of one or more amino acid residues in the amino acid sequence of a (naturally occurring) $V_H$ domain from a conventional 4-chain antibody by one or more of the amino acid residues that occur at the corresponding position(s) in a $V_HH$ domain of a heavy chain antibody. This can be performed in a manner known per se, which will be clear to the skilled person, for example on the basis of the further description herein. Such "camelizing" substitutions are preferably inserted at amino acid positions that form and/or are present at the $V_H$-$V_L$ interface, and/or at the so-called Camelidae hallmark residues, as defined herein (see for example WO 94/04678, Davies and Riechmann FEBS Letters 339: 285-290, 1994; Davies and Riechmann Protein Engineering 9 (6): 531-537, 1996; Riechmann J Mol. Biol. 259: 957-969, 1996; and Riechmann and Muyldermans J. Immunol. Meth. 231: 25-38, 1999).

In some embodiments, the sdAb is a human single-domain antibody produced by transgenic mice or rats expressing human heavy chain segments. See, eg., US20090307787 A1, U.S. Pat. No. 8.754,287, US20150289489A1, US20100122358A1, and WO2004049794. In some embodiments, the sdAb is affinity matured.

In some embodiments, naturally occurring $V_HH$ domains against a particular antigen or target, can be obtained from (naïve or immune) libraries of Camelid $V_HH$ sequences. Such methods may or may not involve screening such a library using said antigen or target, or at least one part, fragment, antigenic determinant or epitope thereof using one or more screening techniques known per se. Such libraries and techniques are for example described in WO 99/37681, WO 01/90190, WO 03/025020 and WO 03/035694. Alternatively, improved synthetic or semi-synthetic libraries derived from (naïve or immune) $V_HH$ libraries may be used, such as $V_HH$ libraries obtained from (naïve or immune) $V_HH$ libraries by techniques such as random mutagenesis and/or CDR shuffling, as for example described in WO 00/43507.

In some embodiments, the single-domain antibodies are generated from conventional four-chain antibodies. See, for example, EP 0 368 684, Ward et al. (Nature 1989 Oct. 12; 341 (6242): 544-6), Holt et al., Trends Biotechnol., 2003, 21(11):484-490; WO 06/030220; and WO 06/003388.

2. Antigens

Each sdAb in the target cell binding domain specifically binds to an antigen on a target cell. In some embodiments, the antigen is a cell surface molecule. The single-domain antibodies may be chosen to recognize an antigen that acts as a cell surface marker on target cells associated with a special disease state. In some embodiments, the antigen, such as the first antigen and/or the second antigen on the target cell(s), is a tumor antigen. In some embodiments, the chimeric antibody immune effector cell engager target a single tumor antigen. In some embodiments, the chimeric antibody immune effector cell engager targets two or more tumor antigens. In some embodiments, the tumor antigen is associated with a B cell malignancy. Tumors express a number of proteins that can serve as a target antigen for an immune response, particularly T cell mediated immune responses. The antigens targeted by the chimeric antibody immune effector cell engager may be antigens on a single diseased cell or antigens that are expressed on different cells that each contribute to the disease. The antigens targeted by the chimeric antibody immune effector cell engager may be directly or indirectly involved in the diseases.

Tumor antigens are proteins that are produced by tumor cells that can elicit an immune response, particularly T cell mediated immune responses. The selection of the targeted antigen of the invention will depend on the particular type of cancer to be treated. Exemplary tumor antigens include, for example, a glioma-associated antigen, carcinoembryonic antigen (CEA), β-human chorionic gonadotropin, alphafetoprotein (AFP), lectin-reactive AFP, thyroglobulin, RAGE-1, MN-CAIX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, HER2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In some embodiments, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and gp100 in melanoma and prostatic acid phosphatase (PAP) and prostate-specific antigen (PSA) in prostate cancer. Other target molecules belong to the group of transformation-related molecules such as the oncogene HER2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma.

In some embodiments, the tumor antigen is a tumor-specific antigen (TSA) or a tumor-associated antigen (TAA). A TSA is unique to tumor cells and does not occur on other cells in the body. A TAA associated antigen is not unique to a tumor cell, and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development, when the immune system is immature, and unable to respond or they may be antigens that are normally present at extremely low levels on normal cells, but which are expressed at much higher levels on tumor cells.

Non-limiting examples of TSA or TAA antigens include the following: Differentiation antigens such as MART-1/MelanA (MART-I), gp 100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23HI, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS 1, SDCCAG16, TA-90\Mac-2 binding protein\cyclophilin C-associated protein, TAAL6, TAG72, TLP, and TPS.

In some embodiments, the antigen (such as the first antigen and/or the second antigen) is selected from the group consisting of CD19, CD20, CD22, CD33, CD38, BCMA, CS1, ROR1, GPC3, CD123, IL-13R, CD138, c-Met, EGFRvIII, GD-2, NY-ESO-1, MAGE A3, and glycolipid F77.

In some embodiments, the antigen is expressed on a B cell. In some embodiments, the antigen (such as the first antigen and/or the second antigen) is BCMA. In some embodiments, the antigen (such as the first antigen and/or the second antigen) is CD38. In some embodiments, the first antigen is BCMA and the second antigen is CD38.

3. Exemplary sdAbs

Sequences of exemplary single-domain antibodies suitable for use in the target cell binding domain include, but are not limited to the single domain antibodies listed in Table 2 below.

TABLE 2

Sequences of exemplary single-domain antibodies.

| Ab | Ex. AA SEQ ID | CDR1 | CDR2 | CDR3 |
|---|---|---|---|---|
| Exemplary Anti-BCMA single-domain antibodies | | | | |
| 269A37346 | 78 | SGFTLDYYAIG (SEQ ID NO: 1) | CISRSDGSTYYADSVKG (SEQ ID NO: 12) | AGADCSGYLRDYEF (SEQ ID NO: 23) |
| 269A37348 | 79 | SGRTFSTYGMA (SEQ ID NO: 2) | SKASMNYSGRTYYADSVKG (SEQ ID NO: 13) | AGTGCSTYGCFDAQIIDY (SEQ ID NO: 24) |
| 269A37917 | 80 | SGRTFTMG (SEQ ID NO: 3) | AISLSPTLAYYAESVKG (SEQ ID NO: 14) | ADRKSVMSIRPDY (SEQ ID NO: 25) |
| 269A37355 | 81 | SGGIFVINAMG (SEQ ID NO: 4) | SIRGLGRTNYDDSVKG (SEQ ID NO: 15) | VYVTLLGGVNRDY (SEQ ID NO: 26) |
| 269A37915 | 82 | SGRTFSSIVMG (SEQ ID NO: 5) | AIMWNDGITYLQDSVKG (SEQ ID NO: 16) | ASKGRYSEYEY (SEQ ID NO: 27) |
| 269A37936 | 83 | SGFTFDRAVIV (SEQ ID NO: 6) | FIKPSDGTIYYIDSLKG (SEQ ID NO: 17) | ASPEDWYTDWIDWSIYR (SEQ ID NO: 28) |
| 269A37953 | 84 | STYTVNSDVMG (SEQ ID NO: 7) | AIMWNDGITYLQDSVKG (SEQ ID NO: 18) | ASKGRYSEYEY (SEQ ID NO: 29) |
| 269A37965 | 85 | SGATLTNDHMA (SEQ ID NO: 8) | AIDWSGRTTNYADPVEG (SEQ ID NO: 19) | VLRAWISYDNDY (SEQ ID NO: 30) |
| 269A37972 | 86 | SGGTLSKNTVA (SEQ ID NO: 9) | SITWDGRTTYYADSVKG (SEQ ID NO: 20) | DLGKWPAGPADY (SEQ ID NO: 31) |

TABLE 2-continued

Sequences of exemplary single-domain antibodies.

| Ab | Ex. AA SEQ ID | CDR1 | CDR2 | CDR3 |
| --- | --- | --- | --- | --- |
| 269A37353 | 87 | SEHTFSSHVMG (SEQ ID NO: 10) | VIGWRDISTSYADSVKG (SEQ ID NO: 21) | ARRIDAADFDS (SEQ ID NO: 32) |
| 269A37948 | 88 | SGRAFSTYFMA (SEQ ID NO: 11) | GIAWSGGSTAYADSVKG (SEQ ID NO: 22) | SRGIEVEEFGA (SEQ ID NO: 33) |
| 269B005 | 290 | INVMA (SEQ ID NO: 209) | AVTRDGRKSCGDSVKG (SEQ ID NO: 236) | DGWGATTLDYTYGMDY (SEQ ID NO: 263) |
| 269B023 | 291 | TFTMG (SEQ ID NO: 210) | SITWDGRSAYYAESVKG (SEQ ID NO: 237) | DRKSVMSIRPDY (SEQ ID NO: 264) |
| 269B024 | 292 | INAMG (SEQ ID NO: 211) | TITRGGSTNYGPSVKG (SEQ ID NO: 238) | ERLDGSGYGYEYDY (SEQ ID NO: 265) |
| 269B028 | 293 | KNTVA (SEQ ID NO: 212) | SITCDGRTTYYANSVNG (SEQ ID NO: 239) | YRKSIMSIQPDY (SEQ ID NO: 266) |
| 269B030 | 294 | SIVMG (SEQ ID NO: 213) | AIMWNDGLTYLQGSVKG (SEQ ID NO: 240) | DRKSVMSIRPDY (SEQ ID NO: 267) |
| 269B038 | 295 | TFTMG (SEQ ID NO: 214) | AISLSPTLAYYAESVKG (SEQ ID NO: 241) | RRIDAADFDS (SEQ ID NO: 268) |
| 269B054 | 296 | KNTVA (SEQ ID NO: 215) | SITWDGRTTYYADSVKG (SEQ ID NO: 242) | LGKWPAGPADY (SEQ ID NO: 269) |
| 269B059 | 297 | INTMD (SEQ ID NO: 216) | AISLSPTLAYYAESVKG (SEQ ID NO: 243) | DRKSVMSIRPDY (SEQ ID NO: 270) |
| 269B060 | 298 | KNTVA (SEQ ID NO: 217) | SITCDGRTTYYANSVKG (SEQ ID NO: 244) | LGKWPAGSADY (SEQ ID NO: 271) |
| 269B069 | 299 | DYWMH (SEQ ID NO: 218) | SIDTSGQTTYYADSLKG (SEQ ID NO: 245) | RYRGGTWYGMAN (SEQ ID NO: 272) |
| 269B074 | 300 | SNTMA (SEQ ID NO: 219) | STTWNGRSTYYADSVKG (SEQ ID NO: 246) | LGKWPAGPADY (SEQ ID NO: 273) |
| 269B076 | 301 | TFTMG (SEQ ID NO: 220) | DISGGRTNYADSVKG (SEQ ID NO: 247) | DRKSVMSIRPDY (SEQ ID NO: 274) |
| 269B079 | 302 | VAAISL (SEQ ID NO: 221) | FTISRDNAKNTVVLQMNSLKP (SEQ ID NO: 248) | DRKSVMSIRPDY (SEQ ID NO: 275) |
| 269B083 | 303 | KNTVA (SEQ ID NO: 222) | SITWDGRTTYYADSVKG (SEQ ID NO: 249) | TASCHLFGLGSGAFVS (SEQ ID NO: 276) |
| 269B085 | 304 | TFTMG (SEQ ID NO: 223) | AISLSPTLAYYAESVKG (SEQ ID NO: 250) | SKDRYSEYEY (SEQ ID NO: 277) |
| 269B093 | 305 | TFTMG (SEQ ID NO: 224) | AISLSPTLAYYAESVKGKG (SEQ ID NO: 251) | KNGGPVDY (SEQ ID NO: 278) |
| 269B094 | 306 | SIVMG (SEQ ID NO: 225) | AIMWNDGITYLQDSVKG (SEQ ID NO: 252) | SKGRYSEYEY (SEQ ID NO: 279) |
| 269B104 | 307 | TFTMG (SEQ ID NO: 226) | AINLSPTLTYYAESVKG (SEQ ID NO: 253) | ERKSVMAIPPDY (SEQ ID NO: 280) |
| 269B109 | 308 | TFTMG (SEQ ID NO: 227) | SITLIPTFPYYAYSVKG (SEQ ID NO: 254) | YRKYLMSILPDY (SEQ ID NO: 281) |
| 269B110 | 309 | TFTMG (SEQ ID NO: 228) | AISLSPTLAYYAESVKG (SEQ ID NO: 255) | NRNSQRVIAALSWIGMNY (SEQ ID NO: 282) |
| 269B113 | 310 | TFTMG (SEQ ID NO: 229) | AISLSPTLAYYAESVKG (SEQ ID NO: 256) | RRIDAADFDS (SEQ ID NO: 283) |
| 269B126 | 311 | TFTMG (SEQ ID NO: 230) | VIGWRDINASYADSVKG (SEQ ID NO: 257) | RRIDATDFDS (SEQ ID NO: 284) |

TABLE 2-continued

Sequences of exemplary single-domain antibodies.

| Ab | Ex. AA SEQ ID | CDR1 | CDR2 | CDR3 |
|---|---|---|---|---|
| 269B129 | 312 | NHVMG (SEQ ID NO: 231) | VIGWRDISTSYADSVKG (SEQ ID NO: 258) | RRIDAADFDS (SEQ ID NO: 285) |
| 269B131 | 313 | NYILA (SEQ ID NO: 232) | HISRSGGKSGYGDSVKG (SEQ ID NO: 259) | PLWYGSPTLIDY (SEQ ID NO: 286) |
| 269B135 | 314 | TFTMG (SEQ ID NO: 233) | AISLSPTLAYYAESVKG (SEQ ID NO: 260) | DRKSVMSIRPDY (SEQ ID NO: 287) |
| 269B136 | 315 | TFTMG (SEQ ID NO: 234) | AISLSPTLAYYAEPVKG (SEQ ID NO: 261) | DRKSVMSIRPDY (SEQ ID NO: 288) |
| 269B139 | 316 | NNFVMG (SEQ ID NO: 235) | AISLSPTLAYYVESVKG (SEQ ID NO: 262) | DRKSVMSIRPDY (SEQ ID NO: 289) |
| Exemplary Anti-CD38 single-domain antibodies | | | | |
| 38A37333 | 89 | SGLTFSSYPMM (SEQ ID NO: 34) | RISDSGGYTNYDDSVKG (SEQ ID NO: 46) | ILGLPT (SEQ ID NO: 58) |
| 38A37336 | 90 | SGFTFSSNWMY (SEQ ID NO: 35) | TISTDGRGTYYKDSVKG (SEQ ID NO: 47) | KEPRVLMAYLRNLGDFGS (SEQ ID NO: 59) |
| 38A37699 | 91 | SGRIFSINAMG (SEQ ID NO: 36) | AISTAGSTNYGDSVKG (SEQ ID NO: 48) | LNFPPYVY (SEQ ID NO: 60) |
| 38A37331 | 92 | SGSIFKVFRVFAMS (SEQ ID NO: 37) | SISSGETTTYADSVKG (SEQ ID NO: 49) | ADHTFTGDF (SEQ ID NO: 61) |
| 38A37717 | 93 | TGKVFSIYDMG (SEQ ID NO: 38) | EITSSGTTHYDDFVSG (SEQ ID NO: 50) | NHVFGGSY (SEQ ID NO: 62) |
| 38A37719 | 94 | SASIFTRLPMG (SEQ ID NO: 39) | GIVPSGRINYADSVKG (SEQ ID NO: 51) | ADTFPLPT (SEQ ID NO: 63) |
| 38A37330 | 95 | SGRAYATMA (SEQ ID NO: 40) | HLRVSGDTTYYTDSVKG (SEQ ID NO: 52) | GPYGILAAARVSNPGNYDY (SEQ ID NO: 64) |
| 38A37334 | 96 | SGLTFSSYIMG (SEQ ID NO: 41) | EISSGGMTSYADSVKG (SEQ ID NO: 53) | APERGSIWYSRYEYKY (SEQ ID NO: 65) |
| 38A37730 | 97 | SQGIFTINAMG (SEQ ID NO: 42) | EVSSGGRTDYADSVKG (SEQ ID NO: 54) | VSGWHVFVGDRIV (SEQ ID NO: 66) |
| 38A37340 | 98 | SGRTFSSYAMA (SEQ ID NO: 43) | SISTSGGITDYADSVKG (SEQ ID NO: 55) | ARTWYLRTSLQYDY (SEQ ID NO: 67) |
| 38A37731 | 99 | SGTIVSISTMG (SEQ ID NO: 44) | TITRRGRTNYTDSVKG (SEQ ID NO: 56) | AEVQLDIWASAYDY (SEQ ID NO: 68) |
| 38A37326 | 100 | SGRTYAMG (SEQ ID NO: 45) | TISGAGNTKYADSVKG (SEQ ID NO: 57) | AGKWFPAANEY (SEQ ID NO: 69) |

Anti-BCMA sdAb

In some embodiments, the target cell binding domain comprises one or more anti-BCMA sdAbs, such as anti-BCMA $V_HH$. In some embodiments, the anti-BCMA sdAb is affinity matured. In some embodiments, the anti-BCMA sdAb is camelid. In some embodiments, the anti-BCMA sdAb is humanized. In some embodiments, the anti-BCMA sdAb comprises an acceptor human framework, e.g., a human immunoglobulin framework or a human consensus framework. In some embodiments, the anti-BCMA sdAb modulates BCMA activity. In some embodiments, the anti-BCMA sdAb is an antagonist antibody. Exemplary anti-BCMA sdAbs have been described, for example, in WO2018/028647, the contents of which are incorporated herein by reference in their entirety.

In some embodiments, the anti-BCMA sdAb comprises one, two, or all three CDRs of the amino acid sequence of SEQ ID NO: 78. In some embodiments, the anti-BCMA sdAb comprises one, two, or all three CDRs of the amino acid sequence of SEQ ID NO: 79. In some embodiments, the anti-BCMA sdAb comprises one, two, or all three CDRs of the amino acid sequence of SEQ ID NO: 80. In some embodiments, the anti-BCMA sdAb comprises one, two, or all three CDRs of the amino acid sequence of SEQ ID NO: 81. In some embodiments, the anti-BCMA sdAb comprises one, two, or all three CDRs of the amino acid sequence of SEQ ID NO: 82. In some embodiments, the anti-BCMA sdAb comprises one, two, or all three CDRs of the amino acid sequence of SEQ ID NO: 83. In some embodiments, the anti-BCMA sdAb comprises one, two, or all three CDRs of the amino acid sequence of SEQ ID NO: 84. In some embodiments, the anti-BCMA sdAb comprises one, two, or all three CDRs of the amino acid sequence of SEQ ID NO: 85. In some embodiments, the anti-BCMA sdAb comprises one, two, or all three CDRs of the amino acid sequence of SEQ ID NO: 86. In some embodiments, the anti-BCMA sdAb comprises one, two, or all three CDRs of the amino acid sequence of SEQ ID NO: 87. In some embodiments, the anti-BCMA sdAb comprises one, two, or all three CDRs of the amino acid sequence of SEQ ID NO: 88. In some embodiments, the anti-BCMA sdAb comprises one, two, or all three CDRs of the amino acid sequence of SEQ ID NO: 290. In some embodiments, the anti-BCMA sdAb comprises one, two, or all three CDRs of the amino acid sequence of SEQ ID NO: 291. In some embodiments, the anti-BCMA sdAb comprises one, two, or all three CDRs of the amino acid sequence of SEQ ID NO: 292. In some embodiments, the anti-BCMA sdAb comprises one, two, or all three CDRs of the amino acid sequence of SEQ ID NO: 293. In some embodiments, the anti-BCMA sdAb comprises one, two, or all three CDRs of the amino acid sequence of SEQ ID NO: 294. In some embodiments, the anti-BCMA sdAb comprises one, two, or all three CDRs of the amino acid sequence of SEQ ID NO: 295. In some embodiments, the anti-BCMA sdAb comprises one, two, or all three CDRs of the amino acid sequence of SEQ ID NO: 296. In some embodiments, the anti-BCMA sdAb comprises one, two, or all three CDRs of the amino acid sequence of SEQ ID NO: 297. In some embodiments, the anti-BCMA sdAb comprises one, two, or all three CDRs of the amino acid sequence of SEQ ID NO: 298. In some embodiments, the anti-BCMA sdAb comprises one, two, or all three CDRs of the amino acid sequence of SEQ ID NO: 299. In some embodiments, the anti-BCMA sdAb comprises one, two, or all three CDRs of the amino acid sequence of SEQ ID NO: 300. In some embodiments, the anti-BCMA sdAb comprises one, two, or all three CDRs of the amino acid sequence of SEQ ID NO: 301. In some embodiments, the anti-BCMA sdAb comprises one, two, or all three CDRs of the amino acid sequence of SEQ ID NO: 302. In some embodiments, the anti-BCMA sdAb comprises one, two, or all three CDRs of the amino acid sequence of SEQ ID NO: 303. In some embodiments, the anti-BCMA sdAb comprises one, two, or all three CDRs of the amino acid sequence of SEQ ID NO: 304. In some embodiments, the anti-BCMA sdAb comprises one, two, or all three CDRs of the amino acid sequence of SEQ ID NO: 305. In some embodiments, the anti-BCMA sdAb comprises one, two, or all three CDRs of the amino acid sequence of SEQ ID NO: 306. In some embodiments, the anti-BCMA sdAb comprises one, two, or all three CDRs of the amino acid sequence of SEQ ID NO: 307. In some embodiments, the anti-BCMA sdAb comprises one, two, or all three CDRs of the amino acid sequence of SEQ ID NO: 308. In some embodiments, the anti-BCMA sdAb comprises one, two, or all three CDRs of the amino acid sequence of SEQ ID NO: 309. In some embodiments, the anti-BCMA sdAb comprises one, two, or all three CDRs of the amino acid sequence of SEQ ID NO: 310. In some embodiments, the anti-BCMA sdAb comprises one, two, or all three CDRs of the amino acid sequence of SEQ ID NO: 311. In some embodiments, the anti-BCMA sdAb comprises one, two, or all three CDRs of the amino acid sequence of SEQ ID NO: 312. In some embodiments, the anti-BCMA sdAb comprises one, two, or all three CDRs of the amino acid sequence of SEQ ID NO: 313. In some embodiments, the anti-BCMA sdAb comprises one, two, or all three CDRs of the amino acid sequence of SEQ ID NO: 314. In some embodiments, the anti-BCMA sdAb comprises one, two, or all three CDRs of the amino acid sequence of SEQ ID NO: 315. In some embodiments, the anti-BCMA sdAb comprises one, two, or all three CDRs of the amino acid sequence of SEQ ID NO: 316.

In some embodiments, the anti-BCMA sdAb comprises at least one, at least two, or all three CDRs selected from (a) a CDR1 comprising an amino acid sequence selected from SEQ ID NOs: 1-11 and 209-235; (b) a CDR2 comprising an amino acid sequence selected from SEQ ID NOs: 12-22 and 236-262; and (c) a CDR3 comprising an amino acid sequence selected from SEQ NOs: 23-33 and 263-289. In some embodiments, the anti-BCMA sdAb comprises three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 1-11 and 209-235; (b) a CDR2 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 12-22 and 236-262; and (c) a CDR3 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 23-33 and 263-289. In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-BCMA sdAb comprising that sequence retains the ability to bind to BCMA. In some embodiments, the anti-BCMA sdAb comprises a substitution (e.g., conservative substitutions), insertions, or deletions of one, two, three or more amino acids in any one of the CDRs described herein, but the anti-BCMA sdAb comprising that sequence retains the ability to bind to BCMA.

In some embodiments, the anti-BCMA sdAb comprises three CDRs comprising: (a) a CDR1 comprising the amino acid sequence of SEQ ID NO: 1; (b) a CDR2 comprising the amino acid sequence of SEQ ID NO: 12; and (c) a CDR3 comprising the amino acid sequence of SEQ ID NO: 23, or a variant thereof comprising up to about 5 amino acid substitutions.

In some embodiments, the anti-BCMA sdAb comprises three CDRs comprising: (a) a CDR1 comprising the amino acid sequence of SEQ ID NO: 2; (b) a CDR2 comprising the amino acid sequence of SEQ ID NO: 13; and (c) a CDR3 comprising the amino acid sequence of SEQ ID NO: 24, or a variant thereof comprising up to about 5 amino acid substitutions.

In some embodiments, the anti-BCMA sdAb comprises three CDRs comprising: (a) a CDR1 comprising the amino acid sequence of SEQ ID NO: 3; (b) a CDR2 comprising the amino acid sequence of SEQ ID NO: 14; and (c) a CDR3 comprising the amino acid sequence of SEQ ID NO: 25, or a variant thereof comprising up to about 5 amino acid substitutions.

In some embodiments, the anti-BCMA sdAb comprises three CDRs comprising: (a) a CDR1 comprising the amino acid sequence of SEQ ID NO: 4; (b) a CDR2 comprising the amino acid sequence of SEQ ID NO: 15; and (c) a CDR3 comprising the amino acid sequence of SEQ ID NO: 26, or a variant thereof comprising up to about 5 amino acid substitutions.

In some embodiments, the anti-BCMA sdAb comprises three CDRs comprising: (a) a CDR1 comprising the amino acid sequence of SEQ ID NO: 5; (b) a CDR2 comprising the amino acid sequence of SEQ ID NO: 16; and (c) a CDR3 comprising the amino acid sequence of SEQ ID NO: 27, or a variant thereof comprising up to about 5 amino acid substitutions.

In some embodiments, the anti-BCMA sdAb comprises three CDRs comprising: (a) a CDR1 comprising the amino acid sequence of SEQ ID NO: 6; (b) a CDR2 comprising the amino acid sequence of SEQ ID NO: 17; and (c) a CDR3 comprising the amino acid sequence of SEQ ID NO:28, or a variant thereof comprising up to about 5 amino acid substitutions.

In some embodiments, the anti-BCMA sdAb comprises three CDRs comprising: (a) a CDR1 comprising the amino acid sequence of SEQ ID NO: 7; (b) a CDR2 comprising the amino acid sequence of SEQ ID NO: 18; and (c) a CDR3 comprising the amino acid sequence of SEQ ID NO: 29, or a variant thereof comprising up to about 5 amino acid substitutions.

In some embodiments, the anti-BCMA sdAb comprises three CDRs comprising: (a) a CDR1 comprising the amino acid sequence of SEQ ID NO: 8; (b) a CDR2 comprising the amino acid sequence of SEQ ID NO: 19; and (c) a CDR3 comprising the amino acid sequence of SEQ ID NO: 30, or a variant thereof comprising up to about 5 amino acid substitutions.

In some embodiments, the anti-BCMA sdAb comprises three CDRs comprising: (a) a CDR1 comprising the amino acid sequence of SEQ ID NO: 9; (b) a CDR2 comprising the amino acid sequence of SEQ ID NO: 20; and (c) a CDR3 comprising the amino acid sequence of SEQ ID NO: 31, or a variant thereof comprising up to about 5 amino acid substitutions.

In some embodiments, the anti-BCMA sdAb comprises three CDRs comprising: (a) a CDR1 comprising the amino acid sequence of SEQ ID NO: 10; (b) a CDR2 comprising the amino acid sequence of SEQ ID NO: 21; and (c) a CDR3 comprising the amino acid sequence of SEQ ID NO: 32, or a variant thereof comprising up to about 5 amino acid substitutions.

In some embodiments, the anti-BCMA sdAb comprises three CDRs comprising: (a) a CDR1 comprising the amino acid sequence of SEQ ID NO: 11; (b) a CDR2 comprising the amino acid sequence of SEQ ID NO: 22; and (c) a CDR3 comprising the amino acid sequence of SEQ ID NO: 33, or a variant thereof comprising up to about 5 amino acid substitutions.

In some embodiments, the anti-BCMA sdAb comprises three CDRs comprising: (a) a CDR1 comprising the amino acid sequence of SEQ ID NO: 209; (b) a CDR2 comprising the amino acid sequence of SEQ TIS NO: 236; and (c) a CDR3 comprising the amino acid sequence of SEQ ID NO: 263, or a variant thereof comprising up to about 5 amino acid substitutions.

In some embodiments, ale anti-BCMA sdAb comprises three CDRs comprising: (a) a CDR1 comprising the amino acid sequence of SEQ ID NO: 210; (b) a CDR2 comprising the amino acid sequence of SEQ ID NO: 237; and (c) a CDR3 comprising the amino acid sequence of SEQ ID NO: 264, or a variant thereof comprising up to about 5 amino acid substitutions.

In some embodiments, the anti-BCMA sdAb comprises three CDRs comprising: (a) a CDR1 comprising the amino acid sequence of SEQ ID NO: 211; (b) a CDR2 comprising the amino acid sequence of SEQ ID NO: 238; and (c) a CDR3 comprising the amino acid sequence of SEQ ID NO: 265, or a variant thereof comprising up to about 5 amino acid substitutions.

In some embodiments, the anti-BCMA sdAb comprises three CDRs comprising: (a) a CDR1 comprising the amino acid sequence of SEQ ID NO: 212; (b) a CDR2 comprising the amino acid sequence of SEQ ID NO: 239; and (c) a CDR3 comprising the amino acid sequence of SEQ ID NO: 266, or a variant thereof comprising up to about 5 amino acid substitutions.

In some embodiments, the anti-BCMA sdAb comprises three CDRs comprising: (a) a CDR1 comprising the amino acid sequence of SEQ ID NO: 213; (b) a CDR2 comprising the amino acid sequence of SEQ ID NO: 240; and (c) a CDR3 comprising the amino acid sequence of SEQ ID NO: 267, or a variant thereof comprising up to about 5 amino acid substitutions.

In some embodiments, the anti-BCMA sdAb comprises three CDRs comprising: (a) a CDR1 comprising, the amino acid sequence of SEQ ID NO: 214; (b) a CDR2 comprising the amino acid sequence of SEQ ID NO: 241; and (c) a CDR3 comprising the amino acid sequence of SEQ ID NO: 268, or a variant thereof comprising up to about 5 amino acid substitutions.

In some embodiments, the anti-BCMA sdAb comprises three CDRs comprising: (a) a CDR1 comprising the amino acid sequence of SEQ ID NO: 215; (b) a CDR2 comprising the amino acid sequence of SEQ ID NO: 242; and (c) a CDR3 comprising the amino acid sequence of SEQ ID NO: 269, or a variant thereof comprising up to about 5 amino acid substitutions.

In some embodiments, the anti-BCMA sdAb comprises three CDRs comprising: (a) a CDR1 comprising the amino acid sequence of SEQ ID NO: 216; (b) a CDR2 comprising the amino acid sequence of SEQ ID NO: 243; and (c) a CDR3 comprising the amino acid sequence of SEQ ID NO: 270, or a variant thereof comprising up to about 5 amino acid substitutions.

In some embodiments, the anti-BCMA sdAb comprises three CDRs comprising: (a) a CDR1 comprising the amino acid sequence of SEQ ID NO: 217; (b) a CDR2 comprising the amino acid sequence of SEQ IIS NO: 244; and (c) a CDR3 comprising the amino acid sequence of SEQ ID NO: 271, or a variant thereof comprising up to about 5 amino acid substitutions.

In some embodiments, the anti-BCMA sdAb comprises three CDRs comprising: (a) a CDR1 comprising the amino acid sequence of SEQ ID NO: 218; (b) a CDR2 comprising the amino acid sequence of SEQ IIS NO: 245; and (c) a CDR3 comprising the amino acid sequence of SEQ ID NO: 272, or a variant thereof comprising up to about 5 amino acid substitutions.

In some embodiments, the anti-BCMA sdAb comprises three CDRs comprising: (a) a CDR1 comprising the amino acid sequence of SEQ ID NO: 219; (b) a CDR2 comprising the amino acid sequence of SEQ ID NO: 246; and (c) a CDR3 comprising the amino acid sequence of SEQ ID NO: 273, or a variant thereof comprising up to about 5 amino acid substitutions.

In some embodiments, the anti-BCMA sdAb comprises three CDRs comprising: (a) a CDR1 comprising the amino acid sequence of SEQ ID NO: 220; (b) a CDR2 comprising the amino acid sequence of SEQ ID NO: 247; and (c) a CDR3 comprising the amino acid sequence of SEQ ID NO: 274, or a variant thereof comprising up to about 5 amino acid substitutions.

In some embodiments, the anti-BCMA sdAb comprises three CDRs comprising: (a) a CDR1 comprising the amino acid sequence of SEQ ID NO: 221; (b) a CDR2 comprising the amino acid sequence of SEQ ID NO: 248; and (c) a CDR3 comprising the amino acid sequence of SEQ ID NO: 275, or a variant thereof comprising up to about 5 amino acid substitutions.

In some embodiments, the anti-BCMA sdAb comprises three CDRs comprising: (a) a CDR1 comprising the amino acid sequence of SEQ ID NO: 222; (b) a CDR2 comprising the amino acid sequence of SEQ ID NO: 249; and (c) a CDR3 comprising the amino acid sequence of SEQ ID NO: 276, or a variant thereof comprising up to about 5 amino acid substitutions.

In some embodiments, the anti-BCMA sdAb comprises three CDRs comprising: (a) a CDR1 comprising the amino acid sequence of SEQ ID NO: 223; (b) a CDR2 comprising the amino acid sequence of SEQ ID NO: 250; and (c) a CDR3 comprising the amino acid sequence of SEQ ID NO: 277, or a variant thereof comprising up to about 5 amino acid substitutions.

In some embodiments, the anti-BCMA sdAb comprises three CDRs comprising: (a) a CDR1 comprising the amino acid sequence of SEQ ID NO: 224; (b) a CDR2 comprising the amino acid sequence of SEQ IIS NO: 251; and (c) a CDR3 comprising the amino acid sequence of SEQ ID NO: 278, or a variant thereof comprising up to about 5 amino acid substitutions.

In some embodiments, the anti-BCMA sdAb comprises three CDRs comprising: (a) a CDR1 comprising the amino acid sequence of SEQ ID NO: 225; (b) a CDR2 comprising the amino acid sequence of SEQ IIS NO: 252; and (c) a CDR3 comprising the amino acid sequence of SEQ ID NO: 279, or a variant thereof comprising up to about 5 amino acid substitutions.

In some embodiments, the anti-BCMA sdAb comprises three CDRs comprising: (a) a CDR1 comprising the amino acid sequence of SEQ ID NO: 226; (b) a CDR2 comprising the amino acid sequence of SEQ ID NO: 253; and (c) a CDR3 comprising the amino acid sequence of SEQ ID NO: 280, or a variant thereof comprising up to about 5 amino acid substitutions.

In some embodiments, the anti-BCMA sdAb comprises three CDRs comprising: (a) a CDR1 comprising the amino acid sequence of SEQ ID NO: 227; (b) a CDR2 comprising the amino acid sequence of SEQ ID NO: 254; and (c) a CDR3 comprising the amino acid sequence of SEQ ID NO: 281, or a variant thereof comprising up to about 5 amino acid substitutions.

In some embodiments, the anti-BCMA sdAb comprises three CDRs comprising: (a) a CDR1 comprising the amino acid sequence of SEQ ID NO: 228; (b) a CDR2 comprising the amino acid sequence of SEQ ID NO: 255; and (c) a CDR3 comprising the amino acid sequence of SEQ ID NO: 282, or a variant thereof comprising up to about 5 amino acid substitutions.

In some embodiments, the anti-BCMA sdAb comprises three CDRs comprising: (a) a CDR1 comprising the amino acid sequence of SEQ ID NO: 229; (b) a CDR2 comprising the amino acid sequence of SEQ ID NO: 256; and (c) a CDR3 comprising the amino acid sequence of SEQ ID NO: 283, or a variant thereof comprising up to about 5 amino acid substitutions.

In some embodiments, the anti-BCMA sdAb comprises three CDRs comprising: (a) a CDR1 comprising the amino acid sequence of SEQ ID NO: 230; (b) a CDR2 comprising the amino acid sequence of SEQ ID NO: 257; and (c) a CDR3 comprising the amino acid sequence of SEQ ID NO: 284, or a variant thereof comprising up to about 5 amino acid substitutions.

In some embodiments, the anti-BCMA sdAb comprises three CDRs comprising: (a) a CDR1 comprising the amino acid sequence of SEQ ID NO: 231; (b) a CDR2 comprising the amino acid sequence of SEQ ID NO: 258; and (c) a CDR3 comprising the amino acid sequence of SEQ ID NO: 285, or a variant thereof comprising up to about 5 amino acid substitutions.

In some embodiments, the anti-BCMA sdAb comprises three CDRs comprising: (a) a CDR1 comprising the amino acid sequence of SEQ ID NO: 232; (b) a CDR2 comprising the amino acid sequence of SEQ ID NO: 259; and (c) a CDR3 comprising the amino acid sequence of SEQ ID NO: 286, or a variant thereof comprising up to about 5 amino acid substitutions.

In some embodiments, the anti-BCMA sdAb comprises three CDRs comprising: (a) a CDR1 comprising the amino acid sequence of SEQ ID NO: 233; (b) a CDR2 comprising the amino acid sequence of SEQ ID NO: 260; and (c) a CDR3 comprising the amino acid sequence of SEQ ID NO: 287, or a variant thereof comprising up to about 5 amino acid substitutions.

In some embodiments, the anti-BCMA sdAb comprises three CDRs comprising: (a) a CDR1 comprising the amino acid sequence of SEQ ID NO: 234; (b) a CDR2 comprising the amino acid sequence of SEQ ID NO: 261; and (c) a CDR3 comprising the amino acid sequence of SEQ ID NO: 288, or a variant thereof comprising up to about 5 amino acid substitutions.

In some embodiments, the anti-BCMA sdAb comprises three CDRs comprising: (a) a CDR1 comprising the amino acid sequence of SEQ ID NO: 235; (b) a CDR2 comprising the amino acid sequence of SEQ ID NO: 262; and (c) a CDR3 comprising the amino acid sequence of SEQ ID NO: 289, or a variant thereof comprising up to about 5 amino acid substitutions.

In some embodiments, the anti-BCMA sdAb comprises a $V_HH$ domain having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 78-88. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-BCMA sdAb comprising that sequence retains the ability to bind to BCMA. In some embodiments, a total of 1 to 10 amino acids have been substituted, inserted and/or deleted in an amino acid sequence selected from SEQ ID NOs: 78-88 and 290-316. In some embodiments, substitutions, insertions, or deletions occur in regions outside the CDRs (i.e., in the FRs). Optionally, the anti-BCMA sdAb comprises an amino acid sequence selected from SEQ ID NOs: 78-88 and 290-316, including post-translational modifications of that sequence.

In some embodiments, the anti-BCMA sdAb comprises comprising a $V_HH$ domain having the amino acid sequence of SEQ ID NO: 78. In some embodiments, the anti-BCMA sdAb comprises a $V_HH$ domain having the amino acid sequence of SEQ ID NO: 79. In some embodiments, the anti-BCMA sdAb comprises a $V_HH$ domain having the amino acid sequence of SEQ ID NO: 80. In some embodiments, the anti-BCMA sdAb comprises a $V_HH$ domain having the amino acid sequence of SEQ ID NO: 81. In some embodiments, the anti-BCMA sdAb comprises a $V_HH$ domain having the amino acid sequence of SEQ ID NO: 82. In some embodiments, the anti-BCMA sdAb comprises a V<sub>H</sub>H domain having the amino acid sequence of SEQ ID NO: 83. In some embodiments, the anti-BCMA sdAb comprises a V<sub>H</sub>H domain having the amino acid sequence of SEQ ID NO: 84. In some embodiments, the anti-BCMA sdAb comprises a V<sub>H</sub>H domain having the amino acid sequence of SEQ ID NO: 85. In some embodiments, the anti-BCMA sdAb comprises a V<sub>H</sub>H domain having the amino acid sequence of SEQ ID NO: 86. In some embodiments, the anti-BCMA sdAb comprises a V<sub>H</sub>H domain having the amino acid sequence of SEQ ID NO: 87. In some embodiments, the anti-BCMA sdAb comprises a V<sub>H</sub>H domain having the amino acid sequence of SEQ ID NO: 88. In some embodiments, the anti-BCMA sdAb comprises a V<sub>H</sub>H domain having the amino acid sequence of SEQ ID NO: 290. In some embodiments, the anti-BCMA sdAb comprises a V<sub>H</sub>H domain having the amino acid sequence of SEQ ID NO: 291. In some embodiments, the anti-BCMA sdAb comprises a V<sub>H</sub>H domain having the amino acid sequence of SEQ ID NO: 292. In some embodiments, the anti-BCMA sdAb comprises a V<sub>H</sub>H domain having the amino acid sequence of SEQ ID NO: 293. In some embodiments, the anti-BCMA sdAb comprises a V<sub>H</sub>H domain having the amino acid sequence of SEQ ID NO: 294. In some embodiments, the anti-BCMA sdAb comprises a V<sub>H</sub>H domain having the amino acid sequence of SEQ ID NO: 295. In some embodiments, the anti-BCMA sdAb comprises a V<sub>H</sub>H domain having the amino acid sequence of SEQ ID NO: 296. In some embodiments, the anti-BCMA sdAb comprises a V<sub>H</sub>H domain having the amino acid sequence of SEQ ID NO: 297. In some embodiments, the anti-BCMA sdAb comprises a V<sub>H</sub>H domain having the amino acid sequence of SEQ ID NO: 298. In some embodiments, the anti-BCMA sdAb comprises a V<sub>H</sub>H domain having the amino acid sequence of SEQ ID NO: 299. In some embodiments, the anti-BCMA sdAb comprises a V<sub>H</sub>H domain having the amino acid sequence of SEQ ID NO: 300. In some embodiments, the anti-BCMA sdAb comprises a V<sub>H</sub>H domain having the amino acid sequence of SEQ ID NO: 301. In some embodiments, the anti-BCMA sdAb comprises a V<sub>H</sub>H domain having the amino acid sequence of SEQ ID NO: 302. In some embodiments, the anti-BCMA sdAb comprises a V<sub>H</sub>H domain having the amino acid sequence of SEQ ID NO: 303. In some embodiments, the anti-BCMA sdAb comprises a V<sub>H</sub>H domain having the amino acid sequence of SEQ ID NO: 304. In some embodiments, the anti-BCMA sdAb comprises a V<sub>H</sub>H domain having the amino acid sequence of SEQ ID NO: 305. In some embodiments, the anti-BCMA sdAb comprises a V<sub>H</sub>H domain having the amino acid sequence of SEQ ID NO: 306. In some embodiments, the anti-BCMA sdAb comprises a V<sub>H</sub>H domain having the amino acid sequence of SEQ ID NO: 307. In some embodiments, the anti-BCMA sdAb comprises a V<sub>H</sub>H domain having the amino acid sequence of SEQ ID NO: 308. In some embodiments, the anti-BCMA sdAb comprises a V<sub>H</sub>H domain having the amino acid sequence of SEQ ID NO: 309. In some embodiments, the anti-BCMA sdAb comprises a V<sub>H</sub>H domain having the amino acid sequence of SEQ ID NO: 310. In some embodiments, the anti-BCMA sdAb comprises a V<sub>H</sub>H domain having the amino acid sequence of SEQ ID NO: 311. In some embodiments, the anti-BCMA sdAb comprises a V<sub>H</sub>H domain having the amino acid sequence of SEQ ID NO: 312. In some embodiments, the anti-BCMA sdAb comprises a V<sub>H</sub>H domain having the amino acid sequence of SEQ ID NO: 313. In some embodiments, the anti-BCMA sdAb comprises a V<sub>H</sub>H domain having the amino acid sequence of SEQ ID NO: 314. In some embodiments, the anti-BCMA sdAb comprises a V<sub>H</sub>H domain having the amino acid sequence of SEQ ID NO: 315. In some embodiments, the anti-BCMA sdAb comprises a V<sub>H</sub>H domain having the amino acid sequence of SEQ ID NO: 316.

In some embodiments, functional epitopes can be mapped by combinatorial alanine scanning. In this process, a combinatorial alanine-scanning strategy can be used to identify amino acids in the BCMA protein that are necessary for interaction with anti-BCMA single-domain antibodies. In some embodiments, the epitope is conformational and crystal structure of anti-BCMA single-domain antibody bound to BCMA may be employe to identify the epitopes. In some embodiments, the anti-BCMA sdAb specifically binds to the same epitope (including substantially the same epitope) as any of the anti-BCMA single-domain antibodies provided herein. For example, in some embodiments, the anti-BCMA sdAb binds to the same epitope as an anti-BCMA single-domain antibody comprising the amino acid sequence of SEQ ID NO: 78. In some embodiments, the anti-BCMA sdAb binds to the same epitope as an anti-BCMA single-domain antibody comprising the amino acid sequence of SEQ ID NO: 79. In some embodiments, the anti-BCMA sdAb binds to the same epitope as an anti-BCMA single-domain antibody comprising the amino acid sequence of SEQ ID NO: 80. In some embodiments, the anti-BCMA sdAb binds to the same epitope as an anti-BCMA single-domain antibody comprising the amino acid sequence of SEQ ID NO: 81. In some embodiments, the anti-BCMA sdAb binds to the same epitope as an anti-BCMA single-domain antibody comprising the amino acid sequence of SEQ ID NO: 82. In some embodiments, the anti-BCMA sdAb binds to the same epitope as an anti-BCMA single-domain antibody comprising the amino acid sequence of SEQ ID NO: 83. In some embodiments, the anti-BCMA sdAb binds to the same epitope as an anti-BCMA single-domain antibody comprising the amino acid sequence of SEQ ID NO: 84. In some embodiments, the anti-BCMA sdAb binds to the same epitope as an anti-BCMA single-domain antibody comprising the amino acid sequence of SEQ ID NO: 85. In some embodiments, the anti-BCMA sdAb binds to the same epitope as an anti-BCMA single-domain antibody comprising the amino acid sequence of SEQ ID NO: 86. In some embodiments, the anti-BCMA sdAb binds to the same epitope as an anti-BCMA single-domain antibody comprising the amino acid sequence of SEQ ID NO: 87. In some embodiments, the anti-BCMA sdAb binds to the same epitope as an anti-BCMA single-domain antibody comprising the amino acid sequence of SEQ ID NO: 88. In some embodiments, the anti-BCMA sdAb binds to the same epitope as an anti-BCMA single-domain antibody comprising the amino acid sequence of SEQ ID NO: 290. In some embodiments, the anti-BCMA sdAb binds to the same epitope as an anti-BCMA single-domain antibody comprising the amino acid sequence of SEQ ID NO: 291. In some embodiments, the anti-BCMA sdAb binds to the same epitope as an anti-BCMA single-domain antibody comprising the amino acid sequence of SEQ ID NO: 292. In some embodiments, the anti-BCMA sdAb binds to the same epitope as an anti-BCMA single-domain antibody comprising the amino acid sequence of SEQ ID NO: 293. In some embodiments, the anti-BCMA sdAb binds to the same epitope as an anti-BCMA single-domain antibody comprising the amino acid sequence of SEQ ID NO: 294. In some embodiments, the anti-BCMA sdAb binds to the same epitope as an anti-BCMA single-domain antibody comprising the amino acid sequence of SEQ ID NO: 295. In some embodiments, the anti-BCMA sdAb binds to the same epitope as an anti-BCMA single-domain antibody comprising the amino acid sequence of SEQ ID NO: 296. In some embodiments, the anti-BCMA sdAb binds to the same epitope as an anti-BCMA single-domain antibody comprising the amino acid sequence of SEQ ID NO: 297. In some embodiments, the anti-BCMA sdAb binds to the same epitope as an anti-BCMA single-domain antibody comprising the amino acid sequence of SEQ ID NO: 298. In some embodiments, the anti-BCMA sdAb binds to the same epitope as an anti-BCMA single-domain antibody comprising the amino acid sequence of SEQ ID NO: 299. In some embodiments, the anti-BCMA sdAb binds to the same epitope as an anti-BCMA single-domain antibody comprising the amino acid sequence of SEQ ID NO: 300. In some embodiments, the anti-BCMA sdAb binds to the same epitope as an anti-BCMA single-domain antibody comprising the amino acid sequence of SEQ ID NO: 301. In some embodiments, the anti-BCMA sdAb binds to the same epitope as an anti-BCMA single-domain antibody comprising the amino acid sequence of SEQ ID NO: 302. In some embodiments, the anti-BCMA sdAb binds to the same epitope as an anti-BCMA single-domain antibody comprising the amino acid sequence of SEQ ID NO: 303. In some embodiments, the anti-BCMA sdAb binds to the same epitope as an anti-BCMA single-domain antibody comprising the amino acid sequence of SEQ ID NO: 304. In some embodiments, the anti-BCMA sdAb binds to the same epitope as an anti-BCMA single-domain antibody comprising the amino acid sequence of SEQ ID NO: 305. In some embodiments, the anti-BCMA sdAb binds to the same epitope as an anti-BCMA single-domain antibody comprising the amino acid sequence of SEQ ID NO: 306. In some embodiments, the anti-BCMA sdAb binds to the same epitope as an anti-BCMA single-domain antibody comprising the amino acid sequence of SEQ ID NO: 307. In some embodiments, the anti-BCMA sdAb binds to the same epitope as an anti-BCMA single-domain antibody comprising the amino acid sequence of SEQ ID NO: 308. In some embodiments, the anti-BCMA sdAb binds to the same epitope as an anti-BCMA single-domain antibody comprising the amino acid sequence of SEQ ID NO: 309. In some embodiments, the anti-BCMA sdAb binds to the same epitope as an anti-BCMA single-domain antibody comprising the amino acid sequence of SEQ ID NO: 310. In some embodiments, the anti-BCMA sdAb binds to the same epitope as an anti-BCMA single-domain antibody comprising the amino acid sequence of SEQ ID NO: 311. In some embodiments, the anti-BCMA sdAb binds to the same epitope as an anti-BCMA single-domain antibody comprising the amino acid sequence of SEQ ID NO: 312. In some embodiments, the anti-BCMA sdAb binds to the same epitope as an anti-BCMA single-domain antibody comprising the amino acid sequence of SEQ ID NO: 313. In some embodiments, the anti-BCMA sdAb binds to the same epitope as an anti-BCMA single-domain antibody comprising the amino acid sequence of SEQ ID NO: 314. In some embodiments, the anti-BCMA sdAb binds to the same epitope as an anti-BCMA single-domain antibody comprising the amino acid sequence of SEQ ID NO: 315. In some embodiments, the anti-BCMA sdAb binds to the same epitope as an anti-BCMA single-domain antibody comprising the amino acid sequence of SEQ ID NO: 316.

In some embodiments, the anti-BCMA sdAb specifically binds to BCMA competitively with any one of the anti-BCMA single-domain antibodies described herein. In some embodiments, competitive binding may be determined using an ELISA assay. For example, in some embodiments, the anti-BCMA sdAb specifically binds to BCMA competitively with an anti-BCMA single-domain antibody comprising the amino acid sequence of SEQ ID NO:78. In some embodiments, the anti-BCMA sdAb specifically binds to BCMA competitively with an anti-BCMA single-domain antibody comprising the amino acid sequence of SEQ ID NO:79. In some embodiments, the anti-BCMA sdAb specifically binds to BCMA competitively with an anti-BCMA single-domain antibody comprising the amino acid sequence of SEQ ID NO:80. In some embodiments, the anti-BCMA sdAb specifically binds to BCMA competitively with an anti-BCMA single-domain antibody comprising the amino acid sequence of SEQ ID NO:81. In some embodiments, the anti-BCMA sdAb specifically binds to BCMA competitively with an anti-BCMA single-domain antibody comprising the amino acid sequence of SEQ ID NO:82. In some embodiments, the anti-BCMA sdAb specifically binds to BCMA competitively with an anti-BCMA single-domain antibody comprising the amino acid sequence of SEQ ID NO:83. In some embodiments, the anti-BCMA sdAb specifically binds to BCMA competitively with an anti-BCMA single-domain antibody comprising the amino acid sequence of SEQ ID NO:84. In some embodiments, the anti-BCMA sdAb specifically binds to BCMA competitively with an anti-BCMA single-domain antibody comprising the amino acid sequence of SEQ ID NO:85. In some embodiments, the anti-BCMA sdAb specifically binds to BCMA competitively with an anti-BCMA single-domain antibody comprising the amino acid sequence of SEQ ID NO:86. In some embodiments, the anti-BCMA sdAb specifically binds to BCMA competitively with an anti-BCMA single-domain antibody comprising the amino acid sequence of SEQ ID NO:87. In some embodiments, the anti-BCMA sdAb specifically binds to BCMA competitively with an anti-BCMA single-domain antibody comprising the amino acid sequence of SEQ ID NO:88. In some embodiments, the anti-BCMA sdAb specifically binds to BCMA competitively with an anti-BCMA single-domain antibody comprising the amino acid sequence of SEQ ID NO:290. In some embodiments, the anti-BCMA sdAb specifically binds to BCMA competitively with an anti-BCMA single-domain antibody comprising the amino acid sequence of SEQ ID NO:291. In some embodiments, the anti-BCMA sdAb specifically binds to BCMA competitively with an anti-BCMA single-domain antibody comprising the amino acid sequence of SEQ ID NO:292. In some embodiments, the anti-BCMA sdAb specifically binds to BCMA competitively with an anti-BCMA single-domain antibody comprising the amino acid sequence of SEQ ID NO:293. In some embodiments, the anti-BCMA sdAb specifically binds to BCMA competitively with an anti-BCMA single-domain antibody comprising the amino acid sequence of SEQ ID NO:294. In some embodiments, the anti-BCMA sdAb specifically binds to BCMA competitively with an anti-BCMA single-domain antibody comprising the amino acid sequence of SEQ ID NO:295. In some embodiments, the anti-BCMA sdAb specifically binds to BCMA competitively with an anti-BCMA single-domain antibody comprising the amino acid sequence of SEQ ID NO:296. In some embodiments, the anti-BCMA sdAb specifically binds to BCMA competitively with an anti-BCMA single-domain antibody comprising the amino acid sequence of SEQ ID NO:297. In some embodiments, the anti-BCMA sdAb specifically binds to BCMA competitively with an anti-BCMA single-domain antibody comprising the amino acid sequence of SEQ ID NO:298. In some embodiments, the anti-BCMA sdAb specifically binds to BCMA competitively with an anti-BCMA single-domain antibody comprising the amino acid sequence of SEQ ID NO:299. In some embodiments, the anti-BCMA sdAb specifically binds to BCMA competitively with an anti-BCMA single-domain antibody comprising the amino acid sequence of SEQ ID NO:300. In some embodiments, the anti-BCMA sdAb specifically binds to BCMA competitively with an anti-BCMA single-domain antibody comprising the amino acid sequence of SEQ ID NO:301. In some embodiments, the anti-BCMA sdAb specifically binds to BCMA competitively with an anti-BCMA single-domain antibody comprising the amino acid sequence of SEQ ID NO:302. In some embodiments, the anti-BCMA sdAb specifically binds to BCMA competitively with an anti-BCMA single-domain antibody comprising the amino acid sequence of SEQ ID NO:303. In some embodiments, the anti-BCMA sdAb specifically binds to BCMA competitively with an anti-BCMA single-domain antibody comprising the amino acid sequence of SEQ ID NO:304. In some embodiments, the anti-BCMA sdAb specifically binds to BCMA competitively with an anti-BCMA single-domain antibody comprising the amino acid sequence of SEQ ID NO:305. In some embodiments, the anti-BCMA sdAb specifically binds to BCMA competitively with an anti-BCMA single-domain antibody comprising the amino acid sequence of SEQ ID NO:306. In some embodiments, the anti-BCMA sdAb specifically binds to BCMA competitively with an anti-BCMA single-domain antibody comprising the amino acid sequence of SEQ ID NO:307. In some embodiments, the anti-BCMA sdAb specifically binds to BCMA competitively with an anti-BCMA single-domain antibody comprising the amino acid sequence of SEQ ID NO:308. In some embodiments, the anti-BCMA sdAb specifically binds to BCMA competitively with an anti-BCMA single-domain antibody comprising the amino acid sequence of SEQ ID NO:309. In some embodiments, the anti-BCMA sdAb specifically binds to BCMA competitively with an anti-BCMA single-domain antibody comprising the amino acid sequence of SEQ ID NO:310. In some embodiments, the anti-BCMA sdAb specifically binds to BCMA competitively with an anti-BCMA single-domain antibody comprising the amino acid sequence of SEQ ID NO:311. In some embodiments, the anti-BCMA sdAb specifically binds to BCMA competitively with an anti-BCMA single-domain antibody comprising the amino acid sequence of SEQ ID NO:312. In some embodiments, the anti-BCMA sdAb specifically binds to BCMA competitively with an anti-BCMA single-domain antibody comprising the amino acid sequence of SEQ ID NO:313. In some embodiments, the anti-BCMA sdAb specifically binds to BCMA competitively with an anti-BCMA single-domain antibody comprising the amino acid sequence of SEQ ID NO:314. In some embodiments, the anti-BCMA sdAb specifically binds to BCMA competitively with an anti-BCMA single-domain antibody comprising the amino acid sequence of SEQ ID NO:315. In some embodiments, the anti-BCMA sdAb specifically binds to BCMA competitively with an anti-BCMA single-domain antibody comprising the amino acid sequence of SEQ ID NO:316.

Anti-CD38 sdAb

In some embodiments, the target cell binding domain comprises one or more anti-CD38 sdAbs, such as anti-CD38 $V_HH$. In some embodiments, the anti-CD38 sdAb is affinity matured. In some embodiments, the anti-CD38 sdAb is camelid. In some embodiments, the anti-CD38 sdAb is humanized. In some embodiments, the anti-CD38 sdAb comprises an acceptor human framework, e.g., a human immunoglobulin framework or a human consensus framework. In some embodiments, the anti-CD38 sdAb modulates CD38 activity. In some embodiments, the anti-CD38 sdAb is an antagonist antibody.

In some embodiments, the anti-CD38 sdAb comprises one, two, or all three CDRs of the amino acid sequence of SEQ ID NO: 89. In some embodiments, the anti-CD38 sdAb comprises one, two, or all three CDRs of the amino acid sequence of SEQ ID NO: 90. In some embodiments, the anti-CD38 sdAb comprises one, two, or all three CDRs of the amino acid sequence of SEQ ID NO: 91. In some embodiments, the anti-CD38 sdAb comprises one, two, or all three CDRs of the amino acid sequence of SEQ ID NO: 92. In some embodiments, the anti-CD38 sdAb comprises one, two, or all three CDRs of the amino acid sequence of SEQ ID NO: 93. In some embodiments, the anti-CD38 sdAb comprises one, two, or all three CDRs of the amino acid sequence of SEQ ID NO: 94. In some embodiments, the anti-CD38 sdAb comprises one, two, or all three CDRs of the amino acid sequence of SEQ ID NO: 95. In some embodiments, the anti-CD38 sdAb comprises one, two, or all three CDRs of the amino acid sequence of SEQ ID NO: 96. In some embodiments, the anti-CD38 sdAb comprises one, two, or all three CDRs of the amino acid sequence of SEQ ID NO: 97. In some embodiments, the anti-CD38 sdAb comprises one, two, or all three CDRs of the amino acid sequence of SEQ ID NO: 98. In some embodiments, the anti-CD38 sdAb comprises one, two, or all three CDRs of the amino acid sequence of SEQ ID NO: 99. In some embodiments, the anti-CD38 sdAb comprises one, two, or all three CDRs of the amino acid sequence of SEQ ID NO: 100.

In some embodiments, the anti-CD38 sdAb comprises at least one, at least two, or all three CDRs selected from (a) a CDR1 comprising an amino acid sequence selected from SEQ ID NOs: 34-45; (b) a CDR2 comprising an amino acid sequence selected from SEQ ID Nils: 46-57; and (c) a CDR3 comprising an amino acid sequence selected from SEQ ID Nils:58-69. In some embodiments, the anti-CD38 sdAb comprises three CDRs comprising: (a) a CDR1 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs:34-45; (b) a CDR2 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs:46-57; and (c) a CDR3 having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs:58-69. In some embodiments, a CDR having at least about any one of 85%, 86%, 87%, 88%, 89%, 90%, 91%, 92%, 93%, 94%, 95%, 96%, 97%, 98%, or 99% identity contains substitutions (e.g., conservative substitutions), insertions, or deletions relative to the reference sequence, but the anti-CD38 sdAb comprising that sequence retains the ability to bind to CD38. In some embodiments, the anti-CD38 sdAb comprises a substitution (e.g., conservative substitutions), insertions, or deletions of one, two, three or more amino acids in any one of the CDRs described herein, but the anti-CD38 sdAb comprising that sequence retains the ability to bind to CD38.

In some embodiments, the anti-CD38 sdAb comprises three CDRs comprising: (a) a CDR1 comprising the amino acid sequence of SEQ ID NO: 34; (b) a CDR2 comprising the amino acid sequence of SEQ ID NO: 46; and (c) a CDR3 comprising the amino acid sequence of SEQ ID NO: 58, or a variant thereof comprising up to about 5 amino acid substitutions.

In some embodiments, the anti-CD38 sdAb comprises three CDRs comprising: (a) a CDR1 comprising the amino acid sequence of SEQ ID NO: 35; (b) a CDR2 comprising the amino acid sequence of SEQ ID NO: 47; and (c) a CDR3 comprising the amino acid sequence of SEQ ID NO: 59, or a variant thereof comprising up to about 5 amino acid substitutions.

In some embodiments, the anti-CD38 sdAb comprises three CDRs comprising: (a) a CDR1 comprising the amino acid sequence of SEQ ID NO: 36; (b) a CDR2 comprising the amino acid sequence of SEQ ID NO: 48; and (c) a CDR3 comprising the amino acid sequence of SEQ ID NO: 60, or a variant thereof comprising up to about 5 amino acid substitutions.

In some embodiments, the anti-CD38 sdAb comprises three CDRs comprising: (a) a CDR1 comprising the amino acid sequence of SEQ ID NO: 37; (b) a CDR2 comprising the amino acid sequence of SEQ ID NO: 49; and (c) a CDR3 comprising the amino acid sequence of SEQ ID NO: 61, or a variant thereof comprising up to about 5 amino acid substitutions.

In some embodiments, the anti-CD38 sdAb comprises three CDRs comprising: (a) a CDR1 comprising the amino acid sequence of SEQ ID NO: 38; (b) a CDR2 comprising the amino acid sequence of SEQ ID NO: 50; and (c) a CDR3 comprising the amino acid sequence of SEQ ID NO: 62, or a variant thereof comprising up to about 5 amino acid substitutions.

In some embodiments, the anti-CD38 sdAb comprises three CDRs comprising: (a) a CDR1 comprising the amino acid sequence of SEQ ID NO: 39; (b) a CDR2 comprising the amino acid sequence of SEQ ID NO: 51; and (c) a CDR3 comprising the amino acid sequence of SEQ ID NO: 63, or a variant thereof comprising up to about 5 amino acid substitutions.

In some embodiments, the anti-CD38 sdAb comprises three CDRs comprising: (a) a CDR1 comprising the amino acid sequence of SEQ ID NO: 40; (b) a CDR2 comprising the amino acid sequence of SEQ ID NO: 52; and (c) a CDR3 comprising the amino acid sequence of SEQ ID NO: 64, or a variant thereof comprising up to about 5 amino acid substitutions.

In some embodiments, the anti-CD38 sdAb comprises three CDRs comprising: (a) a CDR1 comprising the amino acid sequence of SEQ ID NO: 41; (b) a CDR2 comprising the amino acid sequence of SEQ ID NO: 53; and (c) a CDR3 comprising the amino acid sequence of SEQ ID NO: 65, or a variant thereof comprising up to about 5 amino acid substitutions.

In some embodiments, the anti-CD38 sdAb comprises three CDRs comprising: (a) a CDR1 comprising the amino acid sequence of SEQ ID NO: 42; (b) a CDR2 comprising the amino acid sequence of SEQ ID NO: 54; and (c) a CDR3 comprising the amino acid sequence of SEQ ID NO: 66, or a variant thereof comprising up to about 5 amino acid substitutions.

In some embodiments, the anti-CD38 sdAb comprises three CDRs comprising: (a) a CDR1 comprising the amino acid sequence of SEQ ID NO: 43; (b) a CDR2 comprising the amino acid sequence of SEQ ID NO: 55; and (c) a CDR3 comprising the amino acid sequence of SEQ ID NO: 67, or a variant thereof comprising up to about 5 amino acid substitutions.

In some embodiments, the anti-CD38 sdAb comprises three CDRs comprising: (a) a. CDR1 comprising the amino acid sequence of SEQ ID NO: 44; (b) a CDR2 comprising the amino acid sequence of SEQ ID NO: 56; and (c) a CDR3 comprising the amino acid sequence of SEQ ID NO: 68, or a variant thereof comprising up to about 5 amino acid substitutions.

In some embodiments, the anti-CD38 sdAb comprises three CDRs comprising: (a) a CDR1 comprising the amino acid sequence of SEQ ID NO: 45; (b) a CDR2 comprising the amino acid sequence of SEQ ID NO: 57; and (c) a CDR3 comprising the amino acid sequence of SEQ ID NO: 69, or a variant thereof comprising up to about 5 amino acid substitutions.

In some embodiments, the anti-CD38 sdAb comprises a $V_HH$ domain having at least about any one of 85%, 86%, 87%, 88%, 89%, 90%, 91%, 92%, 93%, 94%, 95%, 96%, 97%, 98%, 99%, or 100% sequence identity to an amino acid sequence selected from SEQ ID NOs: 89-100. In some embodiments, a $V_HH$ sequence having at least about any one of 85%, 86%, 87%, 88%, 89%, 90%, 91%, 92%, 93%, 94%, 95%, 96%, 97%, 98%, or 99% identity contains substitutions e.g., conservative substitutions), insertions, or deletions relative to the reference sequence, but the anti-CD38 sdAb comprising that sequence retains the ability to bind to CD38. In some embodiments, a total of 1 to 10 amino acids have been substituted, inserted and/or deleted in an amino acid sequence selected from SEQ ID NOs: 89-100. In some embodiments, substitutions, insertions, or deletions occur in regions outside the CDRs (i.e., in the FRs). Optionally, the anti-CD38 sdAb comprises an amino acid sequence selected from SEQ ID NOs: 89-100, including post-translational modifications of that sequence.

In some embodiments, the anti-CD38 sdAb comprises a $V_HH$ domain having the amino acid sequence of SEQ ID NO: 89. In some embodiments, the anti-CD38 sdAb comprises a $V_HH$ domain having the amino acid sequence of SEQ ID NO: 90. In some embodiments, the anti-CD38 sdAb comprises a $V_HH$ domain having the amino acid sequence of SEQ ID NO: 91. In some embodiments, the anti-CD38 sdAb comprises a $V_HH$ domain having the amino acid sequence of SEQ ID NO: 92. In some embodiments, the anti-CD38 sdAb comprises a $V_HH$ domain having the amino acid sequence of SEQ ID NO: 93. In some embodiments, the anti-CD38 sdAb comprises a $V_HH$ domain having the amino acid sequence of SEQ ID NO: 94. In some embodiments, the anti-CD38 sdAb comprises a $V_HH$ domain having the amino acid sequence of SEQ ID NO: 95. In some embodiments, the anti-CD38 sdAb comprises a $V_HH$ domain having the amino acid sequence of SEQ ID NO: 96. In some embodiments, the anti-CD38 sdAb comprises a $V_HH$ domain having the amino acid sequence of SEQ ID NO: 97. In some embodiments, the anti-CD38 sdAb comprises a $V_HH$ domain having the amino acid sequence of SEQ ID NO: 98. In some embodiments, the anti-CD38 sdAb comprises a $V_HH$ domain having the amino acid sequence of SEQ ID NO: 99. In some embodiments, the anti-CD38 sdAb comprises a $V_HH$ domain having the amino acid sequence of SEQ ID NO: 100.

In some embodiments, functional epitopes can be mapped by combinatorial alanine scanning. In this process, a combinatorial alanine-scanning strategy can be used to identify amino acids in the CD38 protein that are necessary for interaction with the anti-CD38 single-domain antibodies. In some embodiments, the epitope is conformational and crystal structure of anti-CD38 single-domain antibody bound to CD38 may be employed to identify the epitopes. In some embodiments, the anti-CD38 sdAb specifically binds to the same epitope (including substantially the same epitope) as any of the anti-CD38 single-domain antibodies provided herein. For example, in some embodiments, the anti-CD38 sdAb binds to the same epitope as an anti-CD38 single-domain antibody comprising the amino acid sequence of SEQ ID NO: 89. In some embodiments, the anti-CD38 sdAb binds to the same epitope as an anti-CD38 single-domain antibody comprising the amino acid sequence of SEQ ID NO: 90. In some embodiments, the anti-CD38 sdAb binds to the same epitope as an anti-CD38 single-domain antibody comprising the amino acid sequence of SEQ ID NO: 91. In some embodiments, the anti-CD38 sdAb binds to the same epitope as an anti-CD38 single-domain antibody comprising the amino acid sequence of SEQ ID NO: 92. In some embodiments, the anti-CD38 sdAb binds to the same epitope as an anti-CD38 single-domain antibody comprising the amino acid sequence of SEQ ID NO: 93. In some embodiments, the anti-CD38 sdAb binds to the same epitope as an anti-CD38 single-domain antibody comprising the amino acid sequence of SEQ ID NO: 94. In some embodiments, the anti-CD38 sdAb binds to the same epitope as an anti-CD38 single-domain antibody comprising the amino acid sequence of SEQ ID NO: 95. In some embodiments, the anti-CD38 sdAb binds to the same epitope as an anti-CD38 single-domain antibody comprising the amino acid sequence of SEQ ID NO: 96. In some embodiments, the anti-CD38 sdAb binds to the same epitope as an anti-CD38 single-domain antibody comprising the amino acid sequence of SEQ ID NO: 97. In some embodiments, the anti-CD38 sdAb binds to the same epitope as an anti-CD38 single-domain antibody comprising the amino acid sequence of SEQ ID NO: 98. In some embodiments, the anti-CD38 sdAb binds to the same epitope as an anti-CD38 single-domain antibody comprising the amino acid sequence of SEQ ID NO: 99. In some embodiments, the anti-CD38 sdAb binds to the same epitope as an anti-CD38 single-domain antibody comprising the amino acid sequence of SEQ ID NO: 100.

In some embodiments, the present application provides an anti-CD38 antibody, or antigen binding fragment thereof, that specifically binds to CD38 competitively with any one of the anti-CD38 single-domain antibodies described herein. In some embodiments, competitive binding may be determined using an ELISA assay. For example, in some embodiments, the anti-CD38 sdAb specifically binds to CD38 competitively with an anti-CD38 single-domain antibody comprising the amino acid sequence of SEQ ID NO:89. In some embodiments, the anti-CD38 sdAb specifically binds to CD38 competitively with an anti-CD38 single-domain antibody comprising the amino acid sequence of SEQ ID NO:90. In some embodiments, the anti-CD38 sdAb specifically binds to CD38 competitively with an anti-CD38 single-domain antibody comprising the amino acid sequence of SEQ ID NO:91. In some embodiments, the anti-CD38 sdAb specifically binds to CD38 competitively with an anti-CD38 single-domain antibody comprising the amino acid sequence of SEQ ID NO:92. In some embodiments, the anti-CD38 sdAb specifically binds to CD38 competitively with an anti-CD38 single-domain antibody comprising the amino acid sequence of SEQ ID NO:93. In some embodiments, the anti-CD38 sdAb specifically binds to CD38 competitively with an anti-CD38 single-domain antibody comprising the amino acid sequence of SEQ ID NO:94. In some embodiments, the anti-CD38 sdAb specifically binds to CD38 competitively with an anti-CD38 single-domain antibody comprising the amino acid sequence of SEQ ID NO:95. In some embodiments, the anti-CD38 sdAb specifically binds to CD38 competitively with an anti-CD38 single-domain antibody comprising the amino acid sequence of SEQ ID NO:96. In some embodiments, the anti-CD38 sdAb specifically binds to CD38 competitively with an anti-CD38 single-domain antibody comprising the amino acid sequence of SEQ ID NO:97. In some embodiments, the anti-CD38 sdAb specifically binds to CD38 competitively with an anti-CD38 single-domain antibody comprising the amino acid sequence of SEQ ID NO:98. In some embodiments, the anti-CD38 sdAb specifically binds to CD38 competitively with an anti-CD38 single-domain antibody comprising the amino acid sequence of SEQ ID NO:99. In some embodiments, the anti-CD38 sdAb specifically binds to CD38 competitively with an anti-CD38 single-domain antibody comprising the amino acid sequence of SEQ ID NO:100.

4. Other Antigen-Binding Fragments

In some embodiments, the target cell binding domain comprises an antigen-binding fragment derived from a four-chain antibody that specifically binds to an antigen on a target cell. Exemplary antigen-binding fragments include, but are not limited to, Fab, Fab', Fab'-SH, $F(ab')_2$, Fv, and scFv fragments. For a review of certain antibody fragments, see Hudson et al. *Nat. Med.* 9:129-134 (2003). For a review of scFv fragments, see, e.g., Pluckthün, in *The Pharmacology of Monoclonal Antibodies, vol.* 113, Rosenburg and Moore eds., (Springer-Verlag, New York), pp. 269-315 (1994); see also WO 93/16185; and U.S. Pat. Nos. 5,571,894 and 5,587,458. For discussion of Fab and $F(ab')_2$ fragments comprising salvage receptor binding epitope residues and having increased in vivo half-life, see U.S. Pat. No. 5,869, 046. In some embodiments, the antibody fragment does not comprise an Fc region.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Antibody fragments can be made by various techniques, including but not limited to proteolytic digestion of an intact antibody as well as production by recombinant host cells (e.g. *E. coli* or phage), as described herein.

In some embodiments, the target cell binding domain comprises an anti-BCMA scFv. The anti-BCMA scFv may be derived from any known anti-BCMA four-chain antibodies, including, but not limited to, C11D5.3 and J22.9-xi. In some embodiments, the anti-BCMA comprises the amino acid sequence of SEQ ID NO: 101, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 101. In some embodiments, the anti-BCMA comprises the amino acid sequence of SEQ ID NO: 102, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 102. In some embodiments, the CATE comprises an immune effector cell binding domain comprising an anti-CD3 $V_HH$ derived from 60E11 or 117G03. In some embodiments, the CATE comprises the amino acid sequence of SEQ ID NO: 204 or 205. In some embodiments, the CATE comprises a His tag (e.g., SEQ ID NO: 208) at the N or C-terminus. In some embodiments, the CATE comprises a signal peptide (e.g., SEQ ID NO: 70 or 71) at the N-terminus 5. Multivalent Target Cell Binding Domain In some embodiments, the target cell binding domain has two or more (such as about any one of 2, 3, 4, 5, 6, or more) antigen binding fragments such as single-domain antibodies. In some embodiments, the multivalent target cell binding domain targets a single antigen, and comprises two or more antigen binding fragments for the single antigen. In some embodiments, the multivalent target cell binding domain targets more than one antigen, and the multivalent target cell binding domain comprises two or more antigen binding fragments for at least one antigen. The antigen binding fragments specific for the same antigen may bind to the same epitope of the antigen or bind to different epitopes of the antigen. The antigen binding fragments specific for the same antigen may comprise the same or different single-domain antibodies.

The chimeric antibody immune effector cell engagers comprising multivalent target cell binding domains describe herein may be especially suitable for targeting multimeric antigens via synergistic binding by the different antigen binding sites, or for enhancing binding affinity or avidity to the antigen. Any of the single-domain antibodies described herein as well as other antigen-binding fragments (e.g., scFv), such as the anti-BCMA, or anti-CD38 antibodies, may be used to provide a multivalent target cell binding domain.

In some embodiments, the target cell binding domain comprises a plurality of anti-BCMA sdAbs. In some embodiments, the plurality of the anti-BCMA sdAb is fused to each other via peptide bonds or peptide linkers. In some embodiments, each peptide linker is no more than about 50 (such as no more than about any one of 35, 25, 20, 15, 10, or 5) amino acids long.

6. Multispecific Target Cell Binding Domain

In some embodiments, the target cell binding domain can specifically bind to two or more (such as about any one of 2, 3, 4, 5, 6, or more) different antigens. In some embodiments, the multispecific target cell binding domain has one antigen binding fragments for each antigen. In some embodiments, the multispecific target cell binding domain has more than two antigen binding fragments for at least one antigen. Each antigen binding fragment may comprise a single-domain antibody.

Depending on the desired antigens to be targeted, the target cell binding domain can be engineered to include the appropriate single-domain antibodies that are specific to the desired antigens. Any one or more of the anti-BCMA or anti-CD38 antibodies described herein may be used in the target cell binding domain in the chimeric antibody immune effector engagers of the present application. In some embodiments, the target cell binding domain comprises an anti-BCMA sdAb and an anti-CD-38 sdAb. The antigen binding fragments (such as sdAbs) can be arranged in any suitable order. For example, the first sdAb is fused to the N-terminus or the C-terminus of the second sdAb. A suitable peptide linker may be placed between different sdAbs to avoid steric hindrance between the sdAbs.

Immune Effector Cell Binding Domain

The chimeric antibody immune effector cell engagers described herein comprise an immune effector cell binding domain. The immune effector cell binding domain comprises an antigen-binding fragment that specifically binds to an antigen on an immune effector cell. Immune effector cells include, but are not limited to, T cells and NK cells.

In some embodiments, the immune effector cell binding domain specifically binds to CD3, such as human CD3. "CD3" is known in the art as a multi-protein complex of six chains (see, Abbas and Lichtman, 2003; Janeway et al., p172 and 178, 1999). In mammals, the complex comprises a CD3 gamma chain, a CD3 delta chain, two CD3 epsilon chains, and a homodimer of CD3 zeta chains. CD3 as used herein may be from various animal species, including human, primate, mouse, rat, or other mammals. In some embodiments, the immune effector cell binding domain comprises an antigen-binding fragment that specifically binds to an individual CD3 chain, such as CD3 gamma chain, CD3 delta chain, or CD3 epsilon chain. In some embodiments, the antigen-binding fragment specifically binds to a complex formed from two or more individual CD3 chains (e.g., a complex of more than one CD3 epsilon chains, a complex of a CD3 gamma and CD3 epsilon chain, a complex of a CD3 delta and CD3 epsilon chain). In some embodiments, the antigen-binding fragment specifically binds to a CD3 epsilon chain.

The antigen-binding fragment targeting CD3 can be of any suitable antigen-binding fragments, including but not limited to Fab, scFv, and sdAb (e.g., $V_HH$). In some embodiments, the antigen-binding fragment is murine, camelid, chimeric, human or humanized. The antigen-binding fragment can be designed based on any known CD3 antibodies in the art, including, but not limited to, SP34 mouse monoclonal antibody, (see, for example, Pressano, S. The EMBO J. 4:337-344, 1985; Alarcon, B. EMBO J. 10:903-912, 1991; Salmeron A. et al., J. Immunol. 147:3047-52, 1991; Yoshino N. et al., Exp. Anim 49:97-110, 2000; Conrad M L. et al., Cytometry 71A:925-33, 2007; and Yang et al., J. Immunol. 137:1097-1100: 1986), Cris-7 monoclonal antibody (Reinherz, E. L. et al. (eds.), Leukocyte typing II, Springer Verlag, New York, (1986)), BC3 monoclonal antibody (Anasetti et al. (1990) J. Exp. Med. 172:1691), OKT3 (Ortho multicenter Transplant Study Group (1985) N. Engl. J. Med. 313:337) and derivatives thereof such as OKT3 ala-ala (Herold et al. (2003) J. Clin. Invest. 11:409), visilizumab (Carpenter et al. (2002) Blood 99:2712), 145-2C11 monoclonal antibody (Hirsch et al. (1988) J. Immunol. 140: 3766), UCHT-1 (Beverley, P C and Callard, R. E. (1981) Eur. J. Immunol. 11: 329-334), anti-CD3 sdAbs (such as 60E11 and 117G03) described in WO2016180982, and CD3 binding molecules described in WO2004/106380; WO2004/106381; WO2010/037838; WO2008/119567; WO2007/042261; WO2010/0150918; the contents of each of the references are incorporated herein by reference in their entireties. In some embodiments, the anti-CD3 antigen-binding fragment is derived from OKT3, L2K, UCHT1, 60E11 or 117G03. In some embodiments, the anti-CD3 antigen-binding fragment is a scFv derived from OKT3, L2K or UCHT. In some embodiments, the anti-CD3 antigen-binding fragment is a $V_HH$ derived from 60E11 or 117G03. In some embodiments, the anti-CD3 antigen-binding fragment is derived from an antibody that binds to the same epitope as OKT3, L2K, UCHT1, 60E11 or 117G03. In some embodiments, the anti-CD3 antigen-binding fragment is derived from an antibody that specifically binds to CD3 competitively with OKT3, L2K, UCHT1, 60E11 or 117G03. Sequences of exemplary anti-CD3 antigen-binding fragments are shown in Table 3 below.

TABLE 3

Sequences of exemplary anti-CD3 antibodies.

| Ab fragment | CDR1 | CDR2 | CDR3 |
|---|---|---|---|
| OKT3 $V_H$ | YTMHW (SEQ ID NO: 164) | INPSRGYTNYNQKFKDKAT (SEQ ID NO: 165) | YYDDHYCLDY (SEQ ID NO: 166) |
| OKT3 $Y_L$ | SASSSVSYMN (SEQ ID NO: 167) | YDTSKLA (SEQ ID NO: 168) | CQQWSSNPF (SEQ ID NO: 169) |
| L2K.07 $V_H$ | YTMHW (SEQ ID NO: 170) | INPSRGYTNYNQKFKDKAT (SEQ ID NO: 171) | YYDDHYCLDY (SEQ ID NO: 172) |
| L2K.07 $Y_L$ | RASSSVSYMN (SEQ ID NO: 173) | YDTSKVA (SEQ ID NO: 174) | QQWSSNPLTF (SEQ ID NO: 175) |
| UCHT 1 $V_H$ | YTMHW (SEQ ID NO: 176) | INPYKGVSTYNQKFKDKAT (SEQ ID NO: 177) | SGYYGDSDWYFDV (SEQ ID NO: 178) |
| UCHT1 $Y_L$ | RASQDIRNYLN (SEQ ID NO: 179) | YTSRLHS (SEQ ID NO: 180) | QQGNTLPWT (SEQ ID NO: 181) |
| 60E11 $V_H$H | SFDMG (SEQ ID NO: 317) | VIGSRGNNRGRTNYADSVKG (SEQ ID NO: 318) | APLVAGRP (SEQ ID NO: 319) |
| 117G03 $V_H$H | GYSMG (SEQ ID NO: 320) | AIVWSGGNTYYEDSVKG (SEQ ID NO: 321) | KIRPYIFKIAGQYDY (SEQ ID NO: 322) |

In some embodiments, the anti-CD3 antigen-binding fragment is derived from OKT3. In some embodiments, the anti-CD3 antigen-binding fragment comprises a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166, or a variant thereof comprising up to about 5 amino acid substitutions; and/or a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169, or a variant thereof comprising up to about 5 amino acid substitutions. In some embodiments, the anti-CD3 antigen-binding fragment is a scFv comprising the amino acid sequence of SEQ ID NO: 103, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 103.

In some embodiments, the anti-CD3 antigen-binding fragment is derived from L2K. In some embodiments, the anti-CD3 antigen-binding fragment comprises a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172, or a variant thereof comprising up to about 5 amino acid substitutions; and/or a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175, or a variant thereof comprising up to about 5 amino acid substitutions. In some embodiments, the anti-CD3 antigen-binding fragment is a scFv comprising the amino acid sequence of SEQ ID NO: 104, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 104.

In some embodiments, the anti-CD3 antigen-binding fragment is derived from UCHT. In some embodiments, the anti-CD3 antigen-binding fragment comprises a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178, or a variant thereof comprising up to about 5 amino acid substitutions; and/or a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181, or a variant thereof comprising up to about 5 amino acid substitutions. In some embodiments, the anti-CD3 antigen-binding fragment is a scFv comprising the amino acid sequence of SEQ ID NO: 105, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 105.

In some embodiments, the anti-CD3 antigen binding fragment is an sdAb, such as $V_H$H. In some embodiments, the anti-CD3 antigen-binding fragment is derived from 60E11. In some embodiments, the anti-CD3 antigen-binding fragment comprises a $V_H$H comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319, or a variant thereof comprising up to about 5 amino acid substitutions. In some embodiments, the anti-CD3 antigen-binding fragment is a $V_H$H comprising the amino acid sequence of SEQ ID NO: 182, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 182.

In some embodiments, the anti-CD3 antigen-binding fragment is derived from 117G03. In some embodiments, the anti-CD3 antigen-binding fragment comprises a $V_H$H comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322, or a variant thereof comprising up to about 5 amino acid substitutions. In some embodiments, the anti-CD3 antigen-binding fragment is a $V_H$H comprising the amino acid sequence of SEQ ID NO: 183, or a variant thereof having at least about 80% (such as at least about any one of 85%, 86%, 87%, 88%, 89%, 90%, 91%, 92%, 93%, 94%, 95%, 96%, 97%, 98%, or 99%) sequence identify to SEQ ID NO: 183.

Peptide Linkers

The target cell binding domain and the immune effector cell binding domain may be fused to each other via a peptide linker. In some embodiments, the target cell binding domain and the immune effector cell binding domain are directly fused to each other without any peptide linker.

In some embodiments, the various antigen-binding fragments (such as sdAbs) in the multispecific or multivalent target cell binding domain are fused to each other via peptide linker(s). In some embodiments, the antigen-binding fragments (such as sdAbs) are directly fused to each other without any peptide linkers. The peptide linkers connecting different antigen-binding fragments (such as sdAbs) may be the same or different.

Each peptide linker in a chimeric antibody immune effector cell engager may have the same or different length and/or sequence depending on the structural and/or functional features of the antigen-binding fragments (such as sdAbs) and/or the various domains. Each peptide linker may be selected and optimized independently. The length, the degree of flexibility and/or other properties of the peptide linker(s) used in the chimeric antibody immune effector cell engagers may have some influence on properties, including but not limited to the affinity, specificity or avidity for one or more particular antigens or epitopes. For example, longer peptide linkers may be selected to ensure that two adjacent domains do not sterically interfere with one another. For example, in a multivalent or multispecific target cell binding domain that comprises sdAbs directed against a multimeric antigen, the length and flexibility of the peptide linkers are preferably such that it allows each antigen-binding fragment (such as sdAb) to bind to the antigenic determinant on each of the subunits of the multimer.

In some embodiment, a peptide linker comprises flexible residues (such as glycine and serine) so that the adjacent domains are free to move relative to each other. For example, a (GGGGS)$_3$ linker (SEQ ID NO: 74) can be a suitable peptide linker between the target cell binding domain and the immune effector cell binding domain. In some embodiments, the peptide linker is no more than about 50 (such as no more than about any one of 35, 25, 20, 15, 10, or 5) amino acids long. In some embodiments, the target cell binding domain is fused to the immune effector cell binding domain via a peptide linker comprising an amino acid sequence selected from the group consisting of SEQ ID NOs: 72-77.

The peptide linker can be of any suitable length. In some embodiments, the peptide linker is at least about any of 1, 2, 3, 4, 5, 6, 7, 8, 9, 10, 11, 12, 13, 14, 15, 16, 17, 18, 19, 20, 25, 30, 35, 40, 50, 75, 100 or more amino acids long. In some embodiments, the peptide linker is no more than about any of 100, 75, 50, 40, 35, 30, 25, 20, 19, 18, 17, 16, 15, 14, 13, 12, 11, 10, 9, 8, 7, 6, 5 or fewer amino acids long. In some embodiments, the length of the peptide linker is any of about 1 amino acid to about 10 amino acids, about 1 amino acids to about 20 amino acids, about 1 amino acid to about 30 amino acids, about 5 amino acids to about 15 amino acids, about 10 amino acids to about 25 amino acids, about 5 amino acids to about 30 amino acids, about 10 amino acids to about 30 amino acids long, about 30 amino acids to about 50 amino acids, about 50 amino acids to about 100 amino acids, or about 1 amino acid to about 100 amino acids.

The peptide linker may have a naturally occurring sequence, or a non-naturally occurring sequence. For example, a sequence derived from the hinge region of heavy chain only antibodies may be used as the linker. See, for example, WO1996/34103. In some embodiments, the peptide linker is a flexible linker. Exemplary flexible linkers include glycine polymers (G)$_N$, glycine-serine polymers (including, for example, (GS)$_n$ (SEQ ID NO: 323), (GSGGS)$_n$ (SEQ ID NO: 324), (GGGS)$_n$ (SEQ ID NO: 325), and (GGGGS)$_n$ (SEQ ID NO: 326), where n is an integer of at least one), glycine-alanine polymers, alanine-serine polymers, and other flexible linkers known in the art. In some embodiments, the peptide linker comprises the amino acid sequence GGGGS (SEQ ID NO: 72), (GGGGS)$_2$ (SEQ ID NO: 73), (GGGGS)$_3$ (SEQ ID NO: 74), (GGGS)$_2$ (SEQ ID NO: 75), (GGGS)$_4$ (SEQ ID NO: 76), or GST-SGSGKPGSGEGSTKG(SEQ ID NO: 77).

Signal Peptide

The chimeric antibody immune effector cell engagers of the present application may comprise a signal peptide (also known as a signal sequence) at the N-terminus of the polypeptide. In general, signal peptides are peptide sequences that target a polypeptide to the desired site in a cell. In some embodiments, the signal peptide targets the chimeric antibody immune effector cell engager to the secretory pathway of the cell and will allow secretion of the chimeric antibody immune effector cell engager into the cell culture media. Signal peptides including signal sequences of naturally occurring proteins or synthetic, non-naturally occurring signal sequences. In some embodiments, the signal peptide is derived from a human albumin signal peptide (e.g., MKWVTFISLLFLFSSAYS, SEQ ID NO: 70). In some embodiments, the signal peptide is derived from a human azurocidin secretion signal (e.g., MTRLTVLAL-LAGLLASSRA, SEQ ID NO: 71).

Exemplary Chimeric Antibody Immune Effector Engagers

Exemplary chimeric antibody immune effector engagers are provided herein.

In some embodiments, there is provided a chimeric antibody immune effector engager comprising at least one anti-BCMA V$_H$H and an anti-CD3 scFv. In some embodiments, the chimeric antibody immune effector engager comprises at least one anti-BCMA V$_H$H domain and an L2K.07 scFv ("BCMA-L2K.07 CATE"). In some embodiments, the chimeric antibody immune effector engager comprises a single anti-BCMA V$_H$H domain. In some embodiments, the chimeric antibody immune effector engager comprises an amino acid sequence selected from the group consisting of SEQ ID NOs: 106-116. In some embodiments, the chimeric antibody immune effector engager comprises two, three or more anti-BCMA V$_H$H domains. In some embodiments, the chimeric antibody immune effector engager comprises the amino acid sequence of SEQ ID NO: 152, 154, 189, 194, 198, 202. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-BCMA V$_H$H and an OKT3 scFv ("BCMA-OKT3 CATE"). In some embodiments, the chimeric antibody immune effector engager comprises a single anti-BCMA V$_H$H domain. In some embodiments, the chimeric antibody immune effector engager comprises an amino acid sequence selected from the group consisting of SEQ ID NOs: 117-127. In some embodiments, the chimeric antibody immune effector engager comprises two, three or more anti-BCMA V$_H$H domains. In some embodiments, the chimeric antibody immune effector engager comprises the amino acid sequence of SEQ ID NO:153, 155, 188, 193, 197, or 201. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-BCMA V$_H$H domain and an UCHT1 scFv ("BCMA-UCHT1 CATE"). In some embodiments, the chimeric antibody immune effector engager comprises a single anti-BCMA V$_H$H domain. In some embodiments, the chimeric antibody immune effector engager comprises two, three or more anti-BCMA V$_H$H domains. In some embodiments, the chimeric antibody immune effector engager comprises the amino acid sequence of SEQ ID NO: 190, 195, 199, or 203. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-BCMA V$_H$H and an anti-CD3 V$_H$H. In some embodiments, the chimeric antibody immune effector engager comprises at least one anti-BCMA V$_H$H domain and a 60E11 V$_H$H ("BCMA-60E11 CATE"). In some embodiments, the chimeric antibody immune effector engager comprises a single anti-BCMA V$_H$H domain. In some embodiments, the chimeric antibody immune effector engager comprises the amino acid sequence of SEQ ID NO: 184. In some embodiments, the chimeric antibody immune effector engager comprises two, three or more anti-BCMA V$_H$H domains. In some embodiments, the chimeric antibody immune effector engager comprises the amino acid sequence of SEQ ID NO: 186, 191, or 196. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-BCMA V$_H$H domain and a 117G03 V$_H$H ("BCMA-117G03 CATE"). In some embodiments, the chimeric antibody immune effector engager comprises a single anti-BCMA V$_H$H domain. In some embodiments, the chimeric antibody immune effector engager comprises the amino acid sequence of SEQ ID NO: 185. In some embodiments, the chimeric antibody immune effector engager comprises two, three or more anti-BCMA V$_H$H domains. In some embodiments, the chimeric antibody immune effector engager comprises the amino acid sequence of SEQ ID NO: 187, 192, or 200. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-CD38 V$_H$H and an anti-CD3 scFv. In some embodiments, the chimeric antibody immune effector engager comprises at least one anti-CD38 V$_H$H and an L2K.07 scFv ("CD38-L2K.07 CATE"). In some embodiments, the chimeric antibody immune effector engager comprises a single anti-CD38 V$_H$H domain. In some embodiments, the chimeric antibody immune effector engager comprises an amino acid sequence selected from the group consisting of SEQ ID NOs: 128-139. In some embodiments, the chimeric antibody immune effector engager comprises two, three or more anti-CD38 V$_H$H domains. In some embodiments, the chimeric antibody immune effector engager comprises an amino acid sequence of SEQ ID NO:156 or 158. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-CD38 V$_H$H and an OKT3 scFv ("CD38-OKT3 CATE"). In some embodiments, the chimeric antibody immune effector engager comprises a single anti-CD38 V$_H$H domain. In some embodiments, the chimeric antibody immune effector engager comprises an amino acid sequence selected from the group consisting of SEQ ID NOs: 140-151. In some embodiments, the chimeric antibody immune effector engager comprises two, three or more anti-CD38 V$_H$H domains. In some embodiments, the chimeric antibody immune effector engager comprises an amino acid sequence of SEQ ID NO:157 or 159. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

In some embodiments, the chimeric antibody immune effector engager comprises at least one anti-CD38 V$_H$H and an UCHT1 scFv ("CD38-UCHT1 CATE").

In some embodiments, the chimeric antibody immune effector engager comprises at least one anti-CD38 V$_H$H and an anti-CD3 V$_H$H.

In some embodiments, the chimeric antibody immune effector engager comprises an anti-BCMA V$_H$H, an anti-CD38 V$_H$H, and an anti-CD3 antigen-binding fragment ("BCMA*CD38-CD3 CAPE"). In some embodiments, the anti-CD3 antigen-binding fragment is a Fab, scFv or sdAb (such as V$_H$H). In some embodiments, the anti-CD3 antigen-binding fragment is camelid, chimeric, human or humanized. In some embodiments, the anti-CD3 antigen-binding fragment is derived from of OKT3, L2K, UCHT1, 60E11 or 117G03. In some embodiments, the chimeric antibody immune effector engager comprises an amino acid sequence selected from SEQ ID NOs: 160-163 and 206-207. In some embodiments, the CATE further comprises a His tag (e.g., SEQ ID NO: 208) at the N or C-terminus. In some embodiments, the CATE comprises a signal peptide (e.g., SEQ ID NO: 70 or 71) at the N-terminus.

Sequence Variants

In some embodiments, amino acid sequence variants of the chimeric antibody immune effector engagers provided herein are contemplated. For example, it may be desirable to improve the binding affinity and/or other biological properties of any one of the sdAbs or antigen-binding fragments. Amino acid sequence variants of an antigen-binding fragment may be prepared by introducing appropriate modifications into the nucleic acid sequence encoding the antigen-binding fragment, or by peptide synthesis. Such modifications include, for example, deletions from, insertions into and/or substitutions of residues within the amino acid sequences of the antigen-binding fragments. Any combination of deletion, insertion, and substitution can be made to arrive at the final construct, provided that the final construct possesses the desired characteristics, e.g., antigen-binding and immune effector cell activation.

In some embodiments, the chimeric antibody immune effector engager variant has one or more amino acid substitutions are provided. Sites of interest for substitutional mutagenesis include the HVRs and FRs. Conservative substitutions are shown in Table 4 under the heading of "Preferred substitutions." More substantial changes are provided in Table 4 under the heading of "exemplary substitutions," and as further described below in reference to amino acid side chain classes.

TABLE 4

Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class.

One type of substitutional variant involves substituting one or more hypervariable region residues of a parent antibody or fragment thereof (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques known in the art. Briefly, one or more HVR residues are mutated and the variant antibodies displayed on phage and screened for a particular biological activity (e.g. binding affinity).

Alterations (e.g., substitutions) may be made in HVRs, e.g., to improve antigen-binding affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, NJ, (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody or antigen-binding fragment thereof to bind antigen. For example, conservative alterations (e.g., conservative substitutions as provided herein) that do not substantially reduce binding affinity may be made in HVRs. Such alterations may be outside of HVR "hotspots" or CDRs. In some embodiments of the variant $V_HH$ sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue. Other insertional variants of the chimeric antibody immune effector engager include the fusion to the N- or C-terminus of the chimeric antibody immune effector engager to an enzyme (e.g., for ADEPT) or a polypeptide which increases the serum half-life of the chimeric antibody immune effector engager. Peptide tags, such as Hisx6 tags, may be added to the chimeric antibody immune effector engager (e.g., at the C-terminus) to facilitate its purification and detection.

III. Methods of Preparation

The chimeric antibody immune effector cell engagers may be prepared using any methods known in the art for recombinant preparation of antibodies or as described herein.
Nucleic Acid Molecules Encoding Chimeric Antibody Immune Effector Cell Engagers Nucleic acid molecules comprising polynucleotides that encode one or more chains of the chimeric antibody immune effector cell engagers are provided. In some embodiments, wherein the chimeric antibody immune effector cell engager comprises a single polypeptide, a nucleic acid molecule comprises a polynucleotide that encodes the target cell binding domain fused to the immune cell binding domain is provided.

In some embodiments, a polynucleotide encoding the chimeric antibody immune effector cell engager comprises a nucleotide sequence that encodes a leader sequence, which, when translated, is located at the N terminus of the chimeric antibody immune effector cell engager. The leader sequence may be the native heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell.

Vectors comprising polynucleotides that encode chimeric antibody immune effector cell engagers are provided. Such vectors include, but are not limited to, DNA vectors, phage vectors, viral vectors, retroviral vectors, etc.

In some embodiments, a vector is selected that is optimized for expression of polypeptides in CHO or CHO-derived cells, or in other mammalian cells. Exemplary such vectors are described, e.g., in Running Deer et al., *Biotechnol. Prog.* 20:880-889 (2004).

Host Cells

In various embodiments, the chimeric antibody immune effector cell engagers may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the chimeric antibody immune effector cell engagers may be expressed in yeast. See, e.g., U.S. Publication No. US 2006/0270045 A1. In some embodiments, a particular eukaryotic host cell is selected based on its ability to make desired post-translational modifications to the chimeric antibody immune effector cell engagers.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, e.g., in Sambrook et al., Molecular Cloning, A Laboratory Manual, 3$^{rd}$ ed. Cold Spring Harbor Laboratory Press (2001). Nucleic acids may be transiently or stably transfected in the desired host cells, according to any suitable method.

The present application also provides host cells comprising any of the polynucleotides or vectors described herein. In some embodiments, the present application provides a host cell comprising a chimeric antibody immune effector cell engager. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Purification of Chimeric Antibody Immune Effector Cell Engagers

The chimeric antibody immune effector cell engagers may be purified by any suitable method. Such methods include, but are not limited to, the use of affinity matrices or hydrophobic interaction chromatography. Hydrophobic interactive chromatography, for example, a butyl or phenyl column, may be suitable for purifying some chimeric antibody immune effector cell engagers. Ion exchange chromatography (e.g. anion exchange chromatography and/or cation exchange chromatography) may also be suitable for purifying some chimeric antibody immune effector cell engagers. Mixed-mode chromatography (e.g. reversed phase/anion exchange, reversed phase/cation exchange, hydrophilic interaction/anion exchange, hydrophilic interaction/cation exchange, etc.) may also be suitable for purifying chimeric antibody immune effector cell engagers. Many methods of purifying polypeptides are known in the art.

Cell-Free Production of Chimeric Antibody Immune Effector Cell Engagers

In some embodiments, the chimeric antibody immune effector cell engager is produced in a cell-free system. Nonlimiting exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

IV. Pharmaceutical Compositions

Further provided by the present application are pharmaceutical compositions comprising any one of the chimeric antibody immune effector cell engagers described herein, and a pharmaceutically acceptable carrier. Pharmaceutical compositions can be prepared by mixing a chimeric antibody immune effector cell engager having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions.

Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g. Zn-protein complexes); chelating agents such as EDTA and/or non-ionic surfactants.

Buffers are used to control the pH in a range which optimizes the therapeutic effectiveness, especially if stability is pH dependent. Buffers are preferably present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may comprise histidine and trimethylamine salts such as Tris.

Preservatives are added to retard microbial growth, and are typically present in a range from 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" are present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between 0.1% to 25% by weight, preferably 1 to 5%, taking into account the relative amounts of the other ingredients. Preferred tonicity agents include polyhydric sugar alcohols, preferably trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") are present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml, preferably about 0.07 mg/ml to about 0.2 mg/ml.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the pharmaceutical compositions to be used for in vivo administration, they must be sterile. The pharmaceutical composition may be rendered sterile by filtration through sterile filtration membranes. The pharmaceutical compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

Sustained-release preparations may be prepared. Suitable examples of sustained-release preparations include semipermeable matrices of solid hydrophobic polymers containing the antagonist, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and ethyl-L-glutamate, non-degradable ethylenevinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The pharmaceutical compositions described herein may also contain more than one active compound or agent as necessary for the particular indication being treated, preferably those with complementary activities that do not adversely affect each other. Alternatively, or in addition, the composition may comprise a cytotoxic agent, chemotherapeutic agent, cytokine, immunosuppressive agent, or growth inhibitory agent. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 18th edition.

V. Methods of Treatment

The present application further provides methods of treating a disease (such as cancer or autoimmune disease) in an individual comprising administering to the individual an effective amount of any one of the pharmaceutical compositions or the chimeric antibody immune effector cell engagers described herein. In some embodiments, the disease is a B cell-related disorder. In some embodiments, the disease is a cancer. In some embodiments the disease is an autoimmune disease.

In some embodiments, there is provided a method of treating a disease (such as a B cell-related disorder) in an individual (such as a human individual), comprising administering to the individual an effective amount of a chimeric antibody immune effector cell engager comprising: (a) a target cell binding domain comprising a sdAb (such as $V_HH$) that specifically binds to an antigen on a target cell; and (b) an immune effector cell binding domain comprising an anti-CD3 antigen-binding fragment. In some embodiments, the target cell is a tumor cell or a B cell. In some embodiments, the anti-CD3 antigen-binding fragment is a Fab, scFv, or sdAb. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_H H$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_H H$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

The methods described herein are suitable for treating various B cell-related disorders, including, but not limited to, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, small lymphocytic lymphoma, B cell proliferations of uncertain malignant potential, lymphomatoid granulomatosis, post-transplant lymphoproliferative disorder, an immunoregulatory disorder, rheumatoid arthritis, myasthenia gravis, idiopathic thrombocytopenia purpura, anti-phospholipid syndrome, Chagas' disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy of undetermined significance. In some embodiments, the plasma cell malignancy is multiple myeloma. In some embodiments, the autoimmune disease is systemic lupus erythematosus.

The methods described herein are suitable for treating various cancers, including solid cancers and liquid cancers. Exemplary cancers include, but are not limited to, plasmacytoma, Hodgkins' lymphoma, follicular lymphomas, small non-cleaved cell lymphomas, endemic Burkitt's lymphoma, sporadic Burkitt's lymphoma, marginal zone lymphoma, extranodal mucosa-associated lymphoid tissue lymphoma, nodal monocytoid B cell lymphoma, splenic lymphoma, mantle cell lymphoma, large cell lymphoma, diffuse mixed cell lymphoma, immunoblastic lymphoma, primary mediastinal B cell lymphoma, pulmonary B cell angiocentric lymphoma, and small lymphocytic lymphoma. In some embodiments, the method is applicable to cancers of at a particular stage, such as early stage, advanced stage and/or metastatic cancer. In some embodiments, the method is used as a first therapy, second therapy, third therapy, or combination therapy with other types of cancer therapies known in the art, such as chemotherapy, surgery, radiation, gene therapy, immunotherapy, bone marrow transplantation, stem cell transplantation, targeted therapy, cryotherapy, ultrasound therapy, photodynamic therapy, radio-frequency ablation or the like, in an adjuvant setting or a neoadjuvant setting. In some embodiments, the method is used for treating a plasma cell disorder, such as multiple myeloma, plasmacytoma or plasma cell leukemia. In some embodiments, the method is used for treating a B cell disorder, such as Non-Hodgkin Lymphoma (NHL) or Chronic Lymphocytic Leukemia (CLL).

Thus, in some embodiments, there is provided a method of treating a cancer (such as multiple myeloma) in an individual (such as a human individual), comprising administering to the individual an effective amount of a chimeric antibody immune effector cell engager comprising: (a) a target cell binding domain comprising an anti-BCMA sdAb (such as anti-BCMA $V_H H$); and (b) an immune effector cell binding domain comprising an antigen-binding fragment that specifically binds to an antigen on an immune effector cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-BCMA sdAb is any one of the anti-BCMA sdAbs listed in Table 2. In some embodiments, the anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the anti-BCMA sdAb comprises an amino acid sequence selected from the group consisting of SEQ ID NOs: 78-88. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a method of treating a cancer (such as multiple myeloma) in an individual (such as a human individual), comprising administering to the individual an effective amount of a chimeric antibody immune effector cell engager comprising: (a) a target cell binding domain comprising an anti-CD38 sdAb (such as anti-CD38 $V_HH$); and (b) an immune effector cell binding domain comprising an antigen-binding fragment that specifically binds to an antigen on an immune effector cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-CD38 sdAb comprises any one of the following: (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58; (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59; (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60; (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61; (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62; (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63; (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64; (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65; (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66; (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68; or (12) a CDR1 comprising the amino acid sequence of SEQ ID NO:45; a CDR2 comprising the amino acid sequence of SEQ ID NO:57; and a CDR3 comprising the amino acid sequence of SEQ ID NO:69. In some embodiments, the anti-CD38 sdAb comprises an amino acid sequence selected from the group consisting of SEQ ID NOs: 89-100. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a method of treating a cancer (such as multiple myeloma) in an individual (such as a human individual), comprising administering to the individual an effective amount of a chimeric antibody immune effector cell engager comprising: (a) a target cell binding domain comprising a first anti-BCMA sdAb (such as anti-BCMA $V_HH$) and a second anti-BCMA sdAb (such as anti-BCMA $V_HH$); and (b) an immune effector cell binding domain comprising an anti-CD3 antigen-binding fragment (such as anti-CD3 $V_HH$ or anti-CD3 scFv). In some embodiments, the first anti-BCMA sdAb is fused to the second anti-BCMA sdAb via a peptide linker. In some embodiments, the first anti-BCMA sdAb and the second anti-BCMA sdAb recognizes different epitopes on BCMA. In some embodiments, the anti-CD3 antigen-binding fragment is an anti-CD3 sdAb such as an anti-CD3 $V_HH$. In some embodiments, the anti-CD3 $V_HH$ is derived from 60E11 or 117G03. In some embodiments, the anti-CD3 antigen-binding fragment is an anti-CD3 scFv. In some embodiments, the anti-CD3 scFv is derived from OKT3, L2K, or UCHT1. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-BCMA sdAb is any one of the anti-BCMA sdAbs listed in Table 2. In some embodiments, the first anti-BCMA sdAb and/or the second anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the first anti-BCMA sdAb and/or the second anti-BCMA sdAb comprises an amino acid sequence selected from the group consisting of SEQ ID NOs: 78-88 and 290-316. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a method of treating a cancer (such as multiple myeloma) in an individual (such as a human individual), comprising administering to the individual an effective amount of a chimeric antibody immune effector cell engager comprising: (a) a target cell binding domain comprising a first sdAb (such as $V_HH$) that specifically binds to a first antigen on a first target cell and a second sdAb (such as $V_HH$) that specifically binds to a second antigen on a second target cell; and (b) an immune effector cell binding domain comprising an antigen-binding fragment that specifically binds to an antigen on an immune effector cell. In some embodiments, the first target cell and the second target cell are the same cell. In some embodiments, the first target cell and the second target cell are different cells. In some embodiments, the first cell and the second cell are tumor cells. In some embodiments, the first sdAb is fused to the second sdAb via a peptide linker. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77. In some embodiments, the first sdAb is an anti-BCMA sdAb and the second sdAb is an anti-CD38 sdAb. In some embodiments, the first sdAb and the second sdAb are anti-BCMA sdAbs.

In some embodiments, there is provided a method of treating a cancer (such as multiple myeloma) in an individual (such as a human individual), comprising administering to the individual an effective amount of a chimeric antibody immune effector cell engager comprising: (a) a target cell binding domain comprising an anti-BCMA sdAb (such as anti-BCMA $V_HH$) and an anti-CD38 sdAb (such as anti-CD38 $V_HH$); and (b) an immune effector cell binding domain comprising an anti-CD3 sdAb (such as anti-CD3 $V_HH$). In some embodiments, the anti-BCMA sdAb is fused to the anti-CD38 sdAb via a peptide linker. In some embodiments, the anti-BCMA sdAb is fused to the C-terminus of the anti-CD38 sdAb. In some embodiments, the anti-CD3 antigen-binding fragment is derived from 60E11 or 117G03. In some embodiments, the anti-CD3 antigen-binding fragment comprises: (1) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (2) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises the amino acid sequence of SEQ ID NO: 182 or 183. In some embodiments, the anti-BCMA sdAb comprises a CDR1 comprising the amino acid sequence of SEQ ID NO:1; a CDR2 comprising the amino acid sequence of SEQ ID NO:12; and a CDR3 comprising the amino acid sequence of SEQ ID NO:23. In some embodiments, the anti-BCMA sdAb comprises the amino acid sequence of SEQ ID NO: 78. In some embodiments, the anti-CD38 sdAb comprises a CDR1 comprising the amino acid sequence of SEQ ID NO:38; a CDR2 comprising the amino acid sequence of SEQ ID NO:50; and a CDR3 comprising the amino acid sequence of SEQ ID NO:62. In some embodiments, the anti-CD38 sdAb comprises the amino acid sequence of SEQ ID NO: 93. In some embodiments, the target cell binding domain is fused to the N-terminus of the immune effector cell binding domain. In some embodiments, the target cell binding domain is fused to the immune effector cell binding domain via a peptide linker, such as a peptide linker comprising the amino acid sequence of SEQ ID NO: 206 or 207.

The methods described herein are also suitable for treating various autoimmune diseases, including, but not limited to, rheumatoid arthritis, myasthenia gravis, idiopathic thrombocytopenia purpura, anti-phospholipid syndrome, Chagas1 disease, Grave's disease, Wegener's granulomatosis, poly-arteritis nodosa, Sjogren's syndrome, pemphigus vulgaris, scleroderma, multiple sclerosis, anti-phospholipid syndrome, ANCA associated vasculitis, Goodpasture's disease, Kawasaki disease, autoimmune hemolytic anemia, and rapidly progressive glomerulonephritis, heavy-chain disease, primary or immunocyte-associated amyloidosis, or monoclonal gammopathy of undetermined significance. In some embodiments, the method is used for treating Systemic Lupus Erythematosus (SLE) or Multiple Sclerosis (MS).

Thus, in some embodiments, there is provided a method of treating an autoimmune disease (such as systemic lupus erythematosus) in an individual (such as a human individual), comprising administering to the individual an effective amount of a chimeric antibody immune effector cell engager comprising: (a) a target cell binding domain comprising an anti-BCMA sdAb (such as anti-BCMA $V_HH$); and (b) an immune effector cell binding domain comprising an antigen-binding fragment that specifically binds to an antigen on an immune effector cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-BCMA sdAb is any one of the anti-BCMA sdAbs listed in Table 2. In some embodiments, the anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the anti-BCMA sdAb comprises an amino acid sequence selected from the group consisting of SEQ ID NOs: 78-88. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a method of treating an autoimmune disease (such as systemic lupus erythematosus) in an individual (such as a human individual), comprising administering to the individual an effective amount of a chimeric antibody immune effector cell engager comprising: (a) a target cell binding domain comprising an anti-CD38 sdAb (such as anti-CD38 $V_HH$); and (b) an immune effector cell binding domain comprising an antigen-binding fragment that specifically binds to an antigen on an immune effector cell. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the anti-CD38 sdAb comprises any one of the following: (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58; (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59; (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60; (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61; (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62; (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63; (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64; (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65; (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66; (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68; or (12) a CDR1 comprising the amino acid sequence of SEQ ID NO:45; a CDR2 comprising the amino acid sequence of SEQ ID NO:57; and a CDR3 comprising the amino acid sequence of SEQ ID NO:69. In some embodiments, the anti-CD38 sdAb comprises an amino acid sequence selected from the group consisting of SEQ ID NOs: 89-100. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

In some embodiments, there is provided a method of treating an autoimmune disease (such as systemic lupus erythematosus) in an individual (such as a human individual), comprising administering to the individual an effective amount of a chimeric antibody immune effector cell engager comprising: (a) a target cell binding domain comprising a first sdAb (such as $V_HH$) that specifically binds to a first antigen on a first target cell and a second sdAb (such as $V_HH$) that specifically binds to a second antigen on a second target cell; and (b) an immune effector cell binding domain comprising an antigen-binding fragment that specifically binds to an antigen on an immune effector cell. In some embodiments, the first target cell and the second target cell are the same cell. In some embodiments, the first target cell and the second target cell are different cells. In some embodiments, the first cell and the second cell are tumor cells. In some embodiments, the first sdAb is fused to the second sdAb via a peptide linker. In some embodiments, the immune effector cell is a T cell. In some embodiments, the immune effector cell is an NK cell. In some embodiments, the antigen-binding fragment of the immune effector cell is a Fab, scFv, or sdAb. In some embodiments, the immune effector cell binding domain comprises an anti-CD3 antigen-binding fragment. In some embodiments, the anti-CD3 antigen-binding fragment is derived from OKT3, L2K, UCHT1, 60E11 or 117G03. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77. In some embodiments, the first sdAb is an anti-BCMA sdAb and the second sdAb is an anti-CD38 sdAb. In some embodiments, the first sdAb and the second sdAb are anti-BCMA sdAbs.

In some embodiments, there is provided a method of treating an autoimmune disease (such as systemic lupus erythematosus) in an individual (such as a human individual), comprising administering to the individual an effective amount of a chimeric antibody immune effector cell engager comprising: (a) a target cell binding domain comprising a first anti-BCMA sdAb (such as anti-BCMA $V_HH$) and a second anti-BCMA sdAb (such as anti-BCMA $V_HH$); and (b) an immune effector cell binding domain comprising an anti-CD3 antigen-binding fragment (such as anti-CD3 $V_HH$ or anti-CD3 scFv). In some embodiments, the first anti-BCMA sdAb is fused to the second anti-BCMA sdAb via a peptide linker. In some embodiments, the first anti-BCMA sdAb and the second anti-BCMA sdAb recognizes different epitopes on BCMA. In some embodiments, the anti-CD3 antigen-binding fragment is an anti-CD3 sdAb such as an anti-CD3 $V_HH$. In some embodiments, the anti-CD3 $V_HH$ is derived from 60E11 or 117G03. In some embodiments, the anti-CD3 antigen-binding fragment is an anti-CD3 scFv. In some embodiments, the anti-CD3 scFv is derived from OKT3, L2K, or UCHT1. In some embodiments, the anti-CD3 antigen-binding fragment comprises any one of the following: (1) a $V_H$ comprising a CDR1 comprising the amino acid sequence of SEQ ID NO:164; a CDR2 comprising the amino acid sequence of SEQ ID NO:165; and a CDR3 comprising the amino acid sequence of SEQ ID NO:166; and a $V_L$ comprising a CDR1 comprising the amino acid sequence of SEQ ID NO:167; a CDR2 comprising the amino acid sequence of SEQ ID NO:168; and a CDR3 comprising the amino acid sequence of SEQ ID NO:169; (2) a $V_H$ comprising a CDR1 comprising the amino acid sequence of SEQ ID NO:170; a CDR2 comprising the amino acid sequence of SEQ ID NO:171; and a CDR3 comprising the amino acid sequence of SEQ ID NO:172; and a $V_L$ comprising a CDR1 comprising the amino acid sequence of SEQ ID NO:173; a CDR2 comprising the amino acid sequence of SEQ ID NO:174; and a CDR3 comprising the amino acid sequence of SEQ ID NO:175; (3) a $V_H$ comprising a CDR1 comprising the amino acid sequence of SEQ ID NO:176; a CDR2 comprising the amino acid sequence of SEQ ID NO:177; and a CDR3 comprising the amino acid sequence of SEQ ID NO:178; and a $V_L$ comprising a CDR1 comprising the amino acid sequence of SEQ ID NO:179; a CDR2 comprising the amino acid sequence of SEQ ID NO:180; and a CDR3 comprising the amino acid sequence of SEQ ID NO:181; (4) a $V_HH$ comprising a CDR1 comprising the amino acid sequence of SEQ ID NO:317; a CDR2 comprising the amino acid sequence of SEQ ID NO:318; and a CDR3 comprising the amino acid sequence of SEQ ID NO:319; or (5) a $V_HH$ comprising a CDR1 comprising the amino acid sequence of SEQ ID NO:320; a CDR2 comprising the amino acid sequence of SEQ ID NO:321; and a CDR3 comprising the amino acid sequence of SEQ ID NO:322. In some embodiments, the anti-CD3 antigen-binding fragment comprises an amino acid sequence selected from the group consisting of SEQ ID NOs: 103-105 and 182-183. In some embodiments, the anti-BCMA sdAb is any one of the anti-BCMA sdAbs listed in Table 2. In some embodiments, the first anti-BCMA sdAb and/or the second anti-BCMA sdAb comprises any one of the following: (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23; (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24; (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25; (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26; (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27; (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28; (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29; (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30; (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31; (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33. In some embodiments, the first anti-BCMA sdAb and/or the second anti-BCMA sdAb comprises an amino acid sequence selected from the group consisting of SEQ ID NOs: 78-88 and 290-316. In some embodiments, the target cell binding domain is fused to the N-terminus of the immune effector cell binding domain. In some embodiments, the target cell binding domain is fused to the C-terminus of the immune effector cell binding domain. In some embodiments, the target cell binding domain is fused to the immune effector cell binding domain via a peptide linker, such as a peptide linker comprising an amino acid sequence selected from the group consisting of SEQ ID NOs: 72-77.

Administration of the pharmaceutical compositions may be carried out in any convenient manner, including by injection, ingestion, transfusion, implantation or transplantation. The compositions may be administered to a patient transarterially, subcutaneously, intradermally, intratumorally, intranodally, intramedullary, intramuscularly, intravenously, or intraperitoneally. In some embodiments, the pharmaceutical composition is administered systemically. In some embodiments, the pharmaceutical composition is administered to an individual by infusion, such as intravenous infusion. Infusion techniques for immunotherapy are known in the art (see, e.g., Rosenberg et al., New Eng. J. of Med. 319: 1676 (1988)). In some embodiments, the pharmaceutical composition is administered to an individual by intradermal or subcutaneous injection. In some embodiments, the compositions are administered by intravenous injection. In some embodiments, the compositions are injected directly into a tumor, or a lymph node. In some embodiments, the pharmaceutical composition is administered locally to a site of tumor, such as directly into tumor cells, or to a tissue having tumor cells.

Dosages and desired drug concentration of pharmaceutical compositions of the present invention may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles laid down by Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46. It is within the scope of the present application that different formulations will be effective for different treatments and different disorders, and that administration intended to treat a specific organ or tissue may necessitate delivery in a manner different from that to another organ or tissue.

In some embodiments, the pharmaceutical composition or the chimeric antibody immune effector cell engager is administered at to dosage of about 10 ng/kg up to about 100 mg/kg of body weight of the individual or more per day, for example, at about 1 mg/kg/day to 10 mg/kg/day, depending upon the route of administration. In some embodiments, the pharmaceutical composition is administered for a single time. In some embodiments, the pharmaceutical composition is administered for multiple times (such as any of 2, 3, 4, 5, 6, or more times). In some embodiments, the pharmaceutical composition is administered at a frequency of once per week to once per year. In some embodiments, the interval between administrations is from about 1 week to about a year. The optimal dosage and treatment regime for a particular patient can readily be determined by one skilled in the art of medicine by monitoring the patient for signs of disease and adjusting the treatment accordingly.

In some embodiments, the pharmaceutical composition or the chimeric antibody immune effector cell engager is administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

VI. Kits and Articles of Manufacture

Further provided are kits, unit dosages, and articles of manufacture comprising any one of the chimeric antibody immune effector cell engagers described herein. In some embodiments, a kit is provided which contains any one of the pharmaceutical compositions described herein and preferably provides instructions for its use.

The kits of the present application are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease or disorder (such as cancer or autoimmune disease) as described herein, and may have a sterile access port (for example the container may be an intravenous solution bag or a vial having a stopper pierceable by a hypodermic injection needle). The label or package insert indicates that the composition is used for treating the particular condition in an individual. The label or package insert will further comprise instructions for administering the composition to the individual. The label may indicate directions for reconstitution and/or use. The container holding the pharmaceutical composition may be a multi-use vial, which allows for repeat administrations (e.g. from 2-6 administrations) of the reconstituted formulation. Package insert refers to instructions customarily included in commercial packages of therapeutic products that contain information about the indications, usage, dosage, administration, contraindications and/or warnings concerning the use of such therapeutic products. Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kits or article of manufacture may include multiple unit doses of the pharmaceutical composition and instructions for use, packaged in quantities sufficient for storage and use in pharmacies, for example, hospital pharmacies and compounding pharmacies.

EXAMPLES

The examples and exemplary embodiments below are intended to be purely exemplary of the invention and should therefore not be considered to limit the invention in any way. The following examples and detailed description are offered by way of illustration and not by way of limitation.

Example 1

Preparation of Chimeric Antibody Immune Cell Engagers

This example describes the design and preparation of exemplary chimeric antibody T cell engagers (CATEs) using antigen-binding fragments from previously identified anti-BCMA, anti-CD38 and anti-CD3 antibodies. The exemplary CATEs are referred herein as BCMA CATEs, CD38 CATEs and BCMA*CD38 CATEs respectively.

1. Single Domain Antibody Generation

Single-domain antibody or $V_HH$ repertoires obtained from llamas and cloned as a phage library were used for selection. Methods of sdAb generation have been described, for example, in PCT/CN2017/072723. Briefly, to develop single-domain antibodies with high binding affinity to specified antigens, llamas were immunized and a phage display library was constructed to identify $V_HH$ leads. Distinct clones were picked at random and were classified according to the sequence of the heavy chain complementarity determining region 3 (CDR3), a region that plays a major role in antigen binding. Through library screening for particular characteristics, several anti-BCMA sdAbs and anti-CD38 sdAbs with excellent properties were obtained. The nucleotide sequences of the heavy chain variable domains of anti-BCMA sdAbs and anti-CD38 sdAbs were obtained by gene sequencing. Some of the sdAbs were chosen to design the exemplary CATEs.

2. Design of Exemplary Chimeric Antibody T Cell Engagers

Exemplary CATE molecules were designed, each comprising a target cell binding domain targeting human antigen BCMA and/or CD38, and a T-cell binding domain targeting CD3 epsilon.

Any methods known in the art can be used to prepare an antibody against a given antigen, which comprises immunoglobulin light and/or heavy chain variable regions. Antigen-binding fragments of various formats can be designed based on the full-length antibodies. For example, the antigen-binding fragment of a single domain antibody can be a single heavy chain variable domain ($V_HH$), which can have high affinity to an antigen without the aid of a light chain. Suitable antigen-binding fragments based on four-chain antibodies include scFv and Fab.

In this example, exemplary CATE molecules #001-#012 and #019-#030 were designed to have an immune effector cell binding domain comprising an anti-CD3 scFv derived from known anti-CD3 antibodies, OKT3, L2K and UCHT1. The $V_H$ and $V_L$ of the anti-CD3 antibodies were gene-edited to prepare the corresponding scFvs, which were fused to a target cell binding domain comprising an anti-BCMA $V_HH$ (CATEs#001-009), two anti-BCMA $V_HH$ (CATEs#010-012), an anti-CD38 $V_HH$ (CATEs#028-030), and an anti-BCMA $V_HH$ fused to an anti-CD38 $V_HH$ (CATEs#025-027) to provide sdAb-based CATEs. Additionally, BCMA scFv-based CATEs comprising an anti-BCMA scFv derived from anti-BCMA antibody J22.9-xi (PDB database: 4ZFO; CATEs#022-024) or C11D5.3 (see, WO2010104949; CATEs#019-021) were prepared.

Exemplary CATE molecules #031-038 were designed to have an immune effector cell binding domain comprising an anti-CD3 $V_HH$ derived from an anti-CD3 single domain antibody 60E11 (also referred to as T0170060E11; SEQ ID NO: 182) or 117G03 (also referred to as T0170117G03; SEQ ID NO: 183). The anti-CD3 single domain antibodies have previously been described in WO2016180982. CATE#031 and CATE#032 were designed to have a monovalent target cell binding domain comprising a single BCMA $V_HH$. CATE#035 and CATE#036 were designed to have a monovalent target cell binding domain comprising a single BCMA scFv derived from J22.9-xi. CATE#033 and CATE#034 were designed to have a bivalent target cell binding domain comprising two different anti-BCMA $V_HH$s. CATE#037 and CATE#038 were designed to have a bispecific target cell binding domain comprising an anti-BCMA $V_HH$ and a CD38 $V_HH$.

3. Vectors Encoding CATEs

For CATEs#001-#012 and #019-#030, three CATE backbone plasmids carrying three different anti-CD3 scFv nucleotide sequences were designed based on the mammalian protein expression vector pTT5 (NRC Biotechnology Research Institute). These three CATE backbone plasmids were named pTT5-LIB-BB1, pTT5-LIB-BB2, and pTT5-LIB-BB3 respectively. The CATE backbone vectors were prepared as follows.

Construction of pTT5-LIB-BB1 vector: nucleotide sequence encoding anti-CD3 scFv with a 6×His tag (SEQ ID NO: 208) at the C-terminus from the clone L2K.07 (Drugbank access NO. DB09052) was codon optimized for expression in human and CHO cell systems. The codon-optimized nucleotide sequence was chemically synthesized and subcloned into a pTT5 vector via XbaI and HindIII cloning sites using known molecular cloning techniques in the art.

Construction of pTT5-LIB-BB2 vector: nucleotide sequence encoding anti-CD3 scFv with a 6×His tag (SEQ ID NO: 208) at the C-terminus from the clone mOKT3 (PDB access NO. 1SY6) was codon optimized for expression in human and CHO cell systems. The codon-optimized nucleotide sequence was chemically synthesized and subcloned into a pTT5 vector via XbaI and HindIII cloning sites using known molecular cloning techniques in the art.

Construction of pTT5-LIB-BB3 vector: nucleotide sequence encoding anti-CD3 scFv with a 6×His tag (SEQ ID NO: 208) at the C-terminus from the clone mUCHT1 (PDB access NO. 1X1W) were codon optimized for better expression in human and CHO cell systems. The codon-optimized nucleotide sequence was chemically synthesized and subcloned to a pTT5 vector via XbaI and HindIII cloning sites using known molecular cloning techniques in the art.

Two different signal peptides, human albumin secretion signal peptide (e.g., SEQ ID NO: 70) and human azurocidin secretion signal (e.g., SEQ ID NO: 71) were selected. See, Biotechnol Bioeng. 2013 April; 110(4):1164-73.

To construct the CATE expression plasmids, nucleotides encoding a signal peptide, at least one anti-BCMA $V_HH$ and/or an anti-CD38 $V_HH$, and a peptide linker were fused together in sequence. The nucleotide sequences were codon optimized for expression in human and CHO cell systems. The codon-optimized nucleotide sequences having a Kozak sequence at 5' end were chemically synthesized and subcloned into each CATE backbone vector (pTT5-LIB-BB1, pTT5-LIB-BB2, and pTT5-LIB-BB3), via EcoRI and XbaI restriction endonuclease sites known molecular cloning techniques in the art. CATEs#001-#012 and #019-#030 are shown in Table 5 below.

TABLE 5

Exemplary CATE constructs (#001-#012 and #019-#030).

| CATE code | Signal peptide | Target cell binding domain | Linker | Anti-CD3 scFv | CATE backbone plasmids |
|---|---|---|---|---|---|
| CATE#001 | Human albumin SP | BCMA $V_HH$1 | (G4S)$_3$ | L2K.07 | pTT5-LIB-BB1 |
| CATE#002 | Human albumin SP | | (SEQ ID | OKT3 | pTT5-LIB-BB2 |
| CATE#003 | Human albumin SP | | NO: 74) | UCHT1 | pTT5-LIB-BB3 |
| CATE#004 | Human azurocidin SP | | | L2K.07 | pTT5-LIB-BB1 |
| CATE#005 | Human azurocidin SP | | | OKT3 | pTT5-LIB-BB2 |
| CATE#006 | Human azurocidin SP | | | UCHT1 | pTT5-LIB-BB3 |
| CATE#007 | Human albumin SP | BCMA $V_HH$2 | (G4S)$_3$ | L2K.07 | pTT5-LIB-BB1 |
| CATE#008 | Human albumin SP | | (SEQ ID | OKT3 | pTT5-LIB-BB2 |
| CATE#009 | Human albumin SP | | NO: 74) | UCHT1 | pTT5-LIB-BB3 |
| CATE#010 | Human albumin SP | BCMA | | L2K.07 | pTT5-LIB-BB1 |
| CATE#011 | Human albumin SP | $V_HH$1*BCMA | | OKT3 | pTT5-LIB-BB2 |
| CATE#012 | Human albumin SP | $V_HH$2 | | UCHT1 | pTT5-LIB-BB3 |
| CATE#019 | Human albumin SP | BCMA scFv | (G4S)$_3$ | L2K.07 | pTT5-LIB-BB1 |
| CATE#020 | Human albumin SP | (C11D5.3) $V_L$- | (SEQ ID | OKT3 | pTT5-LIB-BB2 |
| CATE#021 | Human albumin SP | $V_H$ | NO: 74) | UCHT1 | pTT5-LIB-BB3 |

TABLE 5-continued

Exemplary CATE constructs (#001-#012 and #019-#030).

| CATE code | Signal peptide | Target cell binding domain | Linker | Anti-CD3 scFv | CATE backbone plasmids |
|---|---|---|---|---|---|
| CATE#022 | Human albumin SP | BCMA scFv | (G4S)$_3$ | L2K.07 | pTT5-LIB-BB1 |
| CATE#023 | Human albumin SP | (J22.9-xi) V$_H$- | (SEQ ID | OKT3 | pTT5-LIB-BB2 |
| CATE#024 | Human albumin SP | V$_L$ | NO: 74) | UCHT1 | pTT5-LIB-BB3 |
| CATE#025 | Human albumin SP | BCMA | (G4S)$_3$ | L2K.07 | pTT5-LIB-BB1 |
| CATE#026 | Human albumin SP | V$_H$H*CD38 | (SEQ ID | OKT3 | pTT5-LIB-BB2 |
| CATE#027 | Human albumin SP | V$_H$H | NO: 74) | UCHT1 | pTT5-LIB-BB3 |
| CATE#028 | Human albumin SP | CD38 V$_H$H | (G4S)$_3$ | L2K.07 | pTT5-LIB-BB1 |
| CATE#029 | Human albumin SP |  | (SEQ ID | OKT3 | pTT5-LIB-BB2 |
| CATE#030 | Human albumin SP |  | NO: 74) | UCHT1 | pTT5-LIB-BB3 |

For CATE#031-CATE#038, vectors carrying nucleotide sequences encoding a Glycine-Serine linker (GGGGS)$_3$ (SEQ ID NO: 74) linking a target cell binding domain and an anti-CD3 single domain antibody (V$_H$H) were synthesized and cloned into a mammalian protein expression vector pcDNA3.4 (Thermo Fisher Scientific). The human albumin secretion signal peptide (SEQ ID NO: 70) was included for protein secretion, as referred to in "Optimized signal peptides for the development of high expressing CHO cell lines (Biotechnol Bioeng. 2013 April; 110(4):1164-73). A polyhistidine-tag (6×His tag, SEQ ID NO: 208) was placed at the C' terminus of each CATE molecule. Ready-to-transfect plasmids were maxi-prepped using routine molecular biology techniques. CATE#031-CATE#038 are shown in Table 6 below.

TABLE 6

Exemplary CATE Constructs (#031-038).

| CATE Code | Signal Peptide | Target cell binding domain | Linker | Anti-CD3 V$_H$H domain |
|---|---|---|---|---|
| CATE#031 | Human albumin SP | BCMA V$_H$H1 | (G4S)$_3$ (SEQ ID NO: 74) | 60E11 (SEQ ID NO: 182) |
| CATE#032 | Human albumin SP |  |  | 117G03 (SEQ ID NO: 183) |
| CATE#033 | Human albumin SP | BCMA V$_H$H1*BCMA | (G4S)$_3$ (SEQ ID NO: 74) | 60E11 (SEQ ID NO: 182) |
| CATE#034 | Human albumin SP | V$_H$H2 |  | 117G03 (SEQ ID NO: 183) |
| CATE#035 | Human albumin SP | BCMA scFv (J22.9-xi) V$_H$- | (G4S)$_3$ (SEQ ID NO: 74) | 60E11 (SEQ ID NO: 182) |
| CATE#036 | Human albumin SP | V$_L$ |  | 117G03 (SEQ ID NO: 183) |
| CATE#037 | Human albumin SP | BCMA V$_H$H*CD38 | (G4S)$_3$ (SEQ ID NO: 74) | 60E11 (SEQ ID NO: 182) |
| CATE#038 | Human albumin SP | V$_H$H |  | 117G03 (SEQ ID NO: 183) |

Example 2

Expression and Purification of Exemplary CATEs in Mammalian Host Cells

We established cell lines to express the exemplary CATEs.

Briefly, plasmids encoding exemplary CATEs #001-#012 and #019-#030 were transiently transfected into 293-6E cells respectively. Briefly, 3×10$^5$ 293-6E cells were seeded into 12-well plates. 2 µg of each ready-to-transfect CATE plasmid was mixed at a pre-optimized ratio with polyetherimide (PEI), then mixed thoroughly and incubated at room temperature for 5 minutes. The transfection mix was then added dropwise to the 293-6E cells and mixed gently. Afterwards, cells were incubated overnight in a 37° C. and 5% CO$_2$ cell incubator.

On the next day, the wells containing transfected cells were refreshed with fresh freestyle medium, and then the transfected cells were allowed to grow in a cell incubator for 4 additional days. On the last day, supernatants from the wells were collected and centrifuged at 500 g 4° C. for 10 min. Supernatants were then aliquoted and stored at −80° C. The pMAX-GFP plasmids (Lonza) were used as controls with identical transfection protocol to monitor the transfection efficiency on each plate. The expression level of GFP in each transfection was analyzed using an ATTUNE™ Nxt flow cytometer (Thermo fisher Scientific). The GFP expression level in each control well was over 95% indicating successful transfections.

The expression levels of the exemplary CATEs #001-#012 and #019-#030 in the supernatants of the 293-6E cells were determined using an anti-6×His tag-HRP based ELISA. FIG. 1 shows the expression levels of the exemplary CATEs #001-#012 and #019-#030, which were about 1-2 µg/mL on average.

CATE #031-038 antibodies were obtained by transient transfection of Expi293F suspension cells. Briefly, Expi293F suspension cells were prepared and seeded into Polycarbonate Erlenmeyer Flasks. 100 µg of ready to transfect CATE plasmids and EXPIFECTAMINE™ 293 Transfection kits (Thermo Fisher Scientific #A14351) were premixed with Opti-MEM I reduced Serum Medium (Thermo Fisher Scientific#31985070) separately and incubated at room temperature for 5 minutes. Then the two mixtures were mixed together gently and incubated at room temperature for 25 minutes. The transfection mix was then added dropwise to the Expi293F cells and mixed gently. Afterwards, cells were incubated overnight in a 37° C. and 8% $CO_2$ cell incubator on a shaker at a speed of 100 rpm. 16-18 hours post transfection, 500 µL EXPIFECTAMINE™ 293 Transfection enhancer 1 and 5 mL EXPIFECTAMINE™ 293 Transfection enhancer 2 from EXPIFECTAMINE™ 293 Transfection kits (Thermo Fisher Scientific #A14351) were added to each flask. Cell viability was monitored every 1-2 days post transfection. On day 4-5 post transfection, supernatants from each well were harvested. Supernatants were centrifuged at 4° C., 4500 rpm for 25 min followed by filtration on a 0.22 µm filter to deplete the cells and debris. Proteins obtained from supernatant of cell culture were then processed for target antibody purification using one-step purification by HITRAP™ MabSelect SuRe (GE #11-0034-93 or 11-0034-095) on AKTA Pure 25. Final protein was re-suspended in Storage Buffer (1×PBS, pH 7.2), sterilized via a 0.22 µm filter and aseptically aliquoted and stored at −80° C. Protein concentrations were determined by Bradford protein assay with BSA as a standard (Thermo Fisher, Cat. No. 23236). Protein purities were estimated by densitometry analysis of the Coomassie Blue-stained SDS-PAGE gel under non-reducing conditions. Endotoxin levels were evaluated using LAL Endotoxin Assay Kit (GenScript, Cat-.No.L00350).

Figure 2A:
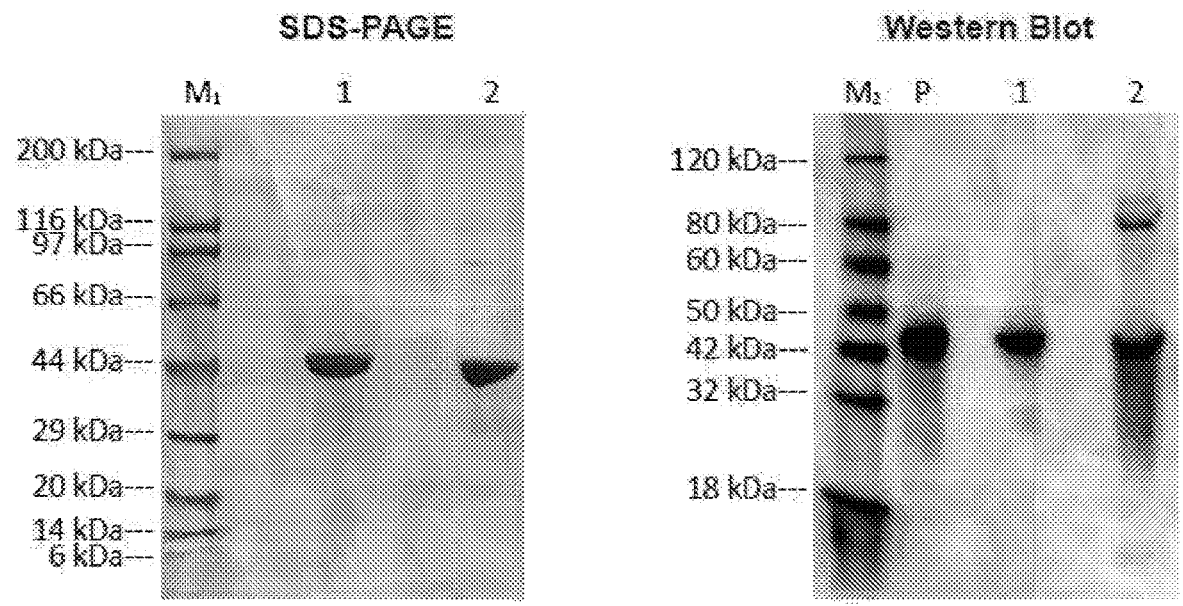
FIG. 2A shows SDS-PAGE and Western blot analysis of CATE #033.
Figure 2B:
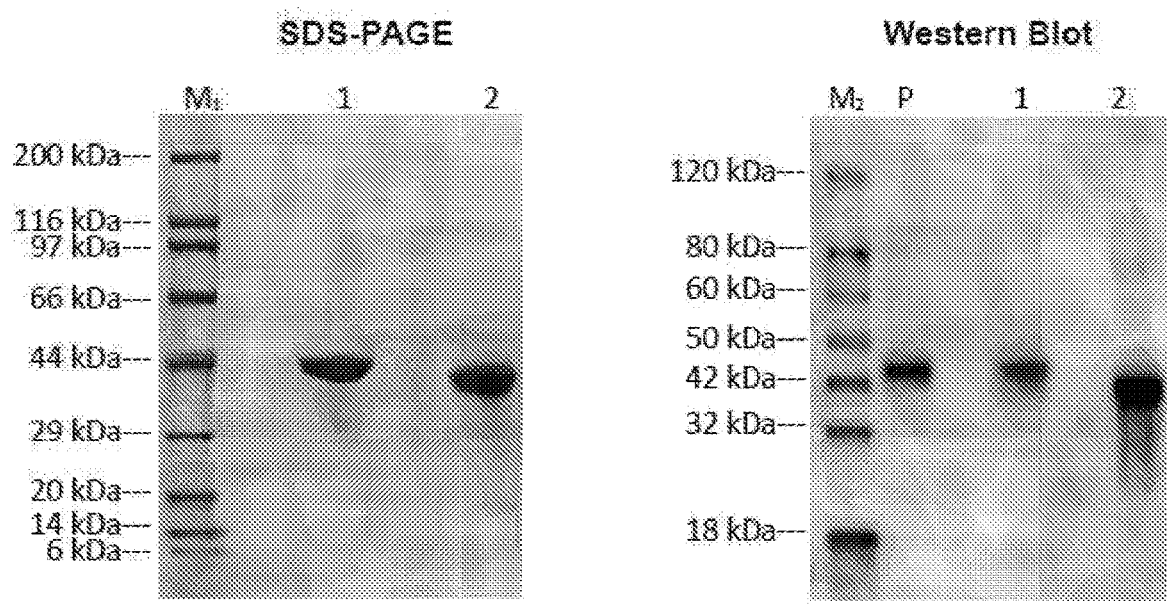
FIG. 2B shows SDS-PAGE and Western blot analysis of CATE #038. SDS-PAGE/Western blot analysis of CATEs #031, #032, 034 and #037 yielded similar results. Lane $M_1$: Protein Marker; Lane $M_2$: Protein Marker; Lane 1: Reducing condition; Lane 2: Non-reducing condition; Lane P: Multiple-tag as a positive control; Primary antibody: Mouse-anti-His mAb.

As shown in Table 7 and FIGS. 2A-2B, CATE proteins #031-038 were successfully expressed using procedures as described above.

TABLE 7

Recombinant expression of CATEs#031-038.

| Protein name | Concentration (mg/mL) | Purity (%) by PAGE | Endotoxin level (EU/mL) |
|---|---|---|---|
| CATE#031 | 1.11 | 95 | 0.3 |
| CATE#032 | 1.01 | 95 | 0.3 |
| CATE#033 | 1.19 | 95 | 0.3 |
| CATE#034 | 0.45 | 95 | 0.3 |
| CATE#035 | 0.05 | 55 | 0.8 |
| CATE#036 | 0.08 | 70 | 0.8 |
| CATE#037 | 1.16 | 95 | 0.3 |
| CATE#038 | 1.13 | 95 | 0.4 |

Example 3

In Vitro Cytotoxicity of Exemplary CATEs Against Multiple Myeloma Cells

1. Primary Human T Cell Preparation

Leukocytes were collected from healthy donors by apheresis, and cell concentration was adjusted to $5 \times 10^6$ cells/ml in R10 medium. Leukocytes were then mixed with 0.9% NaCl solution at 1:1 (v/v) ratio. 3 mL lymphoprep medium was added to a 15 mL centrifuge tube, and 6 ml of diluted lymphocyte mix was slowly layered on top of the lymphoprep medium. The lymphocyte mix was centrifuged at 800 g for 30 minutes without break at 20° C. Lymphocyte buffy coat was then collected with a 200 µL pipette. The harvested fraction was diluted at least 6 fold with 0.9% NaCl or R10 to reduce density of the solution. The harvested fraction was then centrifuged at 250 g for 10 minutes at 20° C. The supernatant was aspirated completely, and 10 mL of R10 was added for re-suspending the cell pellet. The mixture was further centrifuged at 250 g for 10 minutes at 20° C. The supernatant was again aspirated. 2 mL of 37° C. pre-warmed R10 with 100 IU/mL IL-2 was added to the cell pellet, and the cell pellet was re-suspended softly. The cell number was determined following Trypan Blue staining. The obtained PBMC sample was ready for later experiments.

Human T cells were purified from PBMCs using Miltenyi Pan T cell isolation kit (Cat#130-096-535), following the manufacturer's protocol. Briefly, cell number was first determined and the cell suspension was centrifuged at 300 g for 10 minutes. The supernatant was then aspirated completely, and the cell pellets were re-suspended in 40 µL buffer per $10^7$ total cells. 10 µL of Pan T Cell Biotin-Antibody Cocktail was added per $10^7$ total cells, mixed thoroughly and incubated for about 5 minutes in the refrigerator (2-8° C.). 30 µL of buffer was then added per $10^7$ cells. 20 µL of Pan T Cell MicroBead Cocktail was added per $10^7$ cells. The cell suspension mixture was mixed well and incubated for an additional 10 minutes in the refrigerator (2-8° C.). A minimum of 500 µL is required for magnetic separation. For magnetic separation, an LS column was placed in the magnetic field of a suitable MACS™ Separator. The column was prepared by rinsing with 3 ml buffer. The cell suspension was then applied onto the column, and flow-through containing the unlabeled cells was collected, which represented the enriched T cell fractions. Additional T cells were collected by washing the column with 3 ml buffer and collecting unlabeled cells that passed through. These unlabeled cells again represented the enriched T cells, and were combined with the flow-through from the previous step. The pooled enriched T cells were then centrifuged and re-suspended in R10 supplemented with 100 IU/mL IL-2.

The prepared T cells were subsequently pre-activated for 48-96 hours with human T cell activation/expansion kit (Miltenyi#130-091-441) according to the manufacturer's protocol, in which anti-CD3/CD28 MACSI™ Beads were added to the T cells at a bead-to-cell ratio of 1:2.

2. In Vitro T Cell-Mediated Cytotoxicity Assays

Human multiple myeloma cell line RPMI8226.Luc was developed by transduction of firefly luciferase gene into RPMI8226 host cells. In vitro T cell-mediated cytotoxicity assays were performed on RPMI8226.Luc cells either cultured alone or co-cultured with pre-stimulated T cells.

To assess the T cell-mediated cytotoxicity of exemplary CATEs against tumor cells, ONE-GLO™ luminescent luciferase assay reagents (Promega#E6110) were prepared according to the manufacturer's protocol and added to the cell samples (i.e., RPMI8226.Luc alone, or RPMI8226.Luc+ pre-stimulated T cells). The remaining luciferase activity in each well was determined. Since luciferase is expressed only in RPMI8226.Luc cells, the remaining luciferase activity in each well correlates directly with the number of viable RPMI8226.Luc cells (i.e., target cells) in the well. The maximum luciferase activity was obtained by adding culture media to target cells in absence of the pre-stimulated T cells (i.e., effector cells). The minimum luciferase activity was determined by adding Triton X-100 at a final concentration of 1% at the beginning of the cytotoxicity assay to lyse all target cells. Specific cytotoxicity was calculated using the formula: Specific Cytotoxicity %=100%*(1-(RLUsample-RLUmin)/(RLUmax-RLUmin)). Data were analyzed and presented using GraphPad Prism using non-linear regression "log(inhibitor) vs. response-Variable slope (four parameters)."

For CATEs #001-012 and #019-030, a preliminary screen was first performed using the in vitro T cell-mediated cytotoxicity assay as described above. The supernatant containing each exemplary CATE was diluted with assay medium (RPMI1640+10% FBS) with a dilution factor of 1:5 or 1:50 and incubated with 2000 RPMI8226.Luc cells in a 384-well format microplate. Pre-stimulated T cells were added to each well at an effector to target cell ratio of 5:1 to initiate the T cell-mediated cytotoxicity of CATE against RPMI8226.Luc cells. Freestyle medium from pMax-GFP transfected 293-6E cells were used as negative controls. After incubation overnight in a cell culture incubator, ONE-GLO™ Luciferase Assay System reagents were added to each cell, and the remaining luciferase activities were measured to assess the number of remaining viable tumor cells. From the preliminary screen, several CATEs with high in vitro T-cell mediated cytotoxicity were picked for further experiments.

A dose-dependent T cell-mediated cytotoxicity curve of each selected CATE was determined. The supernatant containing each selected CATE was diluted with assay medium (RPMI1640+10% FBS) and incubated with 2000 RPMI8226.Luc cells in a 384-well format microplate. In group 1, the pre-stimulated T cells were added to each well at an effector to target cell ratio of 5:1 to initiate the T cell-mediated cytotoxicity of CATE against RPMI8226.Luc cells. In group 2, assay medium (RPMI1640+10%FBS) instead of pre-stimulated T cells was added to each well containing the exemplary CATE and RPMI8226.Luc cells to determine T cell-independent cytotoxicity of CATE against RPMI8226.Luc cells. After overnight incubation, the assay plates were briefly centrifuged at 300 g for 1 min, and then 10 μL of supernatant in each well was collected to detect the level of secreted IFNγ. The remaining cells in the co-culture assay were added with ONE-GLO™ Luciferase Assay System reagents, and the remaining luciferase activities were measured to assess the number of remaining viable tumor cells.

Figure 3A:
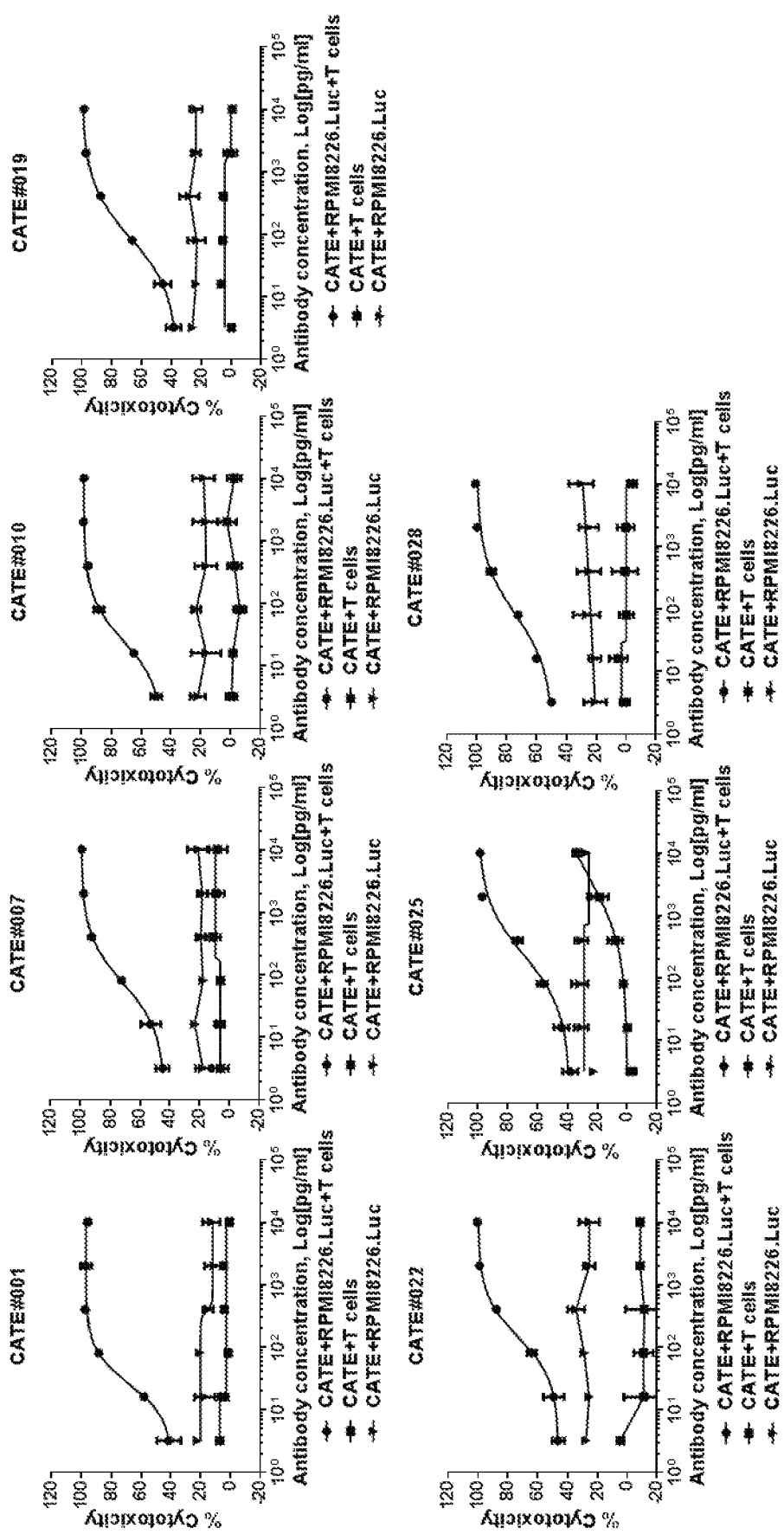
FIG. 3A shows dose-dependent T cell-mediated cytotoxicity against tumor cells by exemplary CATEs in a co-culture assay. The exemplary CATEs (also referred herein as "CATE-L2K.07 scFv") each comprising an anti-CD3 scFv derived from L2K.07.
Figure 3B:
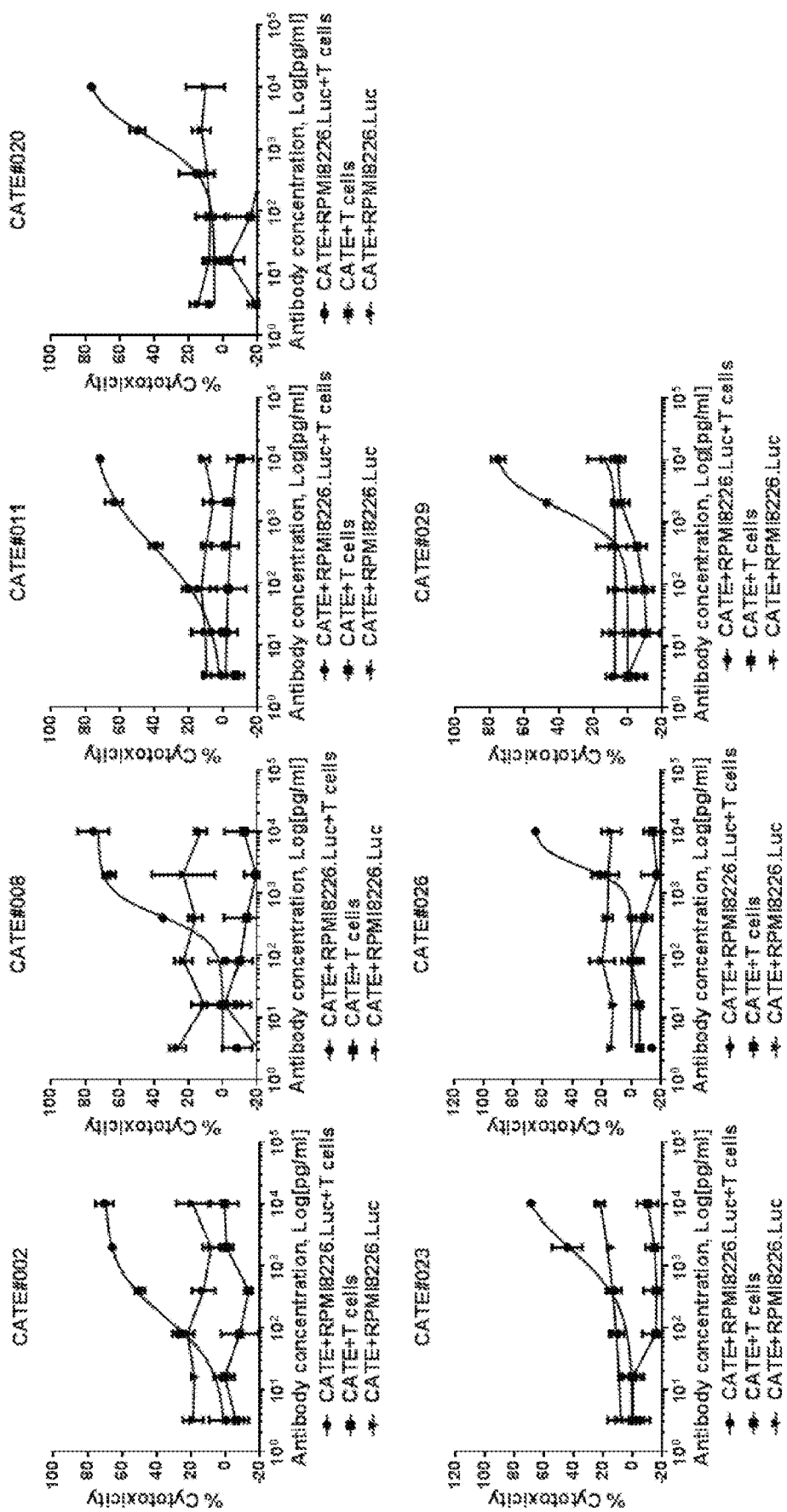
FIG. 3B shows dose-dependent T cell-mediated cytotoxicity against tumor cells by exemplary CATEs in a co-culture assay. The exemplary CATEs (also referred herein as "CATE-OKT3 scFv") each comprising an anti-CD3 scFv derived from OKT3.

FIG. 3A shows dose-dependent T cell-mediated cytotoxicity of CATEs based on L2K.07-derived anti-CD3 scFv (CATE-L2K.07 scFv). FIG. 3B shows dose-dependent T cell-mediated cytotoxicity of CATEs based on OKT3-derived anti-CD3 scFv (CATE-OKT3 scFv). EC50 values of the exemplary CATEs are listed in Table 8 below. Lower EC50 values correspond to higher T-cell mediated cytotoxicity by CATE. The results demonstrate that CATEs comprising $V_HH$ domains targeting BCMA and/or CD38 have potent T-cell mediated cytotoxic effects against multiple myeloma cells. Additionally, CATEs comprising anti-BCMA $V_HH$ domains have higher T-cell mediated cytotoxic effects against multiple myeloma cells, compared to CATEs comprising anti-BCMA scFv domains.

TABLE 8

EC50 values of exemplary CATEs.

|  | CATE#001 | CATE#007 | CATE#010 | CATE#019 | CATE#022 | CATE#025 | CATE#028 |
|---|---|---|---|---|---|---|---|
| Bottom | 39.3 | 43.54 | 45.95 | 36.37 | 45.89 | 38.79 | 48.82 |
| Top | 97.02 | 99.25 | 98.34 | 99.46 | ~100.0 | ~100.0 | ~100.0 |
| LogEC50 | 1.406 | 1.857 | 1.398 | 1.948 | 2.154 | 2.373 | 1.923 |
| HillSlope | 1.582 | 1.116 | 1.22 | 0.9966 | 1.253 | 0.96 | 0.9471 |
| EC50, pg/mL | 25.45 | 72.02 | 25.03 | 88.72 | 142.4 | 235.8 | 83.81 |

|  | CATE#002 | CATE#008 | CATE#011 | CATE#020 | CATE#023 | CATE#026 | CATE#029 |
|---|---|---|---|---|---|---|---|
| Bottom | ~0 | ~0 | ~0 | 4.789 | ~0 | ~0 | ~0 |
| Top | 70.29 | 72.53 | 78.15 | 82.66 | 82.44 | 66.42 | 78.55 |
| LogEC50 | 2.174 | 2.629 | 2.55 | 3.201 | 3.26 | 3.419 | 3.201 |
| HillSlope | 1.056 | 2.046 | 0.7657 | 1.344 | 0.9659 | 2.753 | 1.704 |
| EC50, pg/mL | 149.3 | 425.9 | 354.6 | 1588 | 1822 | 2623 | 1589 |

CATE#037, CATE#038, anti-BCMA antibody (without an anti-CD3 domain), or anti-CD3 antibody (without an anti-BCMA domain) at 10 μg/mL final concentration were co-cultured with RPMI8226.Luc cells overnight in the presence or absence of primary T cells. The effector-to-target cell ratio of the co-culture assays was 5:1. Assays with CATE molecules were performed with a 10-fold serial dilution descending from 10000 ng/mL. The ONE-GLO™ Luciferase Assay was used to assess cytotoxicity as described above.

Figure 4:
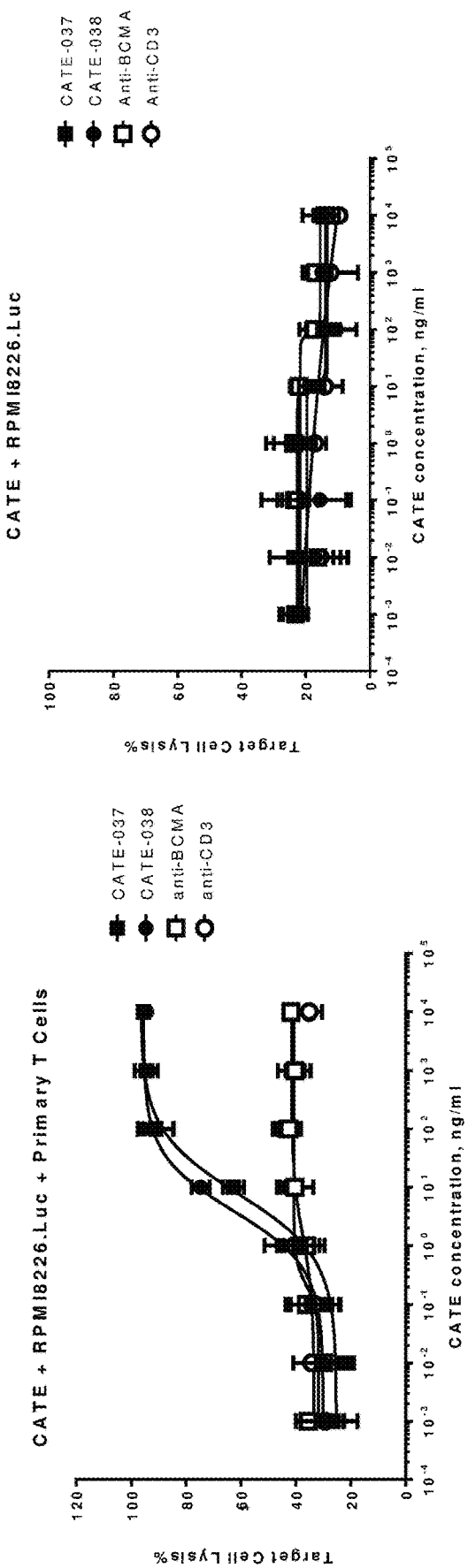
FIG. 4 shows in vitro dose-dependent T cell-mediated cytotoxicity against tumor cells by CATE #037 and #038 in a co-culture assay.

As shown in FIG. 4 and Table 9, CATE#037 and CATE#038 were efficient in mediating primary T cell dependent cytotoxicity against RPMI8226.Luc cells in a dose-dependent manner. The EC50 values were 7.706 ng/mL for CATE#037 and 3.944 ng/mL for CATE#038. Without the presence of primary T cells, CATE proteins were not be able to elicit cytotoxicity against RPMI8226.Luc cells in a dose-dependent manner. Moreover, proteins with anti-BCMA alone (without an anti-CD3 domain) or anti-CD3 alone (without an anti-BCMA domain) were not able to elicit cytotoxicity effects against RPMI8226.Luc cells in a dose-dependent manner. The results demonstrate that CATE#037 and CATE#038 are capable of facilitating T cell-dependent cytotoxicity against target tumor cells in a dose-dependent and antigen-dependent manner.

TABLE 9

Best-fit cytotoxicity values of CATE#037-038

|  | CATE#037 | CATE#038 | anti-BCMA | anti-CD3 |
|---|---|---|---|---|
| | Test sample + RPMI8226.Luc + Primary T Cells | | | |
| Maximum cytotoxicity, % | 96.78 | 95.66 | N.D. | N.D. |
| EC50, ng/mL | 7.706 | 3.944 | N.D. | N.D. |
| | Test sample + RPMI8226.Luc | | | |
| Maximum cytotoxicity, % | N.D. | N.D. | N.D. | N.D. |
| EC50, ng/mL | N.D. | N.D. | N.D. | N.D. |

*N.D., No dose-dependent target cell lysis

3. In Vitro IFN-γ Release Assay

Figure 5:
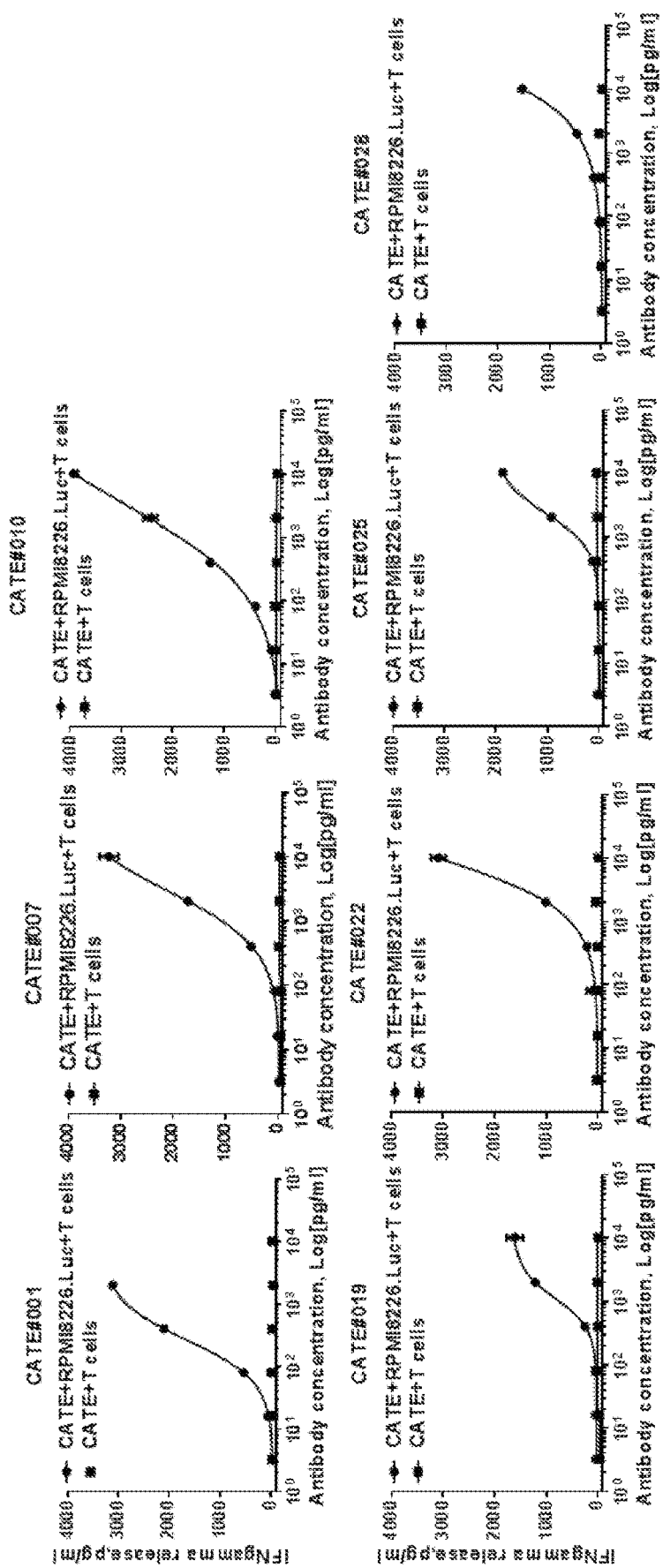
FIG. 5 shows in vitro IFNγ release by primary T cells in response to exemplary CATEs (#001, #007, #010, #019, #022, #025 and #028) in a co-culture assay with tumor cells.

According to the co-culture assay described above, in group 2, 10 µL of supernatant from each well was transferred to a small-volume round bottom white wall 384 well-plate to determine secreted IFNγ level in each co-culture using a HTRF kit (Cisbio, catalog number 62IFNPEB) according to the manual. FIG. 5 shows the IFN-γ levels released by T cells co-cultured with in response to exemplary CATEs #001, #007, #010, #019, #022, #025 and #028. IFNγ release is a sign of T cell activation. The data shows that CATEs comprising anti-BCMA $V_HH$ triggered higher level of IFNγ release from T cells co-incubated with RPMI8226.Luc cells compared to CATEs comprising anti-BCMA scFvs CATE#037, CATE#038, anti-BCMA antibody, or anti-CD3 antibody at 10 µg/mL final concentration were co-cultured with RPMI8226.Luc cells overnight in the presence or absence of primary T cells as described above. After incubation, the assay plates were briefly centrifuged for 1 min (300 g), and then 10 µL of supernatants in each well were transferred to a small volume round bottom white wall 384 well-plate for detection of secreted IFNγ level by HTRF kit (Cisbio, 62IFNPEB) according to the manual of the kit.

Figure 6:
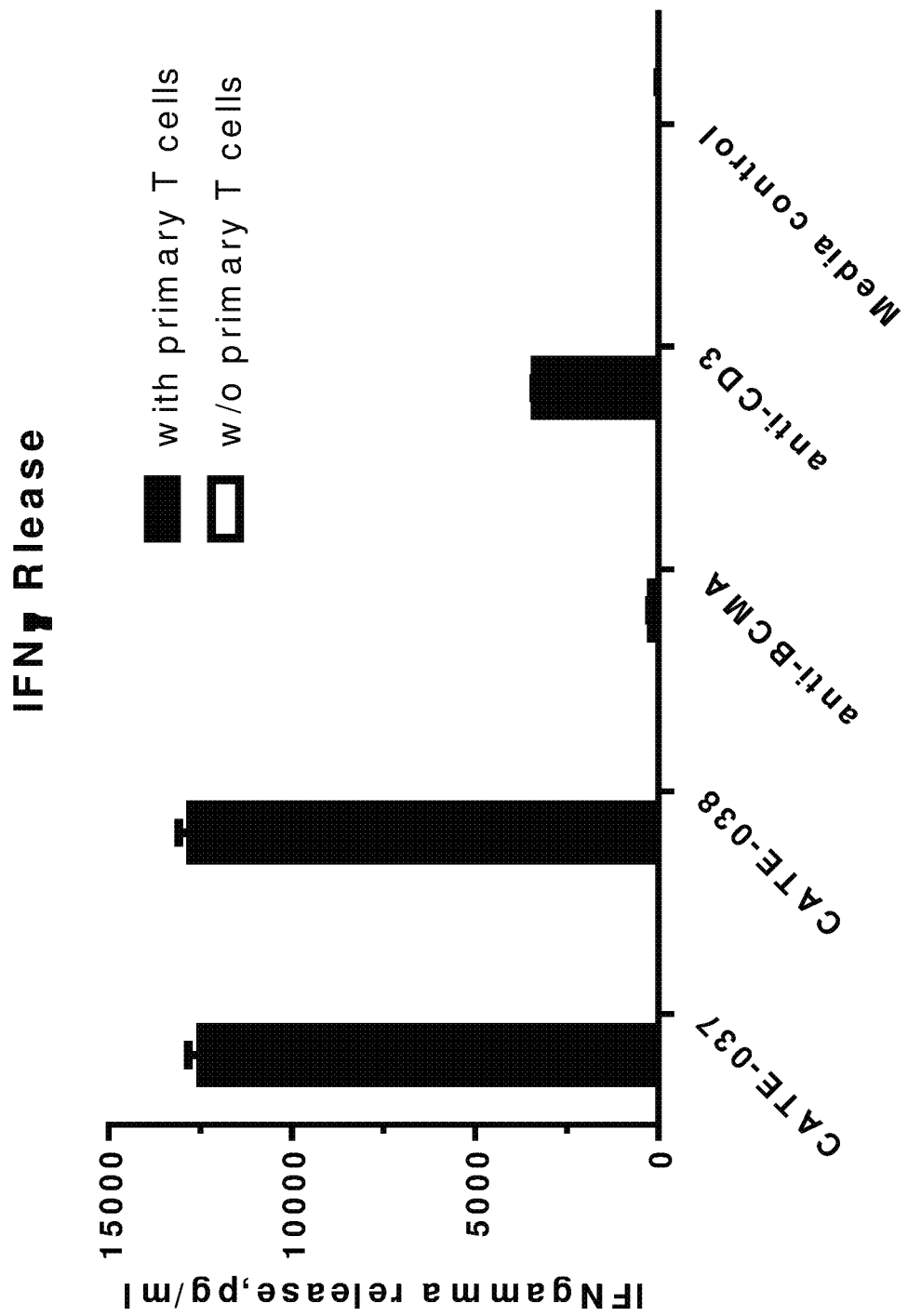
FIG. 6 shows in vitro IFNγ release by primary T cells in response to CATE#037 and CATE#038 in a co-culture assay with tumor cells.

As shown in FIG. 6, IFNγ release elicited by CATE#037 or CATE#038 in the co-culture assay was dependent on the presence of primary T cells. The IFNγ release levels elicited by the anti-BCMA antibody alone (without an anti-CD3 domain) and the anti-CD3 antibody alone (without an anti-BCMA domain) were significantly lower than those of CATE#037 and CATE#038 treated cells, even in the presence of primary T cells. These results demonstrate that CATE#037 and #038 are capable of facilitating T cell-dependent IFNγ release against target tumor cells in an antigen-dependent manner.

Example 7

In Vivo Efficacy of CATEs

The in vivo anti-tumor efficacy of CATE#037 and CATE#038 was assessed in a systemic multiple myeloma mouse model having the RPMI8226.Luc xenograft. RPMI8226.Luc cells were prepared as described above. Cell viability was determined to be ≥95% by trypan blue exclusion. The cells were suspended in HBSS$^{-/-}$ on ice (4° C.) at a concentration of $10^7$ cells/mL on the day of tumor implantation.

NOD-Prkdcem26Cd52Il2rgem26Cd22/Nju, (abbreviation: NCG) mice were used in this study. This mouse model was created by sequential CRISPR/Cas9 editing of the Prkdc and Il2rg loci in the NOD/Nju mouse, generating a mouse co-isogenic to the NOD/Nju mouse. The NOD/Nju mouse carries a mutation in the Sirpa (SIRP α) gene that allows for engrafting of foreign hematopoietic stem cells. The Prkdc knockout generates a SCID-like phenotype lacking proper T cell and B cell formation. The knockout of the Il2rg gene further exacerbates the SCID-like phenotype while additionally resulting in a decrease of NK cell production. This "triple-immunodeficient" mouse strain is more immunocompromised than commonly used immunodeficient mouse strains including SCID and nude mice.

Prkdc and Il2rg are part of the SCID (severe combined immunodeficiency) family of genes affecting maturation and formation of T cells, B cells and NK cells, to a lesser degree, dendritic cells. Disrupting the Prkdc gene, which encodes the catalytic subunit of the DNA-dependent protein kinase enzyme, reduces V(D)J recombination necessary for propagating antibody diversity in maturing T and B cells. Disrupting Il2rg, which encodes the common gamma subunit found in IL-2 and multiple IL receptors (IL-4, IL-7, IL-9, IL-15 and IL-21), prevents immature lymphocytes (T cells, B cells, and NK cells) and other leukocytes from reaching maturation as the receptors are required to bind and induce cytokine-mediated signaling. The NCG mouse strain is similar to other triple-immunodeficient models capable of hosting xenograft cells, tissue and human immune system components, thus enabling studies of tumor biology and immune-oncology, infectious disease, graft-versus-host disease (GvHD), hematopoiesis, and tissue transplant.

Prior to conducting this study, the procedures involving the care and use of animals were reviewed and approved by the Institutional Animal Care and Use Committee (IACUC) to ensure compliance with the regulations of the Association for Assessment and Accreditation of Laboratory Animal Care (AAALAC). The animals were properly maintained and treated according to SOP of GenScript in a controlled facility.

Female NCG mice (age 5-6 weeks) were caged for 1 week before implantation of RPMI8226.Luc cells at a dose of $4\times10^6$ cells/animal by tail i.v. injection. 9 days post tumor cell implantation, the mice were imaged using bioluminescent imaging (BLI) to evaluate tumor engraftment. Mice were randomized into several groups with 6 mice each and received a single dose treatment (i.v.) on Day 0 (i.e., the day of CATE treatment) as shown in Table 10.

TABLE 10

Animal grouping

| Group | Number of animals | Tumor model | Treatment | Dose | Route |
|---|---|---|---|---|---|
| 1 | 6 | systemic | T cells | $2 \times 10^6$ T cells | i.v. |
| 2 | 6 | multiple myeloma | CATE#037 + T cells | 10 mg/kg CATE + $2 \times 10^6$ T cells | injection via tail |
| 3 | 6 | (RPMI8226.Luc) | CATE#038 + T cells | 10 mg/kg CATE + $2 \times 10^6$ T cells | |
| 4 | 6 | | CATE#037 | 10 mg/kg | |
| 5 | 6 | | CATE#038 | 10 mg/kg | |

Following tumor inoculation, the animals were checked daily for morbidity. During routine monitoring, the animals were checked for any effects of tumor growth on normal behavior such as mobility, food and water consumption, body weight gain/loss, eye/hair matting and any other signs of abnormality. Mortality and observable clinical signs were recorded. Body weights of the animals were measured twice per week. Tumor growth was measured by using bioluminescent imaging (BLI) every 14 days. Survival of the animals were also monitored.

Figure 7:
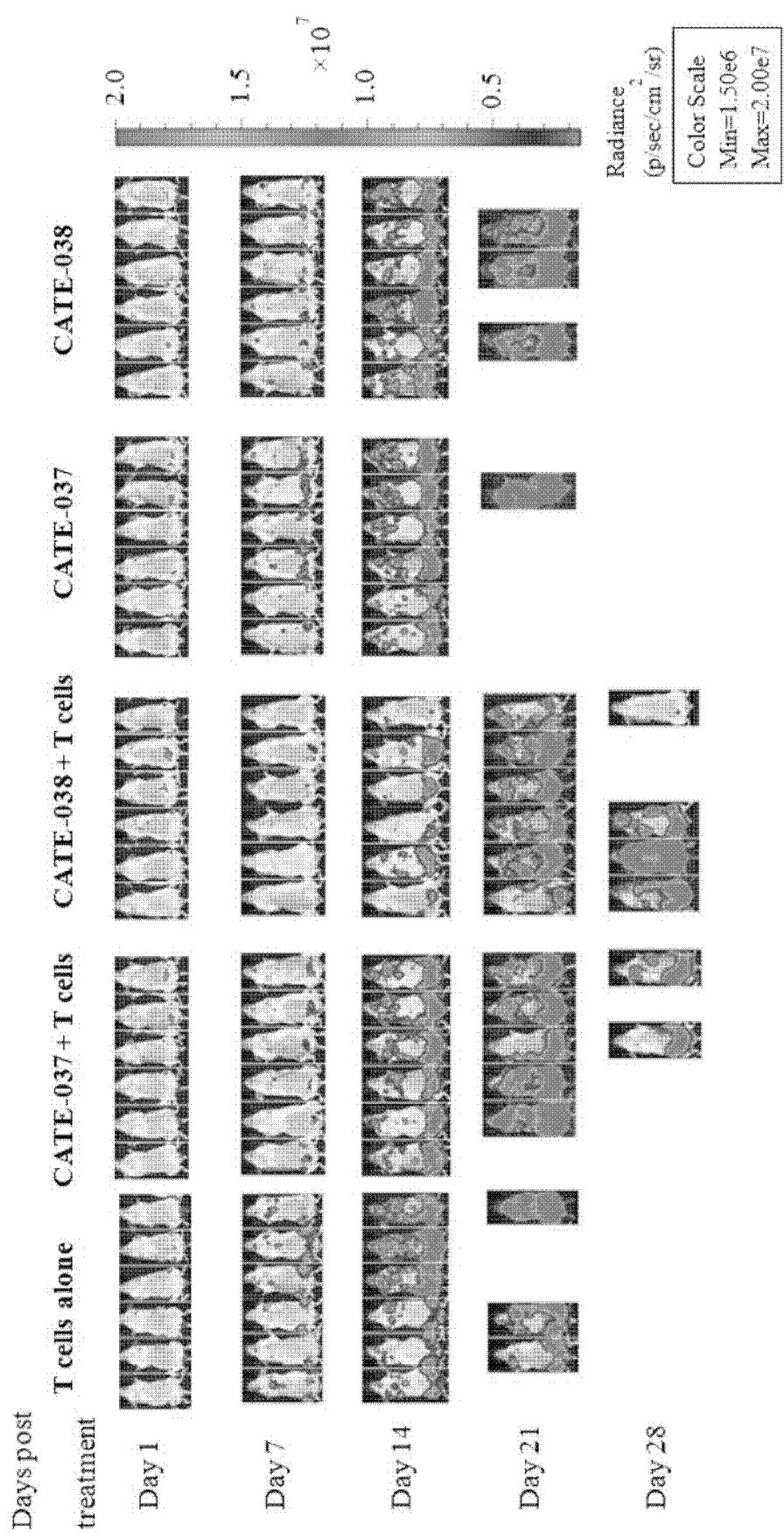
FIG. 7 shows in vivo anti-tumor efficacy of CATE #037 and CATE #038 on a mouse model of multiple myeloma.
Figure 8:
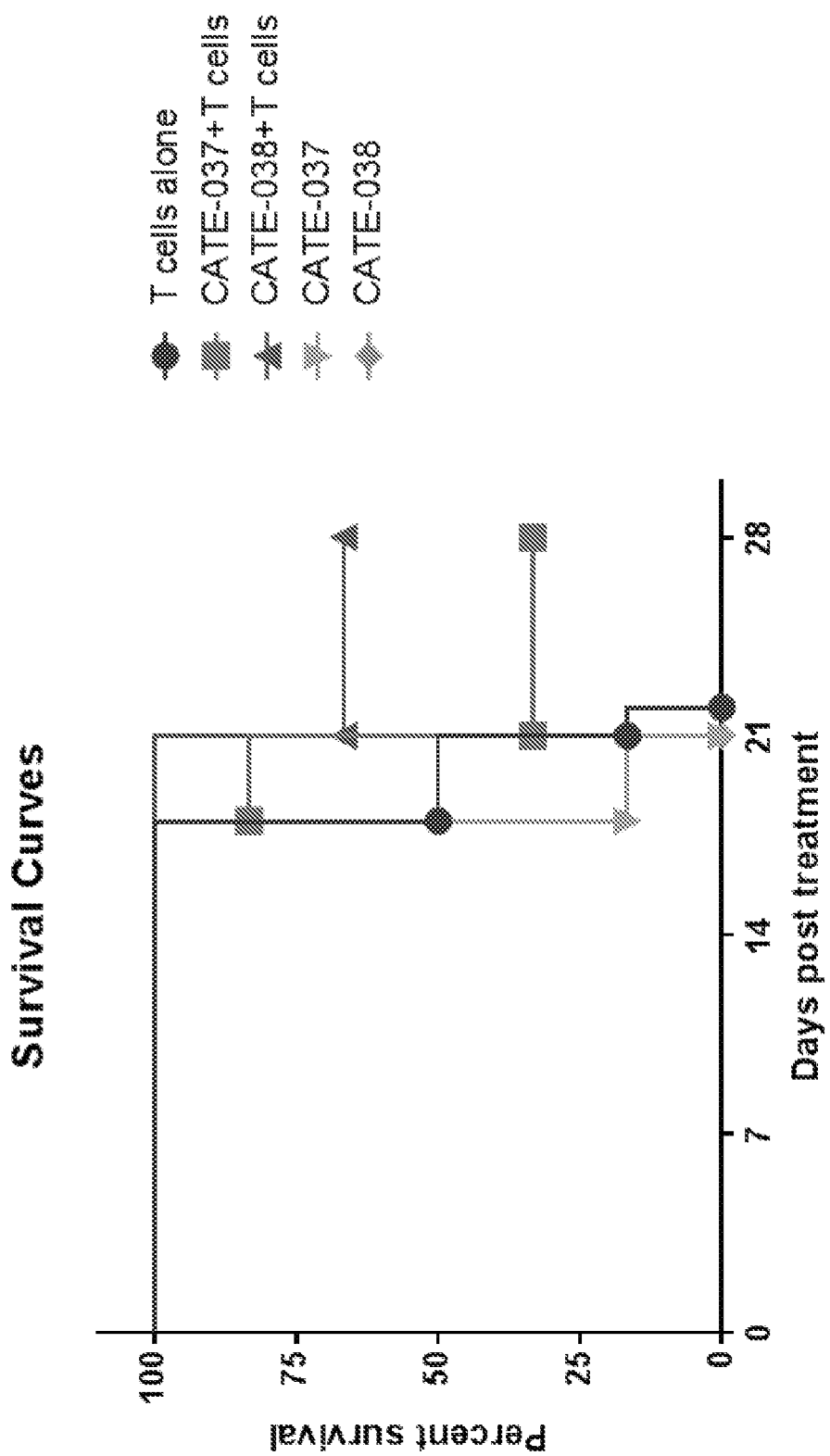
FIG. 8 shows survival curves of mice treated with CATE #037 and CATE#038 (n=6).

As shown in FIG. 7 and FIG. 8, mice treated with CATE#037 and CATE#038 in the presence of T cells showed significantly higher survival rate than mice treated with CATE#037 and CATE#038 without T cells or mice treated with T cells alone. These results demonstrate in vivo efficacy of CATE#037 and CATE#038 in the systemic multiple myeloma mouse model having the RPMI8226.Luc xenograft.

The invention claimed is:

1. A chimeric antibody immune effector cell engager comprising:
   (a) a target cell binding domain, wherein the target cell binding domain comprises an anti-BCMA single-domain antibody (sdAb) comprising:
      (1) a CDR1 comprising the amino acid sequence of SEQ ID NO:1; a CDR2 comprising the amino acid sequence of SEQ ID NO:12; and a CDR3 comprising the amino acid sequence of SEQ ID NO:23;
      (2) a CDR1 comprising the amino acid sequence of SEQ ID NO:2; a CDR2 comprising the amino acid sequence of SEQ ID NO:13; and a CDR3 comprising the amino acid sequence of SEQ ID NO:24;
      (3) a CDR1 comprising the amino acid sequence of SEQ ID NO:3; a CDR2 comprising the amino acid sequence of SEQ ID NO:14; and a CDR3 comprising the amino acid sequence of SEQ ID NO:25;
      (4) a CDR1 comprising the amino acid sequence of SEQ ID NO:4; a CDR2 comprising the amino acid sequence of SEQ ID NO:15; and a CDR3 comprising the amino acid sequence of SEQ ID NO:26;
      (5) a CDR1 comprising the amino acid sequence of SEQ ID NO:5; a CDR2 comprising the amino acid sequence of SEQ ID NO:16; and a CDR3 comprising the amino acid sequence of SEQ ID NO:27;
      (6) a CDR1 comprising the amino acid sequence of SEQ ID NO:6; a CDR2 comprising the amino acid sequence of SEQ ID NO:17; and a CDR3 comprising the amino acid sequence of SEQ ID NO:28;
      (7) a CDR1 comprising the amino acid sequence of SEQ ID NO:7; a CDR2 comprising the amino acid sequence of SEQ ID NO:18; and a CDR3 comprising the amino acid sequence of SEQ ID NO:29;
      (8) a CDR1 comprising the amino acid sequence of SEQ ID NO:8; a CDR2 comprising the amino acid sequence of SEQ ID NO:19; and a CDR3 comprising the amino acid sequence of SEQ ID NO:30;
      (9) a CDR1 comprising the amino acid sequence of SEQ ID NO:9; a CDR2 comprising the amino acid sequence of SEQ ID NO:20; and a CDR3 comprising the amino acid sequence of SEQ ID NO:31;
      (10) a CDR1 comprising the amino acid sequence of SEQ ID NO:10; a CDR2 comprising the amino acid sequence of SEQ ID NO:21; and a CDR3 comprising the amino acid sequence of SEQ ID NO:32; or
      (11) a CDR1 comprising the amino acid sequence of SEQ ID NO:11; a CDR2 comprising the amino acid sequence of SEQ ID NO:22; and a CDR3 comprising the amino acid sequence of SEQ ID NO:33; and,
   (b) an immune effector cell binding domain comprising an anti-CD3 antigen-binding fragment.

2. The chimeric antibody immune effector cell engager of claim 1, wherein the sdAb is camelid, chimeric, or humanized.

3. The chimeric antibody immune effector cell engager of claim 1, wherein the sdAb is a $V_HH$ fragment.

4. A chimeric antibody immune effector cell engager comprising:
   (a) a target cell binding domain, wherein the target cell binding domain comprises an anti-CD38 single domain antibody (sdAb) comprising:
      (1) a CDR1 comprising the amino acid sequence of SEQ ID NO:34; a CDR2 comprising the amino acid sequence of SEQ ID NO:46; and a CDR3 comprising the amino acid sequence of SEQ ID NO:58;
      (2) a CDR1 comprising the amino acid sequence of SEQ ID NO:35; a CDR2 comprising the amino acid sequence of SEQ ID NO:47; and a CDR3 comprising the amino acid sequence of SEQ ID NO:59;
      (3) a CDR1 comprising the amino acid sequence of SEQ ID NO:36; a CDR2 comprising the amino acid sequence of SEQ ID NO:48; and a CDR3 comprising the amino acid sequence of SEQ ID NO:60;
      (4) a CDR1 comprising the amino acid sequence of SEQ ID NO:37; a CDR2 comprising the amino acid sequence of SEQ ID NO:49; and a CDR3 comprising the amino acid sequence of SEQ ID NO:61;
      (5) a CDR1 comprising the amino acid sequence of SEQ ID NO:38; a CDR2 comprising the amino acid sequence of SEQ ID NO:50; and a CDR3 comprising the amino acid sequence of SEQ ID NO:62;
      (6) a CDR1 comprising the amino acid sequence of SEQ ID NO:39; a CDR2 comprising the amino acid sequence of SEQ ID NO:51; and a CDR3 comprising the amino acid sequence of SEQ ID NO:63;
      (7) a CDR1 comprising the amino acid sequence of SEQ ID NO:40; a CDR2 comprising the amino acid sequence of SEQ ID NO:52; and a CDR3 comprising the amino acid sequence of SEQ ID NO:64;
      (8) a CDR1 comprising the amino acid sequence of SEQ ID NO:41; a CDR2 comprising the amino acid sequence of SEQ ID NO:53; and a CDR3 comprising the amino acid sequence of SEQ ID NO:65;
      (9) a CDR1 comprising the amino acid sequence of SEQ ID NO:42; a CDR2 comprising the amino acid sequence of SEQ ID NO:54; and a CDR3 comprising the amino acid sequence of SEQ ID NO:66;
      (10) a CDR1 comprising the amino acid sequence of SEQ ID NO:43; a CDR2 comprising the amino acid sequence of SEQ ID NO:55; and a CDR3 comprising the amino acid sequence of SEQ ID NO:67; or
      (11) a CDR1 comprising the amino acid sequence of SEQ ID NO:44; a CDR2 comprising the amino acid sequence of SEQ ID NO:56; and a CDR3 comprising the amino acid sequence of SEQ ID NO:68; and,
   (b) an immune effector cell binding domain comprising an anti-CD3 antigen-binding fragment.

5. The chimeric antibody immune effector cell engager of claim 1, wherein the target cell binding domain comprises an anti-BCMA sdAb that specifically binds to BCMA and an anti-CD38 sdAb that specifically binds to CD38.

6. The chimeric antibody immune effector cell engager of claim 1, wherein the target cell binding domain comprises a first anti-BCMA sdAb and a second anti-BCMA sdAb.

7. The chimeric antibody immune effector cell engager of claim 1, wherein the target cell binding domain is fused to the N-terminus of the immune effector cell binding domain, or wherein the target cell binding domain is fused to the C-terminus of the immune effector cell binding domain.

8. The chimeric antibody immune effector cell engager of claim 1, wherein the immune effector cell is a T cell or an NK cell.

9. The chimeric antibody immune effector cell engager of claim 1, wherein the anti-CD3 antigen-binding fragment is derived from OKT3, L2K, UCHT1, 60E11, or 117G03.

10. An isolated nucleic acid comprising a nucleic acid sequence encoding the chimeric antibody immune effector cell engager of claim 1.

11. A vector comprising the isolated nucleic acid of claim 10.

12. A pharmaceutical composition, comprising the chimeric antibody immune effector cell engager of claim 1, and a pharmaceutically acceptable carrier.

13. A method of treating a BCMA-expressing cancer in an individual, comprising administering to the individual an effective amount of the pharmaceutical composition of claim 12.

14. The chimeric antibody immune effector cell engager of claim 4, wherein the anti-CD3 antigen-binding fragment is derived from OKT3, L2K, UCHT1, 60E11, or 117G03.

15. The chimeric antibody immune effector cell engager of claim 1, wherein the anti-BCMA sdAb comprises an amino acid sequence selected from the group consisting of SEQ ID NOs: 78-88 and 290-316.

16. The chimeric antibody immune effector cell engager of claim 4, wherein the anti-CD38 sdAb comprises an amino acid sequence selected from the group consisting of SEQ ID NOs: 89-100.

17. The chimeric antibody immune effector cell engager of claim 1, wherein the anti-CD3 binding fragment is a $V_HH$ or an scFv.

18. The chimeric antibody immune effector cell engager of claim 4, wherein the anti-CD3 binding fragment is a $V_HH$ or an scFv.

19. The chimeric antibody immune effector cell engager of claim 1, wherein the anti-CD3 binding fragment comprises an amino acid sequence selected from the group consisting of SEQ ID NOs: 103-105 and 182-183.

20. The chimeric antibody immune effector cell engager of claim 4, wherein the anti-CD3 binding fragment comprises an amino acid sequence selected from the group consisting of SEQ ID NOs: 103-105 and 182-183.

21. The chimeric antibody immune effector cell engager of claim 5, wherein the chimeric antibody immune effector cell engager comprises an the amino acid sequence selected from the group consisting of SEQ ID NOs: 160-163 and 206-207.

22. The chimeric antibody immune effector cell engager of claim 5, wherein the chimeric antibody immune effector cell engager comprises:
   a) a target binding domain comprising:
      (i) an anti-BCMA sdAb comprising a CDR1 comprising the amino acid sequence of SEQ ID NO:1; a CDR2 comprising the amino acid sequence of SEQ ID NO:12; and a CDR3 comprising the amino acid sequence of SEQ ID NO:23; and
      (ii) an anti-CD38 sdAb comprising a CDR1 comprising the amino acid sequence of SEQ ID NO:38; a CDR2 comprising the amino acid sequence of SEQ ID NO:50; and a CDR3 comprising the amino acid sequence of SEQ ID NO:62; and, b) an immune effector cell binding domain comprising an anti-CD3 $V_HH$ comprising a CDR1 comprising the amino acid sequence of SEQ ID NO: 317; a CDR2 comprising the amino acid sequence of SEQ ID NO: 318; and a CDR3 comprising the amino acid sequence of SEQ ID NO: 319.

23. The chimeric antibody immune effector cell engager of claim 5, wherein the chimeric antibody immune effector cell engager comprises:
   a) a target binding domain comprising:
      (i) an anti-BCMA sdAb comprising the amino acid sequence of SEQ ID NO: 78; and
      (ii) an anti-CD38 sdAb comprising the amino acid sequence of SEQ ID NO: 93; and,
   b) an immune effector cell binding domain comprising an anti-CD3 $V_HH$ comprising the amino acid sequence of SEQ ID NO: 182.

24. The chimeric antibody immune effector cell engager of claim 5, wherein the chimeric antibody immune effector cell engager comprises:
   a) a target binding domain comprising:
      (i) an anti-BCMA sdAb comprising a CDR1 comprising the amino acid sequence of SEQ ID NO:1; a CDR2 comprising the amino acid sequence of SEQ ID NO:12; and a CDR3 comprising the amino acid sequence of SEQ ID NO:23; and
      (ii) an anti-CD38 sdAb comprising a CDR1 comprising the amino acid sequence of SEQ ID NO:38; a CDR2 comprising the amino acid sequence of SEQ ID NO:50; and a CDR3 comprising the amino acid sequence of SEQ ID NO:62; and,
   b) an immune effector cell binding domain comprising an anti-CD3 $V_HH$ comprising a CDR1 comprising the amino acid sequence of SEQ ID NO: 320; a CDR2 comprising the amino acid sequence of SEQ ID NO: 321; and a CDR3 comprising the amino acid sequence of SEQ ID NO: 322.

25. The chimeric antibody immune effector cell engager of claim 5, wherein the chimeric antibody immune effector cell engager comprises:
   a) a target binding domain comprising:
      (i) an anti-BCMA sdAb comprising the amino acid sequence of SEQ ID NO: 78; and
      (ii) an anti-CD38 sdAb comprising the amino acid sequence of SEQ ID NO: 93; and,
   b) an immune effector cell binding domain comprising an anti-CD3 $V_HH$ comprising the amino acid sequence of SEQ ID NO: 183.

26. A pharmaceutical composition, comprising the chimeric antibody immune effector cell engager of claim 4, and a pharmaceutically acceptable carrier.

27. The chimeric antibody immune effector cell engager of claim 1, wherein the anti-BCMA sdAb comprises a CDR1 comprising the amino acid sequence of SEQ ID NO:1; a CDR2 comprising the amino acid sequence of SEQ ID NO:12; and a CDR3 comprising the amino acid sequence of SEQ ID NO:23.

28. The chimeric antibody immune effector cell engager of claim 4, wherein the anti-CD38 sdAb comprises a CDR1 comprising the amino acid sequence of SEQ ID NO:38; a CDR2 comprising the amino acid sequence of SEQ ID NO:50; and a CDR3 comprising the amino acid sequence of SEQ ID NO:62.

* * * * *

```
                              SEQUENCE LISTING

<160> NUMBER OF SEQ ID NOS: 326

<210> SEQ ID NO 1
<211> LENGTH: 11
<212> TYPE: PRT
<213> ORGANISM: Artificial Sequence
<220> FEATURE:
<223> OTHER INFORMATION: BCMA 269A37346 VHH CDR1

<400> SEQUENCE: 1

Ser Gly Phe Thr Leu Asp Tyr Tyr Ala Ile Gly
1               5                   10

<210> SEQ ID NO 2
<211> LENGTH: 11
<212> TYPE: PRT
<213> ORGANISM: Artificial Sequence
<220> FEATURE:
<223> OTHER INFORMATION: BCMA 269A37348 VHH CDR1

<400> SEQUENCE: 2

Ser Gly Arg Thr Phe Ser Thr Tyr Gly Met Ala
1               5                   10

<210> SEQ ID NO 3
<211> LENGTH: 8
<212> TYPE: PRT
<213> ORGANISM: Artificial Sequence
<220> FEATURE:
<223> OTHER INFORMATION: BCMA 269A37917 VHH CDR1

<400> SEQUENCE: 3

Ser Gly Arg Thr Phe Thr Met Gly
1               5

<210> SEQ ID NO 4
<211> LENGTH: 11
<212> TYPE: PRT
<213> ORGANISM: Artificial Sequence
<220> FEATURE:
<223> OTHER INFORMATION: BCMA 269A37355 VHH CDR1

<400> SEQUENCE: 4

Ser Gly Gly Ile Phe Val Ile Asn Ala Met Gly
1               5                   10

<210> SEQ ID NO 5
<211> LENGTH: 11
<212> TYPE: PRT
<213> ORGANISM: Artificial Sequence
<220> FEATURE:
<223> OTHER INFORMATION: BCMA 269A37915 VHH CDR1

<400> SEQUENCE: 5

Ser Gly Arg Thr Phe Ser Ser Ile Val Met Gly
1               5                   10

<210> SEQ ID NO 6
<211> LENGTH: 11
<212> TYPE: PRT
<213> ORGANISM: Artificial Sequence
<220> FEATURE:
<223> OTHER INFORMATION: BCMA 269A37936 VHH CDR1
```

```
<400> SEQUENCE: 6

Ser Gly Phe Thr Phe Asp Arg Ala Val Ile Val
1               5                   10

<210> SEQ ID NO 7
<211> LENGTH: 11
<212> TYPE: PRT
<213> ORGANISM: Artificial Sequence
<220> FEATURE:
<223> OTHER INFORMATION: BCMA 269A37953 VHH CDR1

<400> SEQUENCE: 7

Ser Thr Tyr Thr Val Asn Ser Asp Val Met Gly
1               5                   10

<210> SEQ ID NO 8
<211> LENGTH: 11
<212> TYPE: PRT
<213> ORGANISM: Artificial Sequence
<220> FEATURE:
<223> OTHER INFORMATION: BCMA 269A37965 VHH CDR1

<400> SEQUENCE: 8

Ser Gly Ala Thr Leu Thr Asn Asp His Met Ala
1               5                   10

<210> SEQ ID NO 9
<211> LENGTH: 11
<212> TYPE: PRT
<213> ORGANISM: Artificial Sequence
<220> FEATURE:
<223> OTHER INFORMATION: BCMA 269A37972 VHH CDR1

<400> SEQUENCE: 9

Ser Gly Gly Thr Leu Ser Lys Asn Thr Val Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: BCMA 269A37353 VHH CDR1

<400> SEQUENCE: 10

Ser Glu His Thr Phe Ser Ser His Val Met Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: BCMA 269A37948 VHH CDR1

<400> SEQUENCE: 11

Ser Gly Arg Ala Phe Ser Thr Tyr Phe Met Ala
1               5                   10

<210> SEQ ID NO 12
<211> LENGTH: 17
<212> TYPE: PRT
<213> ORGANISM: Artificial Sequence
<220> FEATURE:
<223> OTHER INFORMATION: BCMA 269A37346 VHH CDR2
```

```
<400> SEQUENCE: 12

Cys Ile Ser Arg Ser Asp Gly Ser Thr Tyr Tyr Ala Asp Ser Val Lys
1               5                   10                  15

Gly

<210> SEQ ID NO 13
<211> LENGTH: 19
<212> TYPE: PRT
<213> ORGANISM: Artificial Sequence
<220> FEATURE:
<223> OTHER INFORMATION: BCMA 269A37348 VHH CDR2

<400> SEQUENCE: 13

Ser Lys Ala Ser Met Asn Tyr Ser Gly Arg Thr Tyr Tyr Ala Asp Ser
1               5                   10                  15

Val Lys Gly

<210> SEQ ID NO 14
<211> LENGTH: 17
<212> TYPE: PRT
<213> ORGANISM: Artificial Sequence
<220> FEATURE:
<223> OTHER INFORMATION: BCMA 269A37917 VHH CDR2

<400> SEQUENCE: 14

Ala Ile Ser Leu Ser Pro Thr Leu Ala Tyr Tyr Ala Glu Ser Val Lys
1               5                   10                  15

Gly

<210> SEQ ID NO 15
<211> LENGTH: 16
<212> TYPE: PRT
<213> ORGANISM: Artificial Sequence
<220> FEATURE:
<223> OTHER INFORMATION: BCMA 269A37355 VHH CDR2

<400> SEQUENCE: 15

Ser Ile Arg Gly Leu Gly Arg Thr Asn Tyr Asp Asp Ser Val Lys Gly
1               5                   10                  15

<210> SEQ ID NO 16
<211> LENGTH: 17
<212> TYPE: PRT
<213> ORGANISM: Artificial Sequence
<220> FEATURE:
<223> OTHER INFORMATION: BCMA 269A37915 VHH CDR2

<400> SEQUENCE: 16

Ala Ile Met Trp Asn Asp Gly Ile Thr Tyr Leu Gln Asp Ser Val Lys
1               5                   10                  15

Gly

<210> SEQ ID NO 17
<211> LENGTH: 17
<212> TYPE: PRT
<213> ORGANISM: Artificial Sequence
<220> FEATURE:
<223> OTHER INFORMATION: BCMA 269A37936 VHH CDR2

<400> SEQUENCE: 17

Phe Ile Lys Pro Ser Asp Gly Thr Ile Tyr Tyr Ile Asp Ser Leu Lys
1               5                   10                  15

Gly
```

```
<210> SEQ ID NO 18
<211> LENGTH: 17
<212> TYPE: PRT
<213> ORGANISM: Artificial Sequence
<220> FEATURE:
<223> OTHER INFORMATION: BCMA 269A37953 VHH CDR2

<400> SEQUENCE: 18

Ala Ile Met Trp Asn Asp Gly Ile Thr Tyr Leu Gln Asp Ser Val Lys
1               5                   10                  15

Gly

<210> SEQ ID NO 19
<211> LENGTH: 17
<212> TYPE: PRT
<213> ORGANISM: Artificial Sequence
<220> FEATURE:
<223> OTHER INFORMATION: BCMA 269A37965 VHH CDR2

<400> SEQUENCE: 19

Ala Ile Asp Trp Ser Gly Arg Thr Thr Asn Tyr Ala Asp Pro Val Glu
1               5                   10                  15

Gly

<210> SEQ ID NO 20
<211> LENGTH: 17
<212> TYPE: PRT
<213> ORGANISM: Artificial Sequence
<220> FEATURE:
<223> OTHER INFORMATION: BCMA 269A37972 VHH CDR2

<400> SEQUENCE: 20

Ser Ile Thr Trp Asp Gly Arg Thr Thr Tyr Tyr Ala Asp Ser Val Lys
1               5                   10                  15

Gly

<210> SEQ ID NO 21
<211> LENGTH: 17
<212> TYPE: PRT
<213> ORGANISM: Artificial Sequence
<220> FEATURE:
<223> OTHER INFORMATION: BCMA 269A37353 VHH CDR2

<400> SEQUENCE: 21

Val Ile Gly Trp Arg Asp Ile Ser Thr Ser Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: BCMA 269A37948 VHH CDR2

<400> SEQUENCE: 22

Gly Ile Ala Trp Ser Gly Gly Ser Thr Ala Tyr Ala Asp Ser Val Lys
1               5                   10                  15

Gly

<210> SEQ ID NO 23
<211> LENGTH: 14
```

```
<212> TYPE: PRT
<213> ORGANISM: Artificial Sequence
<220> FEATURE:
<223> OTHER INFORMATION: BCMA 269A37346 VHH CDR3

<400> SEQUENCE: 23

Ala Gly Ala Asp Cys Ser Gly Tyr Leu Arg Asp Tyr Glu Phe
1               5                   10

<210> SEQ ID NO 24
<211> LENGTH: 18
<212> TYPE: PRT
<213> ORGANISM: Artificial Sequence
<220> FEATURE:
<223> OTHER INFORMATION: BCMA 269A37348 VHH CDR3

<400> SEQUENCE: 24

Ala Gly Thr Gly Cys Ser Thr Tyr Gly Cys Phe Asp Ala Gln Ile Ile
1               5                   10                  15

Asp Tyr

<210> SEQ ID NO 25
<211> LENGTH: 13
<212> TYPE: PRT
<213> ORGANISM: Artificial Sequence
<220> FEATURE:
<223> OTHER INFORMATION: BCMA 269A37917 VHH CDR3

<400> SEQUENCE: 25

Ala Asp Arg Lys Ser Val Met Ser Ile Arg Pro Asp Tyr
1               5                   10

<210> SEQ ID NO 26
<211> LENGTH: 13
<212> TYPE: PRT
<213> ORGANISM: Artificial Sequence
<220> FEATURE:
<223> OTHER INFORMATION: BCMA 269A37355 VHH CDR3

<400> SEQUENCE: 26

Val Tyr Val Thr Leu Leu Gly Gly Val Asn Arg Asp Tyr
1               5                   10

<210> SEQ ID NO 27
<211> LENGTH: 11
<212> TYPE: PRT
<213> ORGANISM: Artificial Sequence
<220> FEATURE:
<223> OTHER INFORMATION: BCMA 269A37915 VHH CDR3

<400> SEQUENCE: 27

Ala Ser Lys Gly Arg Tyr Ser Glu Tyr Glu Tyr
1               5                   10

<210> SEQ ID NO 28
<211> LENGTH: 17
<212> TYPE: PRT
<213> ORGANISM: Artificial Sequence
<220> FEATURE:
<223> OTHER INFORMATION: BCMA 269A37936 VHH CDR3

<400> SEQUENCE: 28

Ala Ser Pro Glu Asp Trp Tyr Thr Asp Trp Ile Asp Trp Ser Ile Tyr
1               5                   10                  15

Arg
```

<210> SEQ ID NO 29
<211> LENGTH: 11
<212> TYPE: PRT
<213> ORGANISM: Artificial Sequence
<220> FEATURE:
<223> OTHER INFORMATION: BCMA 269A37953 VHH CDR3

<400> SEQUENCE: 29

Ala Ser Lys Gly Arg Tyr Ser Glu Tyr Glu Tyr
1               5                   10

<210> SEQ ID NO 30
<211> LENGTH: 12
<212> TYPE: PRT
<213> ORGANISM: Artificial Sequence
<220> FEATURE:
<223> OTHER INFORMATION: BCMA 269A37965 VHH CDR3

<400> SEQUENCE: 30

Val Leu Arg Ala Trp Ile Ser Tyr Asp Asn Asp Tyr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: BCMA 269A37972 VHH CDR3

<400> SEQUENCE: 31

Asp Leu Gly Lys Trp Pro Ala Gly Pro Ala Asp Tyr
1               5                   10

<210> SEQ ID NO 32
<211> LENGTH: 11
<212> TYPE: PRT
<213> ORGANISM: Artificial Sequence
<220> FEATURE:
<223> OTHER INFORMATION: BCMA 269A37353 VHH CDR3

<400> SEQUENCE: 32

Ala Arg Arg Ile Asp Ala Ala Asp Phe Asp Ser
1               5                   10

<210> SEQ ID NO 33
<211> LENGTH: 11
<212> TYPE: PRT
<213> ORGANISM: Artificial Sequence
<220> FEATURE:
<223> OTHER INFORMATION: BCMA 269A37948 VHH CDR3

<400> SEQUENCE: 33

Ser Arg Gly Ile Glu Val Glu Glu Phe Gly Ala
1               5                   10

<210> SEQ ID NO 34
<211> LENGTH: 11
<212> TYPE: PRT
<213> ORGANISM: Artificial Sequence
<220> FEATURE:
<223> OTHER INFORMATION: CD38 38A37333 VHH CDR1

<400> SEQUENCE: 34

Ser Gly Leu Thr Phe Ser Ser Tyr Pro Met Met
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CD38 38A37336 VHH CDR1

<400> SEQUENCE: 35

Ser Gly Phe Thr Phe Ser Ser Asn Trp Met Tyr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: CD38 38A37699 VHH CDR1

<400> SEQUENCE: 36

Ser Gly Arg Ile Phe Ser Ile Asn Ala Met Gly
1               5                   10

<210> SEQ ID NO 37
<211> LENGTH: 14
<212> TYPE: PRT
<213> ORGANISM: Artificial Sequence
<220> FEATURE:
<223> OTHER INFORMATION: CD38 38A37331 VHH CDR1

<400> SEQUENCE: 37

Ser Gly Ser Ile Phe Lys Val Phe Arg Val Phe Ala Met Ser
1               5                   10

<210> SEQ ID NO 38
<211> LENGTH: 11
<212> TYPE: PRT
<213> ORGANISM: Artificial Sequence
<220> FEATURE:
<223> OTHER INFORMATION: CD38 38A37717 VHH CDR1

<400> SEQUENCE: 38

Thr Gly Lys Val Phe Ser Ile Tyr Asp Met Gly
1               5                   10

<210> SEQ ID NO 39
<211> LENGTH: 11
<212> TYPE: PRT
<213> ORGANISM: Artificial Sequence
<220> FEATURE:
<223> OTHER INFORMATION: CD38 38A37719 VHH CDR1

<400> SEQUENCE: 39

Ser Ala Ser Ile Phe Thr Arg Leu Pro Met Gly
1               5                   10

<210> SEQ ID NO 40
<211> LENGTH: 9
<212> TYPE: PRT
<213> ORGANISM: Artificial Sequence
<220> FEATURE:
<223> OTHER INFORMATION: CD38 38A37330 VHH CDR1

<400> SEQUENCE: 40

Ser Gly Arg Ala Tyr Ala Thr Met Ala
1               5

<210> SEQ ID NO 41

```
<211> LENGTH: 11
<212> TYPE: PRT
<213> ORGANISM: Artificial Sequence
<220> FEATURE:
<223> OTHER INFORMATION: CD38 38A37334 VHH CDR1

<400> SEQUENCE: 41

Ser Gly Leu Thr Phe Ser Ser Tyr Ile Met Gly
1               5                   10

<210> SEQ ID NO 42
<211> LENGTH: 11
<212> TYPE: PRT
<213> ORGANISM: Artificial Sequence
<220> FEATURE:
<223> OTHER INFORMATION: CD38 38A37730 VHH CDR1

<400> SEQUENCE: 42

Ser Gln Gly Ile Phe Thr Ile Asn Ala Met Gly
1               5                   10

<210> SEQ ID NO 43
<211> LENGTH: 11
<212> TYPE: PRT
<213> ORGANISM: Artificial Sequence
<220> FEATURE:
<223> OTHER INFORMATION: CD38 38A37340 VHH CDR1

<400> SEQUENCE: 43

Ser Gly Arg Thr Phe Ser Ser Tyr Ala Met Ala
1               5                   10

<210> SEQ ID NO 44
<211> LENGTH: 11
<212> TYPE: PRT
<213> ORGANISM: Artificial Sequence
<220> FEATURE:
<223> OTHER INFORMATION: CD38 38A37731 VHH CDR1

<400> SEQUENCE: 44

Ser Gly Thr Ile Val Ser Ile Ser Thr Met Gly
1               5                   10

<210> SEQ ID NO 45
<211> LENGTH: 8
<212> TYPE: PRT
<213> ORGANISM: Artificial Sequence
<220> FEATURE:
<223> OTHER INFORMATION: CD38 38A37326 VHH CDR1

<400> SEQUENCE: 45

Ser Gly Arg Thr Tyr Ala Met Gly
1               5

<210> SEQ ID NO 46
<211> LENGTH: 17
<212> TYPE: PRT
<213> ORGANISM: Artificial Sequence
<220> FEATURE:
<223> OTHER INFORMATION: CD38 38A37333 VHH CDR2

<400> SEQUENCE: 46

Arg Ile Ser Asp Ser Gly Gly Tyr Thr Asn Tyr Asp Asp Ser Val Lys
1               5                   10                  15

Gly
```

```
<210> SEQ ID NO 47
<211> LENGTH: 17
<212> TYPE: PRT
<213> ORGANISM: Artificial Sequence
<220> FEATURE:
<223> OTHER INFORMATION: CD38 38A37336 VHH CDR2

<400> SEQUENCE: 47

Thr Ile Ser Thr Asp Gly Arg Gly Thr Tyr Tyr Lys Asp Ser Val Lys
1               5                   10                  15
Gly

<210> SEQ ID NO 48
<211> LENGTH: 16
<212> TYPE: PRT
<213> ORGANISM: Artificial Sequence
<220> FEATURE:
<223> OTHER INFORMATION: CD38 38A37699 VHH CDR2

<400> SEQUENCE: 48

Ala Ile Ser Thr Ala Gly Ser Thr Asn Tyr Gly Asp Ser Val Lys Gly
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: CD38 38A37331 VHH CDR2

<400> SEQUENCE: 49

Ser Ile Ser Ser Gly Glu Thr Thr Thr Tyr Ala Asp Ser Val Lys Gly
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: CD38 38A37717 VHH CDR2

<400> SEQUENCE: 50

Glu Ile Thr Ser Ser Gly Thr Thr His Tyr Asp Asp Phe Val Ser Gly
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: CD38 38A37719 VHH CDR2

<400> SEQUENCE: 51

Gly Ile Val Pro Ser Gly Arg Ile Asn Tyr Ala Asp Ser Val Lys Gly
1               5                   10                  15

<210> SEQ ID NO 52
<211> LENGTH: 17
<212> TYPE: PRT
<213> ORGANISM: Artificial Sequence
<220> FEATURE:
<223> OTHER INFORMATION: CD38 38A37330 VHH CDR2

<400> SEQUENCE: 52

His Leu Arg Val Ser Gly Asp Thr Thr Tyr Tyr Thr Asp Ser Val Lys
1               5                   10                  15
```

Gly

<210> SEQ ID NO 53
<211> LENGTH: 16
<212> TYPE: PRT
<213> ORGANISM: Artificial Sequence
<220> FEATURE:
<223> OTHER INFORMATION: CD38 38A37334 VHH CDR2

<400> SEQUENCE: 53

Glu Ile Ser Ser Gly Gly Met Thr Ser Tyr Ala Asp Ser Val Lys Gly
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: CD38 38A37730 VHH CDR2

<400> SEQUENCE: 54

Glu Val Ser Ser Gly Gly Arg Thr Asp Tyr Ala Asp Ser Val Lys Gly
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: CD38 38A37340 VHH CDR2

<400> SEQUENCE: 55

Ser Ile Ser Thr Ser Gly Gly Ile Thr Asp Tyr Ala Asp Ser Val Lys
1               5                   10                  15

Gly

<210> SEQ ID NO 56
<211> LENGTH: 16
<212> TYPE: PRT
<213> ORGANISM: Artificial Sequence
<220> FEATURE:
<223> OTHER INFORMATION: CD38 38A37731 VHH CDR2

<400> SEQUENCE: 56

Thr Ile Thr Arg Arg Gly Arg Thr Asn Tyr Thr Asp Ser Val Lys Gly
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: CD38 38A37326 VHH CDR2

<400> SEQUENCE: 57

Thr Ile Ser Gly Ala Gly Asn Thr Lys Tyr Ala Asp Ser Val Lys Gly
1               5                   10                  15

<210> SEQ ID NO 58
<211> LENGTH: 6
<212> TYPE: PRT
<213> ORGANISM: Artificial Sequence
<220> FEATURE:
<223> OTHER INFORMATION: CD38 38A37333 VHH CDR3

<400> SEQUENCE: 58

Ile Leu Gly Leu Pro Thr
1               5

<210> SEQ ID NO 59
<211> LENGTH: 18
<212> TYPE: PRT
<213> ORGANISM: Artificial Sequence
<220> FEATURE:
<223> OTHER INFORMATION: CD38 38A37336 VHH CDR3

<400> SEQUENCE: 59

Lys Glu Pro Arg Val Leu Met Ala Tyr Leu Arg Asn Leu Gly Asp Phe
1               5                   10                  15

Gly Ser

<210> SEQ ID NO 60
<211> LENGTH: 8
<212> TYPE: PRT
<213> ORGANISM: Artificial Sequence
<220> FEATURE:
<223> OTHER INFORMATION: CD38 38A37699 VHH CDR3

<400> SEQUENCE: 60

Leu Asn Phe Pro Pro Tyr Val Tyr
1               5

<210> SEQ ID NO 61
<211> LENGTH: 9
<212> TYPE: PRT
<213> ORGANISM: Artificial Sequence
<220> FEATURE:
<223> OTHER INFORMATION: CD38 38A37331 VHH CDR3

<400> SEQUENCE: 61

Ala Asp His Thr Phe Thr Gly Asp Phe
1               5

<210> SEQ ID NO 62
<211> LENGTH: 8
<212> TYPE: PRT
<213> ORGANISM: Artificial Sequence
<220> FEATURE:
<223> OTHER INFORMATION: CD38 38A37717 VHH CDR3

<400> SEQUENCE: 62

Asn His Val Phe Gly Gly Ser Tyr
1               5

<210> SEQ ID NO 63
<211> LENGTH: 8
<212> TYPE: PRT
<213> ORGANISM: Artificial Sequence
<220> FEATURE:
<223> OTHER INFORMATION: CD38 38A37719 VHH CDR3

<400> SEQUENCE: 63

Ala Asp Thr Phe Pro Leu Pro Thr
1               5

<210> SEQ ID NO 64
<211> LENGTH: 19
<212> TYPE: PRT
<213> ORGANISM: Artificial Sequence
<220> FEATURE:
<223> OTHER INFORMATION: CD38 38A37330 VHH CDR3

<400> SEQUENCE: 64

```
Gly Pro Tyr Gly Ile Leu Ala Ala Ala Arg Val Ser Asn Pro Gly Asn
1               5                   10                  15

Tyr Asp Tyr

<210> SEQ ID NO 65
<211> LENGTH: 16
<212> TYPE: PRT
<213> ORGANISM: Artificial Sequence
<220> FEATURE:
<223> OTHER INFORMATION: CD38 38A37334 VHH CDR3

<400> SEQUENCE: 65

Ala Pro Glu Arg Gly Ser Ile Trp Tyr Ser Arg Tyr Glu Tyr Lys Tyr
1               5                   10                  15

<210> SEQ ID NO 66
<211> LENGTH: 13
<212> TYPE: PRT
<213> ORGANISM: Artificial Sequence
<220> FEATURE:
<223> OTHER INFORMATION: CD38 38A37730 VHH CDR3

<400> SEQUENCE: 66

Val Ser Gly Trp His Val Phe Val Gly Asp Arg Ile Val
1               5                   10

<210> SEQ ID NO 67
<211> LENGTH: 14
<212> TYPE: PRT
<213> ORGANISM: Artificial Sequence
<220> FEATURE:
<223> OTHER INFORMATION: CD38 38A37340 VHH CDR3

<400> SEQUENCE: 67

Ala Arg Thr Trp Tyr Leu Arg Thr Ser Leu Gln Tyr Asp Tyr
1               5                   10

<210> SEQ ID NO 68
<211> LENGTH: 14
<212> TYPE: PRT
<213> ORGANISM: Artificial Sequence
<220> FEATURE:
<223> OTHER INFORMATION: CD38 38A37731 VHH CDR3

<400> SEQUENCE: 68

Ala Glu Val Gln Leu Asp Ile Trp Ala Ser Ala Tyr Asp Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: CD38 38A37326 VHH CDR3

<400> SEQUENCE: 69

Ala Gly Lys Trp Phe Pro Ala Ala Asn Glu Tyr
1               5                   10

<210> SEQ ID NO 70
<211> LENGTH: 18
<212> TYPE: PRT
<213> ORGANISM: Artificial Sequence
<220> FEATURE:
<223> OTHER INFORMATION: Signal peptide
```

```
<400> SEQUENCE: 70

Met Lys Trp Val Thr Phe Ile Ser Leu Leu Phe Leu Phe Ser Ser Ala
1               5                   10                  15

Tyr Ser

<210> SEQ ID NO 71
<211> LENGTH: 19
<212> TYPE: PRT
<213> ORGANISM: Artificial Sequence
<220> FEATURE:
<223> OTHER INFORMATION: Signal peptide

<400> SEQUENCE: 71

Met Thr Arg Leu Thr Val Leu Ala Leu Leu Ala Gly Leu Leu Ala Ser
1               5                   10                  15

Ser Arg Ala

<210> SEQ ID NO 72
<211> LENGTH: 5
<212> TYPE: PRT
<213> ORGANISM: Artificial Sequence
<220> FEATURE:
<223> OTHER INFORMATION: Linker

<400> SEQUENCE: 72

Gly Gly Gly Gly Ser
1               5

<210> SEQ ID NO 73
<211> LENGTH: 10
<212> TYPE: PRT
<213> ORGANISM: Artificial Sequence
<220> FEATURE:
<223> OTHER INFORMATION: Linker

<400> SEQUENCE: 73

Gly Gly Gly Gly Ser Gly Gly Gly Gly Ser
1               5                   10

<210> SEQ ID NO 74
<211> LENGTH: 15
<212> TYPE: PRT
<213> ORGANISM: Artificial Sequence
<220> FEATURE:
<223> OTHER INFORMATION: Linker

<400> SEQUENCE: 74

Gly Gly Gly Gly Ser Gly Gly Gly Gly Ser Gly Gly Gly Gly Ser
1               5                   10                  15

<210> SEQ ID NO 75
<211> LENGTH: 8
<212> TYPE: PRT
<213> ORGANISM: Artificial Sequence
<220> FEATURE:
<223> OTHER INFORMATION: Linker

<400> SEQUENCE: 75

Gly Gly Gly Ser Gly Gly Gly Ser
1               5

<210> SEQ ID NO 76
<211> LENGTH: 16
<212> TYPE: PRT
<213> ORGANISM: Artificial Sequence
```

```
<220> FEATURE:
<223> OTHER INFORMATION: Linker

<400> SEQUENCE: 76

Gly Gly Gly Ser Gly Gly Ser Gly Gly Ser Gly Gly Gly Ser
1               5                   10                  15

<210> SEQ ID NO 77
<211> LENGTH: 18
<212> TYPE: PRT
<213> ORGANISM: Artificial Sequence
<220> FEATURE:
<223> OTHER INFORMATION: Linker

<400> SEQUENCE: 77

Gly Ser Thr Ser Gly Ser Gly Lys Pro Gly Ser Gly Glu Gly Ser Thr
1               5                   10                  15

Lys Gly

<210> SEQ ID NO 78
<211> LENGTH: 122
<212> TYPE: PRT
<213> ORGANISM: Artificial Sequence
<220> FEATURE:
<223> OTHER INFORMATION: BCMA 269A37346 VHH

<400> SEQUENCE: 78

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser
        115                 120

<210> SEQ ID NO 79
<211> LENGTH: 128
<212> TYPE: PRT
<213> ORGANISM: Artificial Sequence
<220> FEATURE:
<223> OTHER INFORMATION: BCMA 269A37348 VHH

<400> SEQUENCE: 79

Gln Val Lys Leu Glu Glu Ser Gly Gly Arg Leu Val Gln Pro Arg Gly
1               5                   10                  15

Ser Leu Arg Leu Ser Cys Ala Gly Ser Gly Arg Thr Phe Ser Thr Tyr
            20                  25                  30

Gly Met Ala Trp Phe Arg Gln Ala Pro Gly Lys Glu Arg Glu Phe Val
        35                  40                  45

Ala Ser Lys Ala Ser Met Asn Tyr Ser Gly Arg Thr Tyr Tyr Ala Asp
    50                  55                  60
```

```
Ser Val Lys Gly Arg Phe Thr Ile Ala Arg Asp Asn Ala Lys Asn Met
 65                  70                  75                  80

Val Phe Leu Gln Met Asn Asn Leu Lys Pro Glu Asp Thr Ala Val Tyr
                 85                  90                  95

Tyr Cys Ala Ala Gly Thr Gly Cys Ser Thr Tyr Gly Cys Phe Asp Ala
            100                 105                 110

Gln Ile Ile Asp Tyr Trp Gly Lys Gly Thr Leu Val Thr Val Ser Ser
        115                 120                 125

<210> SEQ ID NO 80
<211> LENGTH: 118
<212> TYPE: PRT
<213> ORGANISM: Artificial Sequence
<220> FEATURE:
<223> OTHER INFORMATION: BCMA 269A37917 VHH

<400> SEQUENCE: 80

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 81
<211> LENGTH: 120
<212> TYPE: PRT
<213> ORGANISM: Artificial Sequence
<220> FEATURE:
<223> OTHER INFORMATION: BCMA 269A37355 VHH

<400> SEQUENCE: 81

Ala Val Gln Leu Val Asp Ser Gly Gly Gly Leu Val Gln Pro Gly Gly
1               5                   10                  15

Ser Leu Arg Leu Ser Cys Val Ala Ser Gly Gly Ile Phe Val Ile Asn
            20                  25                  30

Ala Met Gly Trp Tyr Arg Gln Ala Pro Gly Lys Gln Arg Glu Leu Val
        35                  40                  45

Ala Ser Ile Arg Gly Leu Gly Arg Thr Asn Tyr Asp Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Ser Leu Glu Pro Glu Asp Thr Ala Val Tyr Tyr Cys Thr
                85                  90                  95

Val Tyr Val Thr Leu Leu Gly Gly Val Asn Arg Asp Tyr Trp Gly Gln
            100                 105                 110

Gly Thr Gln Val Thr Val Ser Ser
        115                 120
```

<210> SEQ ID NO 82
<211> LENGTH: 119
<212> TYPE: PRT
<213> ORGANISM: Artificial Sequence
<220> FEATURE:
<223> OTHER INFORMATION: BCMA 269A37915 VHH

<400> SEQUENCE: 82

Glu Val Gln Leu Val Glu Ser Gly Gly Gly Leu Val Gln Ala Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
            100                 105                 110

Thr Gln Val Thr Val Ser Ser
        115

<210> SEQ ID NO 83
<211> LENGTH: 128
<212> TYPE: PRT
<213> ORGANISM: Artificial Sequence
<220> FEATURE:
<223> OTHER INFORMATION: BCMA 269A37936 VHH

<400> SEQUENCE: 83

Glu Val Gln Leu Val Glu Ser Gly Gly Gly Val Val Gln Ala Gly Gly
1               5                   10                  15

Ser Leu Thr Val Ser Cys Thr Ala Ser Gly Phe Thr Phe Asp Arg Ala
            20                  25                  30

Val Ile Val Trp Phe Arg Gln Ala Pro Gly Lys Gly Arg Glu Gly Val
        35                  40                  45

Ser Phe Ile Lys Pro Ser Asp Gly Thr Ile Tyr Tyr Ile Asp Ser Leu
    50                  55                  60

Lys Gly Arg Phe Thr Ile Ser Ser Asp Ile Ala Lys Asn Thr Val Tyr
65                  70                  75                  80

Leu Gln Met Lys Ser Leu Glu Ser Glu Asp Ser Ala Val Tyr Tyr Cys
                85                  90                  95

Ala Ala Ser Pro Glu Asp Trp Tyr Thr Asp Trp Ile Asp Trp Ser Ile
            100                 105                 110

Tyr Arg Trp Gln His Trp Gly Gln Gly Thr Gln Val Thr Val Ser Ser
        115                 120                 125

<210> SEQ ID NO 84
<211> LENGTH: 119
<212> TYPE: PRT
<213> ORGANISM: Artificial Sequence
<220> FEATURE:
<223> OTHER INFORMATION: BCMA 269A37953 VHH

<400> SEQUENCE: 84

Glu Val Gln Leu Val Glu Ser Gly Gly Gly Met Val Gln Ala Gly Asp
1               5                   10                  15

Ser Leu Arg Leu Ser Cys Val Gln Ser Thr Tyr Thr Asn Ser Asp
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
                100                 105                 110

Thr Gln Val Thr Val Ser Ser
            115

<210> SEQ ID NO 85
<211> LENGTH: 120
<212> TYPE: PRT
<213> ORGANISM: Artificial Sequence
<220> FEATURE:
<223> OTHER INFORMATION: BCMA 269A37965 VHH

<400> SEQUENCE: 85

Ala Val Gln Leu Val Glu Ser Gly Gly Gly Leu Val Gln Ala Gly Asp
1               5                   10                  15

Ser Leu Arg Leu Ser Cys Thr Ala Ser Gly Ala Thr Leu Thr Asn Asp
            20                  25                  30

His Met Ala Trp Phe Arg Gln Ala Pro Gly Lys Gly Arg Glu Phe Val
        35                  40                  45

Ala Ala Ile Asp Trp Ser Gly Arg Thr Thr Asn Tyr Ala Asp Pro Val
    50                  55                  60

Glu Gly Arg Phe Thr Ile Ser Arg Asn Asn Ala Lys Asn Thr Val Tyr
65                  70                  75                  80

Leu Glu Met Asn Ser Leu Lys Leu Glu Asp Thr Ala Val Tyr Tyr Cys
                85                  90                  95

Ala Val Leu Arg Ala Trp Ile Ser Tyr Asp Asn Asp Tyr Trp Gly Gln
                100                 105                 110

Gly Thr Gln Val Thr Val Ser Ser
            115                 120

<210> SEQ ID NO 86
<211> LENGTH: 120
<212> TYPE: PRT
<213> ORGANISM: Artificial Sequence
<220> FEATURE:
<223> OTHER INFORMATION: BCMA 269A37972 VHH

<400> SEQUENCE: 86

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
        35                  40                  45

Ala Ser Ile Thr Trp Asp Gly Arg Thr Thr Tyr Tyr Ala Asp Ser Val
    50                  55                  60

```
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Val Cys
                 85                  90                  95

Ala Asp Leu Gly Lys Trp Pro Ala Gly Pro Ala Asp Tyr Trp Gly Gln
            100                 105                 110

Gly Thr Gln Val Thr Val Ser Ser
        115                 120
```

<210> SEQ ID NO 87
<211> LENGTH: 119
<212> TYPE: PRT
<213> ORGANISM: Artificial Sequence
<220> FEATURE:
<223> OTHER INFORMATION: BCMA 269A37353 VHH

<400> SEQUENCE: 87

```
Gln Val Lys Leu Glu Glu Ser Gly Gly Gly Leu Val Gln Ala Gly Arg
  1               5                  10                  15

Ser Leu Arg Leu Ser Cys Ala Ala Ser Glu His Thr Phe Ser Ser His
                 20                  25                  30

Val Met Gly Trp Phe Arg Gln Ala Pro Gly Lys Glu Arg Glu Ser Val
             35                  40                  45

Ala Val Ile Gly Trp Arg Asp Ile Ser Thr Ser Tyr Ala Asp Ser Val
         50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Arg Ile Asp Ala Ala Asp Phe Asp Ser Trp Gly Gln Gly
            100                 105                 110

Thr Gln Val Thr Val Ser Ser
        115
```

<210> SEQ ID NO 88
<211> LENGTH: 119
<212> TYPE: PRT
<213> ORGANISM: Artificial Sequence
<220> FEATURE:
<223> OTHER INFORMATION: BCMA 269A37948 VHH

<400> SEQUENCE: 88

```
Ala Val Gln Leu Val Glu Ser Gly Gly Gly Leu Val Gln Ala Gly Asp
  1               5                  10                  15

Ser Leu Arg Leu Thr Cys Thr Ala Ser Gly Arg Ala Phe Ser Thr Tyr
                 20                  25                  30

Phe Met Ala Trp Phe Arg Gln Ala Pro Gly Lys Glu Arg Glu Phe Val
             35                  40                  45

Ala Gly Ile Ala Trp Ser Gly Gly Ser Thr Ala Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Ser Glu Asp Thr Ala Val Tyr Tyr Cys
                 85                  90                  95

Ala Ser Arg Gly Ile Glu Val Glu Glu Phe Gly Ala Trp Gly Gln Gly
            100                 105                 110

Thr Gln Val Thr Val Ser Ser
```

<210> SEQ ID NO 89
<211> LENGTH: 114
<212> TYPE: PRT
<213> ORGANISM: Artificial Sequence
<220> FEATURE:
<223> OTHER INFORMATION: CD38 38A37333 VHH

<400> SEQUENCE: 89

Asp Val Gln Leu Val Glu Ser Gly Gly Gly Leu Val Gln Pro Gly Gly
1               5                   10                  15
Ser Leu Arg Leu Ser Cys Val Ala Ser Gly Leu Thr Phe Ser Ser Tyr
            20                  25                  30
Pro Met Met Trp Val Arg Gln Ala Pro Gly Lys Gly Leu Glu Trp Val
        35                  40                  45
Ser Arg Ile Ser Asp Ser Gly Gly Tyr Thr Asn Tyr Asp Asp Ser Val
    50                  55                  60
Lys Gly Arg Phe Thr Ile Ser Arg Asp Asn Ala Lys Asn Thr Leu Tyr
65                  70                  75                  80
Leu Gln Met Asn Ser Leu Thr Pro Glu Asp Thr Ala Val Tyr Tyr Cys
                85                  90                  95
Arg Ile Leu Gly Leu Pro Thr Thr Gly Gln Gly Thr Gln Val Thr Val
            100                 105                 110
Ser Ser

<210> SEQ ID NO 90
<211> LENGTH: 126
<212> TYPE: PRT
<213> ORGANISM: Artificial Sequence
<220> FEATURE:
<223> OTHER INFORMATION: CD38 38A37336 VHH

<400> SEQUENCE: 90

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Asn
            20                  25                  30
Trp Met Tyr Trp Val Arg Gln Ala Pro Gly Lys Gly Leu Glu Trp Val
        35                  40                  45
Ala Thr Ile Ser Thr Asp Gly Arg Gly Thr Tyr Tyr Lys Asp Ser Val
    50                  55                  60
Lys Gly Arg Phe Thr Val Ser Arg Asp Asn Ala Met Ser Thr Leu Leu
65                  70                  75                  80
Leu Gln Met Asn Asn Leu Lys Ser Glu Asp Thr Ala Val Tyr Tyr Cys
                85                  90                  95
Ala Lys Glu Pro Arg Val Leu Met Ala Tyr Leu Arg Asn Leu Gly Asp
            100                 105                 110
Phe Gly Ser Trp Gly Gln Gly Thr Gln Val Thr Val Ser Ser
        115                 120                 125

<210> SEQ ID NO 91
<211> LENGTH: 115
<212> TYPE: PRT
<213> ORGANISM: Artificial Sequence
<220> FEATURE:
<223> OTHER INFORMATION: CD38 38A37699 VHH

<400> SEQUENCE: 91

-continued

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Thr Ala Gly Ser Thr Asn Tyr Gly Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asn Phe Pro Pro Tyr Val Tyr Trp Gly Gln Gly Thr Gln Val Thr
            100                 105                 110

Val Ser Ser
        115

<210> SEQ ID NO 92
<211> LENGTH: 119
<212> TYPE: PRT
<213> ORGANISM: Artificial Sequence
<220> FEATURE:
<223> OTHER INFORMATION: CD38 38A37331 VHH

<400> SEQUENCE: 92

Gln Val Lys Leu Glu Glu Ser Gly Gly Gly Leu Val Gln Pro Gly Glu
1               5                   10                  15

Ser Leu Arg Leu Ser Cys Ser Ala Ser Gly Ser Ile Phe Lys Val Phe
            20                  25                  30

Arg Val Phe Ala Met Ser Trp Tyr Arg Gln Gly Pro Gly Lys Gln Arg
        35                  40                  45

Glu Leu Val Ala Ser Ile Ser Ser Gly Glu Thr Thr Thr Tyr Ala Asp
50                  55                  60

Ser Val Lys Gly Arg Phe Thr Ile Ser Arg Asp Asn Ala Lys Asn Thr
65                  70                  75                  80

Ala Tyr Leu Gln Met Asp Ser Leu Lys Pro Glu Asp Thr Ala Val Tyr
                85                  90                  95

Tyr Cys Asn Ala Asp His Thr Phe Thr Gly Asp Phe Trp Gly Gln Gly
            100                 105                 110

Thr Gln Val Thr Val Ser Ser
        115

<210> SEQ ID NO 93
<211> LENGTH: 116
<212> TYPE: PRT
<213> ORGANISM: Artificial Sequence
<220> FEATURE:
<223> OTHER INFORMATION: CD38 38A37717 VHH

<400> SEQUENCE: 93

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser
        115

<210> SEQ ID NO 94
<211> LENGTH: 115
<212> TYPE: PRT
<213> ORGANISM: Artificial Sequence
<220> FEATURE:
<223> OTHER INFORMATION: CD38 38A37719 VHH

<400> SEQUENCE: 94

Gln Val Lys Leu Glu Glu Ser Gly Gly Gly Ser Val Gln Thr Gly Gly
1               5                   10                  15

Ser Leu Arg Leu Ser Cys Ala Ala Ser Ala Ser Ile Phe Thr Arg Leu
                20                  25                  30

Pro Met Gly Trp Tyr Arg Gln Ala Pro Gly Lys Gln Arg Glu Leu Val
            35                  40                  45

Val Gly Ile Val Pro Ser Gly Arg Ile Asn Tyr Ala Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Arg
                85                  90                  95

Ala Asp Thr Phe Pro Leu Pro Thr Trp Gly Gln Gly Thr Gln Val Thr
            100                 105                 110

Val Ser Ser
        115

<210> SEQ ID NO 95
<211> LENGTH: 126
<212> TYPE: PRT
<213> ORGANISM: Artificial Sequence
<220> FEATURE:
<223> OTHER INFORMATION: CD38 38A37330 VHH

<400> SEQUENCE: 95

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Tyr Ala Thr Met
                20                  25                  30

Ala Trp Phe Arg Gln Ala Pro Gly Lys Glu Arg Glu Phe Val Ala His
            35                  40                  45

Leu Arg Val Ser Gly Asp Thr Thr Tyr Tyr Thr Asp Ser Val Lys Gly
50                  55                  60

Arg Phe Thr Ile Ser Arg Asp Asn Ala Lys Asn Thr Ala Tyr Leu Gln
65                  70                  75                  80

Met Asn Met Leu Lys Pro Glu Asp Thr Ala Val Tyr Tyr Cys Ala Ala
                85                  90                  95

Gly Pro Tyr Gly Ile Leu Ala Ala Ala Arg Val Ser Asn Pro Gly Asn
            100                 105                 110

Tyr Asp Tyr Trp Gly Gln Gly Thr Gln Val Thr Val Ser Ser

<210> SEQ ID NO 96
<211> LENGTH: 123
<212> TYPE: PRT
<213> ORGANISM: Artificial Sequence
<220> FEATURE:
<223> OTHER INFORMATION: CD38 38A37334 VHH

<400> SEQUENCE: 96

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ile Met Gly Trp Phe Arg Gln Ala Pro Gly Glu Glu Arg Glu Leu Val
        35                  40                  45

Ala Glu Ile Ser Ser Gly Gly Met Thr Ser Tyr Ala Asp Ser Val Lys
    50                  55                  60

Gly Arg Phe Thr Ile Ser Arg Asp Asn Ala Lys Lys Thr Gly Tyr Leu
65                  70                  75                  80

Gln Met Asn Ser Leu Lys Pro Glu Asp Thr Ala Val Tyr Tyr Cys Ala
                85                  90                  95

Ala Pro Glu Arg Gly Ser Ile Trp Tyr Ser Arg Tyr Glu Tyr Lys Tyr
            100                 105                 110

Trp Gly Gln Gly Thr Gln Val Thr Val Ser Ser
        115                 120

<210> SEQ ID NO 97
<211> LENGTH: 120
<212> TYPE: PRT
<213> ORGANISM: Artificial Sequence
<220> FEATURE:
<223> OTHER INFORMATION: CD38 38A37730 VHH

<400> SEQUENCE: 97

Ala Val Gln Leu Val Asp Ser Gly Gly Gly Leu Ala Gln Thr Gly Gly
1               5                   10                  15

Ser Leu Arg Leu Ser Cys Ala Ala Ser Gln Ile Phe Thr Ile Asn
            20                  25                  30

Ala Met Gly Trp Tyr Arg Gln Val Pro Gly Lys Gln Arg Glu Leu Val
        35                  40                  45

Ala Glu Val Ser Ser Gly Gly Arg Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Arg
                85                  90                  95

Val Ser Gly Trp His Val Phe Val Gly Asp Arg Ile Val Trp Gly Gln
            100                 105                 110

Gly Thr Leu Val Thr Val Ser Ser
        115                 120

<210> SEQ ID NO 98
<211> LENGTH: 123
<212> TYPE: PRT
<213> ORGANISM: Artificial Sequence
<220> FEATURE:
<223> OTHER INFORMATION: CD38 38A37340 VHH

<400> SEQUENCE: 98

```
Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Ile Val
        35                  40                  45

Ser Ser Ile Ser Thr Ser Gly Gly Ile Thr Asp Tyr Ala Asp Ser Val
50                  55                  60

Lys Gly Arg Phe Thr Ile Ser Lys Asp Ser Ala Lys Met Asn Thr Val
65                  70                  75                  80

Tyr Leu Gln Met Asn Ser Leu Glu Pro Glu Asp Thr Ala Val Tyr Tyr
                85                  90                  95

Cys Ala Ala Arg Thr Trp Tyr Leu Arg Thr Ser Leu Gly Tyr Asp Tyr
            100                 105                 110

Trp Gly Gln Gly Thr Gln Val Thr Val Ser Ser
        115                 120
```

<210> SEQ ID NO 99
<211> LENGTH: 121
<212> TYPE: PRT
<213> ORGANISM: Artificial Sequence
<220> FEATURE:
<223> OTHER INFORMATION: CD38 38A37731 VHH

<400> SEQUENCE: 99

```
Gln Val Lys Leu Glu Glu Ser Gly Gly Gly Leu Val Gln Ala Gly Gly
1               5                   10                  15

Ser Leu Arg Leu Ser Cys Val Ala Ser Gly Thr Ile Val Ser Ile Ser
            20                  25                  30

Thr Met Gly Trp Tyr Arg Gln Ala Pro Gly Lys Gln Arg Glu Leu Val
        35                  40                  45

Ala Thr Ile Thr Arg Arg Gly Arg Thr Asn Tyr Thr Asp Ser Val Lys
50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Val Gln Leu Asp Ile Trp Ala Ser Ala Tyr Asp Tyr Trp Gly
            100                 105                 110

Gln Gly Thr Gln Val Thr Val Ala Ser
        115                 120
```

<210> SEQ ID NO 100
<211> LENGTH: 115
<212> TYPE: PRT
<213> ORGANISM: Artificial Sequence
<220> FEATURE:
<223> OTHER INFORMATION: CD38 38A37326 VHH

<400> SEQUENCE: 100

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Tyr Ala Met Gly
            20                  25                  30

Trp Tyr Arg Gln Ala Pro Gly Lys Gln Arg Asp Leu Val Ala Thr Ile
        35                  40                  45

Ser Gly Ala Gly Asn Thr Lys Tyr Ala Asp Ser Val Lys Gly Arg Phe
```

```
                50                  55                  60
Thr Ile Ser Arg Asp Asn Ala Lys Asn Thr Met Tyr Leu Gln Met Asn
 65                  70                  75                  80

Ser Leu Lys Pro Glu Asp Thr Ala Val Tyr Tyr Cys Ala Ala Gly Lys
                 85                  90                  95

Trp Phe Pro Ala Ala Asn Glu Tyr Trp Gly Gln Gly Thr Gln Val Thr
                100                 105                 110

Val Ser Ser
        115

<210> SEQ ID NO 101
<211> LENGTH: 253
<212> TYPE: PRT
<213> ORGANISM: Artificial Sequence
<220> FEATURE:
<223> OTHER INFORMATION: C11D5.3 scFv

<400> SEQUENCE: 101

Asp Ile Val Leu Thr Gln Ser Pro Pro Ser Leu Ala Met Ser Leu Gly
 1               5                  10                  15

Lys Arg Ala Thr Ile Ser Cys Arg Ala Ser Glu Ser Val Thr Ile Leu
                20                  25                  30

Gly Ser His Leu Ile His Trp Tyr Gln Gln Lys Pro Gly Gln Pro Pro
            35                  40                  45

Thr Leu Leu Ile Gln Leu Ala Ser Asn Val Gln Thr Gly Val Pro Ala
        50                  55                  60

Arg Phe Ser Gly Ser Gly Ser Arg Thr Asp Phe Thr Leu Thr Ile Asp
 65                  70                  75                  80

Pro Val Glu Glu Asp Asp Val Ala Val Tyr Tyr Cys Leu Gln Ser Arg
                 85                  90                  95

Thr Ile Pro Arg Thr Phe Gly Gly Gly Thr Lys Leu Glu Ile Lys Gly
                100                 105                 110

Ser Thr Ser Gly Ser Gly Lys Pro Gly Ser Gly Glu Gly Ser Thr Lys
            115                 120                 125

Gly Gln Ile Gln Leu Val Gln Ser Gly Pro Glu Leu Lys Lys Pro Gly
        130                 135                 140

Glu Thr Val Lys Ile Ser Cys Lys Ala Ser Gly Tyr Thr Phe Thr Asp
145                 150                 155                 160

Tyr Ser Ile Asn Trp Val Lys Arg Ala Pro Gly Lys Gly Leu Lys Trp
                165                 170                 175

Met Gly Trp Ile Asn Thr Glu Thr Arg Glu Pro Ala Tyr Ala Tyr Asp
            180                 185                 190

Phe Arg Gly Arg Phe Ala Phe Ser Leu Glu Thr Ser Ala Ser Thr Ala
        195                 200                 205

Tyr Leu Gln Ile Asn Asn Leu Lys Tyr Glu Asp Thr Ala Thr Tyr Phe
    210                 215                 220

Cys Ala Leu Asp Tyr Ser Tyr Ala Met Asp Tyr Trp Gly Gln Gly Thr
225                 230                 235                 240

Ser Val Thr Val Ser Ser Phe Val Pro Val Phe Leu Pro
                245                 250

<210> SEQ ID NO 102
<211> LENGTH: 242
<212> TYPE: PRT
<213> ORGANISM: Artificial Sequence
<220> FEATURE:
<223> OTHER INFORMATION: J22.1-xi scFv
```

<400> SEQUENCE: 102

```
Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Gly Asp Ala Met Asp Tyr Trp Gly Gln
            100                 105                 110

Gly Thr Ser Val Thr Val Ser Ser Gly Gly Gly Ser Gly Gly Gly
        115                 120                 125

Gly Ser Gly Gly Gly Gly Ser Asp Ile Val Met Thr Gln Ser Gln Arg
    130                 135                 140

Phe Met Thr Thr Ser Val Gly Asp Arg Val Ser Val Thr Cys Lys Ala
145                 150                 155                 160

Ser Gln Ser Val Asp Ser Asn Val Ala Trp Tyr Gln Gln Lys Pro Arg
                165                 170                 175

Gln Ser Pro Lys Ala Leu Ile Phe Ser Ala Ser Leu Arg Phe Ser Gly
            180                 185                 190

Val Pro Ala Arg Phe Thr Gly Ser Gly Ser Gly Thr Asp Phe Thr Leu
        195                 200                 205

Thr Ile Ser Asn Leu Gln Ser Glu Asp Leu Ala Glu Tyr Phe Cys Gln
    210                 215                 220

Gln Tyr Asn Asn Tyr Pro Leu Thr Phe Gly Ala Gly Thr Lys Leu Glu
225                 230                 235                 240

Leu Lys
```

<210> SEQ ID NO 103
<211> LENGTH: 247
<212> TYPE: PRT
<213> ORGANISM: Artificial Sequence
<220> FEATURE:
<223> OTHER INFORMATION: OKT3 scFv

<400> SEQUENCE: 103

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
```

```
             100                 105                 110
Thr Thr Leu Thr Val Ser Ser Gly Gly Gly Ser Gly Gly Gly
            115                 120                 125

Ser Gly Gly Gly Gly Ser Gln Ile Val Leu Thr Gln Ser Pro Ala Ile
            130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
            195                 200                 205

Ser Gly Met Glu Ala Glu Asp Ala Ala Thr Tyr Tyr Cys Gln Gln Trp
            210                 215                 220

Ser Ser Asn Pro Phe Thr Phe Gly Ser Gly Thr Lys Leu Glu Ile Asn
225                 230                 235                 240

Arg His His His His His
            245

<210> SEQ ID NO 104
<211> LENGTH: 249
<212> TYPE: PRT
<213> ORGANISM: Artificial Sequence
<220> FEATURE:
<223> OTHER INFORMATION: L2K.07 scFv

<400> SEQUENCE: 104

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
            115                 120                 125

Gly Ser Gly Gly Ser Gly Gly Val Asp Asp Ile Gln Leu Thr Gln Ser
            130                 135                 140

Pro Ala Ile Met Ser Ala Ser Pro Gly Glu Lys Val Thr Met Thr Cys
145                 150                 155                 160

Arg Ala Ser Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
            180                 185                 190

Gly Val Pro Tyr Arg Phe Ser Gly Ser Gly Ser Gly Thr Ser Tyr Ser
            195                 200                 205

Leu Thr Ile Ser Ser Met Glu Ala Glu Asp Ala Ala Thr Tyr Tyr Cys
```

```
                210                 215                 220
Gln Gln Trp Ser Ser Asn Pro Leu Thr Phe Gly Ala Gly Thr Lys Leu
225                 230                 235                 240

Glu Leu Lys His His His His His His
                245

<210> SEQ ID NO 105
<211> LENGTH: 250
<212> TYPE: PRT
<213> ORGANISM: Artificial Sequence
<220> FEATURE:
<223> OTHER INFORMATION: UCHT1 scFv

<400> SEQUENCE: 105

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
                20                  25                  30

Thr Met Asn Trp Val Lys Gln Ser His Gly Lys Asn Leu Glu Trp Met
            35                  40                  45

Gly Leu Ile Asn Pro Tyr Lys Gly Val Ser Thr Tyr Asn Gln Lys Phe
        50                  55                  60

Lys Asp Lys Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Ser Gly Tyr Tyr Gly Asp Ser Asp Trp Tyr Phe Asp Val Trp
                100                 105                 110

Gly Gln Gly Thr Thr Leu Thr Val Phe Ser Gly Gly Gly Gly Ser Gly
            115                 120                 125

Gly Gly Gly Ser Gly Gly Gly Ser Asp Ile Gln Met Thr Gln Thr
        130                 135                 140

Thr Ser Ser Leu Ser Ala Ser Leu Gly Asp Arg Val Thr Ile Ser Cys
145                 150                 155                 160

Arg Ala Ser Gln Asp Ile Arg Asn Tyr Leu Asn Trp Tyr Gln Gln Lys
                165                 170                 175

Pro Asp Gly Thr Val Lys Leu Leu Ile Tyr Tyr Thr Ser Arg Leu His
            180                 185                 190

Ser Gly Val Pro Ser Lys Phe Ser Gly Ser Gly Ser Gly Thr Asp Tyr
        195                 200                 205

Ser Leu Thr Ile Ser Asn Leu Glu Gln Glu Asp Ile Ala Thr Tyr Phe
    210                 215                 220

Cys Gln Gln Gly Asn Thr Leu Pro Trp Thr Phe Ala Gly Gly Thr Lys
225                 230                 235                 240

Leu Glu Ile Lys His His His His His His
                245                 250

<210> SEQ ID NO 106
<211> LENGTH: 386
<212> TYPE: PRT
<213> ORGANISM: Artificial Sequence
<220> FEATURE:
<223> OTHER INFORMATION: BCMA 269A37346 VHH-L2K.07 CATE

<400> SEQUENCE: 106

Gln Val Gln Leu Val Glu Ser Gly Gly Gly Leu Val Gln Pro Gly Gly
1               5                   10                  15
```

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser Gly Gly Gly Gly Ser Gly
        115                 120                 125

Gly Gly Gly Ser Gly Gly Gly Gly Ser Asp Ile Lys Leu Gln Gln Ser
    130                 135                 140

Gly Ala Glu Leu Ala Arg Pro Gly Ala Ser Val Lys Met Ser Cys Lys
145                 150                 155                 160

Thr Ser Gly Tyr Thr Phe Thr Arg Tyr Thr Met His Trp Val Lys Gln
                165                 170                 175

Arg Pro Gly Gln Gly Leu Glu Trp Ile Gly Tyr Ile Asn Pro Ser Arg
            180                 185                 190

Gly Tyr Thr Asn Tyr Asn Gln Lys Phe Lys Asp Lys Ala Thr Leu Thr
        195                 200                 205

Thr Asp Lys Ser Ser Ser Thr Ala Tyr Met Gln Leu Ser Ser Leu Thr
    210                 215                 220

Ser Glu Asp Ser Ala Val Tyr Tyr Cys Ala Arg Tyr Tyr Asp Asp His
225                 230                 235                 240

Tyr Cys Leu Asp Tyr Trp Gly Gln Gly Thr Thr Leu Thr Val Ser Ser
                245                 250                 255

Val Glu Gly Gly Ser Gly Gly Ser Gly Gly Ser Gly Gly Ser Gly Gly
            260                 265                 270

Val Asp Asp Ile Gln Leu Thr Gln Ser Pro Ala Ile Met Ser Ala Ser
        275                 280                 285

Pro Gly Glu Lys Val Thr Met Thr Cys Arg Ala Ser Ser Ser Val Ser
    290                 295                 300

Tyr Met Asn Trp Tyr Gln Gln Lys Ser Gly Thr Ser Pro Lys Arg Trp
305                 310                 315                 320

Ile Tyr Asp Thr Ser Lys Val Ala Ser Gly Val Pro Tyr Arg Phe Ser
                325                 330                 335

Gly Ser Gly Ser Gly Thr Ser Tyr Ser Leu Thr Ile Ser Ser Met Glu
            340                 345                 350

Ala Glu Asp Ala Ala Thr Tyr Tyr Cys Gln Gln Trp Ser Ser Asn Pro
        355                 360                 365

Leu Thr Phe Gly Ala Gly Thr Lys Leu Glu Leu Lys His His His His
    370                 375                 380

His His
385

<210> SEQ ID NO 107
<211> LENGTH: 392
<212> TYPE: PRT
<213> ORGANISM: Artificial Sequence
<220> FEATURE:
<223> OTHER INFORMATION: BCMA 269A37348 VHH-L2K.07 CATE

<400> SEQUENCE: 107

```
Gln Val Lys Leu Glu Glu Ser Gly Gly Arg Leu Val Gln Pro Arg Gly
1               5                   10                  15

Ser Leu Arg Leu Ser Cys Ala Gly Ser Gly Arg Thr Phe Ser Thr Tyr
            20                  25                  30

Gly Met Ala Trp Phe Arg Gln Ala Pro Gly Lys Glu Arg Glu Phe Val
        35                  40                  45

Ala Ser Lys Ala Ser Met Asn Tyr Ser Gly Arg Thr Tyr Tyr Ala Asp
    50                  55                  60

Ser Val Lys Gly Arg Phe Thr Ile Ala Arg Asp Asn Ala Lys Asn Met
65                  70                  75                  80

Val Phe Leu Gln Met Asn Asn Leu Lys Pro Glu Asp Thr Ala Val Tyr
                85                  90                  95

Tyr Cys Ala Ala Gly Thr Gly Cys Ser Thr Tyr Gly Cys Phe Asp Ala
            100                 105                 110

Gln Ile Ile Asp Tyr Trp Gly Lys Gly Thr Leu Val Thr Val Ser Ser
        115                 120                 125

Gly Gly Gly Gly Ser Gly Gly Gly Ser Gly Gly Gly Gly Ser Asp
130                 135                 140

Ile Lys Leu Gln Gln Ser Gly Ala Glu Leu Ala Arg Pro Gly Ala Ser
145                 150                 155                 160

Val Lys Met Ser Cys Lys Thr Ser Gly Tyr Thr Phe Thr Arg Tyr Thr
                165                 170                 175

Met His Trp Val Lys Gln Arg Pro Gly Gln Gly Leu Glu Trp Ile Gly
            180                 185                 190

Tyr Ile Asn Pro Ser Arg Gly Tyr Thr Asn Tyr Asn Gln Lys Phe Lys
        195                 200                 205

Asp Lys Ala Thr Leu Thr Thr Asp Lys Ser Ser Ser Thr Ala Tyr Met
    210                 215                 220

Gln Leu Ser Ser Leu Thr Ser Glu Asp Ser Ala Val Tyr Tyr Cys Ala
225                 230                 235                 240

Arg Tyr Tyr Asp Asp His Tyr Cys Leu Asp Tyr Trp Gly Gln Gly Thr
                245                 250                 255

Thr Leu Thr Val Ser Ser Val Glu Gly Gly Ser Gly Gly Ser Gly Gly
            260                 265                 270

Ser Gly Gly Ser Gly Gly Val Asp Asp Ile Gln Leu Thr Gln Ser Pro
        275                 280                 285

Ala Ile Met Ser Ala Ser Pro Gly Glu Lys Val Thr Met Thr Cys Arg
    290                 295                 300

Ala Ser Ser Ser Val Ser Tyr Met Asn Trp Tyr Gln Gln Lys Ser Gly
305                 310                 315                 320

Thr Ser Pro Lys Arg Trp Ile Tyr Asp Thr Ser Lys Val Ala Ser Gly
                325                 330                 335

Val Pro Tyr Arg Phe Ser Gly Ser Gly Ser Gly Thr Ser Tyr Ser Leu
            340                 345                 350

Thr Ile Ser Ser Met Glu Ala Glu Asp Ala Ala Thr Tyr Tyr Cys Gln
        355                 360                 365

Gln Trp Ser Ser Asn Pro Leu Thr Phe Gly Ala Gly Thr Lys Leu Glu
    370                 375                 380

Leu Lys His His His His His His
385                 390
```

```
<210> SEQ ID NO 108
<211> LENGTH: 382
<212> TYPE: PRT
<213> ORGANISM: Artificial Sequence
<220> FEATURE:
<223> OTHER INFORMATION: BCMA 269A37917 VHH-L2K.07 CATE

<400> SEQUENCE: 108

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser Gly Gly Gly Gly Ser Gly Gly Gly Gly Ser
        115                 120                 125

Gly Gly Gly Gly Ser Asp Ile Lys Leu Gln Gln Ser Gly Ala Glu Leu
    130                 135                 140

Ala Arg Pro Gly Ala Ser Val Lys Met Ser Cys Lys Thr Ser Gly Tyr
145                 150                 155                 160

Thr Phe Thr Arg Tyr Thr Met His Trp Val Lys Gln Arg Pro Gly Gln
                165                 170                 175

Gly Leu Glu Trp Ile Gly Tyr Ile Asn Pro Ser Arg Gly Tyr Thr Asn
            180                 185                 190

Tyr Asn Gln Lys Phe Lys Asp Lys Ala Thr Leu Thr Thr Asp Lys Ser
        195                 200                 205

Ser Ser Thr Ala Tyr Met Gln Leu Ser Ser Leu Thr Ser Glu Asp Ser
    210                 215                 220

Ala Val Tyr Tyr Cys Ala Arg Tyr Tyr Asp Asp His Tyr Cys Leu Asp
225                 230                 235                 240

Tyr Trp Gly Gln Gly Thr Thr Leu Thr Val Ser Ser Val Glu Gly Gly
                245                 250                 255

Ser Gly Gly Ser Gly Gly Ser Gly Gly Ser Gly Gly Val Asp Asp Ile
            260                 265                 270

Gln Leu Thr Gln Ser Pro Ala Ile Met Ser Ala Ser Pro Gly Glu Lys
        275                 280                 285

Val Thr Met Thr Cys Arg Ala Ser Ser Ser Val Ser Tyr Met Asn Trp
    290                 295                 300

Tyr Gln Gln Lys Ser Gly Thr Ser Pro Lys Arg Trp Ile Tyr Asp Thr
305                 310                 315                 320

Ser Lys Val Ala Ser Gly Val Pro Tyr Arg Phe Ser Gly Ser Gly Ser
                325                 330                 335

Gly Thr Ser Tyr Ser Leu Thr Ile Ser Ser Met Glu Ala Glu Asp Ala
            340                 345                 350

Ala Thr Tyr Tyr Cys Gln Gln Trp Ser Ser Asn Pro Leu Thr Phe Gly
        355                 360                 365

Ala Gly Thr Lys Leu Glu Leu Lys His His His His His His
```

<210> SEQ ID NO 109
<211> LENGTH: 384
<212> TYPE: PRT
<213> ORGANISM: Artificial Sequence
<220> FEATURE:
<223> OTHER INFORMATION: BCMA 269A37355 VHH-L2K.07 CATE

<400> SEQUENCE: 109

```
Ala Val Gln Leu Val Asp Ser Gly Gly Gly Leu Val Gln Pro Gly Gly
1               5                   10                  15

Ser Leu Arg Leu Ser Cys Val Ala Ser Gly Gly Ile Phe Val Ile Asn
            20                  25                  30

Ala Met Gly Trp Tyr Arg Gln Ala Pro Gly Lys Gln Arg Glu Leu Val
        35                  40                  45

Ala Ser Ile Arg Gly Leu Gly Arg Thr Asn Tyr Asp Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Ser Leu Glu Pro Glu Asp Thr Ala Val Tyr Tyr Cys Thr
                85                  90                  95

Val Tyr Val Thr Leu Leu Gly Val Asn Arg Asp Tyr Trp Gly Gln
            100                 105                 110

Gly Thr Gln Val Thr Val Ser Ser Gly Gly Gly Gly Ser Gly Gly Gly
        115                 120                 125

Gly Ser Gly Gly Gly Gly Ser Asp Ile Lys Leu Gln Gln Ser Gly Ala
    130                 135                 140

Glu Leu Ala Arg Pro Gly Ala Ser Val Lys Met Ser Cys Lys Thr Ser
145                 150                 155                 160

Gly Tyr Thr Phe Thr Arg Tyr Thr Met His Trp Val Lys Gln Arg Pro
                165                 170                 175

Gly Gln Gly Leu Glu Trp Ile Gly Tyr Ile Asn Pro Ser Arg Gly Tyr
            180                 185                 190

Thr Asn Tyr Asn Gln Lys Phe Lys Asp Lys Ala Thr Leu Thr Thr Asp
        195                 200                 205

Lys Ser Ser Ser Thr Ala Tyr Met Gln Leu Ser Ser Leu Thr Ser Glu
    210                 215                 220

Asp Ser Ala Val Tyr Tyr Cys Ala Arg Tyr Tyr Asp Asp His Tyr Cys
225                 230                 235                 240

Leu Asp Tyr Trp Gly Gln Gly Thr Thr Leu Thr Val Ser Ser Val Glu
                245                 250                 255

Gly Gly Ser Gly Gly Ser Gly Gly Ser Gly Gly Ser Gly Gly Val Asp
            260                 265                 270

Asp Ile Gln Leu Thr Gln Ser Pro Ala Ile Met Ser Ala Ser Pro Gly
        275                 280                 285

Glu Lys Val Thr Met Thr Cys Arg Ala Ser Ser Ser Val Ser Tyr Met
    290                 295                 300

Asn Trp Tyr Gln Gln Lys Ser Gly Thr Ser Pro Lys Arg Trp Ile Tyr
305                 310                 315                 320

Asp Thr Ser Lys Val Ala Ser Gly Val Pro Tyr Arg Phe Ser Gly Ser
                325                 330                 335

Gly Ser Gly Thr Ser Tyr Ser Leu Thr Ile Ser Ser Met Glu Ala Glu
            340                 345                 350

Asp Ala Ala Thr Tyr Tyr Cys Gln Gln Trp Ser Ser Asn Pro Leu Thr
```

```
<210> SEQ ID NO 110
<211> LENGTH: 383
<212> TYPE: PRT
<213> ORGANISM: Artificial Sequence
<220> FEATURE:
<223> OTHER INFORMATION: BCMA 269A37915 VHH-L2K.07 CATE

<400> SEQUENCE: 110
```

| | | | | | | | | | | | | | | |
|---|---|---|---|---|---|---|---|---|---|---|---|---|---|---|
| Phe | Gly | Ala | Gly | Thr | Lys | Leu | Glu | Leu | Lys | His | His | His | His | His |
| 370 | | | | 375 | | | | | 380 | | | | | |
| Glu | Val | Gln | Leu | Val | Glu | Ser | Gly | Gly | Gly | Leu | Val | Gln | Ala | Gly |
| 1 | | | | 5 | | | | | 10 | | | | | 15 |
| Ser | Leu | Arg | Leu | Ser | Cys | Ala | Ala | Ser | Gly | Arg | Thr | Phe | Ser | Ile |
| | | | 20 | | | | | 25 | | | | | 30 | |
| Val | Met | Gly | Trp | Phe | Arg | Gln | Ala | Pro | Gly | Lys | Glu | Arg | Glu | Phe | Val |
| | | 35 | | | | | 40 | | | | | 45 | | | |
| Gly | Ala | Ile | Met | Trp | Asn | Asp | Gly | Ile | Thr | Tyr | Leu | Gln | Asp | Ser | Val |
| | 50 | | | | | 55 | | | | | 60 | | | | |
| Lys | Gly | Arg | Phe | Thr | Ile | Phe | Arg | Asp | Asn | Ala | Lys | Asn | Thr | Val | Tyr |
| 65 | | | | | 70 | | | | | 75 | | | | | 80 |
| Leu | Gln | Met | Asn | Ser | Leu | Lys | Leu | Glu | Asp | Thr | Ala | Val | Tyr | Tyr | Cys |
| | | | | 85 | | | | | 90 | | | | | 95 | |
| Ala | Ala | Ser | Lys | Gly | Arg | Tyr | Ser | Glu | Tyr | Glu | Tyr | Trp | Gly | Gln | Gly |
| | | | 100 | | | | | 105 | | | | | 110 | | |
| Thr | Gln | Val | Thr | Val | Ser | Ser | Gly | Gly | Gly | Ser | Gly | Gly | Gly | Gly |
| | | | 115 | | | | | 120 | | | | | 125 | | |
| Ser | Gly | Gly | Gly | Gly | Ser | Asp | Ile | Lys | Leu | Gln | Gln | Ser | Gly | Ala | Glu |
| | 130 | | | | | 135 | | | | | 140 | | | | |
| Leu | Ala | Arg | Pro | Gly | Ala | Ser | Val | Lys | Met | Ser | Cys | Lys | Thr | Ser | Gly |
| 145 | | | | | 150 | | | | | 155 | | | | | 160 |
| Tyr | Thr | Phe | Thr | Arg | Tyr | Thr | Met | His | Trp | Val | Lys | Gln | Arg | Pro | Gly |
| | | | | 165 | | | | | 170 | | | | | 175 | |
| Gln | Gly | Leu | Glu | Trp | Ile | Gly | Tyr | Ile | Asn | Pro | Ser | Arg | Gly | Tyr | Thr |
| | | | 180 | | | | | 185 | | | | | 190 | | |
| Asn | Tyr | Asn | Gln | Lys | Phe | Lys | Asp | Lys | Ala | Thr | Leu | Thr | Thr | Asp | Lys |
| | | 195 | | | | | 200 | | | | | 205 | | | |
| Ser | Ser | Ser | Thr | Ala | Tyr | Met | Gln | Leu | Ser | Ser | Leu | Thr | Ser | Glu | Asp |
| | 210 | | | | | 215 | | | | | 220 | | | | |
| Ser | Ala | Val | Tyr | Tyr | Cys | Ala | Arg | Tyr | Tyr | Asp | Asp | His | Tyr | Cys | Leu |
| 225 | | | | | 230 | | | | | 235 | | | | | 240 |
| Asp | Tyr | Trp | Gly | Gln | Gly | Thr | Thr | Leu | Thr | Val | Ser | Ser | Val | Glu | Gly |
| | | | | 245 | | | | | 250 | | | | | 255 | |
| Gly | Ser | Gly | Gly | Ser | Gly | Gly | Ser | Gly | Gly | Ser | Gly | Gly | Val | Asp | Asp |
| | | | 260 | | | | | 265 | | | | | 270 | | |
| Ile | Gln | Leu | Thr | Gln | Ser | Pro | Ala | Ile | Met | Ser | Ala | Ser | Pro | Gly | Glu |
| | | 275 | | | | | 280 | | | | | 285 | | | |
| Lys | Val | Thr | Met | Thr | Cys | Arg | Ala | Ser | Ser | Val | Ser | Tyr | Met | Asn |
| | 290 | | | | | 295 | | | | | 300 | | | | |
| Trp | Tyr | Gln | Gln | Lys | Ser | Gly | Thr | Ser | Pro | Lys | Arg | Trp | Ile | Tyr | Asp |
| 305 | | | | | 310 | | | | | 315 | | | | | 320 |
| Thr | Ser | Lys | Val | Ala | Ser | Gly | Val | Pro | Tyr | Arg | Phe | Ser | Gly | Ser | Gly |
| | | | | 325 | | | | | 330 | | | | | 335 | |
| Ser | Gly | Thr | Ser | Tyr | Ser | Leu | Thr | Ile | Ser | Ser | Met | Glu | Ala | Glu | Asp |

```
                   340                 345                 350
Ala Ala Thr Tyr Tyr Cys Gln Gln Trp Ser Ser Asn Pro Leu Thr Phe
            355                 360                 365

Gly Ala Gly Thr Lys Leu Glu Leu Lys His His His His His His
370                 375                 380

<210> SEQ ID NO 111
<211> LENGTH: 392
<212> TYPE: PRT
<213> ORGANISM: Artificial Sequence
<220> FEATURE:
<223> OTHER INFORMATION: BCMA 269A37936 VHH-L2K.07 CATE

<400> SEQUENCE: 111

Glu Val Gln Leu Val Glu Ser Gly Gly Gly Val Val Gln Ala Gly Gly
1               5                   10                  15

Ser Leu Thr Val Ser Cys Thr Ala Ser Gly Phe Thr Phe Asp Arg Ala
            20                  25                  30

Val Ile Val Trp Phe Arg Gln Ala Pro Gly Lys Gly Arg Glu Gly Val
        35                  40                  45

Ser Phe Ile Lys Pro Ser Asp Gly Thr Ile Tyr Tyr Ile Asp Ser Leu
50                  55                  60

Lys Gly Arg Phe Thr Ile Ser Ser Asp Ile Ala Lys Asn Thr Val Tyr
65                  70                  75                  80

Leu Gln Met Lys Ser Leu Glu Ser Glu Asp Ser Ala Val Tyr Tyr Cys
                85                  90                  95

Ala Ala Ser Pro Glu Asp Trp Tyr Thr Asp Trp Ile Asp Trp Ser Ile
            100                 105                 110

Tyr Arg Trp Gln His Trp Gly Gln Gly Thr Gln Val Thr Val Ser Ser
        115                 120                 125

Gly Gly Gly Gly Ser Gly Gly Gly Ser Gly Gly Gly Ser Asp
130                 135                 140

Ile Lys Leu Gln Gln Ser Gly Ala Glu Leu Ala Arg Pro Gly Ala Ser
145                 150                 155                 160

Val Lys Met Ser Cys Lys Thr Ser Gly Tyr Thr Phe Thr Arg Tyr Thr
                165                 170                 175

Met His Trp Val Lys Gln Arg Pro Gly Gln Gly Leu Glu Trp Ile Gly
            180                 185                 190

Tyr Ile Asn Pro Ser Arg Gly Tyr Thr Asn Tyr Asn Gln Lys Phe Lys
        195                 200                 205

Asp Lys Ala Thr Leu Thr Thr Asp Lys Ser Ser Ser Thr Ala Tyr Met
210                 215                 220

Gln Leu Ser Ser Leu Thr Ser Glu Asp Ser Ala Val Tyr Tyr Cys Ala
225                 230                 235                 240

Arg Tyr Tyr Asp Asp His Tyr Cys Leu Asp Tyr Trp Gly Gln Gly Thr
                245                 250                 255

Thr Leu Thr Val Ser Ser Val Glu Gly Gly Ser Gly Gly Ser Gly Gly
            260                 265                 270

Ser Gly Gly Ser Gly Gly Val Asp Asp Ile Gln Leu Thr Gln Ser Pro
        275                 280                 285

Ala Ile Met Ser Ala Ser Pro Gly Glu Lys Val Thr Met Thr Cys Arg
        290                 295                 300

Ala Ser Ser Ser Val Ser Tyr Met Asn Trp Tyr Gln Gln Lys Ser Gly
305                 310                 315                 320

Thr Ser Pro Lys Arg Trp Ile Tyr Asp Thr Ser Lys Val Ala Ser Gly
```

```
                    325                 330                 335
Val Pro Tyr Arg Phe Ser Gly Ser Gly Ser Gly Thr Ser Tyr Ser Leu
            340                 345                 350

Thr Ile Ser Ser Met Glu Ala Glu Asp Ala Ala Thr Tyr Tyr Cys Gln
            355                 360                 365

Gln Trp Ser Ser Asn Pro Leu Thr Phe Gly Ala Gly Thr Lys Leu Glu
            370                 375                 380

Leu Lys His His His His His His
385                 390

<210> SEQ ID NO 112
<211> LENGTH: 383
<212> TYPE: PRT
<213> ORGANISM: Artificial Sequence
<220> FEATURE:
<223> OTHER INFORMATION: BCMA 269A37953 VHH-L2K.07 CATE

<400> SEQUENCE: 112

Glu Val Gln Leu Val Glu Ser Gly Gly Gly Met Val Gln Ala Gly Asp
1               5                   10                  15

Ser Leu Arg Leu Ser Cys Val Gln Ser Thr Tyr Thr Val Asn Ser Asp
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Glu Tyr Trp Gly Gln Gly
            100                 105                 110

Thr Gln Val Thr Val Ser Ser Gly Gly Gly Gly Ser Gly Gly Gly Gly
        115                 120                 125

Ser Gly Gly Gly Gly Ser Asp Ile Lys Leu Gln Gln Ser Gly Ala Glu
    130                 135                 140

Leu Ala Arg Pro Gly Ala Ser Val Lys Met Ser Cys Lys Thr Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
        195                 200                 205

Ser Ser Ser Thr Ala Tyr Met Gln Leu Ser Ser Leu Thr Ser Glu Asp
    210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Val Glu Gly
                245                 250                 255

Gly Ser Gly Gly Ser Gly Gly Ser Gly Gly Ser Gly Gly Val Asp Asp
            260                 265                 270

Ile Gln Leu Thr Gln Ser Pro Ala Ile Met Ser Ala Ser Pro Gly Glu
        275                 280                 285

Lys Val Thr Met Thr Cys Arg Ala Ser Ser Ser Val Ser Tyr Met Asn
```

```
                290             295             300
Trp Tyr Gln Gln Lys Ser Gly Thr Ser Pro Lys Arg Trp Ile Tyr Asp
305                 310                 315                 320

Thr Ser Lys Val Ala Ser Gly Val Pro Tyr Arg Phe Ser Gly Ser Gly
                325                 330                 335

Ser Gly Thr Ser Tyr Ser Leu Thr Ile Ser Ser Met Glu Ala Glu Asp
                340                 345                 350

Ala Ala Thr Tyr Tyr Cys Gln Gln Trp Ser Ser Asn Pro Leu Thr Phe
                355                 360                 365

Gly Ala Gly Thr Lys Leu Glu Leu Lys His His His His His His
                370                 375                 380

<210> SEQ ID NO 113
<211> LENGTH: 384
<212> TYPE: PRT
<213> ORGANISM: Artificial Sequence
<220> FEATURE:
<223> OTHER INFORMATION: BCMA 269A37965 VHH-L2K.07 CATE

<400> SEQUENCE: 113

Ala Val Gln Leu Val Glu Ser Gly Gly Gly Leu Val Gln Ala Gly Asp
1               5                   10                  15

Ser Leu Arg Leu Ser Cys Thr Ala Ser Gly Ala Thr Leu Thr Asn Asp
                20                  25                  30

His Met Ala Trp Phe Arg Gln Ala Pro Gly Lys Gly Arg Glu Phe Val
                35                  40                  45

Ala Ala Ile Asp Trp Ser Gly Arg Thr Thr Asn Tyr Ala Asp Pro Val
            50                  55                  60

Glu Gly Arg Phe Thr Ile Ser Arg Asn Asn Ala Lys Asn Thr Val Tyr
65              70                  75                  80

Leu Glu Met Asn Ser Leu Lys Leu Glu Asp Thr Ala Val Tyr Tyr Cys
                85                  90                  95

Ala Val Leu Arg Ala Trp Ile Ser Tyr Asp Asn Asp Tyr Trp Gly Gln
                100                 105                 110

Gly Thr Gln Val Thr Val Ser Ser Gly Gly Gly Gly Ser Gly Gly Gly
                115                 120                 125

Gly Ser Gly Gly Gly Gly Ser Asp Ile Lys Leu Gln Gln Ser Gly Ala
            130                 135                 140

Glu Leu Ala Arg Pro Gly Ala Ser Val Lys Met Ser Cys Lys Thr Ser
145                 150                 155                 160

Gly Tyr Thr Phe Thr Arg Tyr Thr Met His Trp Val Lys Gln Arg Pro
                165                 170                 175

Gly Gln Gly Leu Glu Trp Ile Gly Tyr Ile Asn Pro Ser Arg Gly Tyr
                180                 185                 190

Thr Asn Tyr Asn Gln Lys Phe Lys Asp Lys Ala Thr Leu Thr Thr Asp
                195                 200                 205

Lys Ser Ser Ser Thr Ala Tyr Met Gln Leu Ser Ser Leu Thr Ser Glu
            210                 215                 220

Asp Ser Ala Val Tyr Tyr Cys Ala Arg Tyr Tyr Asp Asp His Tyr Cys
225                 230                 235                 240

Leu Asp Tyr Trp Gly Gln Gly Thr Thr Leu Thr Val Ser Ser Val Glu
                245                 250                 255

Gly Gly Ser Gly Gly Ser Gly Gly Ser Gly Gly Ser Gly Gly Val Asp
                260                 265                 270

Asp Ile Gln Leu Thr Gln Ser Pro Ala Ile Met Ser Ala Ser Pro Gly
```

```
                275                 280                 285
Glu Lys Val Thr Met Thr Cys Arg Ala Ser Ser Val Ser Tyr Met
290                 295                 300
Asn Trp Tyr Gln Gln Lys Ser Gly Thr Ser Pro Lys Arg Trp Ile Tyr
305                 310                 315                 320
Asp Thr Ser Lys Val Ala Ser Gly Val Pro Tyr Arg Phe Ser Gly Ser
                325                 330                 335
Gly Ser Gly Thr Ser Tyr Ser Leu Thr Ile Ser Ser Met Glu Ala Glu
            340                 345                 350
Asp Ala Ala Thr Tyr Tyr Cys Gln Gln Trp Ser Ser Asn Pro Leu Thr
            355                 360                 365
Phe Gly Ala Gly Thr Lys Leu Glu Leu Lys His His His His His His
370                 375                 380
```

<210> SEQ ID NO 114
<211> LENGTH: 384
<212> TYPE: PRT
<213> ORGANISM: Artificial Sequence
<220> FEATURE:
<223> OTHER INFORMATION: BCMA 269A37972 VHH-L2K.07 CATE

<400> SEQUENCE: 114

```
Gln Val Gln Leu Val Glu Ser Gly Gly Gly Leu Val Gln Ala Gly Gly
1               5                   10                  15
Ser Leu Arg Leu Ser Cys Ala Ala Ser Gly Gly Thr Leu Ser Lys Asn
            20                  25                  30
Thr Val Ala Trp Phe Arg Gln Ala Pro Gly Lys Glu Arg Gly Phe Val
        35                  40                  45
Ala Ser Ile Thr Trp Asp Gly Arg Thr Thr Tyr Tyr Ala Asp Ser Val
    50                  55                  60
Lys Gly Arg Phe Thr Ile Ser Arg Asp Asn Ala Lys Asn Thr Val Tyr
65                  70                  75                  80
Leu Gln Met Asn Ser Leu Lys Pro Glu Asp Thr Ala Val Tyr Val Cys
                85                  90                  95
Ala Asp Leu Gly Lys Trp Pro Ala Gly Pro Ala Asp Tyr Trp Gly Gln
            100                 105                 110
Gly Thr Gln Val Thr Val Ser Ser Gly Gly Gly Gly Ser Gly Gly Gly
        115                 120                 125
Gly Ser Gly Gly Gly Gly Ser Asp Ile Lys Leu Gln Gln Ser Gly Ala
    130                 135                 140
Glu Leu Ala Arg Pro Gly Ala Ser Val Lys Met Ser Cys Lys Thr Ser
145                 150                 155                 160
Gly Tyr Thr Phe Thr Arg Tyr Thr Met His Trp Val Lys Gln Arg Pro
                165                 170                 175
Gly Gln Gly Leu Glu Trp Ile Gly Tyr Ile Asn Pro Ser Arg Gly Tyr
            180                 185                 190
Thr Asn Tyr Asn Gln Lys Phe Lys Asp Lys Ala Thr Leu Thr Thr Asp
        195                 200                 205
Lys Ser Ser Ser Thr Ala Tyr Met Gln Leu Ser Ser Leu Thr Ser Glu
    210                 215                 220
Asp Ser Ala Val Tyr Tyr Cys Ala Arg Tyr Tyr Asp Asp His Tyr Cys
225                 230                 235                 240
Leu Asp Tyr Trp Gly Gln Gly Thr Thr Leu Thr Val Ser Ser Val Glu
                245                 250                 255
Gly Gly Ser Gly Gly Ser Gly Gly Ser Gly Gly Ser Gly Gly Val Asp
```

```
            260                 265                 270
Asp Ile Gln Leu Thr Gln Ser Pro Ala Ile Met Ser Ala Ser Pro Gly
                275                 280                 285
Glu Lys Val Thr Met Thr Cys Arg Ala Ser Ser Ser Val Ser Tyr Met
            290                 295                 300
Asn Trp Tyr Gln Gln Lys Ser Gly Thr Ser Pro Lys Arg Trp Ile Tyr
305                 310                 315                 320
Asp Thr Ser Lys Val Ala Ser Gly Val Pro Tyr Arg Phe Ser Gly Ser
                325                 330                 335
Gly Ser Gly Thr Ser Tyr Ser Leu Thr Ile Ser Ser Met Glu Ala Glu
            340                 345                 350
Asp Ala Ala Thr Tyr Tyr Cys Gln Gln Trp Ser Ser Asn Pro Leu Thr
                355                 360                 365
Phe Gly Ala Gly Thr Lys Leu Glu Leu Lys His His His His His His
            370                 375                 380

<210> SEQ ID NO 115
<211> LENGTH: 383
<212> TYPE: PRT
<213> ORGANISM: Artificial Sequence
<220> FEATURE:
<223> OTHER INFORMATION: BCMA 269A37353 VHH-L2K.07 CATE

<400> SEQUENCE: 115

Gln Val Lys Leu Glu Glu Ser Gly Gly Gly Leu Val Gln Ala Gly Arg
1               5                   10                  15
Ser Leu Arg Leu Ser Cys Ala Ala Ser Glu His Thr Phe Ser Ser His
            20                  25                  30
Val Met Gly Trp Phe Arg Gln Ala Pro Gly Lys Glu Arg Glu Ser Val
        35                  40                  45
Ala Val Ile Gly Trp Arg Asp Ile Ser Thr Ser Tyr Ala Asp Ser Val
    50                  55                  60
Lys Gly Arg Phe Thr Ile Ser Arg Asp Asn Ala Lys Lys Thr Leu Tyr
65                  70                  75                  80
Leu Gln Met Asn Ser Leu Lys Pro Glu Asp Thr Ala Val Tyr Tyr Cys
                85                  90                  95
Ala Ala Arg Arg Ile Asp Ala Ala Asp Phe Asp Ser Trp Gly Gln Gly
            100                 105                 110
Thr Gln Val Thr Val Ser Ser Gly Gly Gly Ser Gly Gly Gly Gly
        115                 120                 125
Ser Gly Gly Gly Ser Asp Ile Lys Leu Gln Gln Ser Gly Ala Glu
            130                 135                 140
Leu Ala Arg Pro Gly Ala Ser Val Lys Met Ser Cys Lys Thr Ser Gly
145                 150                 155                 160
Tyr Thr Phe Thr Arg Tyr Thr Met His Trp Val Lys Gln Arg Pro Gly
                165                 170                 175
Gln Gly Leu Glu Trp Ile Gly Tyr Ile Asn Pro Ser Arg Gly Tyr Thr
            180                 185                 190
Asn Tyr Asn Gln Lys Phe Lys Asp Lys Ala Thr Leu Thr Thr Asp Lys
        195                 200                 205
Ser Ser Ser Thr Ala Tyr Met Gln Leu Ser Ser Leu Thr Ser Glu Asp
    210                 215                 220
Ser Ala Val Tyr Tyr Cys Ala Arg Tyr Tyr Asp Asp His Tyr Cys Leu
225                 230                 235                 240
Asp Tyr Trp Gly Gln Gly Thr Thr Leu Thr Val Ser Ser Val Glu Gly
```

```
                    245                 250                 255
Gly Ser Gly Gly Ser Gly Gly Ser Gly Gly Ser Gly Gly Val Asp Asp
            260                 265                 270

Ile Gln Leu Thr Gln Ser Pro Ala Ile Met Ser Ala Ser Pro Gly Glu
            275                 280                 285

Lys Val Thr Met Thr Cys Arg Ala Ser Ser Ser Val Ser Tyr Met Asn
            290                 295                 300

Trp Tyr Gln Gln Lys Ser Gly Thr Ser Pro Lys Arg Trp Ile Tyr Asp
305                 310                 315                 320

Thr Ser Lys Val Ala Ser Gly Val Pro Tyr Arg Phe Ser Gly Ser Gly
                325                 330                 335

Ser Gly Thr Ser Tyr Ser Leu Thr Ile Ser Ser Met Glu Ala Glu Asp
            340                 345                 350

Ala Ala Thr Tyr Tyr Cys Gln Gln Trp Ser Ser Asn Pro Leu Thr Phe
            355                 360                 365

Gly Ala Gly Thr Lys Leu Glu Leu Lys His His His His His His
            370                 375                 380
```

<210> SEQ ID NO 116
<211> LENGTH: 383
<212> TYPE: PRT
<213> ORGANISM: Artificial Sequence
<220> FEATURE:
<223> OTHER INFORMATION: BCMA 269A37948 VHH-L2K.07 CATE

<400> SEQUENCE: 116

```
Ala Val Gln Leu Val Glu Ser Gly Gly Gly Leu Val Gln Ala Gly Asp
1               5                   10                  15

Ser Leu Arg Leu Thr Cys Thr Ala Ser Gly Arg Ala Phe Ser Thr Tyr
            20                  25                  30

Phe Met Ala Trp Phe Arg Gln Ala Pro Gly Lys Glu Arg Glu Phe Val
            35                  40                  45

Ala Gly Ile Ala Trp Ser Gly Ser Thr Ala Tyr Ala Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Ser Glu Asp Thr Ala Val Tyr Tyr Cys
            85                  90                  95

Ala Ser Arg Gly Ile Glu Val Glu Glu Phe Gly Ala Trp Gly Gln Gly
            100                 105                 110

Thr Gln Val Thr Val Ser Ser Gly Gly Gly Gly Ser Gly Gly Gly Gly
            115                 120                 125

Ser Gly Gly Gly Gly Ser Asp Ile Lys Leu Gln Gln Ser Gly Ala Glu
            130                 135                 140

Leu Ala Arg Pro Gly Ala Ser Val Lys Met Ser Cys Lys Thr Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
            195                 200                 205

Ser Ser Ser Thr Ala Tyr Met Gln Leu Ser Ser Leu Thr Ser Glu Asp
            210                 215                 220

Ser Ala Val Tyr Tyr Cys Ala Arg Tyr Tyr Asp Asp His Tyr Cys Leu
```

```
                    225                 230                 235                 240
Asp Tyr Trp Gly Gln Gly Thr Thr Leu Thr Val Ser Ser Val Glu Gly
                245                 250                 255

Gly Ser Gly Gly Ser Gly Gly Ser Gly Gly Ser Gly Gly Val Asp Asp
                260                 265                 270

Ile Gln Leu Thr Gln Ser Pro Ala Ile Met Ser Ala Ser Pro Gly Glu
                275                 280                 285

Lys Val Thr Met Thr Cys Arg Ala Ser Ser Ser Val Ser Tyr Met Asn
                290                 295                 300

Trp Tyr Gln Gln Lys Ser Gly Thr Ser Pro Lys Arg Trp Ile Tyr Asp
305                 310                 315                 320

Thr Ser Lys Val Ala Ser Gly Val Pro Tyr Arg Phe Ser Gly Ser Gly
                325                 330                 335

Ser Gly Thr Ser Tyr Ser Leu Thr Ile Ser Ser Met Glu Ala Glu Asp
                340                 345                 350

Ala Ala Thr Tyr Tyr Cys Gln Gln Trp Ser Ser Asn Pro Leu Thr Phe
                355                 360                 365

Gly Ala Gly Thr Lys Leu Glu Leu Lys His His His His His His
                370                 375                 380
```

<210> SEQ ID NO 117
<211> LENGTH: 384
<212> TYPE: PRT
<213> ORGANISM: Artificial Sequence
<220> FEATURE:
<223> OTHER INFORMATION: BCMA 269A37346 VHH-OKT3 CATE

<400> SEQUENCE: 117

```
Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
                20                  25                  30

Ala Ile Gly Trp Phe Arg Gln Ala Pro Gly Lys Glu Arg Glu Gly Val
                35                  40                  45

Ile Cys Ile Ser Arg Ser Asp Gly Ser Thr Tyr Tyr Ala Asp Ser Val
                50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
                100                 105                 110

Gly Gln Gly Thr Gln Val Thr Val Ser Ser Gly Gly Gly Gly Ser Gly
                115                 120                 125

Gly Gly Gly Ser Gly Gly Gly Ser Gln Val Gln Leu Gln Gln Ser
                130                 135                 140

Gly Ala Glu Leu Ala Arg Pro Gly Ala Ser Val Lys Met Ser Cys Lys
145                 150                 155                 160

Ala Ser Gly Tyr Thr Phe Thr Arg Tyr Thr Met His Trp Val Lys Gln
                165                 170                 175

Arg Pro Gly Gln Gly Leu Glu Trp Ile Gly Tyr Ile Asn Pro Ser Arg
                180                 185                 190

Gly Tyr Thr Asn Tyr Asn Gln Lys Phe Lys Asp Lys Ala Thr Leu Thr
                195                 200                 205

Thr Asp Lys Ser Ser Ser Thr Ala Tyr Met Gln Leu Ser Ser Leu Thr
```

Ser Glu Asp Ser Ala Val Tyr Tyr Cys Ala Arg Tyr Tyr Asp Asp His
225                 230                 235                 240

Tyr Cys Leu Asp Tyr Trp Gly Gln Gly Thr Thr Leu Thr Val Ser Ser
            245                 250                 255

Gly Gly Gly Gly Ser Gly Gly Gly Gly Ser Gly Gly Gly Gly Ser Gln
        260                 265                 270

Ile Val Leu Thr Gln Ser Pro Ala Ile Met Ser Ala Ser Pro Gly Glu
            275                 280                 285

Lys Val Thr Met Thr Cys Ser Ala Ser Ser Val Ser Tyr Met Asn
        290                 295                 300

Trp Tyr Gln Gln Lys Ser Gly Thr Ser Pro Lys Arg Trp Ile Tyr Asp
305                 310                 315                 320

Thr Ser Lys Leu Ala Ser Gly Val Pro Ala His Phe Arg Gly Ser Gly
            325                 330                 335

Ser Gly Thr Ser Tyr Ser Leu Thr Ile Ser Gly Met Glu Ala Glu Asp
        340                 345                 350

Ala Ala Thr Tyr Tyr Cys Gln Gln Trp Ser Ser Asn Pro Phe Thr Phe
            355                 360                 365

Gly Ser Gly Thr Lys Leu Glu Ile Asn Arg His His His His His His
        370                 375                 380

<210> SEQ ID NO 118
<211> LENGTH: 390
<212> TYPE: PRT
<213> ORGANISM: Artificial Sequence
<220> FEATURE:
<223> OTHER INFORMATION: BCMA 269A37348 VHH-OKT3 CATE

<400> SEQUENCE: 118

Gln Val Lys Leu Glu Glu Ser Gly Gly Arg Leu Val Gln Pro Arg Gly
1               5                   10                  15

Ser Leu Arg Leu Ser Cys Ala Gly Ser Gly Arg Thr Phe Ser Thr Tyr
            20                  25                  30

Gly Met Ala Trp Phe Arg Gln Ala Pro Gly Lys Glu Arg Glu Phe Val
        35                  40                  45

Ala Ser Lys Ala Ser Met Asn Tyr Ser Gly Arg Thr Tyr Tyr Ala Asp
    50                  55                  60

Ser Val Lys Gly Arg Phe Thr Ile Ala Arg Asp Asn Ala Lys Asn Met
65                  70                  75                  80

Val Phe Leu Gln Met Asn Asn Leu Lys Pro Glu Asp Thr Ala Val Tyr
                85                  90                  95

Tyr Cys Ala Ala Gly Thr Gly Cys Ser Thr Tyr Gly Cys Phe Asp Ala
            100                 105                 110

Gln Ile Ile Asp Tyr Trp Gly Lys Gly Thr Leu Val Thr Val Ser Ser
        115                 120                 125

Gly Gly Gly Gly Ser Gly Gly Gly Gly Ser Gly Gly Gly Gly Ser Gln
    130                 135                 140

Val Gln Leu Gln Gln Ser Gly Ala Glu Leu Ala Arg Pro Gly Ala Ser
145                 150                 155                 160

Val Lys Met Ser Cys Lys Ala Ser Gly Tyr Thr Phe Thr Arg Tyr Thr
                165                 170                 175

Met His Trp Val Lys Gln Arg Pro Gly Gln Gly Leu Glu Trp Ile Gly
            180                 185                 190

Tyr Ile Asn Pro Ser Arg Gly Tyr Thr Asn Tyr Asn Gln Lys Phe Lys

```
                195                 200                 205
Asp Lys Ala Thr Leu Thr Thr Asp Lys Ser Ser Thr Ala Tyr Met
        210                 215                 220
Gln Leu Ser Ser Leu Thr Ser Glu Asp Ser Ala Val Tyr Tyr Cys Ala
225                 230                 235                 240
Arg Tyr Tyr Asp Asp His Tyr Cys Leu Asp Tyr Trp Gly Gln Gly Thr
                245                 250                 255
Thr Leu Thr Val Ser Ser Gly Gly Gly Gly Ser Gly Gly Gly Gly Ser
            260                 265                 270
Gly Gly Gly Gly Ser Gln Ile Val Leu Thr Gln Ser Pro Ala Ile Met
        275                 280                 285
Ser Ala Ser Pro Gly Glu Lys Val Thr Met Thr Cys Ser Ala Ser Ser
290                 295                 300
Ser Val Ser Tyr Met Asn Trp Tyr Gln Gln Lys Ser Gly Thr Ser Pro
305                 310                 315                 320
Lys Arg Trp Ile Tyr Asp Thr Ser Lys Leu Ala Ser Gly Val Pro Ala
                325                 330                 335
His Phe Arg Gly Ser Gly Ser Gly Thr Ser Tyr Ser Leu Thr Ile Ser
            340                 345                 350
Gly Met Glu Ala Glu Asp Ala Ala Thr Tyr Tyr Cys Gln Gln Trp Ser
        355                 360                 365
Ser Asn Pro Phe Thr Phe Gly Ser Gly Thr Lys Leu Glu Ile Asn Arg
370                 375                 380
His His His His His His
385                 390

<210> SEQ ID NO 119
<211> LENGTH: 380
<212> TYPE: PRT
<213> ORGANISM: Artificial Sequence
<220> FEATURE:
<223> OTHER INFORMATION: BCMA 269A37917 VHH-OKT3 CATE

<400> SEQUENCE: 119

Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Thr Met Gly
            20                  25                  30
Trp Phe Arg Gln Ala Pro Gly Lys Glu Arg Glu Phe Val Ala Ala Ile
        35                  40                  45
Ser Leu Ser Pro Thr Leu Ala Tyr Tyr Ala Glu Ser Val Lys Gly Arg
50                  55                  60
Phe Thr Ile Ser Arg Asp Asn Ala Lys Asn Thr Val Val Leu Gln Met
65                  70                  75                  80
Asn Ser Leu Lys Pro Glu Asp Thr Ala Leu Tyr Tyr Cys Ala Ala Asp
                85                  90                  95
Arg Lys Ser Val Met Ser Ile Arg Pro Asp Tyr Trp Gly Gln Gly Thr
            100                 105                 110
Gln Val Thr Val Ser Ser Gly Gly Gly Gly Ser Gly Gly Gly Gly Ser
        115                 120                 125
Gly Gly Gly Gly Ser Gln Val Gln Leu Gln Gln Ser Gly Ala Glu Leu
130                 135                 140
Ala Arg Pro Gly Ala Ser Val Lys Met Ser Cys Lys Ala Ser Gly Tyr
145                 150                 155                 160
Thr Phe Thr Arg Tyr Thr Met His Trp Val Lys Gln Arg Pro Gly Gln
```

```
                    165                 170                 175
Gly Leu Glu Trp Ile Gly Tyr Ile Asn Pro Ser Arg Gly Tyr Thr Asn
                180                 185                 190

Tyr Asn Gln Lys Phe Lys Asp Lys Ala Thr Leu Thr Thr Asp Lys Ser
            195                 200                 205

Ser Ser Thr Ala Tyr Met Gln Leu Ser Ser Leu Thr Ser Glu Asp Ser
        210                 215                 220

Ala Val Tyr Tyr Cys Ala Arg Tyr Tyr Asp Asp His Tyr Cys Leu Asp
225                 230                 235                 240

Tyr Trp Gly Gln Gly Thr Thr Leu Thr Val Ser Ser Gly Gly Gly Gly
                245                 250                 255

Ser Gly Gly Gly Gly Ser Gly Gly Gly Ser Gln Ile Val Leu Thr
                260                 265                 270

Gln Ser Pro Ala Ile Met Ser Ala Ser Pro Gly Glu Lys Val Thr Met
                275                 280                 285

Thr Cys Ser Ala Ser Ser Val Ser Tyr Met Asn Trp Tyr Gln Gln
            290                 295                 300

Lys Ser Gly Thr Ser Pro Lys Arg Trp Ile Tyr Asp Thr Ser Lys Leu
305                 310                 315                 320

Ala Ser Gly Val Pro Ala His Phe Arg Gly Ser Gly Ser Gly Thr Ser
                325                 330                 335

Tyr Ser Leu Thr Ile Ser Gly Met Glu Ala Glu Asp Ala Ala Thr Tyr
                340                 345                 350

Tyr Cys Gln Gln Trp Ser Ser Asn Pro Phe Thr Phe Gly Ser Gly Thr
            355                 360                 365

Lys Leu Glu Ile Asn Arg His His His His His
                370                 375                 380

<210> SEQ ID NO 120
<211> LENGTH: 382
<212> TYPE: PRT
<213> ORGANISM: Artificial Sequence
<220> FEATURE:
<223> OTHER INFORMATION: BCMA 269A37355 VHH-OKT3 CATE

<400> SEQUENCE: 120

Ala Val Gln Leu Val Asp Ser Gly Gly Gly Leu Val Gln Pro Gly Gly
1               5                   10                  15

Ser Leu Arg Leu Ser Cys Val Ala Ser Gly Gly Ile Phe Val Ile Asn
            20                  25                  30

Ala Met Gly Trp Tyr Arg Gln Ala Pro Gly Lys Gln Arg Glu Leu Val
        35                  40                  45

Ala Ser Ile Arg Gly Leu Gly Arg Thr Asn Tyr Asp Asp Ser Val Lys
    50                  55                  60

Gly Arg Phe Thr Ile Ser Arg Asp Asn Ala Asn Asn Thr Val Tyr Leu
65                  70                  75                  80

Gln Met Asn Ser Leu Glu Pro Glu Asp Thr Ala Val Tyr Tyr Cys Thr
                85                  90                  95

Val Tyr Val Thr Leu Leu Gly Val Asn Arg Asp Tyr Trp Gly Gln
            100                 105                 110

Gly Thr Gln Val Thr Val Ser Ser Gly Gly Gly Gly Ser Gly Gly Gly
        115                 120                 125

Gly Ser Gly Gly Gly Gly Ser Gln Val Gln Leu Gln Gln Ser Gly Ala
    130                 135                 140

Glu Leu Ala Arg Pro Gly Ala Ser Val Lys Met Ser Cys Lys Ala Ser
```

```
                145                 150                 155                 160
Gly Tyr Thr Phe Thr Arg Tyr Thr Met His Trp Val Lys Gln Arg Pro
                    165                 170                 175
Gly Gln Gly Leu Glu Trp Ile Gly Tyr Ile Asn Pro Ser Arg Gly Tyr
                180                 185                 190
Thr Asn Tyr Asn Gln Lys Phe Lys Asp Lys Ala Thr Leu Thr Thr Asp
                195                 200                 205
Lys Ser Ser Ser Thr Ala Tyr Met Gln Leu Ser Ser Leu Thr Ser Glu
            210                 215                 220
Asp Ser Ala Val Tyr Tyr Cys Ala Arg Tyr Tyr Asp His Tyr Cys
225                 230                 235                 240
Leu Asp Tyr Trp Gly Gln Gly Thr Thr Leu Thr Val Ser Ser Gly Gly
                    245                 250                 255
Gly Gly Ser Gly Gly Gly Gly Ser Gly Gly Gly Gly Ser Gln Ile Val
                260                 265                 270
Leu Thr Gln Ser Pro Ala Ile Met Ser Ala Ser Pro Gly Glu Lys Val
            275                 280                 285
Thr Met Thr Cys Ser Ala Ser Ser Ser Val Ser Tyr Met Asn Trp Tyr
        290                 295                 300
Gln Gln Lys Ser Gly Thr Ser Pro Lys Arg Trp Ile Tyr Asp Thr Ser
305                 310                 315                 320
Lys Leu Ala Ser Gly Val Pro Ala His Phe Arg Gly Ser Gly Ser Gly
                    325                 330                 335
Thr Ser Tyr Ser Leu Thr Ile Ser Gly Met Glu Ala Glu Asp Ala Ala
                340                 345                 350
Thr Tyr Tyr Cys Gln Gln Trp Ser Ser Asn Pro Phe Thr Phe Gly Ser
            355                 360                 365
Gly Thr Lys Leu Glu Ile Asn Arg His His His His His His
        370                 375                 380
```

<210> SEQ ID NO 121
<211> LENGTH: 381
<212> TYPE: PRT
<213> ORGANISM: Artificial Sequence
<220> FEATURE:
<223> OTHER INFORMATION: BCMA 269A37915 VHH-OKT3 CATE

<400> SEQUENCE: 121

```
Glu Val Gln Leu Val Glu Ser Gly Gly Gly Leu Val Gln Ala Gly Gly
1               5                   10                  15
Ser Leu Arg Leu Ser Cys Ala Ala Ser Gly Arg Thr Phe Ser Ser Ile
            20                  25                  30
Val Met Gly Trp Phe Arg Gln Ala Pro Gly Lys Glu Arg Glu Phe Val
        35                  40                  45
Gly Ala Ile Met Trp Asn Asp Gly Ile Thr Tyr Leu Gln Asp Ser Val
    50                  55                  60
Lys Gly Arg Phe Thr Ile Phe Arg Asp Asn Ala Lys Asn Thr Val Tyr
65                  70                  75                  80
Leu Gln Met Asn Ser Leu Lys Leu Glu Asp Thr Ala Val Tyr Tyr Cys
                85                  90                  95
Ala Ala Ser Lys Gly Arg Tyr Ser Glu Tyr Glu Tyr Trp Gly Gln Gly
            100                 105                 110
Thr Gln Val Thr Val Ser Ser Gly Gly Gly Ser Gly Gly Gly Gly
        115                 120                 125
Ser Gly Gly Gly Gly Ser Gln Val Gln Leu Gln Gln Ser Gly Ala Glu
```

```
                        130             135                 140
Leu Ala Arg Pro Gly Ala Ser Val Lys Met Ser Cys Lys Ala Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
                195                 200                 205

Ser Ser Ser Thr Ala Tyr Met Gln Leu Ser Ser Leu Thr Ser Glu Asp
210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Gly Gly Gly
                245                 250                 255

Gly Ser Gly Gly Gly Gly Ser Gly Gly Gly Gly Ser Gln Ile Val Leu
            260                 265                 270

Thr Gln Ser Pro Ala Ile Met Ser Ala Ser Pro Gly Glu Lys Val Thr
            275                 280                 285

Met Thr Cys Ser Ala Ser Ser Ser Val Ser Tyr Met Asn Trp Tyr Gln
290                 295                 300

Gln Lys Ser Gly Thr Ser Pro Lys Arg Trp Ile Tyr Asp Thr Ser Lys
305                 310                 315                 320

Leu Ala Ser Gly Val Pro Ala His Phe Arg Gly Ser Gly Ser Gly Thr
                325                 330                 335

Ser Tyr Ser Leu Thr Ile Ser Gly Met Glu Ala Glu Asp Ala Ala Thr
                340                 345                 350

Tyr Tyr Cys Gln Gln Trp Ser Ser Asn Pro Phe Thr Phe Gly Ser Gly
                355                 360                 365

Thr Lys Leu Glu Ile Asn Arg His His His His His
        370                 375                 380

<210> SEQ ID NO 122
<211> LENGTH: 390
<212> TYPE: PRT
<213> ORGANISM: Artificial Sequence
<220> FEATURE:
<223> OTHER INFORMATION: BCMA 269A37936 VHH-OKT3 CATE

<400> SEQUENCE: 122

Glu Val Gln Leu Val Glu Ser Gly Gly Gly Val Val Gln Ala Gly Gly
1               5                   10                  15

Ser Leu Thr Val Ser Cys Thr Ala Ser Gly Phe Thr Phe Asp Arg Ala
                20                  25                  30

Val Ile Val Trp Phe Arg Gln Ala Pro Gly Lys Gly Arg Glu Gly Val
            35                  40                  45

Ser Phe Ile Lys Pro Ser Asp Gly Thr Ile Tyr Tyr Ile Asp Ser Leu
        50                  55                  60

Lys Gly Arg Phe Thr Ile Ser Ser Asp Ile Ala Lys Asn Thr Val Tyr
65                  70                  75                  80

Leu Gln Met Lys Ser Leu Glu Ser Glu Asp Ser Ala Val Tyr Tyr Cys
                85                  90                  95

Ala Ala Ser Pro Glu Asp Trp Tyr Thr Asp Trp Ile Asp Trp Ser Ile
            100                 105                 110

Tyr Arg Trp Gln His Trp Gly Gln Gly Thr Gln Val Thr Val Ser Ser
```

```
            115                 120                 125
Gly Gly Gly Gly Ser Gly Gly Gly Ser Gly Gly Gly Ser Gln
    130                 135                 140
Val Gln Leu Gln Gln Ser Gly Ala Glu Leu Ala Arg Pro Gly Ala Ser
145                 150                 155                 160
Val Lys Met Ser Cys Lys Ala Ser Gly Tyr Thr Phe Thr Arg Tyr Thr
                165                 170                 175
Met His Trp Val Lys Gln Arg Pro Gly Gln Gly Leu Glu Trp Ile Gly
            180                 185                 190
Tyr Ile Asn Pro Ser Arg Gly Tyr Thr Asn Tyr Asn Gln Lys Phe Lys
        195                 200                 205
Asp Lys Ala Thr Leu Thr Thr Asp Lys Ser Ser Ser Thr Ala Tyr Met
    210                 215                 220
Gln Leu Ser Ser Leu Thr Ser Glu Asp Ser Ala Val Tyr Tyr Cys Ala
225                 230                 235                 240
Arg Tyr Tyr Asp Asp His Tyr Cys Leu Asp Tyr Trp Gly Gln Gly Thr
                245                 250                 255
Thr Leu Thr Val Ser Ser Gly Gly Gly Gly Ser Gly Gly Gly Gly Ser
            260                 265                 270
Gly Gly Gly Gly Ser Gln Ile Val Leu Thr Gln Ser Pro Ala Ile Met
        275                 280                 285
Ser Ala Ser Pro Gly Glu Lys Val Thr Met Thr Cys Ser Ala Ser Ser
    290                 295                 300
Ser Val Ser Tyr Met Asn Trp Tyr Gln Gln Lys Ser Gly Thr Ser Pro
305                 310                 315                 320
Lys Arg Trp Ile Tyr Asp Thr Ser Lys Leu Ala Ser Gly Val Pro Ala
                325                 330                 335
His Phe Arg Gly Ser Gly Ser Gly Thr Ser Tyr Ser Leu Thr Ile Ser
            340                 345                 350
Gly Met Glu Ala Glu Asp Ala Ala Thr Tyr Tyr Cys Gln Gln Trp Ser
        355                 360                 365
Ser Asn Pro Phe Thr Phe Gly Ser Gly Thr Lys Leu Glu Ile Asn Arg
    370                 375                 380
His His His His His
385                 390

<210> SEQ ID NO 123
<211> LENGTH: 381
<212> TYPE: PRT
<213> ORGANISM: Artificial Sequence
<220> FEATURE:
<223> OTHER INFORMATION: BCMA 269A37953 VHH-OKT3 CATE

<400> SEQUENCE: 123

Glu Val Gln Leu Val Glu Ser Gly Gly Gly Met Val Gln Ala Gly Asp
1               5                   10                  15
Ser Leu Arg Leu Ser Cys Val Gln Ser Thr Tyr Thr Val Asn Ser Asp
            20                  25                  30
Val Met Gly Trp Phe Arg Gln Ala Pro Gly Lys Glu Arg Glu Phe Val
        35                  40                  45
Gly Ala Ile Met Trp Asn Asp Gly Ile Thr Tyr Leu Gln Asp Ser Val
    50                  55                  60
Lys Gly Arg Phe Thr Ile Phe Arg Asp Asn Ala Lys Asn Thr Val Tyr
65                  70                  75                  80
Leu Gln Met Asn Ser Leu Lys Leu Glu Asp Thr Ala Val Tyr Tyr Cys
```

```
                    85                  90                  95
Ala Ala Ser Lys Gly Arg Tyr Ser Glu Tyr Glu Tyr Trp Gly Gln Gly
                100                 105                 110

Thr Gln Val Thr Val Ser Ser Gly Gly Gly Ser Gly Gly Gly Gly
            115                 120                 125

Ser Gly Gly Gly Gly Ser Gln Val Gln Leu Gln Gln Ser Gly Ala Glu
            130                 135                 140

Leu Ala Arg Pro Gly Ala Ser Val Lys Met Ser Cys Lys Ala Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
                180                 185                 190

Asn Tyr Asn Gln Lys Phe Lys Asp Lys Ala Thr Leu Thr Thr Asp Lys
                195                 200                 205

Ser Ser Ser Thr Ala Tyr Met Gln Leu Ser Ser Leu Thr Ser Glu Asp
            210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Gly Gly Gly
                245                 250                 255

Gly Ser Gly Gly Gly Gly Ser Gly Gly Gly Gly Ser Gln Ile Val Leu
            260                 265                 270

Thr Gln Ser Pro Ala Ile Met Ser Ala Ser Pro Gly Glu Lys Val Thr
            275                 280                 285

Met Thr Cys Ser Ala Ser Ser Ser Val Ser Tyr Met Asn Trp Tyr Gln
            290                 295                 300

Gln Lys Ser Gly Thr Ser Pro Lys Arg Trp Ile Tyr Asp Thr Ser Lys
305                 310                 315                 320

Leu Ala Ser Gly Val Pro Ala His Phe Arg Gly Ser Gly Ser Gly Thr
                325                 330                 335

Ser Tyr Ser Leu Thr Ile Ser Gly Met Glu Ala Glu Asp Ala Ala Thr
            340                 345                 350

Tyr Tyr Cys Gln Gln Trp Ser Ser Asn Pro Phe Thr Phe Gly Ser Gly
            355                 360                 365

Thr Lys Leu Glu Ile Asn Arg His His His His His
            370                 375                 380

<210> SEQ ID NO 124
<211> LENGTH: 382
<212> TYPE: PRT
<213> ORGANISM: Artificial Sequence
<220> FEATURE:
<223> OTHER INFORMATION: BCMA 269A37965 VHH-OKT3 CATE

<400> SEQUENCE: 124

Ala Val Gln Leu Val Glu Ser Gly Gly Gly Leu Val Gln Ala Gly Asp
1               5                   10                  15

Ser Leu Arg Leu Ser Cys Thr Ala Ser Gly Ala Thr Leu Thr Asn Asp
            20                  25                  30

His Met Ala Trp Phe Arg Gln Ala Pro Gly Lys Gly Arg Glu Phe Val
            35                  40                  45

Ala Ala Ile Asp Trp Ser Gly Arg Thr Thr Asn Tyr Ala Asp Pro Val
50                  55                  60

Glu Gly Arg Phe Thr Ile Ser Arg Asn Asn Ala Lys Asn Thr Val Tyr
```

```
                65                  70                  75                  80
Leu Glu Met Asn Ser Leu Lys Leu Glu Asp Thr Ala Val Tyr Tyr Cys
                    85                  90                  95

Ala Val Leu Arg Ala Trp Ile Ser Tyr Asp Asn Asp Tyr Trp Gly Gln
                100                 105                 110

Gly Thr Gln Val Thr Val Ser Ser Gly Gly Gly Gly Ser Gly Gly Gly
                115                 120                 125

Gly Ser Gly Gly Gly Gly Ser Gln Val Gln Leu Gln Gln Ser Gly Ala
            130                 135                 140

Glu Leu Ala Arg Pro Gly Ala Ser Val Lys Met Ser Cys Lys Ala Ser
145                 150                 155                 160

Gly Tyr Thr Phe Thr Arg Tyr Thr Met His Trp Val Lys Gln Arg Pro
                165                 170                 175

Gly Gln Gly Leu Glu Trp Ile Gly Tyr Ile Asn Pro Ser Arg Gly Tyr
                180                 185                 190

Thr Asn Tyr Asn Gln Lys Phe Lys Asp Lys Ala Thr Leu Thr Thr Asp
                195                 200                 205

Lys Ser Ser Ser Thr Ala Tyr Met Gln Leu Ser Ser Leu Thr Ser Glu
210                 215                 220

Asp Ser Ala Val Tyr Tyr Cys Ala Arg Tyr Tyr Asp Asp His Tyr Cys
225                 230                 235                 240

Leu Asp Tyr Trp Gly Gln Gly Thr Thr Leu Thr Val Ser Ser Gly Gly
                245                 250                 255

Gly Gly Ser Gly Gly Gly Gly Ser Gly Gly Gly Gly Ser Gln Ile Val
                260                 265                 270

Leu Thr Gln Ser Pro Ala Ile Met Ser Ala Ser Pro Gly Glu Lys Val
            275                 280                 285

Thr Met Thr Cys Ser Ala Ser Ser Ser Val Ser Tyr Met Asn Trp Tyr
                290                 295                 300

Gln Gln Lys Ser Gly Thr Ser Pro Lys Arg Trp Ile Tyr Asp Thr Ser
305                 310                 315                 320

Lys Leu Ala Ser Gly Val Pro Ala His Phe Arg Gly Ser Gly Ser Gly
                325                 330                 335

Thr Ser Tyr Ser Leu Thr Ile Ser Gly Met Glu Ala Glu Asp Ala Ala
                340                 345                 350

Thr Tyr Tyr Cys Gln Gln Trp Ser Ser Asn Pro Phe Thr Phe Gly Ser
                355                 360                 365

Gly Thr Lys Leu Glu Ile Asn Arg His His His His His His
    370                 375                 380

<210> SEQ ID NO 125
<211> LENGTH: 382
<212> TYPE: PRT
<213> ORGANISM: Artificial Sequence
<220> FEATURE:
<223> OTHER INFORMATION: BCMA 269A37972 VHH-OKT3 CATE

<400> SEQUENCE: 125

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
                20                  25                  30

Thr Val Ala Trp Phe Arg Gln Ala Pro Gly Lys Glu Arg Gly Phe Val
                35                  40                  45

Ala Ser Ile Thr Trp Asp Gly Arg Thr Thr Tyr Tyr Ala Asp Ser Val
```

```
                50                  55                  60
Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Val Cys
                 85                  90                  95

Ala Asp Leu Gly Lys Trp Pro Ala Gly Pro Ala Asp Tyr Trp Gly Gln
                100                 105                 110

Gly Thr Gln Val Thr Val Ser Gly Gly Gly Ser Gly Gly Gly
            115                 120                 125

Gly Ser Gly Gly Gly Ser Gln Val Gln Leu Gln Gln Ser Gly Ala
            130                 135                 140

Glu Leu Ala Arg Pro Gly Ala Ser Val Lys Met Ser Cys Lys Ala Ser
145                 150                 155                 160

Gly Tyr Thr Phe Thr Arg Tyr Thr Met His Trp Val Lys Gln Arg Pro
                165                 170                 175

Gly Gln Gly Leu Glu Trp Ile Gly Tyr Ile Asn Pro Ser Arg Gly Tyr
            180                 185                 190

Thr Asn Tyr Asn Gln Lys Phe Lys Asp Lys Ala Thr Leu Thr Thr Asp
            195                 200                 205

Lys Ser Ser Ser Thr Ala Tyr Met Gln Leu Ser Ser Leu Thr Ser Glu
 210                 215                 220

Asp Ser Ala Val Tyr Tyr Cys Ala Arg Tyr Tyr Asp Asp His Tyr Cys
225                 230                 235                 240

Leu Asp Tyr Trp Gly Gln Gly Thr Thr Leu Thr Val Ser Ser Gly Gly
                245                 250                 255

Gly Gly Ser Gly Gly Gly Ser Gly Gly Gly Ser Gln Ile Val
            260                 265                 270

Leu Thr Gln Ser Pro Ala Ile Met Ser Ala Ser Pro Gly Glu Lys Val
            275                 280                 285

Thr Met Thr Cys Ser Ala Ser Ser Ser Val Ser Tyr Met Asn Trp Tyr
            290                 295                 300

Gln Gln Lys Ser Gly Thr Ser Pro Lys Arg Trp Ile Tyr Asp Thr Ser
305                 310                 315                 320

Lys Leu Ala Ser Gly Val Pro Ala His Phe Arg Gly Ser Gly Ser Gly
                325                 330                 335

Thr Ser Tyr Ser Leu Thr Ile Ser Gly Met Glu Ala Glu Asp Ala Ala
            340                 345                 350

Thr Tyr Tyr Cys Gln Gln Trp Ser Ser Asn Pro Phe Thr Phe Gly Ser
            355                 360                 365

Gly Thr Lys Leu Glu Ile Asn Arg His His His His His
            370                 375                 380

<210> SEQ ID NO 126
<211> LENGTH: 381
<212> TYPE: PRT
<213> ORGANISM: Artificial Sequence
<220> FEATURE:
<223> OTHER INFORMATION: BCMA 269A37353 VHH-OKT3 CATE

<400> SEQUENCE: 126

Gln Val Lys Leu Glu Glu Ser Gly Gly Gly Leu Val Gln Ala Gly Arg
 1                5                 10                  15

Ser Leu Arg Leu Ser Cys Ala Ala Ser Glu His Thr Phe Ser Ser His
             20                  25                  30

Val Met Gly Trp Phe Arg Gln Ala Pro Gly Lys Glu Arg Glu Ser Val
```

-continued

```
                35                  40                  45
Ala Val Ile Gly Trp Arg Asp Ile Ser Thr Ser Tyr Ala Asp Ser Val
 50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Arg Ile Asp Ala Asp Phe Asp Ser Trp Gly Gln Gly
                100                 105                 110

Thr Gln Val Thr Val Ser Ser Gly Gly Gly Ser Gly Gly Gly Gly
                115                 120                 125

Ser Gly Gly Gly Ser Gln Val Gln Leu Gln Gln Ser Gly Ala Glu
 130                 135                 140

Leu Ala Arg Pro Gly Ala Ser Val Lys Met Ser Cys Lys Ala Ser Gly
 145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
                180                 185                 190

Asn Tyr Asn Gln Lys Phe Lys Asp Lys Ala Thr Leu Thr Thr Asp Lys
                195                 200                 205

Ser Ser Ser Thr Ala Tyr Met Gln Leu Ser Ser Leu Thr Ser Glu Asp
 210                 215                 220

Ser Ala Val Tyr Tyr Cys Ala Arg Tyr Tyr Asp Asp His Tyr Cys Leu
 225                 230                 235                 240

Asp Tyr Trp Gly Gln Gly Thr Thr Leu Thr Val Ser Ser Gly Gly Gly
                245                 250                 255

Gly Ser Gly Gly Gly Gly Ser Gly Gly Gly Ser Gln Ile Val Leu
                260                 265                 270

Thr Gln Ser Pro Ala Ile Met Ser Ala Ser Pro Gly Glu Lys Val Thr
                275                 280                 285

Met Thr Cys Ser Ala Ser Ser Val Ser Tyr Met Asn Trp Tyr Gln
                290                 295                 300

Gln Lys Ser Gly Thr Ser Pro Lys Arg Trp Ile Tyr Asp Thr Ser Lys
 305                 310                 315                 320

Leu Ala Ser Gly Val Pro Ala His Phe Arg Gly Ser Gly Ser Gly Thr
                325                 330                 335

Ser Tyr Ser Leu Thr Ile Ser Gly Met Glu Ala Glu Asp Ala Ala Thr
                340                 345                 350

Tyr Tyr Cys Gln Gln Trp Ser Ser Asn Pro Phe Thr Phe Gly Ser Gly
                355                 360                 365

Thr Lys Leu Glu Ile Asn Arg His His His His His
                370                 375                 380
```

<210> SEQ ID NO 127
<211> LENGTH: 381
<212> TYPE: PRT
<213> ORGANISM: Artificial Sequence
<220> FEATURE:
<223> OTHER INFORMATION: BCMA 269A37948 VHH-OKT3 CATE

<400> SEQUENCE: 127

```
Ala Val Gln Leu Val Glu Ser Gly Gly Gly Leu Val Gln Ala Gly Asp
 1               5                  10                  15

Ser Leu Arg Leu Thr Cys Thr Ala Ser Gly Arg Ala Phe Ser Thr Tyr
```

```
                20                  25                  30
Phe Met Ala Trp Phe Arg Gln Ala Pro Gly Lys Glu Arg Glu Phe Val
                35                  40                  45
Ala Gly Ile Ala Trp Ser Gly Ser Thr Ala Tyr Ala Asp Ser Val
        50                  55                  60
Lys Gly Arg Phe Thr Ile Ser Arg Asp Asn Ala Lys Asn Thr Val Tyr
65                  70                  75                  80
Leu Gln Met Asn Ser Leu Lys Ser Glu Asp Thr Ala Val Tyr Tyr Cys
                85                  90                  95
Ala Ser Arg Gly Ile Glu Val Glu Phe Gly Ala Trp Gly Gln Gly
            100                 105                 110
Thr Gln Val Thr Val Ser Ser Gly Gly Gly Ser Gly Gly Gly Gly
                115                 120                 125
Ser Gly Gly Gly Ser Gln Val Gln Leu Gln Ser Gly Ala Glu
        130                 135                 140
Leu Ala Arg Pro Gly Ala Ser Val Lys Met Ser Cys Lys Ala Ser Gly
145                 150                 155                 160
Tyr Thr Phe Thr Arg Tyr Thr Met His Trp Val Lys Gln Arg Pro Gly
                165                 170                 175
Gln Gly Leu Glu Trp Ile Gly Tyr Ile Asn Pro Ser Arg Gly Tyr Thr
            180                 185                 190
Asn Tyr Asn Gln Lys Phe Lys Asp Lys Ala Thr Leu Thr Thr Asp Lys
                195                 200                 205
Ser Ser Ser Thr Ala Tyr Met Gln Leu Ser Ser Leu Thr Ser Glu Asp
    210                 215                 220
Ser Ala Val Tyr Tyr Cys Ala Arg Tyr Tyr Asp Asp His Tyr Cys Leu
225                 230                 235                 240
Asp Tyr Trp Gly Gln Gly Thr Thr Leu Thr Val Ser Ser Gly Gly Gly
                245                 250                 255
Gly Ser Gly Gly Gly Gly Ser Gly Gly Gly Gly Ser Gln Ile Val Leu
            260                 265                 270
Thr Gln Ser Pro Ala Ile Met Ser Ala Ser Pro Gly Glu Lys Val Thr
        275                 280                 285
Met Thr Cys Ser Ala Ser Ser Ser Val Ser Tyr Met Asn Trp Tyr Gln
    290                 295                 300
Gln Lys Ser Gly Thr Ser Pro Lys Arg Trp Ile Tyr Asp Thr Ser Lys
305                 310                 315                 320
Leu Ala Ser Gly Val Pro Ala His Phe Arg Gly Ser Gly Ser Gly Thr
                325                 330                 335
Ser Tyr Ser Leu Thr Ile Ser Gly Met Glu Ala Glu Asp Ala Ala Thr
            340                 345                 350
Tyr Tyr Cys Gln Gln Trp Ser Ser Asn Pro Phe Thr Phe Gly Ser Gly
        355                 360                 365
Thr Lys Leu Glu Ile Asn Arg His His His His His
    370                 375                 380

<210> SEQ ID NO 128
<211> LENGTH: 378
<212> TYPE: PRT
<213> ORGANISM: Artificial Sequence
<220> FEATURE:
<223> OTHER INFORMATION: CD38 38A37333 VHH-L2K.07 CATE

<400> SEQUENCE: 128

Asp Val Gln Leu Val Glu Ser Gly Gly Gly Leu Val Gln Pro Gly Gly
```

```
1               5                   10                  15
Ser Leu Arg Leu Ser Cys Val Ala Ser Gly Leu Thr Phe Ser Ser Tyr
            20                  25                  30

Pro Met Met Trp Val Arg Gln Ala Pro Gly Lys Gly Leu Glu Trp Val
            35                  40                  45

Ser Arg Ile Ser Asp Ser Gly Tyr Thr Asn Tyr Asp Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Thr Pro Glu Asp Thr Ala Val Tyr Tyr Cys
            85                  90                  95

Arg Ile Leu Gly Leu Pro Thr Gly Gln Gly Thr Gln Val Thr Val
            100                 105                 110

Ser Ser Gly Gly Gly Ser Gly Gly Gly Ser Gly Gly Gly
            115                 120                 125

Ser Asp Ile Lys Leu Gln Gln Ser Gly Ala Glu Leu Ala Arg Pro Gly
 130                 135                 140

Ala Ser Val Lys Met Ser Cys Lys Thr Ser Gly Tyr Thr Phe Thr Arg
145                 150                 155                 160

Tyr Thr Met His Trp Val Lys Gln Arg Pro Gly Gln Gly Leu Glu Trp
                165                 170                 175

Ile Gly Tyr Ile Asn Pro Ser Arg Gly Tyr Thr Asn Tyr Asn Gln Lys
            180                 185                 190

Phe Lys Asp Lys Ala Thr Leu Thr Thr Asp Lys Ser Ser Ser Thr Ala
            195                 200                 205

Tyr Met Gln Leu Ser Ser Leu Thr Ser Glu Asp Ser Ala Val Tyr Tyr
 210                 215                 220

Cys Ala Arg Tyr Tyr Asp Asp His Tyr Cys Leu Asp Tyr Trp Gly Gln
225                 230                 235                 240

Gly Thr Thr Leu Thr Val Ser Ser Val Glu Gly Gly Ser Gly Gly Ser
                245                 250                 255

Gly Gly Ser Gly Gly Ser Gly Gly Val Asp Asp Ile Gln Leu Thr Gln
            260                 265                 270

Ser Pro Ala Ile Met Ser Ala Ser Pro Gly Glu Lys Val Thr Met Thr
 275                 280                 285

Cys Arg Ala Ser Ser Ser Val Ser Tyr Met Asn Trp Tyr Gln Gln Lys
 290                 295                 300

Ser Gly Thr Ser Pro Lys Arg Trp Ile Tyr Asp Thr Ser Lys Val Ala
305                 310                 315                 320

Ser Gly Val Pro Tyr Arg Phe Ser Gly Ser Gly Ser Gly Thr Ser Tyr
                325                 330                 335

Ser Leu Thr Ile Ser Ser Met Glu Ala Glu Asp Ala Ala Thr Tyr Tyr
            340                 345                 350

Cys Gln Gln Trp Ser Ser Asn Pro Leu Thr Phe Gly Ala Gly Thr Lys
            355                 360                 365

Leu Glu Leu Lys His His His His His His
 370                 375
```

<210> SEQ ID NO 129
<211> LENGTH: 390
<212> TYPE: PRT
<213> ORGANISM: Artificial Sequence
<220> FEATURE:
<223> OTHER INFORMATION: CD38 38A37336 VHH-L2K.07 CATE

<400> SEQUENCE: 129

| | | | | | | | | | | | | | | |
|---|---|---|---|---|---|---|---|---|---|---|---|---|---|---|
| Glu | Val | Gln | Leu | Val | Glu | Ser | Gly | Gly | Gly | Leu | Val | Gln | Pro | Gly | Gly |
| 1 | | | | 5 | | | | | 10 | | | | | 15 | |
| Ser | Leu | Arg | Leu | Ser | Cys | Ala | Ala | Ser | Gly | Phe | Thr | Phe | Ser | Ser | Asn |
| | | | 20 | | | | | 25 | | | | | 30 | | |
| Trp | Met | Tyr | Trp | Val | Arg | Gln | Ala | Pro | Gly | Lys | Gly | Leu | Glu | Trp | Val |
| | | 35 | | | | | 40 | | | | | 45 | | | |
| Ala | Thr | Ile | Ser | Thr | Asp | Gly | Arg | Gly | Thr | Tyr | Tyr | Lys | Asp | Ser | Val |
| | 50 | | | | | 55 | | | | | 60 | | | | |
| Lys | Gly | Arg | Phe | Thr | Val | Ser | Arg | Asp | Asn | Ala | Met | Ser | Thr | Leu | Leu |
| 65 | | | | | 70 | | | | | 75 | | | | | 80 |
| Leu | Gln | Met | Asn | Asn | Leu | Lys | Ser | Glu | Asp | Thr | Ala | Val | Tyr | Tyr | Cys |
| | | | | 85 | | | | | 90 | | | | | 95 | |
| Ala | Lys | Glu | Pro | Arg | Val | Leu | Met | Ala | Tyr | Leu | Arg | Asn | Leu | Gly | Asp |
| | | | 100 | | | | | 105 | | | | | 110 | | |
| Phe | Gly | Ser | Trp | Gly | Gln | Gly | Thr | Gln | Val | Thr | Val | Ser | Ser | Gly | Gly |
| | | 115 | | | | | 120 | | | | | 125 | | | |
| Gly | Gly | Ser | Gly | Gly | Gly | Gly | Ser | Gly | Gly | Gly | Gly | Ser | Asp | Ile | Lys |
| | 130 | | | | | 135 | | | | | 140 | | | | |
| Leu | Gln | Gln | Ser | Gly | Ala | Glu | Leu | Ala | Arg | Pro | Gly | Ala | Ser | Val | Lys |
| 145 | | | | | 150 | | | | | 155 | | | | | 160 |
| Met | Ser | Cys | Lys | Thr | Ser | Gly | Tyr | Thr | Phe | Thr | Arg | Tyr | Thr | Met | His |
| | | | | 165 | | | | | 170 | | | | | 175 | |
| Trp | Val | Lys | Gln | Arg | Pro | Gly | Gln | Gly | Leu | Glu | Trp | Ile | Gly | Tyr | Ile |
| | | | 180 | | | | | 185 | | | | | 190 | | |
| Asn | Pro | Ser | Arg | Gly | Tyr | Thr | Asn | Tyr | Asn | Gln | Lys | Phe | Lys | Asp | Lys |
| | | 195 | | | | | 200 | | | | | 205 | | | |
| Ala | Thr | Leu | Thr | Thr | Asp | Lys | Ser | Ser | Thr | Ala | Tyr | Met | Gln | Leu |
| | 210 | | | | | 215 | | | | | 220 | | | | |
| Ser | Ser | Leu | Thr | Ser | Glu | Asp | Ser | Ala | Val | Tyr | Tyr | Cys | Ala | Arg | Tyr |
| 225 | | | | | 230 | | | | | 235 | | | | | 240 |
| Tyr | Asp | Asp | His | Tyr | Cys | Leu | Asp | Tyr | Trp | Gly | Gln | Gly | Thr | Thr | Leu |
| | | | | 245 | | | | | 250 | | | | | 255 | |
| Thr | Val | Ser | Ser | Val | Glu | Gly | Gly | Ser | Gly | Gly | Ser | Gly | Gly | Ser | Gly |
| | | | 260 | | | | | 265 | | | | | 270 | | |
| Gly | Ser | Gly | Gly | Val | Asp | Asp | Ile | Gln | Leu | Thr | Gln | Ser | Pro | Ala | Ile |
| | | 275 | | | | | 280 | | | | | 285 | | | |
| Met | Ser | Ala | Ser | Pro | Gly | Glu | Lys | Val | Thr | Met | Thr | Cys | Arg | Ala | Ser |
| | 290 | | | | | 295 | | | | | 300 | | | | |
| Ser | Ser | Val | Ser | Tyr | Met | Asn | Trp | Tyr | Gln | Gln | Lys | Ser | Gly | Thr | Ser |
| 305 | | | | | 310 | | | | | 315 | | | | | 320 |
| Pro | Lys | Arg | Trp | Ile | Tyr | Asp | Thr | Ser | Lys | Val | Ala | Ser | Gly | Val | Pro |
| | | | | 325 | | | | | 330 | | | | | 335 | |
| Tyr | Arg | Phe | Ser | Gly | Ser | Gly | Ser | Gly | Thr | Ser | Tyr | Ser | Leu | Thr | Ile |
| | | | 340 | | | | | 345 | | | | | 350 | | |
| Ser | Ser | Met | Glu | Ala | Glu | Asp | Ala | Ala | Thr | Tyr | Tyr | Cys | Gln | Gln | Trp |
| | | 355 | | | | | 360 | | | | | 365 | | | |
| Ser | Ser | Asn | Pro | Leu | Thr | Phe | Gly | Ala | Gly | Thr | Lys | Leu | Glu | Leu | Lys |
| | 370 | | | | | 375 | | | | | 380 | | | | |
| His | His | His | His | His | His | | | | | | | | | | |
| 385 | | | | | 390 | | | | | | | | | | |

<210> SEQ ID NO 130

```
<211> LENGTH: 379
<212> TYPE: PRT
<213> ORGANISM: Artificial Sequence
<220> FEATURE:
<223> OTHER INFORMATION: CD38 38A37699 VHH-L2K.07 CATE

<400> SEQUENCE: 130

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Thr Ala Gly Ser Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asn Phe Pro Pro Tyr Val Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Asp Ile Lys Leu Gln Gln Ser Gly Ala Glu Leu Ala Arg Pro
    130                 135                 140

Gly Ala Ser Val Lys Met Ser Cys Lys Thr Ser Gly Tyr Thr Phe Thr
145                 150                 155                 160

Arg Tyr Thr Met His Trp Val Lys Gln Arg Pro Gly Gln Gly Leu Glu
                165                 170                 175

Trp Ile Gly Tyr Ile Asn Pro Ser Arg Gly Tyr Thr Asn Tyr Asn Gln
            180                 185                 190

Lys Phe Lys Asp Lys Ala Thr Leu Thr Thr Asp Lys Ser Ser Ser Thr
        195                 200                 205

Ala Tyr Met Gln Leu Ser Ser Leu Thr Ser Glu Asp Ser Ala Val Tyr
    210                 215                 220

Tyr Cys Ala Arg Tyr Tyr Asp Asp His Tyr Cys Leu Asp Tyr Trp Gly
225                 230                 235                 240

Gln Gly Thr Thr Leu Thr Val Ser Ser Val Glu Gly Gly Ser Gly Gly
                245                 250                 255

Ser Gly Gly Ser Gly Gly Ser Gly Gly Val Asp Asp Ile Gln Leu Thr
            260                 265                 270

Gln Ser Pro Ala Ile Met Ser Ala Ser Pro Gly Glu Lys Val Thr Met
        275                 280                 285

Thr Cys Arg Ala Ser Ser Ser Val Ser Tyr Met Asn Trp Tyr Gln Gln
    290                 295                 300

Lys Ser Gly Thr Ser Pro Lys Arg Trp Ile Tyr Asp Thr Ser Lys Val
305                 310                 315                 320

Ala Ser Gly Val Pro Tyr Arg Phe Ser Gly Ser Gly Ser Gly Thr Ser
                325                 330                 335

Tyr Ser Leu Thr Ile Ser Ser Met Glu Ala Glu Asp Ala Ala Thr Tyr
            340                 345                 350

Tyr Cys Gln Gln Trp Ser Ser Asn Pro Leu Thr Phe Gly Ala Gly Thr
        355                 360                 365

Lys Leu Glu Leu Lys His His His His His His
    370                 375
```

<210> SEQ ID NO 131
<211> LENGTH: 383
<212> TYPE: PRT
<213> ORGANISM: Artificial Sequence
<220> FEATURE:
<223> OTHER INFORMATION: CD38 38A37331 VHH-L2K.07 CATE

<400> SEQUENCE: 131

```
Gln Val Lys Leu Glu Glu Ser Gly Gly Gly Leu Val Gln Pro Gly Glu
1               5                   10                  15

Ser Leu Arg Leu Ser Cys Ser Ala Ser Gly Ser Ile Phe Lys Val Phe
            20                  25                  30

Arg Val Phe Ala Met Ser Trp Tyr Arg Gln Gly Pro Gly Lys Gln Arg
        35                  40                  45

Glu Leu Val Ala Ser Ile Ser Ser Gly Glu Thr Thr Thr Tyr Ala Asp
    50                  55                  60

Ser Val Lys Gly Arg Phe Thr Ile Ser Arg Asp Asn Ala Lys Asn Thr
65                  70                  75                  80

Ala Tyr Leu Gln Met Asp Ser Leu Lys Pro Glu Asp Thr Ala Val Tyr
                85                  90                  95

Tyr Cys Asn Ala Asp His Thr Phe Thr Gly Asp Phe Trp Gly Gln Gly
            100                 105                 110

Thr Gln Val Thr Val Ser Ser Gly Gly Gly Ser Gly Gly Gly Gly
        115                 120                 125

Ser Gly Gly Gly Gly Ser Asp Ile Lys Leu Gln Gln Ser Gly Ala Glu
    130                 135                 140

Leu Ala Arg Pro Gly Ala Ser Val Lys Met Ser Cys Lys Thr Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
        195                 200                 205

Ser Ser Ser Thr Ala Tyr Met Gln Leu Ser Ser Leu Thr Ser Glu Asp
    210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Val Glu Gly
                245                 250                 255

Gly Ser Gly Gly Ser Gly Gly Ser Gly Gly Ser Gly Gly Val Asp Asp
            260                 265                 270

Ile Gln Leu Thr Gln Ser Pro Ala Ile Met Ser Ala Ser Pro Gly Glu
        275                 280                 285

Lys Val Thr Met Thr Cys Arg Ala Ser Ser Ser Val Ser Tyr Met Asn
    290                 295                 300

Trp Tyr Gln Gln Lys Ser Gly Thr Ser Pro Lys Arg Trp Ile Tyr Asp
305                 310                 315                 320

Thr Ser Lys Val Ala Ser Gly Val Pro Tyr Arg Phe Ser Gly Ser Gly
                325                 330                 335

Ser Gly Thr Ser Tyr Ser Leu Thr Ile Ser Ser Met Glu Ala Glu Asp
            340                 345                 350

Ala Ala Thr Tyr Tyr Cys Gln Gln Trp Ser Ser Asn Pro Leu Thr Phe
        355                 360                 365
```

Gly Ala Gly Thr Lys Leu Glu Leu Lys His His His His His His
    370                 375                 380

<210> SEQ ID NO 132
<211> LENGTH: 380
<212> TYPE: PRT
<213> ORGANISM: Artificial Sequence
<220> FEATURE:
<223> OTHER INFORMATION: CD38 38A37717 VHH-L2K.07 CATE

<400> SEQUENCE: 132

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Asp Ile Lys Leu Gln Gln Ser Gly Ala Glu Leu Ala Arg
    130                 135                 140

Pro Gly Ala Ser Val Lys Met Ser Cys Lys Thr Ser Gly Tyr Thr Phe
145                 150                 155                 160

Thr Arg Tyr Thr Met His Trp Val Lys Gln Arg Pro Gly Gln Gly Leu
                165                 170                 175

Glu Trp Ile Gly Tyr Ile Asn Pro Ser Arg Gly Tyr Thr Asn Tyr Asn
            180                 185                 190

Gln Lys Phe Lys Asp Lys Ala Thr Leu Thr Thr Asp Lys Ser Ser Ser
        195                 200                 205

Thr Ala Tyr Met Gln Leu Ser Ser Leu Thr Ser Glu Asp Ser Ala Val
    210                 215                 220

Tyr Tyr Cys Ala Arg Tyr Tyr Asp Asp His Tyr Cys Leu Asp Tyr Trp
225                 230                 235                 240

Gly Gln Gly Thr Thr Leu Thr Val Ser Val Glu Gly Gly Ser Gly
                245                 250                 255

Gly Ser Gly Gly Ser Gly Gly Ser Gly Gly Val Asp Asp Ile Gln Leu
            260                 265                 270

Thr Gln Ser Pro Ala Ile Met Ser Ala Ser Pro Gly Glu Lys Val Thr
        275                 280                 285

Met Thr Cys Arg Ala Ser Ser Val Ser Tyr Met Asn Trp Tyr Gln
    290                 295                 300

Gln Lys Ser Gly Thr Ser Pro Lys Arg Trp Ile Tyr Asp Thr Ser Lys
305                 310                 315                 320

Val Ala Ser Gly Val Pro Tyr Arg Phe Ser Gly Ser Gly Ser Gly Thr
                325                 330                 335

Ser Tyr Ser Leu Thr Ile Ser Ser Met Glu Ala Glu Asp Ala Ala Thr
            340                 345                 350

Tyr Tyr Cys Gln Gln Trp Ser Ser Asn Pro Leu Thr Phe Gly Ala Gly
        355                 360                 365

Thr Lys Leu Glu Leu Lys His His His His His
        370                 375                 380

<210> SEQ ID NO 133
<211> LENGTH: 379
<212> TYPE: PRT
<213> ORGANISM: Artificial Sequence
<220> FEATURE:
<223> OTHER INFORMATION: CD38 38A37719 VHH-L2K.07 CATE

<400> SEQUENCE: 133

Gln Val Lys Leu Glu Glu Ser Gly Gly Gly Ser Val Gln Thr Gly Gly
1               5                   10                  15

Ser Leu Arg Leu Ser Cys Ala Ala Ser Ala Ser Ile Phe Thr Arg Leu
            20                  25                  30

Pro Met Gly Trp Tyr Arg Gln Ala Pro Gly Lys Gln Arg Glu Leu Val
        35                  40                  45

Val Gly Ile Val Pro Ser Gly Arg Ile Asn Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Arg
                85                  90                  95

Ala Asp Thr Phe Pro Leu Pro Thr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Asp Ile Lys Leu Gln Gln Ser Gly Ala Glu Leu Ala Arg Pro
130                 135                 140

Gly Ala Ser Val Lys Met Ser Cys Lys Thr Ser Gly Tyr Thr Phe Thr
145                 150                 155                 160

Arg Tyr Thr Met His Trp Val Lys Gln Arg Pro Gly Gln Gly Leu Glu
                165                 170                 175

Trp Ile Gly Tyr Ile Asn Pro Ser Arg Gly Tyr Thr Asn Tyr Asn Gln
            180                 185                 190

Lys Phe Lys Asp Lys Ala Thr Leu Thr Thr Asp Lys Ser Ser Ser Thr
        195                 200                 205

Ala Tyr Met Gln Leu Ser Ser Leu Thr Ser Glu Asp Ser Ala Val Tyr
    210                 215                 220

Tyr Cys Ala Arg Tyr Tyr Asp Asp His Tyr Cys Leu Asp Tyr Trp Gly
225                 230                 235                 240

Gln Gly Thr Thr Leu Thr Val Ser Ser Val Glu Gly Gly Ser Gly Gly
                245                 250                 255

Ser Gly Gly Ser Gly Gly Ser Gly Gly Val Asp Asp Ile Gln Leu Thr
            260                 265                 270

Gln Ser Pro Ala Ile Met Ser Ala Ser Pro Gly Glu Lys Val Thr Met
        275                 280                 285

Thr Cys Arg Ala Ser Ser Val Ser Tyr Met Asn Trp Tyr Gln Gln
    290                 295                 300

Lys Ser Gly Thr Ser Pro Lys Arg Trp Ile Tyr Asp Thr Ser Lys Val
305                 310                 315                 320

Ala Ser Gly Val Pro Tyr Arg Phe Ser Gly Ser Gly Ser Gly Thr Ser
                325                 330                 335

Tyr Ser Leu Thr Ile Ser Ser Met Glu Ala Glu Asp Ala Ala Thr Tyr
                340                 345                 350

Tyr Cys Gln Gln Trp Ser Ser Asn Pro Leu Thr Phe Gly Ala Gly Thr
            355                 360                 365

Lys Leu Glu Leu Lys His His His His His His
    370                 375

<210> SEQ ID NO 134
<211> LENGTH: 390
<212> TYPE: PRT
<213> ORGANISM: Artificial Sequence
<220> FEATURE:
<223> OTHER INFORMATION: CD38 38A37330 VHH-L2K.07 CATE

<400> SEQUENCE: 134

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Tyr Ala Thr Met
            20                  25                  30

Ala Trp Phe Arg Gln Ala Pro Gly Lys Glu Arg Glu Phe Val Ala His
        35                  40                  45

Leu Arg Val Ser Gly Asp Thr Thr Tyr Tyr Thr Asp Ser Val Lys Gly
    50                  55                  60

Arg Phe Thr Ile Ser Arg Asp Asn Ala Lys Asn Thr Ala Tyr Leu Gln
65                  70                  75                  80

Met Asn Met Leu Lys Pro Glu Asp Thr Ala Val Tyr Tyr Cys Ala Ala
                85                  90                  95

Gly Pro Tyr Gly Ile Leu Ala Ala Arg Val Ser Asn Pro Gly Asn
            100                 105                 110

Tyr Asp Tyr Trp Gly Gln Gly Thr Gln Val Thr Val Ser Ser Gly Gly
            115                 120                 125

Gly Gly Ser Gly Gly Gly Gly Ser Gly Gly Gly Gly Ser Asp Ile Lys
        130                 135                 140

Leu Gln Gln Ser Gly Ala Glu Leu Ala Arg Pro Gly Ala Ser Val Lys
145                 150                 155                 160

Met Ser Cys Lys Thr Ser Gly Tyr Thr Phe Thr Arg Tyr Thr Met His
                165                 170                 175

Trp Val Lys Gln Arg Pro Gly Gln Gly Leu Glu Trp Ile Gly Tyr Ile
            180                 185                 190

Asn Pro Ser Arg Gly Tyr Thr Asn Tyr Asn Gln Lys Phe Lys Asp Lys
        195                 200                 205

Ala Thr Leu Thr Thr Asp Lys Ser Ser Ser Thr Ala Tyr Met Gln Leu
    210                 215                 220

Ser Ser Leu Thr Ser Glu Asp Ser Ala Val Tyr Tyr Cys Ala Arg Tyr
225                 230                 235                 240

Tyr Asp Asp His Tyr Cys Leu Asp Tyr Trp Gly Gln Gly Thr Thr Leu
            245                 250                 255

Thr Val Ser Ser Val Glu Gly Gly Ser Gly Gly Ser Gly Gly Ser Gly
            260                 265                 270

Gly Ser Gly Gly Val Asp Asp Ile Gln Leu Thr Gln Ser Pro Ala Ile
        275                 280                 285

Met Ser Ala Ser Pro Gly Glu Lys Val Thr Met Thr Cys Arg Ala Ser
    290                 295                 300

Ser Ser Val Ser Tyr Met Asn Trp Tyr Gln Gln Lys Ser Gly Thr Ser
305                 310                 315                 320

```
Pro Lys Arg Trp Ile Tyr Asp Thr Ser Lys Val Ala Ser Gly Val Pro
            325                 330                 335

Tyr Arg Phe Ser Gly Ser Gly Ser Gly Thr Ser Tyr Ser Leu Thr Ile
            340                 345                 350

Ser Ser Met Glu Ala Glu Asp Ala Ala Thr Tyr Tyr Cys Gln Gln Trp
            355                 360                 365

Ser Ser Asn Pro Leu Thr Phe Gly Ala Gly Thr Lys Leu Glu Leu Lys
            370                 375                 380

His His His His His His
385                 390

<210> SEQ ID NO 135
<211> LENGTH: 387
<212> TYPE: PRT
<213> ORGANISM: Artificial Sequence
<220> FEATURE:
<223> OTHER INFORMATION: CD38 38A37334 VHH-L2K.07 CATE

<400> SEQUENCE: 135

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ile Met Gly Trp Phe Arg Gln Ala Pro Gly Glu Glu Arg Glu Leu Val
            35                  40                  45

Ala Glu Ile Ser Ser Gly Gly Met Thr Ser Tyr Ala Asp Ser Val Lys
        50                  55                  60

Gly Arg Phe Thr Ile Ser Arg Asp Asn Ala Lys Lys Thr Gly Tyr Leu
65              70                  75                  80

Gln Met Asn Ser Leu Lys Pro Glu Asp Thr Ala Val Tyr Tyr Cys Ala
            85                  90                  95

Ala Pro Glu Arg Gly Ser Ile Trp Tyr Ser Arg Tyr Glu Tyr Lys Tyr
            100                 105                 110

Trp Gly Gln Gly Thr Gln Val Thr Val Ser Ser Gly Gly Gly Gly Ser
            115                 120                 125

Gly Gly Gly Gly Ser Gly Gly Gly Ser Asp Ile Lys Leu Gln Gln
        130                 135                 140

Ser Gly Ala Glu Leu Ala Arg Pro Gly Ala Ser Val Lys Met Ser Cys
145                 150                 155                 160

Lys Thr Ser Gly Tyr Thr Phe Thr Arg Tyr Thr Met His Trp Val Lys
            165                 170                 175

Gln Arg Pro Gly Gln Gly Leu Glu Trp Ile Gly Tyr Ile Asn Pro Ser
            180                 185                 190

Arg Gly Tyr Thr Asn Tyr Asn Gln Lys Phe Lys Asp Lys Ala Thr Leu
            195                 200                 205

Thr Thr Asp Lys Ser Ser Ser Thr Ala Tyr Met Gln Leu Ser Ser Leu
            210                 215                 220

Thr Ser Glu Asp Ser Ala Val Tyr Tyr Cys Ala Arg Tyr Tyr Asp Asp
225                 230                 235                 240

His Tyr Cys Leu Asp Tyr Trp Gly Gln Gly Thr Thr Leu Thr Val Ser
            245                 250                 255

Ser Val Glu Gly Gly Ser Gly Gly Ser Gly Gly Ser Gly Gly Ser Gly
            260                 265                 270

Gly Val Asp Asp Ile Gln Leu Thr Gln Ser Pro Ala Ile Met Ser Ala
            275                 280                 285
```

```
Ser Pro Gly Glu Lys Val Thr Met Thr Cys Arg Ala Ser Ser Val
    290                 295                 300

Ser Tyr Met Asn Trp Tyr Gln Gln Lys Ser Gly Thr Ser Pro Lys Arg
305                 310                 315                 320

Trp Ile Tyr Asp Thr Ser Lys Val Ala Ser Gly Val Pro Tyr Arg Phe
                325                 330                 335

Ser Gly Ser Gly Ser Gly Thr Ser Tyr Ser Leu Thr Ile Ser Ser Met
                340                 345                 350

Glu Ala Glu Asp Ala Ala Thr Tyr Tyr Cys Gln Gln Trp Ser Ser Asn
        355                 360                 365

Pro Leu Thr Phe Gly Ala Gly Thr Lys Leu Glu Leu Lys His His His
    370                 375                 380

His His His
385

<210> SEQ ID NO 136
<211> LENGTH: 384
<212> TYPE: PRT
<213> ORGANISM: Artificial Sequence
<220> FEATURE:
<223> OTHER INFORMATION: CD38 38A37730 VHH-L2K.07 CATE

<400> SEQUENCE: 136

Ala Val Gln Leu Val Asp Ser Gly Gly Gly Leu Ala Gln Thr Gly Gly
1               5                   10                  15

Ser Leu Arg Leu Ser Cys Ala Ala Ser Gln Gly Ile Phe Thr Ile Asn
            20                  25                  30

Ala Met Gly Trp Tyr Arg Gln Val Pro Gly Lys Gln Arg Glu Leu Val
        35                  40                  45

Ala Glu Val Ser Ser Gly Gly Arg Thr Asp Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Gly Val Tyr Tyr Cys Arg
                85                  90                  95

Val Ser Gly Trp His Val Phe Val Gly Asp Arg Ile Val Trp Gly Gln
            100                 105                 110

Gly Thr Leu Val Thr Val Ser Ser Gly Gly Gly Ser Gly Gly Gly
        115                 120                 125

Gly Ser Gly Gly Gly Ser Asp Ile Lys Leu Gln Gln Ser Gly Ala
    130                 135                 140

Glu Leu Ala Arg Pro Gly Ala Ser Val Lys Met Ser Cys Lys Thr Ser
145                 150                 155                 160

Gly Tyr Thr Phe Thr Arg Tyr Thr Met His Trp Val Lys Gln Arg Pro
                165                 170                 175

Gly Gln Gly Leu Glu Trp Ile Gly Tyr Ile Asn Pro Ser Arg Gly Tyr
            180                 185                 190

Thr Asn Tyr Asn Gln Lys Phe Lys Asp Lys Ala Thr Leu Thr Thr Asp
        195                 200                 205

Lys Ser Ser Ser Thr Ala Tyr Met Gln Leu Ser Ser Leu Thr Ser Glu
    210                 215                 220

Asp Ser Ala Val Tyr Tyr Cys Ala Arg Tyr Tyr Asp Asp His Tyr Cys
225                 230                 235                 240

Leu Asp Tyr Trp Gly Gln Gly Thr Leu Thr Val Ser Ser Val Glu
                245                 250                 255
```

```
Gly Gly Ser Gly Gly Ser Gly Gly Ser Gly Gly Val Asp
            260             265             270

Asp Ile Gln Leu Thr Gln Ser Pro Ala Ile Met Ser Ala Ser Pro Gly
                275                 280                 285

Glu Lys Val Thr Met Thr Cys Arg Ala Ser Ser Val Ser Tyr Met
290                 295                 300

Asn Trp Tyr Gln Gln Lys Ser Gly Thr Ser Pro Lys Arg Trp Ile Tyr
305                 310                 315                 320

Asp Thr Ser Lys Val Ala Ser Gly Val Pro Tyr Arg Phe Ser Gly Ser
                325                 330                 335

Gly Ser Gly Thr Ser Tyr Ser Leu Thr Ile Ser Ser Met Glu Ala Glu
                340                 345                 350

Asp Ala Ala Thr Tyr Tyr Cys Gln Gln Trp Ser Ser Asn Pro Leu Thr
                355                 360                 365

Phe Gly Ala Gly Thr Lys Leu Glu Leu Lys His His His His His His
                370                 375                 380
```

<210> SEQ ID NO 137
<211> LENGTH: 387
<212> TYPE: PRT
<213> ORGANISM: Artificial Sequence
<220> FEATURE:
<223> OTHER INFORMATION: CD38 38A37340 VHH-L2K.07 CATE

<400> SEQUENCE: 137

```
Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
                20                  25                  30

Ala Met Ala Trp Phe Arg Gln Ala Pro Gly Lys Glu Arg Glu Ile Val
                35                  40                  45

Ser Ser Ile Ser Thr Ser Gly Gly Ile Thr Asp Tyr Ala Asp Ser Val
                50                  55                  60

Lys Gly Arg Phe Thr Ile Ser Lys Asp Ser Ala Lys Met Asn Thr Val
65                  70                  75                  80

Tyr Leu Gln Met Asn Ser Leu Glu Pro Glu Asp Thr Ala Val Tyr Tyr
                85                  90                  95

Cys Ala Ala Arg Thr Trp Tyr Leu Arg Thr Ser Leu Gln Tyr Asp Tyr
                100                 105                 110

Trp Gly Gln Gly Thr Gln Val Thr Val Ser Ser Gly Gly Gly Gly Ser
                115                 120                 125

Gly Gly Gly Gly Ser Gly Gly Gly Ser Asp Ile Lys Leu Gln Gln
            130             135                 140

Ser Gly Ala Glu Leu Ala Arg Pro Gly Ala Ser Val Lys Met Ser Cys
145                 150                 155                 160

Lys Thr Ser Gly Tyr Thr Phe Thr Arg Tyr Thr Met His Trp Val Lys
                165                 170                 175

Gln Arg Pro Gly Gln Gly Leu Glu Trp Ile Gly Tyr Ile Asn Pro Ser
                180                 185                 190

Arg Gly Tyr Thr Asn Tyr Asn Gln Lys Phe Lys Asp Lys Ala Thr Leu
                195                 200                 205

Thr Thr Asp Lys Ser Ser Thr Ala Tyr Met Gln Leu Ser Ser Leu
                210                 215                 220

Thr Ser Glu Asp Ser Ala Val Tyr Tyr Cys Ala Arg Tyr Tyr Asp Asp
225                 230                 235                 240
```

-continued

His Tyr Cys Leu Asp Tyr Trp Gly Gln Gly Thr Thr Leu Thr Val Ser
            245                 250                 255

Ser Val Glu Gly Gly Ser Gly Gly Ser Gly Gly Ser Gly Gly Ser Gly
            260                 265                 270

Gly Val Asp Asp Ile Gln Leu Thr Gln Ser Pro Ala Ile Met Ser Ala
            275                 280                 285

Ser Pro Gly Glu Lys Val Thr Met Thr Cys Arg Ala Ser Ser Ser Val
            290                 295                 300

Ser Tyr Met Asn Trp Tyr Gln Gln Lys Ser Gly Thr Ser Pro Lys Arg
305                 310                 315                 320

Trp Ile Tyr Asp Thr Ser Lys Val Ala Ser Gly Val Pro Tyr Arg Phe
                325                 330                 335

Ser Gly Ser Gly Ser Gly Thr Ser Tyr Ser Leu Thr Ile Ser Ser Met
                340                 345                 350

Glu Ala Glu Asp Ala Ala Thr Tyr Tyr Cys Gln Gln Trp Ser Ser Asn
                355                 360                 365

Pro Leu Thr Phe Gly Ala Gly Thr Lys Leu Glu Leu Lys His His His
            370                 375                 380

His His His
385

<210> SEQ ID NO 138
<211> LENGTH: 385
<212> TYPE: PRT
<213> ORGANISM: Artificial Sequence
<220> FEATURE:
<223> OTHER INFORMATION: CD38 38A37731 VHH-L2K.07 CATE

<400> SEQUENCE: 138

Gln Val Lys Leu Glu Glu Ser Gly Gly Gly Leu Val Gln Ala Gly Gly
1               5                   10                  15

Ser Leu Arg Leu Ser Cys Val Ala Ser Gly Thr Ile Val Ser Ile Ser
            20                  25                  30

Thr Met Gly Trp Tyr Arg Gln Ala Pro Gly Lys Gln Arg Glu Leu Val
        35                  40                  45

Ala Thr Ile Thr Arg Arg Gly Arg Thr Asn Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Val Gln Leu Asp Ile Trp Ala Ser Ala Tyr Asp Tyr Trp Gly
            100                 105                 110

Gln Gly Thr Gln Val Thr Val Ala Ser Gly Gly Gly Gly Ser Gly Gly
        115                 120                 125

Gly Gly Ser Gly Gly Gly Gly Ser Asp Ile Lys Leu Gln Gln Ser Gly
    130                 135                 140

Ala Glu Leu Ala Arg Pro Gly Ala Ser Val Lys Met Ser Cys Lys Thr
145                 150                 155                 160

Ser Gly Tyr Thr Phe Thr Arg Tyr Thr Met His Trp Val Lys Gln Arg
                165                 170                 175

Pro Gly Gln Gly Leu Glu Trp Ile Gly Tyr Ile Asn Pro Ser Arg Gly
            180                 185                 190

Tyr Thr Asn Tyr Asn Gln Lys Phe Lys Asp Lys Ala Thr Leu Thr Thr
        195                 200                 205

```
Asp Lys Ser Ser Ser Thr Ala Tyr Met Gln Leu Ser Ser Leu Thr Ser
    210                 215                 220

Glu Asp Ser Ala Val Tyr Tyr Cys Ala Arg Tyr Tyr Asp His Tyr
225                 230                 235                 240

Cys Leu Asp Tyr Trp Gly Gln Gly Thr Thr Leu Thr Val Ser Ser Val
                    245                 250                 255

Glu Gly Gly Ser Gly Gly Ser Gly Gly Ser Gly Gly Ser Gly Gly Val
                260                 265                 270

Asp Asp Ile Gln Leu Thr Gln Ser Pro Ala Ile Met Ser Ala Ser Pro
                275                 280                 285

Gly Glu Lys Val Thr Met Thr Cys Arg Ala Ser Ser Ser Val Ser Tyr
    290                 295                 300

Met Asn Trp Tyr Gln Gln Lys Ser Gly Thr Ser Pro Lys Arg Trp Ile
305                 310                 315                 320

Tyr Asp Thr Ser Lys Val Ala Ser Gly Val Pro Tyr Arg Phe Ser Gly
                325                 330                 335

Ser Gly Ser Gly Thr Ser Tyr Ser Leu Thr Ile Ser Ser Met Glu Ala
                340                 345                 350

Glu Asp Ala Ala Thr Tyr Tyr Cys Gln Gln Trp Ser Ser Asn Pro Leu
                355                 360                 365

Thr Phe Gly Ala Gly Thr Lys Leu Glu Leu Lys His His His His
    370                 375                 380

His
385

<210> SEQ ID NO 139
<211> LENGTH: 379
<212> TYPE: PRT
<213> ORGANISM: Artificial Sequence
<220> FEATURE:
<223> OTHER INFORMATION: CD38 38A37326 VHH-L2K.07 CATE

<400> SEQUENCE: 139

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Tyr Ala Met Gly
            20                  25                  30

Trp Tyr Arg Gln Ala Pro Gly Lys Gln Arg Asp Leu Val Ala Thr Ile
        35                  40                  45

Ser Gly Ala Gly Asn Thr Lys Tyr Ala Asp Ser Val Lys Gly Arg Phe
    50                  55                  60

Thr Ile Ser Arg Asp Asn Ala Lys Asn Thr Met Tyr Leu Gln Met Asn
65                  70                  75                  80

Ser Leu Lys Pro Glu Asp Thr Ala Val Tyr Tyr Cys Ala Ala Gly Lys
                85                  90                  95

Trp Phe Pro Ala Ala Asn Glu Tyr Trp Gly Gln Gly Thr Gln Val Thr
                100                 105                 110

Val Ser Ser Gly Gly Gly Gly Ser Gly Gly Gly Gly Ser Gly Gly Gly
            115                 120                 125

Gly Ser Asp Ile Lys Leu Gln Gln Ser Gly Ala Glu Leu Ala Arg Pro
    130                 135                 140

Gly Ala Ser Val Lys Met Ser Cys Lys Thr Ser Gly Tyr Thr Phe Thr
145                 150                 155                 160

Arg Tyr Thr Met His Trp Val Lys Gln Arg Pro Gly Gln Gly Leu Glu
                165                 170                 175
```

```
Trp Ile Gly Tyr Ile Asn Pro Ser Arg Gly Tyr Thr Asn Tyr Asn Gln
            180                 185                 190

Lys Phe Lys Asp Lys Ala Thr Leu Thr Thr Asp Lys Ser Ser Ser Thr
        195                 200                 205

Ala Tyr Met Gln Leu Ser Ser Leu Thr Ser Glu Asp Ser Ala Val Tyr
    210                 215                 220

Tyr Cys Ala Arg Tyr Tyr Asp Asp His Tyr Cys Leu Asp Tyr Trp Gly
225                 230                 235                 240

Gln Gly Thr Thr Leu Thr Val Ser Ser Val Glu Gly Ser Gly Gly
                245                 250                 255

Ser Gly Gly Ser Gly Gly Ser Gly Gly Val Asp Asp Ile Gln Leu Thr
                260                 265                 270

Gln Ser Pro Ala Ile Met Ser Ala Ser Pro Gly Glu Lys Val Thr Met
            275                 280                 285

Thr Cys Arg Ala Ser Ser Ser Val Ser Tyr Met Asn Trp Tyr Gln Gln
        290                 295                 300

Lys Ser Gly Thr Ser Pro Lys Arg Trp Ile Tyr Asp Thr Ser Lys Val
305                 310                 315                 320

Ala Ser Gly Val Pro Tyr Arg Phe Ser Gly Ser Gly Ser Gly Thr Ser
                325                 330                 335

Tyr Ser Leu Thr Ile Ser Ser Met Glu Ala Glu Asp Ala Ala Thr Tyr
                340                 345                 350

Tyr Cys Gln Gln Trp Ser Ser Asn Pro Leu Thr Phe Gly Ala Gly Thr
            355                 360                 365

Lys Leu Glu Leu Lys His His His His His His
        370                 375

<210> SEQ ID NO 140
<211> LENGTH: 376
<212> TYPE: PRT
<213> ORGANISM: Artificial Sequence
<220> FEATURE:
<223> OTHER INFORMATION: CD38 38A37333 VHH-OKT3 CATE

<400> SEQUENCE: 140

Asp Val Gln Leu Val Glu Ser Gly Gly Gly Leu Val Gln Pro Gly Gly
1               5                   10                  15

Ser Leu Arg Leu Ser Cys Val Ala Ser Gly Leu Thr Phe Ser Ser Tyr
            20                  25                  30

Pro Met Met Trp Val Arg Gln Ala Pro Gly Lys Gly Leu Glu Trp Val
        35                  40                  45

Ser Arg Ile Ser Asp Ser Gly Gly Tyr Thr Asn Tyr Asp Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Thr Pro Glu Asp Thr Ala Val Tyr Tyr Cys
                85                  90                  95

Arg Ile Leu Gly Leu Pro Thr Thr Gly Gln Gly Thr Gln Val Thr Val
            100                 105                 110

Ser Ser Gly Gly Gly Gly Ser Gly Gly Gly Ser Gly Gly Gly Gly
        115                 120                 125

Ser Gln Val Gln Leu Gln Gln Ser Gly Ala Glu Leu Ala Arg Pro Gly
    130                 135                 140

Ala Ser Val Lys Met Ser Cys Lys Ala Ser Gly Tyr Thr Phe Thr Arg
145                 150                 155                 160
```

Tyr Thr Met His Trp Val Lys Gln Arg Pro Gly Gln Gly Leu Glu Trp
                165                 170                 175

Ile Gly Tyr Ile Asn Pro Ser Arg Gly Tyr Thr Asn Tyr Asn Gln Lys
            180                 185                 190

Phe Lys Asp Lys Ala Thr Leu Thr Thr Asp Lys Ser Ser Ser Thr Ala
        195                 200                 205

Tyr Met Gln Leu Ser Ser Leu Thr Ser Glu Asp Ser Ala Val Tyr Tyr
    210                 215                 220

Cys Ala Arg Tyr Tyr Asp Asp His Tyr Cys Leu Asp Tyr Trp Gly Gln
225                 230                 235                 240

Gly Thr Thr Leu Thr Val Ser Ser Gly Gly Gly Gly Ser Gly Gly Gly
                245                 250                 255

Gly Ser Gly Gly Gly Gly Ser Gln Ile Val Leu Thr Gln Ser Pro Ala
                260                 265                 270

Ile Met Ser Ala Ser Pro Gly Glu Lys Val Thr Met Thr Cys Ser Ala
                275                 280                 285

Ser Ser Ser Val Ser Tyr Met Asn Trp Tyr Gln Gln Lys Ser Gly Thr
            290                 295                 300

Ser Pro Lys Arg Trp Ile Tyr Asp Thr Ser Lys Leu Ala Ser Gly Val
305                 310                 315                 320

Pro Ala His Phe Arg Gly Ser Gly Ser Gly Thr Ser Tyr Ser Leu Thr
                325                 330                 335

Ile Ser Gly Met Glu Ala Glu Asp Ala Ala Thr Tyr Tyr Cys Gln Gln
                340                 345                 350

Trp Ser Ser Asn Pro Phe Thr Phe Gly Ser Gly Thr Lys Leu Glu Ile
            355                 360                 365

Asn Arg His His His His His His
    370                 375

<210> SEQ ID NO 141
<211> LENGTH: 388
<212> TYPE: PRT
<213> ORGANISM: Artificial Sequence
<220> FEATURE:
<223> OTHER INFORMATION: CD38 38A37336 VHH-OKT3 CATE

<400> SEQUENCE: 141

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Asn
            20                  25                  30

Trp Met Tyr Trp Val Arg Gln Ala Pro Gly Lys Gly Leu Glu Trp Val
        35                  40                  45

Ala Thr Ile Ser Thr Asp Gly Arg Gly Thr Tyr Tyr Lys Asp Ser Val
    50                  55                  60

Lys Gly Arg Phe Thr Val Ser Arg Asp Asn Ala Met Ser Thr Leu Leu
65                  70                  75                  80

Leu Gln Met Asn Asn Leu Lys Ser Glu Asp Thr Ala Val Tyr Tyr Cys
                85                  90                  95

Ala Lys Glu Pro Arg Val Leu Met Ala Tyr Leu Arg Asn Leu Gly Asp
            100                 105                 110

Phe Gly Ser Trp Gly Gln Gly Thr Gln Val Thr Val Ser Ser Gly Gly
        115                 120                 125

Gly Gly Ser Gly Gly Gly Gly Ser Gly Gly Gly Gly Ser Gln Val Gln
    130                 135                 140

```
Leu Gln Gln Ser Gly Ala Glu Leu Ala Arg Pro Gly Ala Ser Val Lys
145                 150                 155                 160

Met Ser Cys Lys Ala Ser Gly Tyr Thr Phe Thr Arg Tyr Thr Met His
                165                 170                 175

Trp Val Lys Gln Arg Pro Gly Gln Gly Leu Glu Trp Ile Gly Tyr Ile
            180                 185                 190

Asn Pro Ser Arg Gly Tyr Thr Asn Tyr Asn Gln Lys Phe Lys Asp Lys
        195                 200                 205

Ala Thr Leu Thr Thr Asp Lys Ser Ser Thr Ala Tyr Met Gln Leu
    210                 215                 220

Ser Ser Leu Thr Ser Glu Asp Ser Ala Val Tyr Tyr Cys Ala Arg Tyr
225                 230                 235                 240

Tyr Asp Asp His Tyr Cys Leu Asp Tyr Trp Gly Gln Gly Thr Thr Leu
                245                 250                 255

Thr Val Ser Ser Gly Gly Gly Ser Gly Gly Gly Ser Gly Gly
            260                 265                 270

Gly Gly Ser Gln Ile Val Leu Thr Gln Ser Pro Ala Ile Met Ser Ala
        275                 280                 285

Ser Pro Gly Glu Lys Val Thr Met Thr Cys Ser Ala Ser Ser Ser Val
    290                 295                 300

Ser Tyr Met Asn Trp Tyr Gln Gln Lys Ser Gly Thr Ser Pro Lys Arg
305                 310                 315                 320

Trp Ile Tyr Asp Thr Ser Lys Leu Ala Ser Gly Val Pro Ala His Phe
                325                 330                 335

Arg Gly Ser Gly Ser Gly Thr Ser Tyr Ser Leu Thr Ile Ser Gly Met
            340                 345                 350

Glu Ala Glu Asp Ala Ala Thr Tyr Tyr Cys Gln Gln Trp Ser Ser Asn
        355                 360                 365

Pro Phe Thr Phe Gly Ser Gly Thr Lys Leu Glu Ile Asn Arg His His
    370                 375                 380

His His His His
385

<210> SEQ ID NO 142
<211> LENGTH: 377
<212> TYPE: PRT
<213> ORGANISM: Artificial Sequence
<220> FEATURE:
<223> OTHER INFORMATION: CD38 38A37699 VHH-OKT3 CATE

<400> SEQUENCE: 142

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Phe Ser Ile Asn
            20                  25                  30

Ala Met Gly Trp Tyr Arg Gln Ala Pro Gly Lys Gln Arg Glu Leu Val
        35                  40                  45

Ala Ala Ile Ser Thr Ala Gly Ser Thr Asn Tyr Gly Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Leu Asn Phe Pro Pro Tyr Val Tyr Trp Gly Gln Gly Thr Gln Val Thr
            100                 105                 110
```

```
Val Ser Ser Gly Gly Gly Ser Gly Gly Gly Ser Gly Gly
        115                 120                 125

Gly Ser Gln Val Gln Leu Gln Gln Ser Gly Ala Glu Leu Ala Arg Pro
    130                 135                 140

Gly Ala Ser Val Lys Met Ser Cys Lys Ala Ser Gly Tyr Thr Phe Thr
145                 150                 155                 160

Arg Tyr Thr Met His Trp Val Lys Gln Arg Pro Gly Gln Gly Leu Glu
                165                 170                 175

Trp Ile Gly Tyr Ile Asn Pro Ser Arg Gly Tyr Thr Asn Tyr Asn Gln
            180                 185                 190

Lys Phe Lys Asp Lys Ala Thr Leu Thr Thr Asp Lys Ser Ser Ser Thr
        195                 200                 205

Ala Tyr Met Gln Leu Ser Ser Leu Thr Ser Glu Asp Ser Ala Val Tyr
    210                 215                 220

Tyr Cys Ala Arg Tyr Tyr Asp Asp His Tyr Cys Leu Asp Tyr Trp Gly
225                 230                 235                 240

Gln Gly Thr Thr Leu Thr Val Ser Ser Gly Gly Gly Ser Gly Gly
                245                 250                 255

Gly Gly Ser Gly Gly Gly Ser Gln Ile Val Leu Thr Gln Ser Pro
        260                 265                 270

Ala Ile Met Ser Ala Ser Pro Gly Glu Lys Val Thr Met Thr Cys Ser
    275                 280                 285

Ala Ser Ser Ser Val Ser Tyr Met Asn Trp Tyr Gln Gln Lys Ser Gly
    290                 295                 300

Thr Ser Pro Lys Arg Trp Ile Tyr Asp Thr Ser Lys Leu Ala Ser Gly
305                 310                 315                 320

Val Pro Ala His Phe Arg Gly Ser Gly Ser Gly Thr Ser Tyr Ser Leu
                325                 330                 335

Thr Ile Ser Gly Met Glu Ala Glu Asp Ala Ala Thr Tyr Tyr Cys Gln
            340                 345                 350

Gln Trp Ser Ser Asn Pro Phe Thr Phe Gly Ser Gly Thr Lys Leu Glu
        355                 360                 365

Ile Asn Arg His His His His His His
        370                 375

<210> SEQ ID NO 143
<211> LENGTH: 381
<212> TYPE: PRT
<213> ORGANISM: Artificial Sequence
<220> FEATURE:
<223> OTHER INFORMATION: CD38 38A37331 VHH-OKT3 CATE

<400> SEQUENCE: 143

Gln Val Lys Leu Glu Glu Ser Gly Gly Gly Leu Val Gln Pro Gly Glu
1               5                   10                  15

Ser Leu Arg Leu Ser Cys Ser Ala Ser Gly Ser Ile Phe Lys Val Phe
            20                  25                  30

Arg Val Phe Ala Met Ser Trp Tyr Arg Gln Gly Pro Gly Lys Gln Arg
        35                  40                  45

Glu Leu Val Ala Ser Ile Ser Ser Gly Glu Thr Thr Thr Tyr Ala Asp
    50                  55                  60

Ser Val Lys Gly Arg Phe Thr Ile Ser Arg Asp Asn Ala Lys Asn Thr
65                  70                  75                  80

Ala Tyr Leu Gln Met Asp Ser Leu Lys Pro Glu Asp Thr Ala Val Tyr
                85                  90                  95
```

Tyr Cys Asn Ala Asp His Thr Phe Thr Gly Asp Phe Trp Gly Gln Gly
                100                 105                 110

Thr Gln Val Thr Val Ser Ser Gly Gly Gly Ser Gly Gly Gly Gly
        115                 120                 125

Ser Gly Gly Gly Gly Ser Gln Val Gln Leu Gln Gln Ser Gly Ala Glu
130                 135                 140

Leu Ala Arg Pro Gly Ala Ser Val Lys Met Ser Cys Lys Ala Ser Gly
145                 150                 155                 160

Tyr Thr Phe Thr Arg Tyr Thr Met His Trp Val Lys Gln Arg Pro Gly
                165                 170                 175

Gln Gly Leu Glu Trp Ile Gly Tyr Ile Asn Pro Ser Arg Gly Tyr Thr
            180                 185                 190

Asn Tyr Asn Gln Lys Phe Lys Asp Lys Ala Thr Leu Thr Thr Asp Lys
        195                 200                 205

Ser Ser Ser Thr Ala Tyr Met Gln Leu Ser Ser Leu Thr Ser Glu Asp
210                 215                 220

Ser Ala Val Tyr Tyr Cys Ala Arg Tyr Tyr Asp Asp His Tyr Cys Leu
225                 230                 235                 240

Asp Tyr Trp Gly Gln Gly Thr Thr Leu Thr Val Ser Ser Gly Gly Gly
                245                 250                 255

Gly Ser Gly Gly Gly Gly Ser Gly Gly Gly Ser Gln Ile Val Leu
            260                 265                 270

Thr Gln Ser Pro Ala Ile Met Ser Ala Ser Pro Gly Glu Lys Val Thr
        275                 280                 285

Met Thr Cys Ser Ala Ser Ser Ser Val Ser Tyr Met Asn Trp Tyr Gln
290                 295                 300

Gln Lys Ser Gly Thr Ser Pro Lys Arg Trp Ile Tyr Asp Thr Ser Lys
305                 310                 315                 320

Leu Ala Ser Gly Val Pro Ala His Phe Arg Gly Ser Gly Ser Gly Thr
                325                 330                 335

Ser Tyr Ser Leu Thr Ile Ser Gly Met Glu Ala Glu Asp Ala Ala Thr
            340                 345                 350

Tyr Tyr Cys Gln Gln Trp Ser Ser Asn Pro Phe Thr Phe Gly Ser Gly
        355                 360                 365

Thr Lys Leu Glu Ile Asn Arg His His His His His
370                 375                 380

<210> SEQ ID NO 144
<211> LENGTH: 378
<212> TYPE: PRT
<213> ORGANISM: Artificial Sequence
<220> FEATURE:
<223> OTHER INFORMATION: CD38 38A37717 VHH-OKT3 CATE

<400> SEQUENCE: 144

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

```
Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Gly Gly Gly Gly Ser Gly Gly
        115                 120                 125

Gly Gly Ser Gln Val Gln Leu Gln Gln Ser Gly Ala Glu Leu Ala Arg
    130                 135                 140

Pro Gly Ala Ser Val Lys Met Ser Cys Lys Ala Ser Gly Tyr Thr Phe
145                 150                 155                 160

Thr Arg Tyr Thr Met His Trp Val Lys Gln Arg Pro Gly Gln Gly Leu
                165                 170                 175

Glu Trp Ile Gly Tyr Ile Asn Pro Ser Arg Gly Tyr Thr Asn Tyr Asn
            180                 185                 190

Gln Lys Phe Lys Asp Lys Ala Thr Leu Thr Thr Asp Lys Ser Ser Ser
        195                 200                 205

Thr Ala Tyr Met Gln Leu Ser Ser Leu Thr Ser Glu Asp Ser Ala Val
    210                 215                 220

Tyr Tyr Cys Ala Arg Tyr Tyr Asp Asp His Tyr Cys Leu Asp Tyr Trp
225                 230                 235                 240

Gly Gln Gly Thr Thr Leu Thr Val Ser Ser Gly Gly Gly Gly Ser Gly
                245                 250                 255

Gly Gly Gly Ser Gly Gly Gly Ser Gln Ile Val Leu Thr Gln Ser
            260                 265                 270

Pro Ala Ile Met Ser Ala Ser Pro Gly Glu Lys Val Thr Met Thr Cys
    275                 280                 285

Ser Ala Ser Ser Val Ser Tyr Met Asn Trp Tyr Gln Gln Lys Ser
290                 295                 300

Gly Thr Ser Pro Lys Arg Trp Ile Tyr Asp Thr Ser Lys Leu Ala Ser
305                 310                 315                 320

Gly Val Pro Ala His Phe Arg Gly Ser Gly Ser Gly Thr Ser Tyr Ser
                325                 330                 335

Leu Thr Ile Ser Gly Met Glu Ala Glu Asp Ala Ala Thr Tyr Tyr Cys
            340                 345                 350

Gln Gln Trp Ser Ser Asn Pro Phe Thr Phe Gly Ser Gly Thr Lys Leu
        355                 360                 365

Glu Ile Asn Arg His His His His His His
    370                 375

<210> SEQ ID NO 145
<211> LENGTH: 377
<212> TYPE: PRT
<213> ORGANISM: Artificial Sequence
<220> FEATURE:
<223> OTHER INFORMATION: CD38 38A37719 VHH-OKT3 CATE

<400> SEQUENCE: 145

Gln Val Lys Leu Glu Glu Ser Gly Gly Gly Ser Val Gln Thr Gly Gly
1               5                   10                  15

Ser Leu Arg Leu Ser Cys Ala Ala Ser Ala Ser Ile Phe Thr Arg Leu
            20                  25                  30

Pro Met Gly Trp Tyr Arg Gln Ala Pro Gly Lys Gln Arg Glu Leu Val
        35                  40                  45

Val Gly Ile Val Pro Ser Gly Arg Ile Asn Tyr Ala Asp Ser Val Lys
    50                  55                  60
```

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Arg
                85                  90                  95

Ala Asp Thr Phe Pro Leu Pro Thr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gln Val Gln Leu Gln Gln Ser Gly Ala Glu Leu Ala Arg Pro
130                 135                 140

Gly Ala Ser Val Lys Met Ser Cys Lys Ala Ser Gly Tyr Thr Phe Thr
145                 150                 155                 160

Arg Tyr Thr Met His Trp Val Lys Gln Arg Pro Gly Gln Gly Leu Glu
                165                 170                 175

Trp Ile Gly Tyr Ile Asn Pro Ser Arg Gly Tyr Thr Asn Tyr Asn Gln
            180                 185                 190

Lys Phe Lys Asp Lys Ala Thr Leu Thr Thr Asp Lys Ser Ser Ser Thr
        195                 200                 205

Ala Tyr Met Gln Leu Ser Ser Leu Thr Ser Glu Asp Ser Ala Val Tyr
210                 215                 220

Tyr Cys Ala Arg Tyr Tyr Asp Asp His Tyr Cys Leu Asp Tyr Trp Gly
225                 230                 235                 240

Gln Gly Thr Thr Leu Thr Val Ser Ser Gly Gly Gly Gly Ser Gly Gly
                245                 250                 255

Gly Gly Ser Gly Gly Gly Gly Ser Gln Ile Val Leu Thr Gln Ser Pro
            260                 265                 270

Ala Ile Met Ser Ala Ser Pro Gly Glu Lys Val Thr Met Thr Cys Ser
        275                 280                 285

Ala Ser Ser Ser Val Ser Tyr Met Asn Trp Tyr Gln Gln Lys Ser Gly
290                 295                 300

Thr Ser Pro Lys Arg Trp Ile Tyr Asp Thr Ser Lys Leu Ala Ser Gly
305                 310                 315                 320

Val Pro Ala His Phe Arg Gly Ser Gly Ser Gly Thr Ser Tyr Ser Leu
                325                 330                 335

Thr Ile Ser Gly Met Glu Ala Glu Asp Ala Ala Thr Tyr Tyr Cys Gln
            340                 345                 350

Gln Trp Ser Ser Asn Pro Phe Thr Phe Gly Ser Gly Thr Lys Leu Glu
        355                 360                 365

Ile Asn Arg His His His His His His
370                 375

<210> SEQ ID NO 146
<211> LENGTH: 388
<212> TYPE: PRT
<213> ORGANISM: Artificial Sequence
<220> FEATURE:
<223> OTHER INFORMATION: CD38 38A37330 VHH-OKT3 CATE

<400> SEQUENCE: 146

Gln Val Gln Leu Val Glu Ser Gly Gly Gly Leu Val Gln Ala Gly Asp
1               5                   10                  15

Ser Leu Arg Leu Ser Cys Ala Ala Ser Gly Arg Ala Tyr Ala Thr Met
            20                  25                  30

Ala Trp Phe Arg Gln Ala Pro Gly Lys Glu Arg Glu Phe Val Ala His
        35                  40                  45

Leu Arg Val Ser Gly Asp Thr Tyr Tyr Thr Asp Ser Val Lys Gly
50                  55                  60

Arg Phe Thr Ile Ser Arg Asp Asn Ala Lys Asn Thr Ala Tyr Leu Gln
65                  70                  75                  80

Met Asn Met Leu Lys Pro Glu Asp Thr Ala Val Tyr Tyr Cys Ala Ala
                85                  90                  95

Gly Pro Tyr Gly Ile Leu Ala Ala Arg Val Ser Asn Pro Gly Asn
            100                 105                 110

Tyr Asp Tyr Trp Gly Gln Gly Thr Gln Val Thr Val Ser Gly Gly
            115                 120                 125

Gly Gly Ser Gly Gly Gly Ser Gly Gly Gly Ser Gln Val Gln
        130                 135                 140

Leu Gln Gln Ser Gly Ala Glu Leu Ala Arg Pro Gly Ala Ser Val Lys
145                 150                 155                 160

Met Ser Cys Lys Ala Ser Gly Tyr Thr Phe Thr Arg Tyr Thr Met His
                165                 170                 175

Trp Val Lys Gln Arg Pro Gly Gln Gly Leu Glu Trp Ile Gly Tyr Ile
                180                 185                 190

Asn Pro Ser Arg Gly Tyr Thr Asn Tyr Asn Gln Lys Phe Lys Asp Lys
                195                 200                 205

Ala Thr Leu Thr Thr Asp Lys Ser Ser Ser Thr Ala Tyr Met Gln Leu
210                 215                 220

Ser Ser Leu Thr Ser Glu Asp Ser Ala Val Tyr Tyr Cys Ala Arg Tyr
225                 230                 235                 240

Tyr Asp Asp His Tyr Cys Leu Asp Tyr Trp Gly Gln Gly Thr Thr Leu
                245                 250                 255

Thr Val Ser Ser Gly Gly Gly Gly Ser Gly Gly Gly Gly Ser Gly Gly
                260                 265                 270

Gly Gly Ser Gln Ile Val Leu Thr Gln Ser Pro Ala Ile Met Ser Ala
            275                 280                 285

Ser Pro Gly Glu Lys Val Thr Met Thr Cys Ser Ala Ser Ser Ser Val
290                 295                 300

Ser Tyr Met Asn Trp Tyr Gln Gln Lys Ser Gly Thr Ser Pro Lys Arg
305                 310                 315                 320

Trp Ile Tyr Asp Thr Ser Lys Leu Ala Ser Gly Val Pro Ala His Phe
                325                 330                 335

Arg Gly Ser Gly Ser Gly Thr Ser Tyr Ser Leu Thr Ile Ser Gly Met
            340                 345                 350

Glu Ala Glu Asp Ala Ala Thr Tyr Tyr Cys Gln Gln Trp Ser Ser Asn
            355                 360                 365

Pro Phe Thr Phe Gly Ser Gly Thr Lys Leu Glu Ile Asn Arg His His
    370                 375                 380

His His His His
385

<210> SEQ ID NO 147
<211> LENGTH: 385
<212> TYPE: PRT
<213> ORGANISM: Artificial Sequence
<220> FEATURE:
<223> OTHER INFORMATION: CD38 38A37334 VHH-OKT3 CATE

<400> SEQUENCE: 147

Glu Val Gln Leu Val Glu Ser Gly Gly Gly Leu Val Gln Ala Gly Gly
1               5                   10                  15

Ser Leu Arg Leu Ser Cys Ala Ala Ser Gly Leu Thr Phe Ser Ser Tyr
            20                  25                  30

Ile Met Gly Trp Phe Arg Gln Ala Pro Gly Glu Arg Glu Leu Val
        35                  40                  45

Ala Glu Ile Ser Ser Gly Gly Met Thr Ser Tyr Ala Asp Ser Val Lys
50                  55                  60

Gly Arg Phe Thr Ile Ser Arg Asp Asn Ala Lys Lys Thr Gly Tyr Leu
65                  70                  75                  80

Gln Met Asn Ser Leu Lys Pro Glu Asp Thr Ala Val Tyr Tyr Cys Ala
                85                  90                  95

Ala Pro Glu Arg Gly Ser Ile Trp Tyr Ser Arg Tyr Glu Tyr Lys Tyr
            100                 105                 110

Trp Gly Gln Gly Thr Gln Val Thr Val Ser Ser Gly Gly Gly Gly Ser
            115                 120                 125

Gly Gly Gly Gly Ser Gly Gly Gly Ser Gln Val Gln Leu Gln Gln
        130                 135                 140

Ser Gly Ala Glu Leu Ala Arg Pro Gly Ala Ser Val Lys Met Ser Cys
145                 150                 155                 160

Lys Ala Ser Gly Tyr Thr Phe Thr Arg Tyr Thr Met His Trp Val Lys
                165                 170                 175

Gln Arg Pro Gly Gln Gly Leu Glu Trp Ile Gly Tyr Ile Asn Pro Ser
            180                 185                 190

Arg Gly Tyr Thr Asn Tyr Asn Gln Lys Phe Lys Asp Lys Ala Thr Leu
        195                 200                 205

Thr Thr Asp Lys Ser Ser Ser Thr Ala Tyr Met Gln Leu Ser Ser Leu
        210                 215                 220

Thr Ser Glu Asp Ser Ala Val Tyr Tyr Cys Ala Arg Tyr Tyr Asp Asp
225                 230                 235                 240

His Tyr Cys Leu Asp Tyr Trp Gly Gln Gly Thr Thr Leu Thr Val Ser
                245                 250                 255

Ser Gly Gly Gly Gly Ser Gly Gly Gly Ser Gly Gly Gly Gly Ser
            260                 265                 270

Gln Ile Val Leu Thr Gln Ser Pro Ala Ile Met Ser Ala Ser Pro Gly
        275                 280                 285

Glu Lys Val Thr Met Thr Cys Ser Ala Ser Ser Val Ser Tyr Met
290                 295                 300

Asn Trp Tyr Gln Gln Lys Ser Gly Thr Ser Pro Lys Arg Trp Ile Tyr
305                 310                 315                 320

Asp Thr Ser Lys Leu Ala Ser Gly Val Pro Ala His Phe Arg Gly Ser
                325                 330                 335

Gly Ser Gly Thr Ser Tyr Ser Leu Thr Ile Ser Gly Met Glu Ala Glu
            340                 345                 350

Asp Ala Ala Thr Tyr Tyr Cys Gln Gln Trp Ser Ser Asn Pro Phe Thr
            355                 360                 365

Phe Gly Ser Gly Thr Lys Leu Glu Ile Asn Arg His His His His
        370                 375                 380

His
385

<210> SEQ ID NO 148
<211> LENGTH: 382
<212> TYPE: PRT
<213> ORGANISM: Artificial Sequence
<220> FEATURE:

<223> OTHER INFORMATION: CD38 38A37730 VHH-OKT3 CATE

<400> SEQUENCE: 148

```
Ala Val Gln Leu Val Asp Ser Gly Gly Gly Leu Ala Gln Thr Gly Gly
1               5                   10                  15
Ser Leu Arg Leu Ser Cys Ala Ala Ser Gln Gly Ile Phe Thr Ile Asn
            20                  25                  30
Ala Met Gly Trp Tyr Arg Gln Val Pro Gly Lys Gln Arg Glu Leu Val
        35                  40                  45
Ala Glu Val Ser Ser Gly Gly Arg Thr Asp Tyr Ala Asp Ser Val Lys
    50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Gly Val Tyr Tyr Cys Arg
                85                  90                  95
Val Ser Gly Trp His Val Phe Val Gly Asp Arg Ile Val Trp Gly Gln
            100                 105                 110
Gly Thr Leu Val Thr Val Ser Ser Gly Gly Gly Ser Gly Gly Gly
        115                 120                 125
Gly Ser Gly Gly Gly Ser Gln Val Gln Leu Gln Gln Ser Gly Ala
    130                 135                 140
Glu Leu Ala Arg Pro Gly Ala Ser Val Lys Met Ser Cys Lys Ala Ser
145                 150                 155                 160
Gly Tyr Thr Phe Thr Arg Tyr Thr Met His Trp Val Lys Gln Arg Pro
                165                 170                 175
Gly Gln Gly Leu Glu Trp Ile Gly Tyr Ile Asn Pro Ser Arg Gly Tyr
            180                 185                 190
Thr Asn Tyr Asn Gln Lys Phe Lys Asp Lys Ala Thr Leu Thr Thr Asp
        195                 200                 205
Lys Ser Ser Ser Thr Ala Tyr Met Gln Leu Ser Ser Leu Thr Ser Glu
    210                 215                 220
Asp Ser Ala Val Tyr Tyr Cys Ala Arg Tyr Tyr Asp Asp His Tyr Cys
225                 230                 235                 240
Leu Asp Tyr Trp Gly Gln Gly Thr Thr Leu Thr Val Ser Ser Gly Gly
                245                 250                 255
Gly Gly Ser Gly Gly Gly Gly Ser Gly Gly Gly Gly Ser Gln Ile Val
            260                 265                 270
Leu Thr Gln Ser Pro Ala Ile Met Ser Ala Ser Pro Gly Glu Lys Val
        275                 280                 285
Thr Met Thr Cys Ser Ala Ser Ser Val Ser Tyr Met Asn Trp Tyr
    290                 295                 300
Gln Gln Lys Ser Gly Thr Ser Pro Lys Arg Trp Ile Tyr Asp Thr Ser
305                 310                 315                 320
Lys Leu Ala Ser Gly Val Pro Ala His Phe Arg Gly Ser Gly Ser Gly
                325                 330                 335
Thr Ser Tyr Ser Leu Thr Ile Ser Gly Met Glu Ala Glu Asp Ala Ala
            340                 345                 350
Thr Tyr Tyr Cys Gln Gln Trp Ser Ser Asn Pro Phe Thr Phe Gly Ser
        355                 360                 365
Gly Thr Lys Leu Glu Ile Asn Arg His His His His His His
    370                 375                 380
```

<210> SEQ ID NO 149
<211> LENGTH: 385

<212> TYPE: PRT
<213> ORGANISM: Artificial Sequence
<220> FEATURE:
<223> OTHER INFORMATION: CD38 38A37340 VHH-OKT3 CATE

<400> SEQUENCE: 149

```
Asp Val Gln Leu Val Glu Ser Gly Gly Gly Leu Val Gln Ala Gly Asp
1               5                   10                  15

Ser Leu Arg Leu Ser Cys Ala Ala Ser Gly Arg Thr Phe Ser Ser Tyr
            20                  25                  30

Ala Met Ala Trp Phe Arg Gln Ala Pro Gly Lys Glu Arg Glu Ile Val
        35                  40                  45

Ser Ser Ile Ser Thr Ser Gly Gly Ile Thr Asp Tyr Ala Asp Ser Val
50                  55                  60

Lys Gly Arg Phe Thr Ile Ser Lys Asp Ser Ala Lys Met Asn Thr Val
65                  70                  75                  80

Tyr Leu Gln Met Asn Ser Leu Glu Pro Glu Asp Thr Ala Val Tyr Tyr
                85                  90                  95

Cys Ala Ala Arg Thr Trp Tyr Leu Arg Thr Ser Leu Gln Tyr Asp Tyr
            100                 105                 110

Trp Gly Gln Gly Thr Gln Val Thr Val Ser Ser Gly Gly Gly Gly Ser
        115                 120                 125

Gly Gly Gly Gly Ser Gly Gly Gly Ser Gln Val Gln Leu Gln Gln
130                 135                 140

Ser Gly Ala Glu Leu Ala Arg Pro Gly Ala Ser Val Lys Met Ser Cys
145                 150                 155                 160

Lys Ala Ser Gly Tyr Thr Phe Thr Arg Tyr Thr Met His Trp Val Lys
                165                 170                 175

Gln Arg Pro Gly Gln Gly Leu Glu Trp Ile Gly Tyr Ile Asn Pro Ser
            180                 185                 190

Arg Gly Tyr Thr Asn Tyr Asn Gln Lys Phe Lys Asp Lys Ala Thr Leu
        195                 200                 205

Thr Thr Asp Lys Ser Ser Ser Thr Ala Tyr Met Gln Leu Ser Ser Leu
210                 215                 220

Thr Ser Glu Asp Ser Ala Val Tyr Tyr Cys Ala Arg Tyr Tyr Asp Asp
225                 230                 235                 240

His Tyr Cys Leu Asp Tyr Trp Gly Gln Gly Thr Thr Leu Thr Val Ser
                245                 250                 255

Ser Gly Gly Gly Gly Ser Gly Gly Gly Gly Ser Gly Gly Gly Gly Ser
            260                 265                 270

Gln Ile Val Leu Thr Gln Ser Pro Ala Ile Met Ser Ala Ser Pro Gly
        275                 280                 285

Glu Lys Val Thr Met Thr Cys Ser Ala Ser Ser Val Ser Tyr Met
290                 295                 300

Asn Trp Tyr Gln Gln Lys Ser Gly Thr Ser Pro Lys Arg Trp Ile Tyr
305                 310                 315                 320

Asp Thr Ser Lys Leu Ala Ser Gly Val Pro Ala His Phe Arg Gly Ser
                325                 330                 335

Gly Ser Gly Thr Ser Tyr Ser Leu Thr Ile Ser Gly Met Glu Ala Glu
            340                 345                 350

Asp Ala Ala Thr Tyr Tyr Cys Gln Gln Trp Ser Ser Asn Pro Phe Thr
        355                 360                 365

Phe Gly Ser Gly Thr Lys Leu Glu Ile Asn Arg His His His His
370                 375                 380
```

His
385

<210> SEQ ID NO 150
<211> LENGTH: 383
<212> TYPE: PRT
<213> ORGANISM: Artificial Sequence
<220> FEATURE:
<223> OTHER INFORMATION: CD38 38A37731 VHH-OKT3 CATE

<400> SEQUENCE: 150

```
Gln Val Lys Leu Glu Glu Ser Gly Gly Gly Leu Val Gln Ala Gly Gly
1               5                   10                  15

Ser Leu Arg Leu Ser Cys Val Ala Ser Gly Thr Ile Val Ser Ile Ser
            20                  25                  30

Thr Met Gly Trp Tyr Arg Gln Ala Pro Gly Lys Gln Arg Glu Leu Val
        35                  40                  45

Ala Thr Ile Thr Arg Arg Gly Arg Thr Asn Tyr Thr Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Glu Val Gln Leu Asp Ile Trp Ala Ser Ala Tyr Asp Tyr Trp Gly
            100                 105                 110

Gln Gly Thr Gln Val Thr Val Ala Ser Gly Gly Gly Ser Gly Gly
        115                 120                 125

Gly Gly Ser Gly Gly Gly Ser Gln Val Gln Leu Gln Gln Ser Gly
    130                 135                 140

Ala Glu Leu Ala Arg Pro Gly Ala Ser Val Lys Met Ser Cys Lys Ala
145                 150                 155                 160

Ser Gly Tyr Thr Phe Thr Arg Tyr Thr Met His Trp Val Lys Gln Arg
                165                 170                 175

Pro Gly Gln Gly Leu Glu Trp Ile Gly Tyr Ile Asn Pro Ser Arg Gly
            180                 185                 190

Tyr Thr Asn Tyr Asn Gln Lys Phe Lys Asp Lys Ala Thr Leu Thr Thr
        195                 200                 205

Asp Lys Ser Ser Ser Thr Ala Tyr Met Gln Leu Ser Ser Leu Thr Ser
    210                 215                 220

Glu Asp Ser Ala Val Tyr Tyr Cys Ala Arg Tyr Tyr Asp Asp His Tyr
225                 230                 235                 240

Cys Leu Asp Tyr Trp Gly Gln Gly Thr Thr Leu Thr Val Ser Ser Gly
                245                 250                 255

Gly Gly Gly Ser Gly Gly Gly Ser Gly Gly Gly Ser Gln Ile
            260                 265                 270

Val Leu Thr Gln Ser Pro Ala Ile Met Ser Ala Ser Pro Gly Glu Lys
        275                 280                 285

Val Thr Met Thr Cys Ser Ala Ser Ser Ser Val Ser Tyr Met Asn Trp
    290                 295                 300

Tyr Gln Gln Lys Ser Gly Thr Ser Pro Lys Arg Trp Ile Tyr Asp Thr
305                 310                 315                 320

Ser Lys Leu Ala Ser Gly Val Pro Ala His Phe Arg Gly Ser Gly Ser
                325                 330                 335

Gly Thr Ser Tyr Ser Leu Thr Ile Ser Gly Met Glu Ala Glu Asp Ala
            340                 345                 350
```

Ala Thr Tyr Tyr Cys Gln Gln Trp Ser Ser Asn Pro Phe Thr Phe Gly
            355                 360                 365

Ser Gly Thr Lys Leu Glu Ile Asn Arg His His His His His His
    370                 375                 380

<210> SEQ ID NO 151
<211> LENGTH: 377
<212> TYPE: PRT
<213> ORGANISM: Artificial Sequence
<220> FEATURE:
<223> OTHER INFORMATION: CD38 38A37326 VHH-OKT3 CATE

<400> SEQUENCE: 151

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Tyr Ala Met Gly
            20                  25                  30

Trp Tyr Arg Gln Ala Pro Gly Lys Gln Arg Asp Leu Val Ala Thr Ile
        35                  40                  45

Ser Gly Ala Gly Asn Thr Lys Tyr Ala Asp Ser Val Lys Gly Arg Phe
    50                  55                  60

Thr Ile Ser Arg Asp Asn Ala Lys Asn Thr Met Tyr Leu Gln Met Asn
65                  70                  75                  80

Ser Leu Lys Pro Glu Asp Thr Ala Val Tyr Tyr Cys Ala Ala Gly Lys
                85                  90                  95

Trp Phe Pro Ala Ala Asn Glu Tyr Trp Gly Gln Gly Thr Gln Val Thr
            100                 105                 110

Val Ser Ser Gly Gly Gly Gly Ser Gly Gly Gly Gly Ser Gly Gly Gly
        115                 120                 125

Gly Ser Gln Val Gln Leu Gln Gln Ser Gly Ala Glu Leu Ala Arg Pro
    130                 135                 140

Gly Ala Ser Val Lys Met Ser Cys Lys Ala Ser Gly Tyr Thr Phe Thr
145                 150                 155                 160

Arg Tyr Thr Met His Trp Val Lys Gln Arg Pro Gly Gln Gly Leu Glu
                165                 170                 175

Trp Ile Gly Tyr Ile Asn Pro Ser Arg Gly Tyr Thr Asn Tyr Asn Gln
            180                 185                 190

Lys Phe Lys Asp Lys Ala Thr Leu Thr Thr Asp Lys Ser Ser Ser Thr
        195                 200                 205

Ala Tyr Met Gln Leu Ser Ser Leu Thr Ser Glu Asp Ser Ala Val Tyr
    210                 215                 220

Tyr Cys Ala Arg Tyr Tyr Asp Asp His Tyr Cys Leu Asp Tyr Trp Gly
225                 230                 235                 240

Gln Gly Thr Thr Leu Thr Val Ser Ser Gly Gly Gly Gly Ser Gly Gly
                245                 250                 255

Gly Gly Ser Gly Gly Gly Gly Ser Gln Ile Val Leu Thr Gln Ser Pro
            260                 265                 270

Ala Ile Met Ser Ala Ser Pro Gly Glu Lys Val Thr Met Thr Cys Ser
        275                 280                 285

Ala Ser Ser Ser Val Ser Tyr Met Asn Trp Tyr Gln Gln Lys Ser Gly
    290                 295                 300

Thr Ser Pro Lys Arg Trp Ile Tyr Asp Thr Ser Lys Leu Ala Ser Gly
305                 310                 315                 320

Val Pro Ala His Phe Arg Gly Ser Gly Ser Gly Thr Ser Tyr Ser Leu
                325                 330                 335

Thr Ile Ser Gly Met Glu Ala Glu Asp Ala Ala Thr Tyr Tyr Cys Gln
                340                 345                 350

Gln Trp Ser Ser Asn Pro Phe Thr Phe Gly Ser Gly Thr Lys Leu Glu
        355                 360                 365

Ile Asn Arg His His His His His His
        370                 375

<210> SEQ ID NO 152
<211> LENGTH: 513
<212> TYPE: PRT
<213> ORGANISM: Artificial Sequence
<220> FEATURE:
<223> OTHER INFORMATION: BCMAx2 269A37346-L2K.07 CATE

<400> SEQUENCE: 152

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser Gly Gly Gly Gly Ser Gln
        115                 120                 125

Val Gln Leu Val Glu Ser Gly Gly Gly Leu Val Gln Pro Gly Gly Ser
    130                 135                 140

Leu Arg Leu Ser Cys Glu Ala Ser Gly Phe Thr Leu Asp Tyr Tyr Ala
145                 150                 155                 160

Ile Gly Trp Phe Arg Gln Ala Pro Gly Lys Glu Arg Glu Gly Val Ile
                165                 170                 175

Cys Ile Ser Arg Ser Asp Gly Ser Thr Tyr Tyr Ala Asp Ser Val Lys
            180                 185                 190

Gly Arg Phe Thr Ile Ser Arg Asp Asn Ala Lys Lys Thr Val Tyr Leu
        195                 200                 205

Gln Met Ile Ser Leu Lys Pro Glu Asp Thr Ala Ala Tyr Tyr Cys Ala
    210                 215                 220

Ala Gly Ala Asp Cys Ser Gly Tyr Leu Arg Asp Tyr Glu Phe Arg Gly
225                 230                 235                 240

Gln Gly Thr Gln Val Thr Val Ser Ser Gly Gly Gly Ser Gly Gly
                245                 250                 255

Gly Gly Ser Gly Gly Gly Ser Asp Ile Lys Leu Gln Gln Ser Gly
            260                 265                 270

Ala Glu Leu Ala Arg Pro Gly Ala Ser Val Lys Met Ser Cys Lys Thr
        275                 280                 285

Ser Gly Tyr Thr Phe Thr Arg Tyr Thr Met His Trp Val Lys Gln Arg
    290                 295                 300

Pro Gly Gln Gly Leu Glu Trp Ile Gly Tyr Ile Asn Pro Ser Arg Gly
305                 310                 315                 320

```
Tyr Thr Asn Tyr Asn Gln Lys Phe Lys Asp Lys Ala Thr Leu Thr Thr
                325                 330                 335

Asp Lys Ser Ser Ser Thr Ala Tyr Met Gln Leu Ser Ser Leu Thr Ser
            340                 345                 350

Glu Asp Ser Ala Val Tyr Tyr Cys Ala Arg Tyr Tyr Asp Asp His Tyr
            355                 360                 365

Cys Leu Asp Tyr Trp Gly Gln Gly Thr Thr Leu Thr Val Ser Ser Val
        370                 375                 380

Glu Gly Gly Ser Gly Gly Ser Gly Gly Ser Gly Gly Ser Gly Gly Val
385                 390                 395                 400

Asp Asp Ile Gln Leu Thr Gln Ser Pro Ala Ile Met Ser Ala Ser Pro
                405                 410                 415

Gly Glu Lys Val Thr Met Thr Cys Arg Ala Ser Ser Ser Val Ser Tyr
            420                 425                 430

Met Asn Trp Tyr Gln Gln Lys Ser Gly Thr Ser Pro Lys Arg Trp Ile
            435                 440                 445

Tyr Asp Thr Ser Lys Val Ala Ser Gly Val Pro Tyr Arg Phe Ser Gly
        450                 455                 460

Ser Gly Ser Gly Thr Ser Tyr Ser Leu Thr Ile Ser Ser Met Glu Ala
465                 470                 475                 480

Glu Asp Ala Ala Thr Tyr Tyr Cys Gln Gln Trp Ser Ser Asn Pro Leu
                485                 490                 495

Thr Phe Gly Ala Gly Thr Lys Leu Glu Leu Lys His His His His His
            500                 505                 510

His

<210> SEQ ID NO 153
<211> LENGTH: 511
<212> TYPE: PRT
<213> ORGANISM: Artificial Sequence
<220> FEATURE:
<223> OTHER INFORMATION: BCMAx2 269A37346-OKT3 CATE

<400> SEQUENCE: 153

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser Gly Gly Gly Gly Ser Gln
            115                 120                 125

Val Gln Leu Val Glu Ser Gly Gly Gly Leu Val Gln Pro Gly Gly Ser
        130                 135                 140

Leu Arg Leu Ser Cys Glu Ala Ser Gly Phe Thr Leu Asp Tyr Tyr Ala
145                 150                 155                 160

Ile Gly Trp Phe Arg Gln Ala Pro Gly Lys Glu Arg Glu Gly Val Ile
```

```
            165                 170                 175
Cys Ile Ser Arg Ser Asp Gly Ser Thr Tyr Tyr Ala Asp Ser Val Lys
            180                 185                 190

Gly Arg Phe Thr Ile Ser Arg Asp Asn Ala Lys Lys Thr Val Tyr Leu
        195                 200                 205

Gln Met Ile Ser Leu Lys Pro Glu Asp Thr Ala Ala Tyr Tyr Cys Ala
    210                 215                 220

Ala Gly Ala Asp Cys Ser Gly Tyr Leu Arg Asp Tyr Glu Phe Arg Gly
225                 230                 235                 240

Gln Gly Thr Gln Val Thr Val Ser Ser Gly Gly Gly Ser Gly Gly
                245                 250                 255

Gly Gly Ser Gly Gly Gly Ser Gln Val Gln Leu Gln Gln Ser Gly
            260                 265                 270

Ala Glu Leu Ala Arg Pro Gly Ala Ser Val Lys Met Ser Cys Lys Ala
        275                 280                 285

Ser Gly Tyr Thr Phe Thr Arg Tyr Thr Met His Trp Val Lys Gln Arg
    290                 295                 300

Pro Gly Gln Gly Leu Glu Trp Ile Gly Tyr Ile Asn Pro Ser Arg Gly
305                 310                 315                 320

Tyr Thr Asn Tyr Asn Gln Lys Phe Lys Asp Lys Ala Thr Leu Thr Thr
                325                 330                 335

Asp Lys Ser Ser Ser Thr Ala Tyr Met Gln Leu Ser Ser Leu Thr Ser
            340                 345                 350

Glu Asp Ser Ala Val Tyr Tyr Cys Ala Arg Tyr Tyr Asp Asp His Tyr
        355                 360                 365

Cys Leu Asp Tyr Trp Gly Gln Gly Thr Thr Leu Thr Val Ser Ser Gly
    370                 375                 380

Gly Gly Gly Ser Gly Gly Gly Gly Ser Gly Gly Gly Gly Ser Gln Ile
385                 390                 395                 400

Val Leu Thr Gln Ser Pro Ala Ile Met Ser Ala Ser Pro Gly Glu Lys
                405                 410                 415

Val Thr Met Thr Cys Ser Ala Ser Ser Val Ser Tyr Met Asn Trp
            420                 425                 430

Tyr Gln Gln Lys Ser Gly Thr Ser Pro Lys Arg Trp Ile Tyr Asp Thr
        435                 440                 445

Ser Lys Leu Ala Ser Gly Val Pro Ala His Phe Arg Gly Ser Gly Ser
    450                 455                 460

Gly Thr Ser Tyr Ser Leu Thr Ile Ser Gly Met Glu Ala Glu Asp Ala
465                 470                 475                 480

Ala Thr Tyr Tyr Cys Gln Gln Trp Ser Ser Asn Pro Phe Thr Phe Gly
                485                 490                 495

Ser Gly Thr Lys Leu Glu Ile Asn Arg His His His His His
            500                 505                 510

<210> SEQ ID NO 154
<211> LENGTH: 640
<212> TYPE: PRT
<213> ORGANISM: Artificial Sequence
<220> FEATURE:
<223> OTHER INFORMATION: BCMAx3 269A37346-L2K.07 CATE

<400> SEQUENCE: 154

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
```

```
                   20                  25                  30
Ala Ile Gly Trp Phe Arg Gln Ala Pro Gly Lys Glu Arg Glu Gly Val
            35                  40                  45
Ile Cys Ile Ser Arg Ser Asp Gly Ser Thr Tyr Tyr Ala Asp Ser Val
    50                  55                  60
Lys Gly Arg Phe Thr Ile Ser Arg Asp Asn Ala Lys Lys Thr Val Tyr
65                  70                  75                  80
Leu Gln Met Ile Ser Leu Lys Pro Glu Asp Thr Ala Ala Tyr Tyr Cys
                85                  90                  95
Ala Ala Gly Ala Asp Cys Ser Gly Tyr Leu Arg Asp Tyr Glu Phe Arg
            100                 105                 110
Gly Gln Gly Thr Gln Val Thr Val Ser Ser Gly Gly Gly Ser Gln
        115                 120                 125
Val Gln Leu Val Glu Ser Gly Gly Leu Val Gln Pro Gly Gly Ser
    130                 135                 140
Leu Arg Leu Ser Cys Glu Ala Ser Gly Phe Thr Leu Asp Tyr Tyr Ala
145                 150                 155                 160
Ile Gly Trp Phe Arg Gln Ala Pro Gly Lys Glu Arg Glu Gly Val Ile
                165                 170                 175
Cys Ile Ser Arg Ser Asp Gly Ser Thr Tyr Tyr Ala Asp Ser Val Lys
            180                 185                 190
Gly Arg Phe Thr Ile Ser Arg Asp Asn Ala Lys Lys Thr Val Tyr Leu
        195                 200                 205
Gln Met Ile Ser Leu Lys Pro Glu Asp Thr Ala Ala Tyr Tyr Cys Ala
    210                 215                 220
Ala Gly Ala Asp Cys Ser Gly Tyr Leu Arg Asp Tyr Glu Phe Arg Gly
225                 230                 235                 240
Gln Gly Thr Gln Val Thr Val Ser Ser Gly Gly Gly Ser Gln Val
                245                 250                 255
Gln Leu Val Glu Ser Gly Gly Gly Leu Val Gln Pro Gly Gly Ser Leu
            260                 265                 270
Arg Leu Ser Cys Glu Ala Ser Gly Phe Thr Leu Asp Tyr Tyr Ala Ile
        275                 280                 285
Gly Trp Phe Arg Gln Ala Pro Gly Lys Glu Arg Glu Gly Val Ile Cys
    290                 295                 300
Ile Ser Arg Ser Asp Gly Ser Thr Tyr Tyr Ala Asp Ser Val Lys Gly
305                 310                 315                 320
Arg Phe Thr Ile Ser Arg Asp Asn Ala Lys Lys Thr Val Tyr Leu Gln
                325                 330                 335
Met Ile Ser Leu Lys Pro Glu Asp Thr Ala Ala Tyr Tyr Cys Ala Ala
            340                 345                 350
Gly Ala Asp Cys Ser Gly Tyr Leu Arg Asp Tyr Glu Phe Arg Gly Gln
        355                 360                 365
Gly Thr Gln Val Thr Val Ser Ser Gly Gly Gly Gly Ser Gly Gly Gly
    370                 375                 380
Gly Ser Gly Gly Gly Gly Ser Asp Ile Lys Leu Gln Gln Ser Gly Ala
385                 390                 395                 400
Glu Leu Ala Arg Pro Gly Ala Ser Val Lys Met Ser Cys Lys Thr Ser
                405                 410                 415
Gly Tyr Thr Phe Thr Arg Tyr Thr Met His Trp Val Lys Gln Arg Pro
            420                 425                 430
Gly Gln Gly Leu Glu Trp Ile Gly Tyr Ile Asn Pro Ser Arg Gly Tyr
        435                 440                 445
```

```
Thr Asn Tyr Asn Gln Lys Phe Lys Asp Lys Ala Thr Leu Thr Thr Asp
    450                 455                 460
Lys Ser Ser Ser Thr Ala Tyr Met Gln Leu Ser Ser Leu Thr Ser Glu
465                 470                 475                 480
Asp Ser Ala Val Tyr Tyr Cys Ala Arg Tyr Tyr Asp Asp His Tyr Cys
                485                 490                 495
Leu Asp Tyr Trp Gly Gln Gly Thr Thr Leu Thr Val Ser Ser Val Glu
            500                 505                 510
Gly Gly Ser Gly Gly Ser Gly Gly Ser Gly Gly Val Asp
        515                 520                 525
Asp Ile Gln Leu Thr Gln Ser Pro Ala Ile Met Ser Ala Ser Pro Gly
530                 535                 540
Glu Lys Val Thr Met Thr Cys Arg Ala Ser Ser Ser Val Ser Tyr Met
545                 550                 555                 560
Asn Trp Tyr Gln Gln Lys Ser Gly Thr Ser Pro Lys Arg Trp Ile Tyr
                565                 570                 575
Asp Thr Ser Lys Val Ala Ser Gly Val Pro Tyr Arg Phe Ser Gly Ser
            580                 585                 590
Gly Ser Gly Thr Ser Tyr Ser Leu Thr Ile Ser Ser Met Glu Ala Glu
        595                 600                 605
Asp Ala Ala Thr Tyr Tyr Cys Gln Gln Trp Ser Ser Asn Pro Leu Thr
610                 615                 620
Phe Gly Ala Gly Thr Lys Leu Glu Leu Lys His His His His His
625                 630                 635                 640

<210> SEQ ID NO 155
<211> LENGTH: 638
<212> TYPE: PRT
<213> ORGANISM: Artificial Sequence
<220> FEATURE:
<223> OTHER INFORMATION: BCMAx3 269A37346-OKT3 CATE

<400> SEQUENCE: 155

Gln Val Gln Leu Val Glu Ser Gly Gly Gly Leu Val Gln Pro Gly Gly
1               5                   10                  15
Ser Leu Arg Leu Ser Cys Glu Ala Ser Gly Phe Thr Leu Asp Tyr Tyr
            20                  25                  30
Ala Ile Gly Trp Phe Arg Gln Ala Pro Gly Lys Glu Arg Glu Gly Val
        35                  40                  45
Ile Cys Ile Ser Arg Ser Asp Gly Ser Thr Tyr Tyr Ala Asp Ser Val
    50                  55                  60
Lys Gly Arg Phe Thr Ile Ser Arg Asp Asn Ala Lys Lys Thr Val Tyr
65                  70                  75                  80
Leu Gln Met Ile Ser Leu Lys Pro Glu Asp Thr Ala Ala Tyr Tyr Cys
                85                  90                  95
Ala Ala Gly Ala Asp Cys Ser Gly Tyr Leu Arg Asp Tyr Glu Phe Arg
            100                 105                 110
Gly Gln Gly Thr Gln Val Thr Val Ser Ser Gly Gly Gly Ser Gln
        115                 120                 125
Val Gln Leu Val Glu Ser Gly Gly Gly Leu Val Gln Pro Gly Gly Ser
    130                 135                 140
Leu Arg Leu Ser Cys Glu Ala Ser Gly Phe Thr Leu Asp Tyr Tyr Ala
145                 150                 155                 160
Ile Gly Trp Phe Arg Gln Ala Pro Gly Lys Glu Arg Glu Gly Val Ile
                165                 170                 175
```

```
Cys Ile Ser Arg Ser Asp Gly Ser Thr Tyr Tyr Ala Asp Ser Val Lys
            180                 185                 190

Gly Arg Phe Thr Ile Ser Arg Asp Asn Ala Lys Lys Thr Val Tyr Leu
        195                 200                 205

Gln Met Ile Ser Leu Lys Pro Glu Asp Thr Ala Ala Tyr Tyr Cys Ala
    210                 215                 220

Ala Gly Ala Asp Cys Ser Gly Tyr Leu Arg Asp Tyr Glu Phe Arg Gly
225                 230                 235                 240

Gln Gly Thr Gln Val Thr Val Ser Ser Gly Gly Gly Ser Gln Val
            245                 250                 255

Gln Leu Val Glu Ser Gly Gly Gly Leu Val Gln Pro Gly Gly Ser Leu
        260                 265                 270

Arg Leu Ser Cys Glu Ala Ser Gly Phe Thr Leu Asp Tyr Tyr Ala Ile
    275                 280                 285

Gly Trp Phe Arg Gln Ala Pro Gly Lys Glu Arg Glu Gly Val Ile Cys
    290                 295                 300

Ile Ser Arg Ser Asp Gly Ser Thr Tyr Tyr Ala Asp Ser Val Lys Gly
305                 310                 315                 320

Arg Phe Thr Ile Ser Arg Asp Asn Ala Lys Lys Thr Val Tyr Leu Gln
                325                 330                 335

Met Ile Ser Leu Lys Pro Glu Asp Thr Ala Ala Tyr Tyr Cys Ala Ala
            340                 345                 350

Gly Ala Asp Cys Ser Gly Tyr Leu Arg Asp Tyr Glu Phe Arg Gly Gln
        355                 360                 365

Gly Thr Gln Val Thr Val Ser Ser Gly Gly Gly Gly Ser Gly Gly Gly
    370                 375                 380

Gly Ser Gly Gly Gly Gly Ser Gln Val Gln Leu Gln Gln Ser Gly Ala
385                 390                 395                 400

Glu Leu Ala Arg Pro Gly Ala Ser Val Lys Met Ser Cys Lys Ala Ser
                405                 410                 415

Gly Tyr Thr Phe Thr Arg Tyr Thr Met His Trp Val Lys Gln Arg Pro
            420                 425                 430

Gly Gln Gly Leu Glu Trp Ile Gly Tyr Ile Asn Pro Ser Arg Gly Tyr
        435                 440                 445

Thr Asn Tyr Asn Gln Lys Phe Lys Asp Lys Ala Thr Leu Thr Thr Asp
    450                 455                 460

Lys Ser Ser Ser Thr Ala Tyr Met Gln Leu Ser Ser Leu Thr Ser Glu
465                 470                 475                 480

Asp Ser Ala Val Tyr Tyr Cys Ala Arg Tyr Tyr Asp Asp His Tyr Cys
                485                 490                 495

Leu Asp Tyr Trp Gly Gln Gly Thr Thr Leu Thr Val Ser Ser Gly Gly
            500                 505                 510

Gly Gly Ser Gly Gly Gly Gly Ser Gly Gly Gly Gly Ser Gln Ile Val
        515                 520                 525

Leu Thr Gln Ser Pro Ala Ile Met Ser Ala Ser Pro Gly Glu Lys Val
    530                 535                 540

Thr Met Thr Cys Ser Ala Ser Ser Ser Val Ser Tyr Met Asn Trp Tyr
545                 550                 555                 560

Gln Gln Lys Ser Gly Thr Ser Pro Lys Arg Trp Ile Tyr Asp Thr Ser
                565                 570                 575

Lys Leu Ala Ser Gly Val Pro Ala His Phe Arg Gly Ser Gly Ser Gly
            580                 585                 590
```

```
Thr Ser Tyr Ser Leu Thr Ile Ser Gly Met Glu Ala Glu Asp Ala Ala
            595                 600                 605

Thr Tyr Tyr Cys Gln Gln Trp Ser Ser Asn Pro Phe Thr Phe Gly Ser
            610                 615                 620

Gly Thr Lys Leu Glu Ile Asn Arg His His His His His His
625                 630                 635

<210> SEQ ID NO 156
<211> LENGTH: 501
<212> TYPE: PRT
<213> ORGANISM: Artificial Sequence
<220> FEATURE:
<223> OTHER INFORMATION: CD38x2 38A37717-L2K.07 CATE

<400> SEQUENCE: 156

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Glu Val Gln Leu Val Glu Ser
        115                 120                 125

Gly Gly Gly Leu Val Gln Ala Gly Gly Ser Leu Arg Leu Ser Cys Ile
130                 135                 140

Ala Thr Gly Lys Val Phe Ser Ile Tyr Asp Met Gly Trp Tyr Arg Gln
145                 150                 155                 160

Ala Pro Gly Lys Gln Arg Glu Leu Val Ala Glu Ile Thr Ser Ser Gly
                165                 170                 175

Thr Thr His Tyr Asp Asp Phe Val Ser Gly Arg Phe Thr Ile Ser Arg
            180                 185                 190

Asp Asn Ala Lys Asn Thr Val Tyr Leu Gln Met Asn Thr Leu Lys Ala
        195                 200                 205

Glu Asp Thr Ala Val Tyr Tyr Cys Arg Ala Asn His Val Phe Gly Gly
    210                 215                 220

Ser Tyr Trp Gly Gln Gly Thr Gln Val Thr Val Ser Ser Gly Gly Gly
225                 230                 235                 240

Gly Ser Gly Gly Gly Gly Ser Gly Gly Gly Gly Ser Asp Ile Lys Leu
                245                 250                 255

Gln Gln Ser Gly Ala Glu Leu Ala Arg Pro Gly Ala Ser Val Lys Met
            260                 265                 270

Ser Cys Lys Thr Ser Gly Tyr Thr Phe Thr Arg Tyr Thr Met His Trp
        275                 280                 285

Val Lys Gln Arg Pro Gly Gln Gly Leu Glu Trp Ile Gly Tyr Ile Asn
    290                 295                 300

Pro Ser Arg Gly Tyr Thr Asn Tyr Asn Gln Lys Phe Lys Asp Lys Ala
305                 310                 315                 320
```

```
Thr Leu Thr Thr Asp Lys Ser Ser Thr Ala Tyr Met Gln Leu Ser
            325                 330                 335

Ser Leu Thr Ser Glu Asp Ser Ala Val Tyr Tyr Cys Ala Arg Tyr Tyr
            340                 345                 350

Asp Asp His Tyr Cys Leu Asp Tyr Trp Gly Gln Gly Thr Thr Leu Thr
            355                 360                 365

Val Ser Ser Val Glu Gly Gly Ser Gly Gly Ser Gly Gly Ser Gly Gly
            370                 375                 380

Ser Gly Gly Val Asp Asp Ile Gln Leu Thr Gln Ser Pro Ala Ile Met
385                 390                 395                 400

Ser Ala Ser Pro Gly Glu Lys Val Thr Met Thr Cys Arg Ala Ser Ser
                    405                 410                 415

Ser Val Ser Tyr Met Asn Trp Tyr Gln Gln Lys Ser Gly Thr Ser Pro
                    420                 425                 430

Lys Arg Trp Ile Tyr Asp Thr Ser Lys Val Ala Ser Gly Val Pro Tyr
                    435                 440                 445

Arg Phe Ser Gly Ser Gly Ser Gly Thr Ser Tyr Ser Leu Thr Ile Ser
            450                 455                 460

Ser Met Glu Ala Glu Asp Ala Ala Thr Tyr Tyr Cys Gln Gln Trp Ser
465                 470                 475                 480

Ser Asn Pro Leu Thr Phe Gly Ala Gly Thr Lys Leu Glu Leu Lys His
                    485                 490                 495

His His His His His
            500

<210> SEQ ID NO 157
<211> LENGTH: 499
<212> TYPE: PRT
<213> ORGANISM: Artificial Sequence
<220> FEATURE:
<223> OTHER INFORMATION: CD38x2 38A37717-OKT3 CATE

<400> SEQUENCE: 157

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
                20                  25                  30

Asp Met Gly Trp Tyr Arg Gln Ala Pro Gly Lys Gln Arg Glu Leu Val
            35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Glu Val Gln Leu Val Glu Ser
        115                 120                 125

Gly Gly Gly Leu Val Gln Ala Gly Gly Ser Leu Arg Leu Ser Cys Ile
    130                 135                 140

Ala Thr Gly Lys Val Phe Ser Ile Tyr Asp Met Gly Trp Tyr Arg Gln
145                 150                 155                 160

Ala Pro Gly Lys Gln Arg Glu Leu Val Ala Glu Ile Thr Ser Ser Gly
                165                 170                 175
```

Thr Thr His Tyr Asp Asp Phe Val Ser Gly Arg Phe Thr Ile Ser Arg
            180                 185                 190

Asp Asn Ala Lys Asn Thr Val Tyr Leu Gln Met Asn Thr Leu Lys Ala
        195                 200                 205

Glu Asp Thr Ala Val Tyr Tyr Cys Arg Ala Asn His Val Phe Gly Gly
    210                 215                 220

Ser Tyr Trp Gly Gln Gly Thr Gln Val Thr Val Ser Ser Gly Gly Gly
225                 230                 235                 240

Gly Ser Gly Gly Gly Gly Ser Gly Gly Gly Ser Gln Val Gln Leu
                245                 250                 255

Gln Gln Ser Gly Ala Glu Leu Ala Arg Pro Gly Ala Ser Val Lys Met
            260                 265                 270

Ser Cys Lys Ala Ser Gly Tyr Thr Phe Thr Arg Tyr Thr Met His Trp
        275                 280                 285

Val Lys Gln Arg Pro Gly Gln Gly Leu Glu Trp Ile Gly Tyr Ile Asn
    290                 295                 300

Pro Ser Arg Gly Tyr Thr Asn Tyr Asn Gln Lys Phe Lys Asp Lys Ala
305                 310                 315                 320

Thr Leu Thr Thr Asp Lys Ser Ser Ser Thr Ala Tyr Met Gln Leu Ser
            325                 330                 335

Ser Leu Thr Ser Glu Asp Ser Ala Val Tyr Tyr Cys Ala Arg Tyr Tyr
        340                 345                 350

Asp Asp His Tyr Cys Leu Asp Tyr Trp Gly Gln Gly Thr Thr Leu Thr
    355                 360                 365

Val Ser Ser Gly Gly Gly Gly Ser Gly Gly Gly Gly Ser Gly Gly Gly
370                 375                 380

Gly Ser Gln Ile Val Leu Thr Gln Ser Pro Ala Ile Met Ser Ala Ser
385                 390                 395                 400

Pro Gly Glu Lys Val Thr Met Thr Cys Ser Ala Ser Ser Ser Val Ser
            405                 410                 415

Tyr Met Asn Trp Tyr Gln Gln Lys Ser Gly Thr Ser Pro Lys Arg Trp
        420                 425                 430

Ile Tyr Asp Thr Ser Lys Leu Ala Ser Gly Val Pro Ala His Phe Arg
    435                 440                 445

Gly Ser Gly Ser Gly Thr Ser Tyr Ser Leu Thr Ile Ser Gly Met Glu
450                 455                 460

Ala Glu Asp Ala Ala Thr Tyr Tyr Cys Gln Gln Trp Ser Ser Asn Pro
465                 470                 475                 480

Phe Thr Phe Gly Ser Gly Thr Lys Leu Glu Ile Asn Arg His His His
            485                 490                 495

His His His

<210> SEQ ID NO 158
<211> LENGTH: 622
<212> TYPE: PRT
<213> ORGANISM: Artificial Sequence
<220> FEATURE:
<223> OTHER INFORMATION: CD38x3 38A37717-L2K.07 CATE

<400> SEQUENCE: 158

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val

```
            35                  40                  45
Ala Glu Ile Thr Ser Ser Gly Thr Thr His Tyr Asp Asp Phe Val Ser
 50                  55                  60

Gly Arg Phe Thr Ile Ser Arg Asp Asn Ala Lys Asn Thr Val Tyr Leu
 65                  70                  75                  80

Gln Met Asn Thr Leu Lys Ala Glu Asp Thr Ala Val Tyr Tyr Cys Arg
                 85                  90                  95

Ala Asn His Val Phe Gly Gly Ser Tyr Trp Gly Gln Gly Thr Gln Val
                100                 105                 110

Thr Val Ser Ser Gly Gly Gly Ser Glu Val Gln Leu Val Glu Ser
        115                 120                 125

Gly Gly Gly Leu Val Gln Ala Gly Gly Ser Leu Arg Leu Ser Cys Ile
        130                 135                 140

Ala Thr Gly Lys Val Phe Ser Ile Tyr Asp Met Gly Trp Tyr Arg Gln
145                 150                 155                 160

Ala Pro Gly Lys Gln Arg Glu Leu Val Ala Glu Ile Thr Ser Ser Gly
                165                 170                 175

Thr Thr His Tyr Asp Asp Phe Val Ser Gly Arg Phe Thr Ile Ser Arg
                180                 185                 190

Asp Asn Ala Lys Asn Thr Val Tyr Leu Gln Met Asn Thr Leu Lys Ala
                195                 200                 205

Glu Asp Thr Ala Val Tyr Tyr Cys Arg Ala Asn His Val Phe Gly Gly
210                 215                 220

Ser Tyr Trp Gly Gln Gly Thr Gln Val Thr Val Ser Ser Gly Gly Gly
225                 230                 235                 240

Gly Ser Glu Val Gln Leu Val Glu Ser Gly Gly Gly Leu Val Gln Ala
                245                 250                 255

Gly Gly Ser Leu Arg Leu Ser Cys Ile Ala Thr Gly Lys Val Phe Ser
                260                 265                 270

Ile Tyr Asp Met Gly Trp Tyr Arg Gln Ala Pro Gly Lys Gln Arg Glu
                275                 280                 285

Leu Val Ala Glu Ile Thr Ser Ser Gly Thr Thr His Tyr Asp Asp Phe
290                 295                 300

Val Ser Gly Arg Phe Thr Ile Ser Arg Asp Asn Ala Lys Asn Thr Val
305                 310                 315                 320

Tyr Leu Gln Met Asn Thr Leu Lys Ala Glu Asp Thr Ala Val Tyr Tyr
                325                 330                 335

Cys Arg Ala Asn His Val Phe Gly Gly Ser Tyr Trp Gly Gln Gly Thr
                340                 345                 350

Gln Val Thr Val Ser Ser Gly Gly Gly Gly Ser Gly Gly Gly Gly Ser
                355                 360                 365

Gly Gly Gly Gly Ser Asp Ile Lys Leu Gln Gln Ser Gly Ala Glu Leu
                370                 375                 380

Ala Arg Pro Gly Ala Ser Val Lys Met Ser Cys Lys Thr Ser Gly Tyr
385                 390                 395                 400

Thr Phe Thr Arg Tyr Thr Met His Trp Val Lys Gln Arg Pro Gly Gln
                405                 410                 415

Gly Leu Glu Trp Ile Gly Tyr Ile Asn Pro Ser Arg Gly Tyr Thr Asn
                420                 425                 430

Tyr Asn Gln Lys Phe Lys Asp Lys Ala Thr Leu Thr Thr Asp Lys Ser
                435                 440                 445

Ser Ser Thr Ala Tyr Met Gln Leu Ser Ser Leu Thr Ser Glu Asp Ser
450                 455                 460
```

```
Ala Val Tyr Tyr Cys Ala Arg Tyr Tyr Asp Asp His Tyr Cys Leu Asp
465                 470                 475                 480

Tyr Trp Gly Gln Gly Thr Thr Leu Thr Val Ser Ser Val Glu Gly Gly
                485                 490                 495

Ser Gly Gly Ser Gly Gly Ser Gly Gly Ser Gly Gly Val Asp Asp Ile
            500                 505                 510

Gln Leu Thr Gln Ser Pro Ala Ile Met Ser Ala Ser Pro Gly Glu Lys
                515                 520                 525

Val Thr Met Thr Cys Arg Ala Ser Ser Ser Val Ser Tyr Met Asn Trp
530                 535                 540

Tyr Gln Gln Lys Ser Gly Thr Ser Pro Lys Arg Trp Ile Tyr Asp Thr
545                 550                 555                 560

Ser Lys Val Ala Ser Gly Val Pro Tyr Arg Phe Ser Gly Ser Gly Ser
                565                 570                 575

Gly Thr Ser Tyr Ser Leu Thr Ile Ser Ser Met Glu Ala Glu Asp Ala
            580                 585                 590

Ala Thr Tyr Tyr Cys Gln Gln Trp Ser Ser Asn Pro Leu Thr Phe Gly
                595                 600                 605

Ala Gly Thr Lys Leu Glu Leu Lys His His His His His His
    610                 615                 620

<210> SEQ ID NO 159
<211> LENGTH: 620
<212> TYPE: PRT
<213> ORGANISM: Artificial Sequence
<220> FEATURE:
<223> OTHER INFORMATION: CD38x3 38A37717-OKT3 CATE

<400> SEQUENCE: 159

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
                20                  25                  30

Asp Met Gly Trp Tyr Arg Gln Ala Pro Gly Lys Gln Arg Glu Leu Val
            35                  40                  45

Ala Glu Ile Thr Ser Ser Gly Thr Thr His Tyr Asp Asp Phe Val Ser
        50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Glu Val Gln Leu Val Glu Ser
        115                 120                 125

Gly Gly Gly Leu Val Gln Ala Gly Gly Ser Leu Arg Leu Ser Cys Ile
    130                 135                 140

Ala Thr Gly Lys Val Phe Ser Ile Tyr Asp Met Gly Trp Tyr Arg Gln
145                 150                 155                 160

Ala Pro Gly Lys Gln Arg Glu Leu Val Ala Glu Ile Thr Ser Ser Gly
                165                 170                 175

Thr Thr His Tyr Asp Asp Phe Val Ser Gly Arg Phe Thr Ile Ser Arg
            180                 185                 190

Asp Asn Ala Lys Asn Thr Val Tyr Leu Gln Met Asn Thr Leu Lys Ala
        195                 200                 205
```

```
Glu Asp Thr Ala Val Tyr Tyr Cys Arg Ala Asn His Val Phe Gly Gly
    210                 215                 220
Ser Tyr Trp Gly Gln Gly Thr Gln Val Thr Val Ser Ser Gly Gly Gly
225                 230                 235                 240
Gly Ser Glu Val Gln Leu Val Glu Ser Gly Gly Gly Leu Val Gln Ala
                245                 250                 255
Gly Gly Ser Leu Arg Leu Ser Cys Ile Ala Thr Gly Lys Val Phe Ser
            260                 265                 270
Ile Tyr Asp Met Gly Trp Tyr Arg Gln Ala Pro Gly Lys Gln Arg Glu
        275                 280                 285
Leu Val Ala Glu Ile Thr Ser Ser Gly Thr Thr His Tyr Asp Asp Phe
    290                 295                 300
Val Ser Gly Arg Phe Thr Ile Ser Arg Asp Asn Ala Lys Asn Thr Val
305                 310                 315                 320
Tyr Leu Gln Met Asn Thr Leu Lys Ala Glu Asp Thr Ala Val Tyr Tyr
                325                 330                 335
Cys Arg Ala Asn His Val Phe Gly Gly Ser Tyr Trp Gly Gln Gly Thr
            340                 345                 350
Gln Val Thr Val Ser Ser Gly Gly Gly Ser Gly Gly Gly Gly Gly Ser
        355                 360                 365
Gly Gly Gly Gly Ser Gln Val Gln Leu Gln Gln Ser Gly Ala Glu Leu
    370                 375                 380
Ala Arg Pro Gly Ala Ser Val Lys Met Ser Cys Lys Ala Ser Gly Tyr
385                 390                 395                 400
Thr Phe Thr Arg Tyr Thr Met His Trp Val Lys Gln Arg Pro Gly Gln
                405                 410                 415
Gly Leu Glu Trp Ile Gly Tyr Ile Asn Pro Ser Arg Gly Tyr Thr Asn
            420                 425                 430
Tyr Asn Gln Lys Phe Lys Asp Lys Ala Thr Leu Thr Thr Asp Lys Ser
        435                 440                 445
Ser Ser Thr Ala Tyr Met Gln Leu Ser Ser Leu Thr Ser Glu Asp Ser
    450                 455                 460
Ala Val Tyr Tyr Cys Ala Arg Tyr Tyr Asp Asp His Tyr Cys Leu Asp
465                 470                 475                 480
Tyr Trp Gly Gln Gly Thr Thr Leu Thr Val Ser Ser Gly Gly Gly Gly
                485                 490                 495
Ser Gly Gly Gly Gly Ser Gly Gly Gly Gly Ser Gln Ile Val Leu Thr
            500                 505                 510
Gln Ser Pro Ala Ile Met Ser Ala Ser Pro Gly Glu Lys Val Thr Met
        515                 520                 525
Thr Cys Ser Ala Ser Ser Val Ser Tyr Met Asn Trp Tyr Gln Gln
    530                 535                 540
Lys Ser Gly Thr Ser Pro Lys Arg Trp Ile Tyr Asp Thr Ser Lys Leu
545                 550                 555                 560
Ala Ser Gly Val Pro Ala His Phe Arg Gly Ser Gly Ser Gly Thr Ser
                565                 570                 575
Tyr Ser Leu Thr Ile Ser Gly Met Glu Ala Glu Asp Ala Ala Thr Tyr
            580                 585                 590
Tyr Cys Gln Gln Trp Ser Ser Asn Pro Phe Thr Phe Gly Ser Gly Thr
        595                 600                 605
Lys Leu Glu Ile Asn Arg His His His His His
    610                 615                 620
```

-continued

```
<210> SEQ ID NO 160
<211> LENGTH: 507
<212> TYPE: PRT
<213> ORGANISM: Artificial Sequence
<220> FEATURE:
<223> OTHER INFORMATION: BCMA 269A37346*CD38 38A37717-L2K.07 CATE

<400> SEQUENCE: 160

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Ala Ile Gly Trp Phe Arg Gln Ala Pro Gly Lys Glu Arg Glu Gly Val
        35                  40                  45

Ile Cys Ile Ser Arg Ser Asp Gly Ser Thr Tyr Tyr Ala Asp Ser Val
    50                  55                  60

Lys Gly Arg Phe Thr Ile Ser Arg Asp Asn Ala Lys Lys Thr Val Tyr
65                  70                  75                  80

Leu Gln Met Ile Ser Leu Lys Pro Glu Asp Thr Ala Ala Tyr Tyr Cys
                85                  90                  95

Ala Ala Gly Ala Asp Cys Ser Gly Tyr Leu Arg Asp Tyr Glu Phe Arg
            100                 105                 110

Gly Gln Gly Thr Gln Val Thr Val Ser Ser Gly Gly Gly Gly Ser Glu
        115                 120                 125

Val Gln Leu Val Glu Ser Gly Gly Gly Leu Val Gln Ala Gly Gly Ser
    130                 135                 140

Leu Arg Leu Ser Cys Ile Ala Thr Gly Lys Val Phe Ser Ile Tyr Asp
145                 150                 155                 160

Met Gly Trp Tyr Arg Gln Ala Pro Gly Lys Gln Arg Glu Leu Val Ala
                165                 170                 175

Glu Ile Thr Ser Ser Gly Thr Thr His Tyr Asp Asp Phe Val Ser Gly
            180                 185                 190

Arg Phe Thr Ile Ser Arg Asp Asn Ala Lys Asn Thr Val Tyr Leu Gln
        195                 200                 205

Met Asn Thr Leu Lys Ala Glu Asp Thr Ala Val Tyr Tyr Cys Arg Ala
    210                 215                 220

Asn His Val Phe Gly Gly Ser Tyr Trp Gly Gln Gly Thr Gln Val Thr
225                 230                 235                 240

Val Ser Ser Gly Gly Gly Gly Ser Gly Gly Gly Ser Gly Gly Gly
                245                 250                 255

Gly Ser Asp Ile Lys Leu Gln Gln Ser Gly Ala Glu Leu Ala Arg Pro
            260                 265                 270

Gly Ala Ser Val Lys Met Ser Cys Lys Thr Ser Gly Tyr Thr Phe Thr
        275                 280                 285

Arg Tyr Thr Met His Trp Val Lys Gln Arg Pro Gly Gln Gly Leu Glu
    290                 295                 300

Trp Ile Gly Tyr Ile Asn Pro Ser Arg Gly Tyr Thr Asn Tyr Asn Gln
305                 310                 315                 320

Lys Phe Lys Asp Lys Ala Thr Leu Thr Thr Asp Lys Ser Ser Ser Thr
                325                 330                 335

Ala Tyr Met Gln Leu Ser Ser Leu Thr Ser Glu Asp Ser Ala Val Tyr
            340                 345                 350

Tyr Cys Ala Arg Tyr Tyr Asp Asp His Tyr Cys Leu Asp Tyr Trp Gly
        355                 360                 365
```

Gln Gly Thr Thr Leu Thr Val Ser Ser Val Glu Gly Ser Gly
        370                 375                 380
Ser Gly Gly Ser Gly Gly Ser Gly Gly Val Asp Asp Ile Gln Leu Thr
385                 390                 395                 400
Gln Ser Pro Ala Ile Met Ser Ala Ser Pro Gly Glu Lys Val Thr Met
                405                 410                 415
Thr Cys Arg Ala Ser Ser Ser Val Ser Tyr Met Asn Trp Tyr Gln Gln
                420                 425                 430
Lys Ser Gly Thr Ser Pro Lys Arg Trp Ile Tyr Asp Thr Ser Lys Val
                435                 440                 445
Ala Ser Gly Val Pro Tyr Arg Phe Ser Gly Ser Gly Ser Gly Thr Ser
            450                 455                 460
Tyr Ser Leu Thr Ile Ser Ser Met Glu Ala Glu Asp Ala Ala Thr Tyr
465                 470                 475                 480
Tyr Cys Gln Gln Trp Ser Ser Asn Pro Leu Thr Phe Gly Ala Gly Thr
                485                 490                 495
Lys Leu Glu Leu Lys His His His His His His
                500                 505

<210> SEQ ID NO 161
<211> LENGTH: 505
<212> TYPE: PRT
<213> ORGANISM: Artificial Sequence
<220> FEATURE:
<223> OTHER INFORMATION: BCMA 269A37346*CD38 38A37717-OKT3 CATE

<400> SEQUENCE: 161

Gln Val Gln Leu Val Glu Ser Gly Gly Gly Leu Val Gln Pro Gly Gly
1               5                   10                  15
Ser Leu Arg Leu Ser Cys Glu Ala Ser Gly Phe Thr Leu Asp Tyr Tyr
            20                  25                  30
Ala Ile Gly Trp Phe Arg Gln Ala Pro Gly Lys Glu Arg Glu Gly Val
        35                  40                  45
Ile Cys Ile Ser Arg Ser Asp Gly Ser Thr Tyr Tyr Ala Asp Ser Val
    50                  55                  60
Lys Gly Arg Phe Thr Ile Ser Arg Asp Asn Ala Lys Lys Thr Val Tyr
65                  70                  75                  80
Leu Gln Met Ile Ser Leu Lys Pro Glu Asp Thr Ala Ala Tyr Tyr Cys
                85                  90                  95
Ala Ala Gly Ala Asp Cys Ser Gly Tyr Leu Arg Asp Tyr Glu Phe Arg
            100                 105                 110
Gly Gln Gly Thr Gln Val Thr Val Ser Ser Gly Gly Gly Gly Ser Glu
        115                 120                 125
Val Gln Leu Val Glu Ser Gly Gly Gly Leu Val Gln Ala Gly Gly Ser
    130                 135                 140
Leu Arg Leu Ser Cys Ile Ala Thr Gly Lys Val Phe Ser Ile Tyr Asp
145                 150                 155                 160
Met Gly Trp Tyr Arg Gln Ala Pro Gly Lys Gln Arg Glu Leu Val Ala
                165                 170                 175
Glu Ile Thr Ser Ser Gly Thr Thr His Tyr Asp Asp Phe Val Ser Gly
            180                 185                 190
Arg Phe Thr Ile Ser Arg Asp Asn Ala Lys Asn Thr Val Tyr Leu Gln
        195                 200                 205
Met Asn Thr Leu Lys Ala Glu Asp Thr Ala Val Tyr Tyr Cys Arg Ala
    210                 215                 220

Asn His Val Phe Gly Gly Ser Tyr Trp Gly Gln Gly Thr Gln Val Thr
225                 230                 235                 240

Val Ser Ser Gly Gly Gly Gly Ser Gly Gly Gly Gly Ser Gly Gly Gly
            245                 250                 255

Gly Ser Gln Val Gln Leu Gln Gln Ser Gly Ala Glu Leu Ala Arg Pro
        260                 265                 270

Gly Ala Ser Val Lys Met Ser Cys Lys Ala Ser Gly Tyr Thr Phe Thr
    275                 280                 285

Arg Tyr Thr Met His Trp Val Lys Gln Arg Pro Gly Gln Gly Leu Glu
290                 295                 300

Trp Ile Gly Tyr Ile Asn Pro Ser Arg Gly Tyr Thr Asn Tyr Asn Gln
305                 310                 315                 320

Lys Phe Lys Asp Lys Ala Thr Leu Thr Thr Asp Lys Ser Ser Ser Thr
            325                 330                 335

Ala Tyr Met Gln Leu Ser Ser Leu Thr Ser Glu Asp Ser Ala Val Tyr
        340                 345                 350

Tyr Cys Ala Arg Tyr Tyr Asp Asp His Tyr Cys Leu Asp Tyr Trp Gly
    355                 360                 365

Gln Gly Thr Thr Leu Thr Val Ser Ser Gly Gly Gly Gly Ser Gly Gly
370                 375                 380

Gly Gly Ser Gly Gly Gly Gly Ser Gln Ile Val Leu Thr Gln Ser Pro
385                 390                 395                 400

Ala Ile Met Ser Ala Ser Pro Gly Glu Lys Val Thr Met Thr Cys Ser
            405                 410                 415

Ala Ser Ser Ser Val Ser Tyr Met Asn Trp Tyr Gln Gln Lys Ser Gly
        420                 425                 430

Thr Ser Pro Lys Arg Trp Ile Tyr Asp Thr Ser Lys Leu Ala Ser Gly
    435                 440                 445

Val Pro Ala His Phe Arg Gly Ser Gly Ser Gly Thr Ser Tyr Ser Leu
450                 455                 460

Thr Ile Ser Gly Met Glu Ala Glu Asp Ala Ala Thr Tyr Tyr Cys Gln
465                 470                 475                 480

Gln Trp Ser Ser Asn Pro Phe Thr Phe Gly Ser Gly Thr Lys Leu Glu
            485                 490                 495

Ile Asn Arg His His His His His His
        500                 505

<210> SEQ ID NO 162
<211> LENGTH: 507
<212> TYPE: PRT
<213> ORGANISM: Artificial Sequence
<220> FEATURE:
<223> OTHER INFORMATION: CD38 38A77717*BCMA 269A37346-L2K.07 CATE

<400> SEQUENCE: 162

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

```
Gln Met Asn Thr Leu Lys Ala Glu Asp Thr Ala Val Tyr Tyr Cys Arg
                 85                  90                  95
Ala Asn His Val Phe Gly Gly Ser Tyr Trp Gly Gln Gly Thr Gln Val
            100                 105                 110
Thr Val Ser Ser Gly Gly Gly Ser Gln Val Gln Leu Val Glu Ser
        115                 120                 125
Gly Gly Gly Leu Val Gln Pro Gly Gly Ser Leu Arg Leu Ser Cys Glu
130                 135                 140
Ala Ser Gly Phe Thr Leu Asp Tyr Tyr Ala Ile Gly Trp Phe Arg Gln
145                 150                 155                 160
Ala Pro Gly Lys Glu Arg Glu Gly Val Ile Cys Ile Ser Arg Ser Asp
                165                 170                 175
Gly Ser Thr Tyr Tyr Ala Asp Ser Val Lys Gly Arg Phe Thr Ile Ser
            180                 185                 190
Arg Asp Asn Ala Lys Lys Thr Val Tyr Leu Gln Met Ile Ser Leu Lys
        195                 200                 205
Pro Glu Asp Thr Ala Ala Tyr Tyr Cys Ala Ala Gly Ala Asp Cys Ser
210                 215                 220
Gly Tyr Leu Arg Asp Tyr Glu Phe Arg Gly Gln Gly Thr Gln Val Thr
225                 230                 235                 240
Val Ser Ser Gly Gly Gly Gly Ser Gly Gly Gly Ser Gly Gly Gly
                245                 250                 255
Gly Ser Asp Ile Lys Leu Gln Gln Ser Gly Ala Glu Leu Ala Arg Pro
            260                 265                 270
Gly Ala Ser Val Lys Met Ser Cys Lys Thr Ser Gly Tyr Thr Phe Thr
        275                 280                 285
Arg Tyr Thr Met His Trp Val Lys Gln Arg Pro Gly Gln Gly Leu Glu
290                 295                 300
Trp Ile Gly Tyr Ile Asn Pro Ser Arg Gly Tyr Thr Asn Tyr Asn Gln
305                 310                 315                 320
Lys Phe Lys Asp Lys Ala Thr Leu Thr Thr Asp Lys Ser Ser Ser Thr
                325                 330                 335
Ala Tyr Met Gln Leu Ser Ser Leu Thr Ser Glu Asp Ser Ala Val Tyr
            340                 345                 350
Tyr Cys Ala Arg Tyr Tyr Asp Asp His Tyr Cys Leu Asp Tyr Trp Gly
        355                 360                 365
Gln Gly Thr Thr Leu Thr Val Ser Ser Val Glu Gly Gly Ser Gly Gly
370                 375                 380
Ser Gly Gly Ser Gly Gly Ser Gly Gly Val Asp Asp Ile Gln Leu Thr
385                 390                 395                 400
Gln Ser Pro Ala Ile Met Ser Ala Ser Pro Gly Glu Lys Val Thr Met
                405                 410                 415
Thr Cys Arg Ala Ser Ser Ser Val Ser Tyr Met Asn Trp Tyr Gln Gln
            420                 425                 430
Lys Ser Gly Thr Ser Pro Lys Arg Trp Ile Tyr Asp Thr Ser Lys Val
        435                 440                 445
Ala Ser Gly Val Pro Tyr Arg Phe Ser Gly Ser Gly Ser Gly Thr Ser
450                 455                 460
Tyr Ser Leu Thr Ile Ser Ser Met Glu Ala Glu Asp Ala Ala Thr Tyr
465                 470                 475                 480
Tyr Cys Gln Gln Trp Ser Ser Asn Pro Leu Thr Phe Gly Ala Gly Thr
                485                 490                 495
Lys Leu Glu Leu Lys His His His His His His
```

<210> SEQ ID NO 163
<211> LENGTH: 505
<212> TYPE: PRT
<213> ORGANISM: Artificial Sequence
<220> FEATURE:
<223> OTHER INFORMATION: CD38 38A37717*BCMA 269A37346-OKT3 CATE

<400> SEQUENCE: 163

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Gln Val Gln Leu Val Glu Ser
        115                 120                 125

Gly Gly Gly Leu Val Gln Pro Gly Gly Ser Leu Arg Leu Ser Cys Glu
    130                 135                 140

Ala Ser Gly Phe Thr Leu Asp Tyr Tyr Ala Ile Gly Trp Phe Arg Gln
145                 150                 155                 160

Ala Pro Gly Lys Glu Arg Glu Gly Val Ile Cys Ile Ser Arg Ser Asp
                165                 170                 175

Gly Ser Thr Tyr Tyr Ala Asp Ser Val Lys Gly Arg Phe Thr Ile Ser
            180                 185                 190

Arg Asp Asn Ala Lys Lys Thr Val Tyr Leu Gln Met Ile Ser Leu Lys
        195                 200                 205

Pro Glu Asp Thr Ala Ala Tyr Tyr Cys Ala Ala Gly Ala Asp Cys Ser
    210                 215                 220

Gly Tyr Leu Arg Asp Tyr Glu Phe Arg Gly Gln Gly Thr Gln Val Thr
225                 230                 235                 240

Val Ser Ser Gly Gly Gly Gly Ser Gly Gly Gly Ser Gly Gly Gly
                245                 250                 255

Gly Ser Gln Val Gln Leu Gln Gln Ser Gly Ala Glu Leu Ala Arg Pro
            260                 265                 270

Gly Ala Ser Val Lys Met Ser Cys Lys Ala Ser Gly Tyr Thr Phe Thr
        275                 280                 285

Arg Tyr Thr Met His Trp Val Lys Gln Arg Pro Gly Gln Gly Leu Glu
    290                 295                 300

Trp Ile Gly Tyr Ile Asn Pro Ser Arg Gly Tyr Thr Asn Tyr Asn Gln
305                 310                 315                 320

Lys Phe Lys Asp Lys Ala Thr Leu Thr Thr Asp Lys Ser Ser Ser Thr
                325                 330                 335

Ala Tyr Met Gln Leu Ser Ser Leu Thr Ser Glu Asp Ser Ala Val Tyr
            340                 345                 350

Tyr Cys Ala Arg Tyr Tyr Asp Asp His Tyr Cys Leu Asp Tyr Trp Gly

```
               355                 360                 365
Gln Gly Thr Thr Leu Thr Val Ser Ser Gly Gly Gly Ser Gly Gly
        370                 375                 380
Gly Gly Ser Gly Gly Gly Ser Gln Ile Val Leu Thr Gln Ser Pro
385                 390                 395                 400
Ala Ile Met Ser Ala Ser Pro Gly Glu Lys Val Thr Met Thr Cys Ser
                405                 410                 415
Ala Ser Ser Val Ser Tyr Met Asn Trp Tyr Gln Gln Lys Ser Gly
            420                 425                 430
Thr Ser Pro Lys Arg Trp Ile Tyr Asp Thr Ser Lys Leu Ala Ser Gly
            435                 440                 445
Val Pro Ala His Phe Arg Gly Ser Gly Ser Gly Thr Ser Tyr Ser Leu
        450                 455                 460
Thr Ile Ser Gly Met Glu Ala Glu Asp Ala Ala Thr Tyr Tyr Cys Gln
465                 470                 475                 480
Gln Trp Ser Ser Asn Pro Phe Thr Phe Gly Ser Gly Thr Lys Leu Glu
                485                 490                 495
Ile Asn Arg His His His His His His
            500                 505

<210> SEQ ID NO 164
<211> LENGTH: 5
<212> TYPE: PRT
<213> ORGANISM: Artificial Sequence
<220> FEATURE:
<223> OTHER INFORMATION: OKT3 VH CDR1

<400> SEQUENCE: 164

Tyr Thr Met His Trp
1               5

<210> SEQ ID NO 165
<211> LENGTH: 19
<212> TYPE: PRT
<213> ORGANISM: Artificial Sequence
<220> FEATURE:
<223> OTHER INFORMATION: OKT3 VH CDR2

<400> SEQUENCE: 165

Ile Asn Pro Ser Arg Gly Tyr Thr Asn Tyr Asn Gln Lys Phe Lys Asp
1               5                   10                  15

Lys Ala Thr

<210> SEQ ID NO 166
<211> LENGTH: 10
<212> TYPE: PRT
<213> ORGANISM: Artificial Sequence
<220> FEATURE:
<223> OTHER INFORMATION: OKT3 VH CDR3

<400> SEQUENCE: 166

Tyr Tyr Asp Asp His Tyr Cys Leu Asp Tyr
1               5                   10

<210> SEQ ID NO 167
<211> LENGTH: 10
<212> TYPE: PRT
<213> ORGANISM: Artificial Sequence
<220> FEATURE:
<223> OTHER INFORMATION: OKT3 VL CDR1

<400> SEQUENCE: 167
```

```
Ser Ala Ser Ser Ser Val Ser Tyr Met Asn
1               5                   10

<210> SEQ ID NO 168
<211> LENGTH: 7
<212> TYPE: PRT
<213> ORGANISM: Artificial Sequence
<220> FEATURE:
<223> OTHER INFORMATION: OKT3 VL CDR2

<400> SEQUENCE: 168

Tyr Asp Thr Ser Lys Leu Ala
1               5

<210> SEQ ID NO 169
<211> LENGTH: 9
<212> TYPE: PRT
<213> ORGANISM: Artificial Sequence
<220> FEATURE:
<223> OTHER INFORMATION: OKT3 VL CDR3

<400> SEQUENCE: 169

Cys Gln Gln Trp Ser Ser Asn Pro Phe
1               5

<210> SEQ ID NO 170
<211> LENGTH: 5
<212> TYPE: PRT
<213> ORGANISM: Artificial Sequence
<220> FEATURE:
<223> OTHER INFORMATION: L2K.07 VH CDR1

<400> SEQUENCE: 170

Tyr Thr Met His Trp
1               5

<210> SEQ ID NO 171
<211> LENGTH: 19
<212> TYPE: PRT
<213> ORGANISM: Artificial Sequence
<220> FEATURE:
<223> OTHER INFORMATION: L2K.07 VH CDR2

<400> SEQUENCE: 171

Ile Asn Pro Ser Arg Gly Tyr Thr Asn Tyr Asn Gln Lys Phe Lys Asp
1               5                   10                  15

Lys Ala Thr

<210> SEQ ID NO 172
<211> LENGTH: 10
<212> TYPE: PRT
<213> ORGANISM: Artificial Sequence
<220> FEATURE:
<223> OTHER INFORMATION: L2K.07 VH CDR3

<400> SEQUENCE: 172

Tyr Tyr Asp Asp His Tyr Cys Leu Asp Tyr
1               5                   10

<210> SEQ ID NO 173
<211> LENGTH: 10
<212> TYPE: PRT
<213> ORGANISM: Artificial Sequence
<220> FEATURE:
<223> OTHER INFORMATION: L2K.07 VL CDR1
```

<400> SEQUENCE: 173

Arg Ala Ser Ser Ser Val Ser Tyr Met Asn
1               5                   10

<210> SEQ ID NO 174
<211> LENGTH: 7
<212> TYPE: PRT
<213> ORGANISM: Artificial Sequence
<220> FEATURE:
<223> OTHER INFORMATION: L2K.07 VL CDR2

<400> SEQUENCE: 174

Tyr Asp Thr Ser Lys Val Ala
1               5

<210> SEQ ID NO 175
<211> LENGTH: 10
<212> TYPE: PRT
<213> ORGANISM: Artificial Sequence
<220> FEATURE:
<223> OTHER INFORMATION: L2K.07 VL CDR3

<400> SEQUENCE: 175

Gln Gln Trp Ser Ser Asn Pro Leu Thr Phe
1               5                   10

<210> SEQ ID NO 176
<211> LENGTH: 5
<212> TYPE: PRT
<213> ORGANISM: Artificial Sequence
<220> FEATURE:
<223> OTHER INFORMATION: UCHT1 VH CDR1

<400> SEQUENCE: 176

Tyr Thr Met Asn Trp
1               5

<210> SEQ ID NO 177
<211> LENGTH: 19
<212> TYPE: PRT
<213> ORGANISM: Artificial Sequence
<220> FEATURE:
<223> OTHER INFORMATION: UCHT1 VH CDR2

<400> SEQUENCE: 177

Ile Asn Pro Tyr Lys Gly Val Ser Thr Tyr Asn Gln Lys Phe Lys Asp
1               5                   10                  15

Lys Ala Thr

<210> SEQ ID NO 178
<211> LENGTH: 13
<212> TYPE: PRT
<213> ORGANISM: Artificial Sequence
<220> FEATURE:
<223> OTHER INFORMATION: UCHT1 VH CDR3

<400> SEQUENCE: 178

Ser Gly Tyr Tyr Gly Asp Ser Asp Trp Tyr Phe Asp Val
1               5                   10

<210> SEQ ID NO 179
<211> LENGTH: 11
<212> TYPE: PRT
<213> ORGANISM: Artificial Sequence
<220> FEATURE:
<223> OTHER INFORMATION: UCHT1 VL CDR1

<400> SEQUENCE: 179

Arg Ala Ser Gln Asp Ile Arg Asn Tyr Leu Asn
1               5                   10

<210> SEQ ID NO 180
<211> LENGTH: 7
<212> TYPE: PRT
<213> ORGANISM: Artificial Sequence
<220> FEATURE:
<223> OTHER INFORMATION: UCHT1 VL CDR2

<400> SEQUENCE: 180

Tyr Thr Ser Arg Leu His Ser
1               5

<210> SEQ ID NO 181
<211> LENGTH: 9
<212> TYPE: PRT
<213> ORGANISM: Artificial Sequence
<220> FEATURE:
<223> OTHER INFORMATION: UCHT1 VL CDR3

<400> SEQUENCE: 181

Gln Gln Gly Asn Thr Leu Pro Trp Thr
1               5

<210> SEQ ID NO 182
<211> LENGTH: 120
<212> TYPE: PRT
<213> ORGANISM: Artificial Sequence
<220> FEATURE:
<223> OTHER INFORMATION: 60E11

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Asp Ile Tyr Lys Ser Phe
            20                  25                  30

Asp Met Gly Trp Tyr Arg Gln Ala Pro Gly Lys Gln Arg Asp Leu Val
        35                  40                  45

Ala Val Ile Gly Ser Arg Gly Asn Asn Arg Gly Arg Thr Asn Tyr Ala
    50                  55                  60

Asp Ser Val Lys Gly Arg Phe Thr Ile Ser Arg Asp Gly Thr Gly Asn
65                  70                  75                  80

Thr Val Tyr Leu Leu Met Asn Lys Leu Arg Pro Glu Asp Thr Ala Ile
                85                  90                  95

Tyr Tyr Cys Asn Thr Ala Pro Leu Val Ala Gly Arg Pro Trp Gly Arg
            100                 105                 110

Gly Thr Leu Val Thr Val Ser Ser
        115                 120

<210> SEQ ID NO 183
<211> LENGTH: 124
<212> TYPE: PRT
<213> ORGANISM: Artificial Sequence
<220> FEATURE:
<223> OTHER INFORMATION: 117G03

<400> SEQUENCE: 183

Glu Val Gln Leu Val Glu Ser Gly Gly Gly Pro Val Gln Ala Gly Gly
1               5                   10                  15

Ser Leu Arg Leu Ser Cys Ala Ala Ser Gly Arg Thr Tyr Arg Gly Tyr
            20                  25                  30

Ser Met Gly Trp Phe Arg Gln Ala Pro Gly Lys Glu Arg Glu Phe Val
            35                  40                  45

Ala Ala Ile Val Trp Ser Gly Gly Asn Thr Tyr Tyr Glu Asp Ser Val
 50                  55                  60

Lys Gly Arg Phe Thr Ile Ser Arg Asp Asn Ala Lys Asn Thr Met Tyr
 65                  70                  75                  80

Leu Gln Met Thr Ser Leu Lys Pro Glu Asp Ser Ala Thr Tyr Tyr Cys
                85                  90                  95

Ala Ala Lys Ile Arg Pro Tyr Ile Phe Lys Ile Ala Gly Gln Tyr Asp
            100                 105                 110

Tyr Trp Gly Gln Gly Thr Gln Val Thr Val Ser Ser
            115                 120

<210> SEQ ID NO 184
<211> LENGTH: 254
<212> TYPE: PRT
<213> ORGANISM: Artificial Sequence
<220> FEATURE:
<223> OTHER INFORMATION: BCMA 269A37353 VHH-CD3 VHH (60E11)

<400> SEQUENCE: 184

Gln Val Lys Leu Glu Glu Ser Gly Gly Gly Leu Val Gln Ala Gly Arg
 1               5                  10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
            35                  40                  45

Ala Val Ile Gly Trp Arg Asp Ile Ser Thr Ser Tyr Ala Asp Ser Val
 50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Gly Ser Gly Gly Gly Gly
            115                 120                 125

Ser Gly Gly Gly Gly Ser Glu Val Gln Leu Val Glu Ser Gly Gly Gly
            130                 135                 140

Leu Val Gln Pro Gly Gly Ser Leu Arg Leu Ser Cys Ala Ala Ser Gly
145                 150                 155                 160

Asp Ile Tyr Lys Ser Phe Asp Met Gly Trp Tyr Arg Gln Ala Pro Gly
            165                 170                 175

Lys Gln Arg Asp Leu Val Ala Val Ile Gly Ser Arg Gly Asn Asn Arg
            180                 185                 190

Gly Arg Thr Asn Tyr Ala Asp Ser Val Lys Gly Arg Phe Thr Ile Ser
            195                 200                 205

Arg Asp Gly Thr Gly Asn Thr Val Tyr Leu Leu Met Asn Lys Leu Arg
 210                 215                 220

Pro Glu Asp Thr Ala Ile Tyr Tyr Cys Asn Thr Ala Pro Leu Val Ala
225                 230                 235                 240

Gly Arg Pro Trp Gly Arg Gly Thr Leu Val Thr Val Ser Ser
            245                 250

<210> SEQ ID NO 185
<211> LENGTH: 258
<212> TYPE: PRT
<213> ORGANISM: Artificial Sequence
<220> FEATURE:
<223> OTHER INFORMATION: BCMA 269A37353 VHH-CD3 VHH (117G03)

<400> SEQUENCE: 185

```
Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Pro Val Gln Ala Gly Gly Ser Leu Arg Leu Ser Cys Ala Ala Ser Gly
145                 150                 155                 160

Arg Thr Tyr Arg Gly Tyr Ser Met Gly Trp Phe Arg Gln Ala Pro Gly
                165                 170                 175

Lys Glu Arg Glu Phe Val Ala Ala Ile Val Trp Ser Gly Gly Asn Thr
            180                 185                 190

Tyr Tyr Glu Asp Ser Val Lys Gly Arg Phe Thr Ile Ser Arg Asp Asn
        195                 200                 205

Ala Lys Asn Thr Met Tyr Leu Gln Met Thr Ser Leu Lys Pro Glu Asp
    210                 215                 220

Ser Ala Thr Tyr Tyr Cys Ala Ala Lys Ile Arg Pro Tyr Ile Phe Lys
225                 230                 235                 240

Ile Ala Gly Gln Tyr Asp Tyr Trp Gly Gln Gly Thr Gln Val Thr Val
                245                 250                 255

Ser Ser
```

<210> SEQ ID NO 186
<211> LENGTH: 377
<212> TYPE: PRT
<213> ORGANISM: Artificial Sequence
<220> FEATURE:
<223> OTHER INFORMATION: BCMA 269A37353 VHH*269A37917 VHH-CD3 VHH 60E11)

<400> SEQUENCE: 186

```
Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45
```

```
Ala Val Ile Gly Trp Arg Asp Ile Ser Thr Ser Tyr Ala Asp Ser Val
 50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Arg Ile Asp Ala Ala Asp Phe Asp Ser Trp Gly Gln Gly
                100                 105                 110

Thr Gln Val Thr Val Ser Ser Gly Gly Gly Ser Glu Val Gln Leu
                115                 120                 125

Val Glu Ser Gly Gly Gly Leu Val Gln Ala Gly Ser Leu Arg Leu
130                 135                 140

Ser Cys Ala Ala Ser Gly Arg Thr Phe Thr Met Gly Trp Phe Arg Gln
145                 150                 155                 160

Ala Pro Gly Lys Glu Arg Glu Phe Val Ala Ala Ile Ser Leu Ser Pro
                165                 170                 175

Thr Leu Ala Tyr Tyr Ala Glu Ser Val Lys Gly Arg Phe Thr Ile Ser
                180                 185                 190

Arg Asp Asn Ala Lys Asn Thr Val Val Leu Gln Met Asn Ser Leu Lys
                195                 200                 205

Pro Glu Asp Thr Ala Leu Tyr Tyr Cys Ala Ala Asp Arg Lys Ser Val
                210                 215                 220

Met Ser Ile Arg Pro Asp Tyr Trp Gly Gln Gly Thr Gln Val Thr Val
225                 230                 235                 240

Ser Ser Gly Gly Gly Gly Ser Gly Gly Gly Ser Gly Gly Gly Gly
                245                 250                 255

Ser Glu Val Gln Leu Val Glu Ser Gly Gly Gly Leu Val Gln Pro Gly
                260                 265                 270

Gly Ser Leu Arg Leu Ser Cys Ala Ala Ser Gly Asp Ile Tyr Lys Ser
                275                 280                 285

Phe Asp Met Gly Trp Tyr Arg Gln Ala Pro Gly Lys Gln Arg Asp Leu
                290                 295                 300

Val Ala Val Ile Gly Ser Arg Gly Asn Asn Arg Gly Arg Thr Asn Tyr
305                 310                 315                 320

Ala Asp Ser Val Lys Gly Arg Phe Thr Ile Ser Arg Asp Gly Thr Gly
                325                 330                 335

Asn Thr Val Tyr Leu Leu Met Asn Lys Leu Arg Pro Glu Asp Thr Ala
                340                 345                 350

Ile Tyr Tyr Cys Asn Thr Ala Pro Leu Val Ala Gly Arg Pro Trp Gly
                355                 360                 365

Arg Gly Thr Leu Val Thr Val Ser Ser
    370                 375
```

<210> SEQ ID NO 187
<211> LENGTH: 381
<212> TYPE: PRT
<213> ORGANISM: Artificial Sequence
<220> FEATURE:
<223> OTHER INFORMATION: BCMA 269A37353 VHH*269A37917 VHH-CD3 VHH
      (117G03)

<400> SEQUENCE: 187

```
Gln Val Lys Leu Glu Glu Ser Gly Gly Gly Leu Val Gln Ala Gly Arg
 1               5                  10                  15

Ser Leu Arg Leu Ser Cys Ala Ala Ser Glu His Thr Phe Ser Ser His
                 20                  25                  30
```

Val Met Gly Trp Phe Arg Gln Ala Pro Gly Lys Glu Arg Glu Ser Val
            35                  40                  45

Ala Val Ile Gly Trp Arg Asp Ile Ser Thr Ser Tyr Ala Asp Ser Val
 50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Arg Ile Asp Ala Ala Asp Phe Asp Ser Trp Gly Gln Gly
                100                 105                 110

Thr Gln Val Thr Val Ser Ser Gly Gly Gly Ser Glu Val Gln Leu
                115                 120                 125

Val Glu Ser Gly Gly Gly Leu Val Gln Ala Gly Gly Ser Leu Arg Leu
                130                 135                 140

Ser Cys Ala Ala Ser Gly Arg Thr Phe Thr Met Gly Trp Phe Arg Gln
145                 150                 155                 160

Ala Pro Gly Lys Glu Arg Glu Phe Val Ala Ala Ile Ser Leu Ser Pro
                165                 170                 175

Thr Leu Ala Tyr Tyr Ala Glu Ser Val Lys Gly Arg Phe Thr Ile Ser
                180                 185                 190

Arg Asp Asn Ala Lys Asn Thr Val Val Leu Gln Met Asn Ser Leu Lys
                195                 200                 205

Pro Glu Asp Thr Ala Leu Tyr Tyr Cys Ala Ala Asp Arg Lys Ser Val
                210                 215                 220

Met Ser Ile Arg Pro Asp Tyr Trp Gly Gln Gly Thr Gln Val Thr Val
225                 230                 235                 240

Ser Ser Gly Gly Gly Gly Ser Gly Gly Gly Gly Ser Gly Gly Gly Gly
                245                 250                 255

Ser Glu Val Gln Leu Val Glu Ser Gly Gly Gly Pro Val Gln Ala Gly
                260                 265                 270

Gly Ser Leu Arg Leu Ser Cys Ala Ala Ser Gly Arg Thr Tyr Arg Gly
                275                 280                 285

Tyr Ser Met Gly Trp Phe Arg Gln Ala Pro Gly Lys Glu Arg Glu Phe
                290                 295                 300

Val Ala Ala Ile Val Trp Ser Gly Gly Asn Thr Tyr Tyr Glu Asp Ser
305                 310                 315                 320

Val Lys Gly Arg Phe Thr Ile Ser Arg Asp Asn Ala Lys Asn Thr Met
                325                 330                 335

Tyr Leu Gln Met Thr Ser Leu Lys Pro Glu Asp Ser Ala Thr Tyr Tyr
                340                 345                 350

Cys Ala Ala Lys Ile Arg Pro Tyr Ile Phe Lys Ile Ala Gly Gln Tyr
                355                 360                 365

Asp Tyr Trp Gly Gln Gly Thr Gln Val Thr Val Ser Ser
                370                 375                 380

<210> SEQ ID NO 188
<211> LENGTH: 498
<212> TYPE: PRT
<213> ORGANISM: Artificial Sequence
<220> FEATURE:
<223> OTHER INFORMATION: BCMA 269A37353 VHH*269A37917 VHH-OKT3 scFv

<400> SEQUENCE: 188

Gln Val Lys Leu Glu Glu Ser Gly Gly Gly Leu Val Gln Ala Gly Arg
1               5                   10                  15

```
Ser Leu Arg Leu Ser Cys Ala Ala Ser Glu His Thr Phe Ser Ser His
         20                  25                  30

Val Met Gly Trp Phe Arg Gln Ala Pro Gly Lys Glu Arg Glu Ser Val
         35                  40                  45

Ala Val Ile Gly Trp Arg Asp Ile Ser Thr Ser Tyr Ala Asp Ser Val
 50                  55                  60

Lys Gly Arg Phe Thr Ile Ser Arg Asp Asn Ala Lys Lys Thr Leu Tyr
 65                  70                  75                  80

Leu Gln Met Asn Ser Leu Lys Pro Glu Asp Thr Ala Val Tyr Tyr Cys
                 85                  90                  95

Ala Ala Arg Arg Ile Asp Ala Ala Asp Phe Asp Ser Trp Gly Gln Gly
             100                 105                 110

Thr Gln Val Thr Val Ser Ser Gly Gly Gly Ser Glu Val Gln Leu
             115                 120                 125

Val Glu Ser Gly Gly Gly Leu Val Gln Ala Gly Gly Ser Leu Arg Leu
         130                 135                 140

Ser Cys Ala Ala Ser Gly Arg Thr Phe Thr Met Gly Trp Phe Arg Gln
145                 150                 155                 160

Ala Pro Gly Lys Glu Arg Glu Phe Val Ala Ala Ile Ser Leu Ser Pro
                 165                 170                 175

Thr Leu Ala Tyr Tyr Ala Glu Ser Val Lys Gly Arg Phe Thr Ile Ser
             180                 185                 190

Arg Asp Asn Ala Lys Asn Thr Val Val Leu Gln Met Asn Ser Leu Lys
             195                 200                 205

Pro Glu Asp Thr Ala Leu Tyr Tyr Cys Ala Ala Asp Arg Lys Ser Val
         210                 215                 220

Met Ser Ile Arg Pro Asp Tyr Trp Gly Gln Gly Thr Gln Val Thr Val
225                 230                 235                 240

Ser Ser Gly Gly Gly Gly Ser Gly Gly Gly Gly Ser Gly Gly Gly Gly
             245                 250                 255

Ser Gln Val Gln Leu Gln Gln Ser Gly Ala Glu Leu Ala Arg Pro Gly
         260                 265                 270

Ala Ser Val Lys Met Ser Cys Lys Ala Ser Gly Tyr Thr Phe Thr Arg
         275                 280                 285

Tyr Thr Met His Trp Val Lys Gln Arg Pro Gly Gln Gly Leu Glu Trp
         290                 295                 300

Ile Gly Tyr Ile Asn Pro Ser Arg Gly Tyr Thr Asn Tyr Asn Gln Lys
305                 310                 315                 320

Phe Lys Asp Lys Ala Thr Leu Thr Thr Asp Lys Ser Ser Ser Thr Ala
             325                 330                 335

Tyr Met Gln Leu Ser Ser Leu Thr Ser Glu Asp Ser Ala Val Tyr Tyr
             340                 345                 350

Cys Ala Arg Tyr Tyr Asp Asp His Tyr Cys Leu Asp Tyr Trp Gly Gln
             355                 360                 365

Gly Thr Thr Leu Thr Val Ser Ser Gly Gly Gly Gly Ser Gly Gly Gly
         370                 375                 380

Gly Ser Gly Gly Gly Gly Ser Gln Ile Val Leu Thr Gln Ser Pro Ala
385                 390                 395                 400

Ile Met Ser Ala Ser Pro Gly Glu Lys Val Thr Met Thr Cys Ser Ala
             405                 410                 415

Ser Ser Ser Val Ser Tyr Met Asn Trp Tyr Gln Gln Lys Ser Gly Thr
             420                 425                 430
```

Ser Pro Lys Arg Trp Ile Tyr Asp Thr Ser Lys Leu Ala Ser Gly Val
            435                 440                 445

Pro Ala His Phe Arg Gly Ser Gly Ser Gly Thr Ser Tyr Ser Leu Thr
    450                 455                 460

Ile Ser Gly Met Glu Ala Glu Asp Ala Ala Thr Tyr Tyr Cys Gln Gln
465                 470                 475                 480

Trp Ser Ser Asn Pro Phe Thr Phe Gly Ser Gly Thr Lys Leu Glu Ile
                485                 490                 495

Asn Arg

<210> SEQ ID NO 189
<211> LENGTH: 500
<212> TYPE: PRT
<213> ORGANISM: Artificial Sequence
<220> FEATURE:
<223> OTHER INFORMATION: BCMA 269A37353 VHH*269A37917 VHH-L2K.07 scFv

<400> SEQUENCE: 189

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Ser Glu Val Gln Leu
        115                 120                 125

Val Glu Ser Gly Gly Gly Leu Val Gln Ala Gly Ser Leu Arg Leu
    130                 135                 140

Ser Cys Ala Ala Ser Gly Arg Thr Phe Thr Met Gly Trp Phe Arg Gln
145                 150                 155                 160

Ala Pro Gly Lys Glu Arg Glu Phe Val Ala Ala Ile Ser Leu Ser Pro
                165                 170                 175

Thr Leu Ala Tyr Tyr Ala Glu Ser Val Lys Gly Arg Phe Thr Ile Ser
            180                 185                 190

Arg Asp Asn Ala Lys Asn Thr Val Val Leu Gln Met Asn Ser Leu Lys
        195                 200                 205

Pro Glu Asp Thr Ala Leu Tyr Tyr Cys Ala Ala Asp Arg Lys Ser Val
    210                 215                 220

Met Ser Ile Arg Pro Asp Tyr Trp Gly Gln Gly Thr Gln Val Thr Val
225                 230                 235                 240

Ser Ser Gly Gly Gly Gly Ser Gly Gly Gly Ser Gly Gly Gly Gly
                245                 250                 255

Ser Asp Ile Lys Leu Gln Gln Ser Gly Ala Glu Leu Ala Arg Pro Gly
            260                 265                 270

Ala Ser Val Lys Met Ser Cys Lys Thr Ser Gly Tyr Thr Phe Thr Arg
        275                 280                 285

Tyr Thr Met His Trp Val Lys Gln Arg Pro Gly Gln Gly Leu Glu Trp

```
                290                 295                 300
Ile Gly Tyr Ile Asn Pro Ser Arg Gly Tyr Thr Asn Tyr Asn Gln Lys
305                 310                 315                 320

Phe Lys Asp Lys Ala Thr Leu Thr Thr Asp Lys Ser Ser Thr Ala
                325                 330                 335

Tyr Met Gln Leu Ser Ser Leu Thr Ser Glu Asp Ser Ala Val Tyr Tyr
                340                 345                 350

Cys Ala Arg Tyr Tyr Asp Asp His Tyr Cys Leu Asp Tyr Trp Gly Gln
                355                 360                 365

Gly Thr Thr Leu Thr Val Ser Ser Val Glu Gly Gly Ser Gly Gly Ser
                370                 375                 380

Gly Gly Ser Gly Gly Ser Gly Gly Val Asp Asp Ile Gln Leu Thr Gln
385                 390                 395                 400

Ser Pro Ala Ile Met Ser Ala Ser Pro Gly Glu Lys Val Thr Met Thr
                405                 410                 415

Cys Arg Ala Ser Ser Ser Val Ser Tyr Met Asn Trp Tyr Gln Gln Lys
                420                 425                 430

Ser Gly Thr Ser Pro Lys Arg Trp Ile Tyr Asp Thr Ser Lys Val Ala
                435                 440                 445

Ser Gly Val Pro Tyr Arg Phe Ser Gly Ser Gly Ser Gly Thr Ser Tyr
                450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Leu Thr Phe Gly Ala Gly Thr Lys
                485                 490                 495

Leu Glu Leu Lys
            500

<210> SEQ ID NO 190
<211> LENGTH: 501
<212> TYPE: PRT
<213> ORGANISM: Artificial Sequence
<220> FEATURE:
<223> OTHER INFORMATION: BCMA 269A37353 VHH*269A37917 VHH-UCHT1 scFv

<400> SEQUENCE: 190

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
                20                  25                  30

Val Met Gly Trp Phe Arg Gln Ala Pro Gly Lys Glu Arg Glu Ser Val
                35                  40                  45

Ala Val Ile Gly Trp Arg Asp Ile Ser Thr Ser Tyr Ala Asp Ser Val
                50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
                100                 105                 110

Thr Gln Val Thr Val Ser Ser Gly Gly Gly Ser Glu Val Gln Leu
                115                 120                 125

Val Glu Ser Gly Gly Gly Leu Val Gln Ala Gly Ser Leu Arg Leu
                130                 135                 140

Ser Cys Ala Ala Ser Gly Arg Thr Phe Thr Met Gly Trp Phe Arg Gln
```

```
            145                 150                 155                 160
Ala Pro Gly Lys Glu Arg Glu Phe Val Ala Ile Ser Leu Ser Pro
                165                 170                 175

Thr Leu Ala Tyr Tyr Ala Glu Ser Val Lys Gly Arg Phe Thr Ile Ser
                180                 185                 190

Arg Asp Asn Ala Lys Asn Thr Val Leu Gln Met Asn Ser Leu Lys
                195                 200                 205

Pro Glu Asp Thr Ala Leu Tyr Tyr Cys Ala Ala Asp Arg Lys Ser Val
                210                 215                 220

Met Ser Ile Arg Pro Asp Tyr Trp Gly Gln Gly Thr Gln Val Thr Val
225                 230                 235                 240

Ser Ser Gly Gly Gly Gly Ser Gly Gly Gly Ser Gly Gly Gly Gly
                245                 250                 255

Ser Glu Val Gln Leu Gln Gln Ser Gly Pro Glu Leu Val Lys Pro Gly
                260                 265                 270

Ala Ser Met Lys Ile Ser Cys Lys Ala Ser Gly Tyr Ser Phe Thr Gly
                275                 280                 285

Tyr Thr Met Asn Trp Val Lys Gln Ser His Gly Lys Asn Leu Glu Trp
                290                 295                 300

Met Gly Leu Ile Asn Pro Tyr Lys Gly Val Ser Thr Tyr Asn Gln Lys
305                 310                 315                 320

Phe Lys Asp Lys Ala Thr Leu Thr Val Asp Lys Ser Ser Ser Thr Ala
                325                 330                 335

Tyr Met Glu Leu Leu Ser Leu Thr Ser Glu Asp Ser Ala Val Tyr Tyr
                340                 345                 350

Cys Ala Arg Ser Gly Tyr Tyr Gly Asp Ser Asp Trp Tyr Phe Asp Val
                355                 360                 365

Trp Gly Gln Gly Thr Thr Leu Thr Val Phe Ser Gly Gly Gly Gly Ser
                370                 375                 380

Gly Gly Gly Gly Ser Gly Gly Gly Ser Asp Ile Gln Met Thr Gln
385                 390                 395                 400

Thr Thr Ser Ser Leu Ser Ala Ser Leu Gly Asp Arg Val Thr Ile Ser
                405                 410                 415

Cys Arg Ala Ser Gln Asp Ile Arg Asn Tyr Leu Asn Trp Tyr Gln Gln
                420                 425                 430

Lys Pro Asp Gly Thr Val Lys Leu Leu Ile Tyr Tyr Thr Ser Arg Leu
                435                 440                 445

His Ser Gly Val Pro Ser Lys Phe Ser Gly Ser Gly Ser Gly Thr Asp
                450                 455                 460

Tyr Ser Leu Thr Ile Ser Asn Leu Glu Gln Glu Asp Ile Ala Thr Tyr
465                 470                 475                 480

Phe Cys Gln Gln Gly Asn Thr Leu Pro Trp Thr Phe Ala Gly Gly Thr
                485                 490                 495

Lys Leu Glu Ile Lys
                500

<210> SEQ ID NO 191
<211> LENGTH: 377
<212> TYPE: PRT
<213> ORGANISM: Artificial Sequence
<220> FEATURE:
<223> OTHER INFORMATION: BCMA 269A37917 VHH*269A37353 VHH-CD3 VHH
      (60E11)

<400> SEQUENCE: 191
```

```
Glu Val Gln Leu Val Glu Ser Gly Gly Gly Leu Val Gln Ala Gly
  1               5                  10                  15

Ser Leu Arg Leu Ser Cys Ala Ala Ser Gly Arg Thr Phe Thr Met Gly
             20                  25                  30

Trp Phe Arg Gln Ala Pro Gly Lys Glu Arg Glu Phe Val Ala Ala Ile
             35                  40                  45

Ser Leu Ser Pro Thr Leu Ala Tyr Tyr Ala Glu Ser Val Lys Gly Arg
 50                  55                  60

Phe Thr Ile Ser Arg Asp Asn Ala Lys Asn Thr Val Val Leu Gln Met
 65                  70                  75                  80

Asn Ser Leu Lys Pro Glu Asp Thr Ala Leu Tyr Tyr Cys Ala Ala Asp
                 85                  90                  95

Arg Lys Ser Val Met Ser Ile Arg Pro Asp Tyr Trp Gly Gln Gly Thr
            100                 105                 110

Gln Val Thr Val Ser Ser Gly Gly Gly Ser Gln Val Lys Leu Glu
            115                 120                 125

Glu Ser Gly Gly Gly Leu Val Gln Ala Gly Arg Ser Leu Arg Leu Ser
        130                 135                 140

Cys Ala Ala Ser Glu His Thr Phe Ser His Val Met Gly Trp Phe
145                 150                 155                 160

Arg Gln Ala Pro Gly Lys Glu Arg Glu Ser Val Ala Val Ile Gly Trp
                165                 170                 175

Arg Asp Ile Ser Thr Ser Tyr Ala Asp Ser Val Lys Gly Arg Phe Thr
            180                 185                 190

Ile Ser Arg Asp Asn Ala Lys Lys Thr Leu Tyr Leu Gln Met Asn Ser
        195                 200                 205

Leu Lys Pro Glu Asp Thr Ala Val Tyr Tyr Cys Ala Ala Arg Arg Ile
    210                 215                 220

Asp Ala Ala Asp Phe Asp Ser Trp Gly Gln Gly Thr Gln Val Thr Val
225                 230                 235                 240

Ser Ser Gly Gly Gly Gly Ser Gly Gly Gly Ser Gly Gly Gly
                245                 250                 255

Ser Glu Val Gln Leu Val Glu Ser Gly Gly Gly Leu Val Gln Pro Gly
        260                 265                 270

Gly Ser Leu Arg Leu Ser Cys Ala Ala Ser Gly Asp Ile Tyr Lys Ser
        275                 280                 285

Phe Asp Met Gly Trp Tyr Arg Gln Ala Pro Gly Lys Gln Arg Asp Leu
    290                 295                 300

Val Ala Val Ile Gly Ser Arg Gly Asn Asn Arg Gly Arg Thr Asn Tyr
305                 310                 315                 320

Ala Asp Ser Val Lys Gly Arg Phe Thr Ile Ser Arg Asp Gly Thr Gly
                325                 330                 335

Asn Thr Val Tyr Leu Leu Met Asn Lys Leu Arg Pro Glu Asp Thr Ala
            340                 345                 350

Ile Tyr Tyr Cys Asn Thr Ala Pro Leu Val Ala Gly Arg Pro Trp Gly
        355                 360                 365

Arg Gly Thr Leu Val Thr Val Ser Ser
    370                 375
```

<210> SEQ ID NO 192
<211> LENGTH: 381
<212> TYPE: PRT
<213> ORGANISM: Artificial Sequence
<220> FEATURE:
<223> OTHER INFORMATION: BCMA 269A37917 VHH*269A37353 VHH-CD3 VHH (117G03)

<400> SEQUENCE: 192

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser Gly Gly Gly Ser Gln Val Lys Leu Glu
            115                 120                 125

Glu Ser Gly Gly Gly Leu Val Gln Ala Gly Arg Ser Leu Arg Leu Ser
130                 135                 140

Cys Ala Ala Ser Glu His Thr Phe Ser His Val Met Gly Trp Phe
145                 150                 155                 160

Arg Gln Ala Pro Gly Lys Glu Arg Glu Ser Val Ala Val Ile Gly Trp
            165                 170                 175

Arg Asp Ile Ser Thr Ser Tyr Ala Asp Ser Val Lys Gly Arg Phe Thr
            180                 185                 190

Ile Ser Arg Asp Asn Ala Lys Lys Thr Leu Tyr Leu Gln Met Asn Ser
            195                 200                 205

Leu Lys Pro Glu Asp Thr Ala Val Tyr Tyr Cys Ala Ala Arg Arg Ile
210                 215                 220

Asp Ala Ala Asp Phe Asp Ser Trp Gly Gln Gly Thr Gln Val Thr Val
225                 230                 235                 240

Ser Ser Gly Gly Gly Gly Ser Gly Gly Gly Ser Gly Gly Gly
            245                 250                 255

Ser Glu Val Gln Leu Val Glu Ser Gly Gly Gly Pro Val Gln Ala Gly
            260                 265                 270

Gly Ser Leu Arg Leu Ser Cys Ala Ala Ser Gly Arg Thr Tyr Arg Gly
            275                 280                 285

Tyr Ser Met Gly Trp Phe Arg Gln Ala Pro Gly Lys Glu Arg Glu Phe
290                 295                 300

Val Ala Ala Ile Val Trp Ser Gly Gly Asn Thr Tyr Tyr Glu Asp Ser
305                 310                 315                 320

Val Lys Gly Arg Phe Thr Ile Ser Arg Asp Asn Ala Lys Asn Thr Met
            325                 330                 335

Tyr Leu Gln Met Thr Ser Leu Lys Pro Glu Asp Ser Ala Thr Tyr Tyr
            340                 345                 350

Cys Ala Ala Lys Ile Arg Pro Tyr Ile Phe Lys Ile Ala Gly Gln Tyr
            355                 360                 365

Asp Tyr Trp Gly Gln Gly Thr Gln Val Thr Val Ser Ser
            370                 375                 380

<210> SEQ ID NO 193
<211> LENGTH: 498

```
<212> TYPE: PRT
<213> ORGANISM: Artificial Sequence
<220> FEATURE:
<223> OTHER INFORMATION: BCMA 269A37917 VHH*269A37353 VHH-OKT3 scFv

<400> SEQUENCE: 193
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Ala | Gly | Gly |
| 1 | | | | 5 | | | | | 10 | | | | | 15 | |
| Ser | Leu | Arg | Leu | Ser | Cys | Ala | Ala | Ser | Gly | Arg | Thr | Phe | Thr | Met | Gly |
| | | 20 | | | | 25 | | | | 30 | | | | | |
| Trp | Phe | Arg | Gln | Ala | Pro | Gly | Lys | Glu | Arg | Glu | Phe | Val | Ala | Ala | Ile |
| | | 35 | | | | 40 | | | | 45 | | | | | |
| Ser | Leu | Ser | Pro | Thr | Leu | Ala | Tyr | Tyr | Ala | Glu | Ser | Val | Lys | Gly | Arg |
| 50 | | | | | 55 | | | | | 60 | | | | | |
| Phe | Thr | Ile | Ser | Arg | Asp | Asn | Ala | Lys | Asn | Thr | Val | Val | Leu | Gln | Met |
| 65 | | | | | 70 | | | | | 75 | | | | | 80 |
| Asn | Ser | Leu | Lys | Pro | Glu | Asp | Thr | Ala | Leu | Tyr | Tyr | Cys | Ala | Ala | Asp |
| | | | | 85 | | | | | 90 | | | | | 95 | |
| Arg | Lys | Ser | Val | Met | Ser | Ile | Arg | Pro | Asp | Tyr | Trp | Gly | Gln | Gly | Thr |
| | | | 100 | | | | | 105 | | | | | 110 | | |
| Gln | Val | Thr | Val | Ser | Ser | Gly | Gly | Gly | Ser | Gln | Val | Lys | Leu | Glu | |
| | 115 | | | | | 120 | | | | | 125 | | | | |
| Glu | Ser | Gly | Gly | Gly | Leu | Val | Gln | Ala | Gly | Arg | Ser | Leu | Arg | Leu | Ser |
| 130 | | | | | 135 | | | | | 140 | | | | | |
| Cys | Ala | Ala | Ser | Glu | His | Thr | Phe | Ser | Ser | His | Val | Met | Gly | Trp | Phe |
| 145 | | | | | 150 | | | | | 155 | | | | | 160 |
| Arg | Gln | Ala | Pro | Gly | Lys | Glu | Arg | Glu | Ser | Val | Ala | Val | Ile | Gly | Trp |
| | | | | 165 | | | | | 170 | | | | | 175 | |
| Arg | Asp | Ile | Ser | Thr | Ser | Tyr | Ala | Asp | Ser | Val | Lys | Gly | Arg | Phe | Thr |
| | | | 180 | | | | | 185 | | | | | 190 | | |
| Ile | Ser | Arg | Asp | Asn | Ala | Lys | Lys | Thr | Leu | Tyr | Leu | Gln | Met | Asn | Ser |
| | | 195 | | | | | 200 | | | | | 205 | | | |
| Leu | Lys | Pro | Glu | Asp | Thr | Ala | Val | Tyr | Tyr | Cys | Ala | Ala | Arg | Arg | Ile |
| 210 | | | | | 215 | | | | | 220 | | | | | |
| Asp | Ala | Ala | Asp | Phe | Asp | Ser | Trp | Gly | Gln | Gly | Thr | Gln | Val | Thr | Val |
| 225 | | | | | 230 | | | | | 235 | | | | | 240 |
| Ser | Ser | Gly | Gly | Gly | Gly | Ser | Gly | Gly | Gly | Ser | Gly | Gly | Gly | Gly | |
| | | | | 245 | | | | | 250 | | | | | 255 | |
| Ser | Gln | Val | Gln | Leu | Gln | Gln | Ser | Gly | Ala | Glu | Leu | Ala | Arg | Pro | Gly |
| | | | 260 | | | | | 265 | | | | | 270 | | |
| Ala | Ser | Val | Lys | Met | Ser | Cys | Lys | Ala | Ser | Gly | Tyr | Thr | Phe | Thr | Arg |
| | | 275 | | | | | 280 | | | | | 285 | | | |
| Tyr | Thr | Met | His | Trp | Val | Lys | Gln | Arg | Pro | Gly | Gln | Gly | Leu | Glu | Trp |
| | 290 | | | | | 295 | | | | | 300 | | | | |
| Ile | Gly | Tyr | Ile | Asn | Pro | Ser | Arg | Gly | Tyr | Thr | Asn | Tyr | Asn | Gln | Lys |
| 305 | | | | | 310 | | | | | 315 | | | | | 320 |
| Phe | Lys | Asp | Lys | Ala | Thr | Leu | Thr | Thr | Asp | Lys | Ser | Ser | Ser | Thr | Ala |
| | | | | 325 | | | | | 330 | | | | | 335 | |
| Tyr | Met | Gln | Leu | Ser | Ser | Leu | Thr | Ser | Glu | Asp | Ser | Ala | Val | Tyr | Tyr |
| | | | 340 | | | | | 345 | | | | | 350 | | |
| Cys | Ala | Arg | Tyr | Tyr | Asp | Asp | His | Tyr | Cys | Leu | Asp | Tyr | Trp | Gly | Gln |
| | | 355 | | | | | 360 | | | | | 365 | | | |
| Gly | Thr | Thr | Leu | Thr | Val | Ser | Ser | Gly | Gly | Gly | Ser | Gly | Gly | Gly | |
| | 370 | | | | | 375 | | | | | 380 | | | | |

```
Gly Ser Gly Gly Gly Ser Gln Ile Val Leu Thr Gln Ser Pro Ala
385                 390                 395                 400

Ile Met Ser Ala Ser Pro Gly Glu Lys Val Thr Met Thr Cys Ser Ala
            405                 410                 415

Ser Ser Ser Val Ser Tyr Met Asn Trp Tyr Gln Gln Lys Ser Gly Thr
            420                 425                 430

Ser Pro Lys Arg Trp Ile Tyr Asp Thr Ser Lys Leu Ala Ser Gly Val
            435                 440                 445

Pro Ala His Phe Arg Gly Ser Gly Ser Gly Thr Ser Tyr Ser Leu Thr
            450                 455                 460

Ile Ser Gly Met Glu Ala Glu Asp Ala Ala Thr Tyr Tyr Cys Gln Gln
465                 470                 475                 480

Trp Ser Ser Asn Pro Phe Thr Phe Gly Ser Gly Thr Lys Leu Glu Ile
            485                 490                 495

Asn Arg

<210> SEQ ID NO 194
<211> LENGTH: 500
<212> TYPE: PRT
<213> ORGANISM: Artificial Sequence
<220> FEATURE:
<223> OTHER INFORMATION: BCMA 269A37917 VHH*269A37353 VHH-L2K.07 scFv

<400> SEQUENCE: 194

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
            85                  90                  95

Arg Lys Ser Val Met Ser Ile Arg Pro Asp Tyr Trp Gly Gln Gly Thr
            100                 105                 110

Gln Val Thr Val Ser Ser Gly Gly Gly Ser Gln Val Lys Leu Glu
            115                 120                 125

Glu Ser Gly Gly Gly Leu Val Gln Ala Gly Arg Ser Leu Arg Leu Ser
            130                 135                 140

Cys Ala Ala Ser Glu His Thr Phe Ser Ser His Val Met Gly Trp Phe
145                 150                 155                 160

Arg Gln Ala Pro Gly Lys Glu Arg Glu Ser Val Ala Val Ile Gly Trp
            165                 170                 175

Arg Asp Ile Ser Thr Ser Tyr Ala Asp Ser Val Lys Gly Arg Phe Thr
            180                 185                 190

Ile Ser Arg Asp Asn Ala Lys Lys Thr Leu Tyr Leu Gln Met Asn Ser
            195                 200                 205

Leu Lys Pro Glu Asp Thr Ala Val Tyr Tyr Cys Ala Ala Arg Arg Ile
            210                 215                 220

Asp Ala Ala Asp Phe Asp Ser Trp Gly Gln Gly Thr Gln Val Thr Val
225                 230                 235                 240

Ser Ser Gly Gly Gly Gly Ser Gly Gly Gly Gly Ser Gly Gly Gly Gly
```

```
                        245                 250                 255
Ser Asp Ile Lys Leu Gln Gln Ser Gly Ala Glu Leu Ala Arg Pro Gly
            260                 265                 270

Ala Ser Val Lys Met Ser Cys Lys Thr Ser Gly Tyr Thr Phe Thr Arg
        275                 280                 285

Tyr Thr Met His Trp Val Lys Gln Arg Pro Gly Gln Gly Leu Glu Trp
    290                 295                 300

Ile Gly Tyr Ile Asn Pro Ser Arg Gly Tyr Thr Asn Tyr Asn Gln Lys
305                 310                 315                 320

Phe Lys Asp Lys Ala Thr Leu Thr Thr Asp Lys Ser Ser Ser Thr Ala
                325                 330                 335

Tyr Met Gln Leu Ser Ser Leu Thr Ser Glu Asp Ser Ala Val Tyr Tyr
            340                 345                 350

Cys Ala Arg Tyr Tyr Asp Asp His Tyr Cys Leu Asp Tyr Trp Gly Gln
        355                 360                 365

Gly Thr Thr Leu Thr Val Ser Ser Val Glu Gly Gly Ser Gly Gly Ser
    370                 375                 380

Gly Gly Ser Gly Gly Ser Gly Gly Val Asp Asp Ile Gln Leu Thr Gln
385                 390                 395                 400

Ser Pro Ala Ile Met Ser Ala Ser Pro Gly Glu Lys Val Thr Met Thr
                405                 410                 415

Cys Arg Ala Ser Ser Ser Val Ser Tyr Met Asn Trp Tyr Gln Gln Lys
            420                 425                 430

Ser Gly Thr Ser Pro Lys Arg Trp Ile Tyr Asp Thr Ser Lys Val Ala
        435                 440                 445

Ser Gly Val Pro Tyr Arg Phe Ser Gly Ser Gly Ser Gly Thr Ser Tyr
    450                 455                 460

Ser Leu Thr Ile Ser Ser Met Glu Ala Glu Asp Ala Ala Thr Tyr Tyr
465                 470                 475                 480

Cys Gln Gln Trp Ser Ser Asn Pro Leu Thr Phe Gly Ala Gly Thr Lys
                485                 490                 495

Leu Glu Leu Lys
            500

<210> SEQ ID NO 195
<211> LENGTH: 501
<212> TYPE: PRT
<213> ORGANISM: Artificial Sequence
<220> FEATURE:
<223> OTHER INFORMATION: BCMA 269A37917 VHH*269A37353 VHH-UCHT1 scFv

<400> SEQUENCE: 195

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
```

```
                100             105             110
    Gln Val Thr Val Ser Gly Gly Gly Ser Gln Val Lys Leu Glu
            115             120             125
    Glu Ser Gly Gly Leu Val Gln Ala Gly Arg Ser Leu Arg Leu Ser
            130             135             140
    Cys Ala Ala Ser Glu His Thr Phe Ser Ser His Val Met Gly Trp Phe
    145             150             155             160
    Arg Gln Ala Pro Gly Lys Glu Arg Glu Ser Val Ala Val Ile Gly Trp
                    165             170             175
    Arg Asp Ile Ser Thr Ser Tyr Ala Asp Ser Val Lys Gly Arg Phe Thr
                180             185             190
    Ile Ser Arg Asp Asn Ala Lys Lys Thr Leu Tyr Leu Gln Met Asn Ser
            195             200             205
    Leu Lys Pro Glu Asp Thr Ala Val Tyr Tyr Cys Ala Ala Arg Arg Ile
            210             215             220
    Asp Ala Ala Asp Phe Asp Ser Trp Gly Gln Gly Thr Gln Val Thr Val
    225             230             235             240
    Ser Ser Gly Gly Gly Gly Ser Gly Gly Gly Gly Ser Gly Gly Gly Gly
                    245             250             255
    Ser Glu Val Gln Leu Gln Gln Ser Gly Pro Glu Leu Val Lys Pro Gly
                    260             265             270
    Ala Ser Met Lys Ile Ser Cys Lys Ala Ser Gly Tyr Ser Phe Thr Gly
                    275             280             285
    Tyr Thr Met Asn Trp Val Lys Gln Ser His Gly Lys Asn Leu Glu Trp
            290             295             300
    Met Gly Leu Ile Asn Pro Tyr Lys Gly Val Ser Thr Tyr Asn Gln Lys
    305             310             315             320
    Phe Lys Asp Lys Ala Thr Leu Thr Val Asp Lys Ser Ser Ser Thr Ala
                    325             330             335
    Tyr Met Glu Leu Leu Ser Leu Thr Ser Glu Asp Ser Ala Val Tyr Tyr
                    340             345             350
    Cys Ala Arg Ser Gly Tyr Tyr Gly Asp Ser Asp Trp Tyr Phe Asp Val
                    355             360             365
    Trp Gly Gln Gly Thr Thr Leu Thr Val Phe Ser Gly Gly Gly Gly Ser
            370             375             380
    Gly Gly Gly Gly Ser Gly Gly Gly Gly Ser Asp Ile Gln Met Thr Gln
    385             390             395             400
    Thr Thr Ser Ser Leu Ser Ala Ser Leu Gly Asp Arg Val Thr Ile Ser
                    405             410             415
    Cys Arg Ala Ser Gln Asp Ile Arg Asn Tyr Leu Asn Trp Tyr Gln Gln
                    420             425             430
    Lys Pro Asp Gly Thr Val Lys Leu Leu Ile Tyr Tyr Thr Ser Arg Leu
                    435             440             445
    His Ser Gly Val Pro Ser Lys Phe Ser Gly Ser Gly Ser Gly Thr Asp
            450             455             460
    Tyr Ser Leu Thr Ile Ser Asn Leu Glu Gln Glu Asp Ile Ala Thr Tyr
    465             470             475             480
    Phe Cys Gln Gln Gly Asn Thr Leu Pro Trp Thr Phe Ala Gly Gly Thr
                    485             490             495
    Lys Leu Glu Ile Lys
                500

<210> SEQ ID NO 196
```

<211> LENGTH: 378
<212> TYPE: PRT
<213> ORGANISM: Artificial Sequence
<220> FEATURE:
<223> OTHER INFORMATION: BCMA 269A37353 VHH*269A37948VHH-CD3 VHH (60E11)

<400> SEQUENCE: 196

```
Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Ser Ala Val Gln Leu
        115                 120                 125

Val Glu Ser Gly Gly Gly Leu Val Gln Ala Gly Asp Ser Leu Arg Leu
    130                 135                 140

Thr Cys Thr Ala Ser Gly Arg Ala Phe Ser Thr Tyr Phe Met Ala Trp
145                 150                 155                 160

Phe Arg Gln Ala Pro Gly Lys Glu Arg Glu Phe Val Ala Gly Ile Ala
                165                 170                 175

Trp Ser Gly Gly Ser Thr Ala Tyr Ala Asp Ser Val Lys Gly Arg Phe
            180                 185                 190

Thr Ile Ser Arg Asp Asn Ala Lys Asn Thr Val Tyr Leu Gln Met Asn
        195                 200                 205

Ser Leu Lys Ser Glu Asp Thr Ala Val Tyr Tyr Cys Ala Ser Arg Gly
    210                 215                 220

Ile Glu Val Glu Glu Phe Gly Ala Trp Gly Gln Gly Thr Gln Val Thr
225                 230                 235                 240

Val Ser Ser Gly Gly Gly Gly Ser Gly Gly Gly Ser Gly Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Asp Ile Tyr Lys
        275                 280                 285

Ser Phe Asp Met Gly Trp Tyr Arg Gln Ala Pro Gly Lys Gln Arg Asp
    290                 295                 300

Leu Val Ala Val Ile Gly Ser Arg Gly Asn Asn Arg Gly Arg Thr Asn
305                 310                 315                 320

Tyr Ala Asp Ser Val Lys Gly Arg Phe Thr Ile Ser Arg Asp Gly Thr
                325                 330                 335

Gly Asn Thr Val Tyr Leu Leu Met Asn Lys Leu Arg Pro Glu Asp Thr
            340                 345                 350

Ala Ile Tyr Tyr Cys Asn Thr Ala Pro Leu Val Ala Gly Arg Pro Trp
        355                 360                 365

Gly Arg Gly Thr Leu Val Thr Val Ser Ser
370                 375
```

<210> SEQ ID NO 197
<211> LENGTH: 428
<212> TYPE: PRT
<213> ORGANISM: Artificial Sequence
<220> FEATURE:
<223> OTHER INFORMATION: BCMA 269A37353 VHH*269A37948VHH-OKT3

<400> SEQUENCE: 197

```
Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Ser Ala Val Gln Leu
        115                 120                 125

Val Glu Ser Gly Gly Gly Leu Val Gln Ala Gly Asp Ser Leu Arg Leu
    130                 135                 140

Thr Cys Thr Ala Ser Gly Arg Ala Phe Ser Thr Tyr Phe Met Ala Trp
145                 150                 155                 160

Phe Arg Gln Ala Pro Gly Lys Glu Arg Glu Phe Val Ala Gly Ile Ala
                165                 170                 175

Trp Ser Gly Gly Ser Thr Ala Tyr Ala Asp Ser Val Lys Gly Arg Phe
            180                 185                 190

Thr Ile Ser Arg Asp Asn Ala Lys Asn Thr Val Tyr Leu Gln Met Asn
        195                 200                 205

Ser Leu Lys Ser Glu Asp Thr Ala Val Tyr Tyr Cys Ala Ser Arg Gly
    210                 215                 220

Ile Glu Val Glu Glu Phe Gly Ala Trp Gly Gln Gly Thr Gln Val Thr
225                 230                 235                 240

Val Ser Ser Gly Gly Gly Gly Ser Gly Gly Gly Ser Gly Gly
                245                 250                 255

Gly Ser Thr Asp Lys Ser Ser Thr Ala Tyr Met Gln Leu Ser Ser
            260                 265                 270

Leu Thr Ser Glu Asp Ser Ala Val Tyr Tyr Cys Ala Arg Tyr Tyr Asp
        275                 280                 285

Asp His Tyr Cys Leu Asp Tyr Trp Gly Gln Gly Thr Thr Leu Thr Val
    290                 295                 300

Ser Ser Gly Gly Gly Gly Ser Gly Gly Gly Gly Ser Gly Gly Gly Gly
305                 310                 315                 320

Ser Gln Ile Val Leu Thr Gln Ser Pro Ala Ile Met Ser Ala Ser Pro
                325                 330                 335

Gly Glu Lys Val Thr Met Thr Cys Ser Ala Ser Ser Ser Val Ser Tyr
            340                 345                 350

Met Asn Trp Tyr Gln Gln Lys Ser Gly Thr Ser Pro Lys Arg Trp Ile
        355                 360                 365
```

Tyr Asp Thr Ser Lys Leu Ala Ser Gly Val Pro Ala His Phe Arg Gly
              370                 375                 380

Ser Gly Ser Gly Thr Ser Tyr Ser Leu Thr Ile Ser Gly Met Glu Ala
385                 390                 395                 400

Glu Asp Ala Ala Thr Tyr Tyr Cys Gln Gln Trp Ser Ser Asn Pro Phe
              405                 410                 415

Thr Phe Gly Ser Gly Thr Lys Leu Glu Ile Asn Arg
              420                 425

<210> SEQ ID NO 198
<211> LENGTH: 501
<212> TYPE: PRT
<213> ORGANISM: Artificial Sequence
<220> FEATURE:
<223> OTHER INFORMATION: BCMA 269A37353 VHH*269A37948VHH-L2K.07 scFv

<400> SEQUENCE: 198

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
              20                  25                  30

Val Met Gly Trp Phe Arg Gln Ala Pro Gly Lys Glu Arg Glu Ser Val
          35                  40                  45

Ala Val Ile Gly Trp Arg Asp Ile Ser Thr Ser Tyr Ala Asp Ser Val
     50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
              85                  90                  95

Ala Ala Arg Arg Ile Asp Ala Ala Asp Phe Asp Ser Trp Gly Gln Gly
              100                 105                 110

Thr Gln Val Thr Val Ser Ser Gly Gly Gly Gly Ser Ala Val Gln Leu
              115                 120                 125

Val Glu Ser Gly Gly Gly Leu Val Gln Ala Gly Asp Ser Leu Arg Leu
         130                 135                 140

Thr Cys Thr Ala Ser Gly Arg Ala Phe Ser Thr Tyr Phe Met Ala Trp
145                 150                 155                 160

Phe Arg Gln Ala Pro Gly Lys Glu Arg Glu Phe Val Ala Gly Ile Ala
              165                 170                 175

Trp Ser Gly Gly Ser Thr Ala Tyr Ala Asp Ser Val Lys Gly Arg Phe
              180                 185                 190

Thr Ile Ser Arg Asp Asn Ala Lys Asn Thr Val Tyr Leu Gln Met Asn
              195                 200                 205

Ser Leu Lys Ser Glu Asp Thr Ala Val Tyr Tyr Cys Ala Ser Arg Gly
         210                 215                 220

Ile Glu Val Glu Glu Phe Gly Ala Trp Gly Gln Gly Thr Gln Val Thr
225                 230                 235                 240

Val Ser Ser Gly Gly Gly Gly Ser Gly Gly Gly Ser Gly Gly
              245                 250                 255

Gly Ser Asp Ile Lys Leu Gln Gln Ser Gly Ala Glu Leu Ala Arg Pro
              260                 265                 270

Gly Ala Ser Val Lys Met Ser Cys Lys Thr Ser Gly Tyr Thr Phe Thr
              275                 280                 285

Arg Tyr Thr Met His Trp Val Lys Gln Arg Pro Gly Gln Gly Leu Glu
              290                 295                 300

Trp Ile Gly Tyr Ile Asn Pro Ser Arg Gly Tyr Thr Asn Tyr Asn Gln
305                 310                 315                 320

Lys Phe Lys Asp Lys Ala Thr Leu Thr Thr Asp Lys Ser Ser Ser Thr
                325                 330                 335

Ala Tyr Met Gln Leu Ser Ser Leu Thr Ser Glu Asp Ser Ala Val Tyr
            340                 345                 350

Tyr Cys Ala Arg Tyr Tyr Asp Asp His Tyr Cys Leu Asp Tyr Trp Gly
        355                 360                 365

Gln Gly Thr Thr Leu Thr Val Ser Ser Val Glu Gly Ser Gly Gly
    370                 375                 380

Ser Gly Gly Ser Gly Gly Ser Gly Gly Val Asp Asp Ile Gln Leu Thr
385                 390                 395                 400

Gln Ser Pro Ala Ile Met Ser Ala Ser Pro Gly Glu Lys Val Thr Met
                405                 410                 415

Thr Cys Arg Ala Ser Ser Ser Val Ser Tyr Met Asn Trp Tyr Gln Gln
            420                 425                 430

Lys Ser Gly Thr Ser Pro Lys Arg Trp Ile Tyr Asp Thr Ser Lys Val
        435                 440                 445

Ala Ser Gly Val Pro Tyr Arg Phe Ser Gly Ser Gly Ser Gly Thr Ser
    450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Leu Thr Phe Gly Ala Gly Thr
            485                 490                 495

Lys Leu Glu Leu Lys
            500

<210> SEQ ID NO 199
<211> LENGTH: 430
<212> TYPE: PRT
<213> ORGANISM: Artificial Sequence
<220> FEATURE:
<223> OTHER INFORMATION: BCMA 269A37353 VHH*269A37948VHH-UCHT1 scFv

<400> SEQUENCE: 199

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Ser Ala Val Gln Leu
        115                 120                 125

Val Glu Ser Gly Gly Gly Leu Val Gln Ala Gly Asp Ser Leu Arg Leu
    130                 135                 140

Thr Cys Thr Ala Ser Gly Arg Ala Phe Ser Thr Tyr Phe Met Ala Trp
145                 150                 155                 160

```
Phe Arg Gln Ala Pro Gly Lys Glu Arg Glu Phe Val Ala Gly Ile Ala
                165                 170                 175

Trp Ser Gly Gly Ser Thr Ala Tyr Ala Asp Ser Val Lys Gly Arg Phe
            180                 185                 190

Thr Ile Ser Arg Asp Asn Ala Lys Asn Thr Val Tyr Leu Gln Met Asn
        195                 200                 205

Ser Leu Lys Ser Glu Asp Thr Ala Val Tyr Tyr Cys Ala Ser Arg Gly
    210                 215                 220

Ile Glu Val Glu Glu Phe Gly Ala Trp Gly Gln Gly Thr Gln Val Thr
225                 230                 235                 240

Val Ser Ser Gly Gly Gly Gly Ser Gly Gly Gly Gly Ser Gly Gly Gly
                245                 250                 255

Gly Ser Asp Lys Ser Ser Thr Ala Tyr Met Glu Leu Leu Ser Leu
            260                 265                 270

Thr Ser Glu Asp Ser Ala Val Tyr Tyr Cys Ala Arg Ser Gly Tyr Tyr
        275                 280                 285

Gly Asp Ser Asp Trp Tyr Phe Asp Val Trp Gly Gln Gly Thr Thr Leu
    290                 295                 300

Thr Val Phe Ser Gly Gly Gly Ser Gly Gly Gly Gly Ser Gly Gly
305                 310                 315                 320

Gly Gly Ser Asp Ile Gln Met Thr Gln Thr Thr Ser Ser Leu Ser Ala
                325                 330                 335

Ser Leu Gly Asp Arg Val Thr Ile Ser Cys Arg Ala Ser Gln Asp Ile
            340                 345                 350

Arg Asn Tyr Leu Asn Trp Tyr Gln Gln Lys Pro Asp Gly Thr Val Lys
        355                 360                 365

Leu Leu Ile Tyr Tyr Thr Ser Arg Leu His Ser Gly Val Pro Ser Lys
    370                 375                 380

Phe Ser Gly Ser Gly Ser Gly Thr Asp Tyr Ser Leu Thr Ile Ser Asn
385                 390                 395                 400

Leu Glu Gln Glu Asp Ile Ala Thr Tyr Phe Cys Gln Gln Gly Asn Thr
                405                 410                 415

Leu Pro Trp Thr Phe Ala Gly Gly Thr Lys Leu Glu Ile Lys
            420                 425                 430

<210> SEQ ID NO 200
<211> LENGTH: 382
<212> TYPE: PRT
<213> ORGANISM: Artificial Sequence
<220> FEATURE:
<223> OTHER INFORMATION: BCMA 269A37948VHH*269A37353 VHH-CD3 VHH
      (117G03)

<400> SEQUENCE: 200

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
```

```
                 85                  90                  95
Ala Ala Arg Arg Ile Asp Ala Ala Asp Phe Asp Ser Trp Gly Gln Gly
            100                 105                 110

Thr Gln Val Thr Val Ser Ser Gly Gly Gly Ser Ala Val Gln Leu
            115                 120                 125

Val Glu Ser Gly Gly Gly Leu Val Gln Ala Gly Asp Ser Leu Arg Leu
130                 135                 140

Thr Cys Thr Ala Ser Gly Arg Ala Phe Ser Thr Tyr Phe Met Ala Trp
145                 150                 155                 160

Phe Arg Gln Ala Pro Gly Lys Glu Arg Glu Phe Val Ala Gly Ile Ala
                165                 170                 175

Trp Ser Gly Gly Ser Thr Ala Tyr Ala Asp Ser Val Lys Gly Arg Phe
            180                 185                 190

Thr Ile Ser Arg Asp Asn Ala Lys Asn Thr Val Tyr Leu Gln Met Asn
            195                 200                 205

Ser Leu Lys Ser Glu Asp Thr Ala Val Tyr Tyr Cys Ala Ser Arg Gly
210                 215                 220

Ile Glu Val Glu Glu Phe Gly Ala Trp Gly Gln Gly Thr Gln Val Thr
225                 230                 235                 240

Val Ser Ser Gly Gly Gly Gly Ser Gly Gly Gly Ser Gly Gly Gly
                245                 250                 255

Gly Ser Glu Val Gln Leu Val Glu Ser Gly Gly Pro Val Gln Ala
            260                 265                 270

Gly Gly Ser Leu Arg Leu Ser Cys Ala Ala Ser Gly Arg Thr Tyr Arg
            275                 280                 285

Gly Tyr Ser Met Gly Trp Phe Arg Gln Ala Pro Gly Lys Glu Arg Glu
            290                 295                 300

Phe Val Ala Ala Ile Val Trp Ser Gly Gly Asn Thr Tyr Tyr Glu Asp
305                 310                 315                 320

Ser Val Lys Gly Arg Phe Thr Ile Ser Arg Asp Asn Ala Lys Asn Thr
                325                 330                 335

Met Tyr Leu Gln Met Thr Ser Leu Lys Pro Glu Asp Ser Ala Thr Tyr
            340                 345                 350

Tyr Cys Ala Ala Lys Ile Arg Pro Tyr Ile Phe Lys Ile Ala Gly Gln
            355                 360                 365

Tyr Asp Tyr Trp Gly Gln Gly Thr Gln Val Thr Val Ser Ser
            370                 375                 380

<210> SEQ ID NO 201
<211> LENGTH: 428
<212> TYPE: PRT
<213> ORGANISM: Artificial Sequence
<220> FEATURE:
<223> OTHER INFORMATION: BCMA 269A37948VHH*269A37353 VHH-OKT3

<400> SEQUENCE: 201

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
```

65                  70                  75                  80
Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
               100                 105                 110

Thr Gln Val Thr Val Ser Ser Gly Gly Gly Ser Ala Val Gln Leu
               115                 120                 125

Val Glu Ser Gly Gly Gly Leu Val Gln Ala Gly Asp Ser Leu Arg Leu
               130                 135                 140

Thr Cys Thr Ala Ser Gly Arg Ala Phe Ser Thr Tyr Phe Met Ala Trp
145                150                 155                 160

Phe Arg Gln Ala Pro Gly Lys Glu Arg Glu Phe Val Ala Gly Ile Ala
               165                 170                 175

Trp Ser Gly Gly Ser Thr Ala Tyr Ala Asp Ser Val Lys Gly Arg Phe
               180                 185                 190

Thr Ile Ser Arg Asp Asn Ala Lys Asn Thr Val Tyr Leu Gln Met Asn
               195                 200                 205

Ser Leu Lys Ser Glu Asp Thr Ala Val Tyr Tyr Cys Ala Ser Arg Gly
210                215                 220

Ile Glu Val Glu Glu Phe Gly Ala Trp Gly Gln Gly Thr Gln Val Thr
225                230                 235                 240

Val Ser Ser Gly Gly Gly Gly Ser Gly Gly Gly Ser Gly Gly Gly
               245                 250                 255

Gly Ser Thr Asp Lys Ser Ser Ser Thr Ala Tyr Met Gln Leu Ser Ser
               260                 265                 270

Leu Thr Ser Glu Asp Ser Ala Val Tyr Tyr Cys Ala Arg Tyr Tyr Asp
               275                 280                 285

Asp His Tyr Cys Leu Asp Tyr Trp Gly Gln Gly Thr Thr Leu Thr Val
               290                 295                 300

Ser Ser Gly Gly Gly Gly Ser Gly Gly Gly Gly Ser Gly Gly Gly Gly
305                310                 315                 320

Ser Gln Ile Val Leu Thr Gln Ser Pro Ala Ile Met Ser Ala Ser Pro
               325                 330                 335

Gly Glu Lys Val Thr Met Thr Cys Ser Ala Ser Ser Val Ser Tyr
               340                 345                 350

Met Asn Trp Tyr Gln Gln Lys Ser Gly Thr Ser Pro Lys Arg Trp Ile
               355                 360                 365

Tyr Asp Thr Ser Lys Leu Ala Ser Gly Val Pro Ala His Phe Arg Gly
               370                 375                 380

Ser Gly Ser Gly Thr Ser Tyr Ser Leu Thr Ile Ser Gly Met Glu Ala
385                390                 395                 400

Glu Asp Ala Ala Thr Tyr Tyr Cys Gln Gln Trp Ser Ser Asn Pro Phe
               405                 410                 415

Thr Phe Gly Ser Gly Thr Lys Leu Glu Ile Asn Arg
               420                 425

<210> SEQ ID NO 202
<211> LENGTH: 501
<212> TYPE: PRT
<213> ORGANISM: Artificial Sequence
<220> FEATURE:
<223> OTHER INFORMATION: BCMA 269A37948VHH*269A37353 VHH-L2K.07 scFv

<400> SEQUENCE: 202

Gln Val Lys Leu Glu Glu Ser Gly Gly Gly Leu Val Gln Ala Gly Arg

-continued

```
1               5                   10                  15
Ser Leu Arg Leu Ser Cys Ala Ala Ser Glu His Thr Phe Ser Ser His
                20                  25                  30
Val Met Gly Trp Phe Arg Gln Ala Pro Gly Lys Glu Arg Glu Ser Val
                35                  40                  45
Ala Val Ile Gly Trp Arg Asp Ile Ser Thr Ser Tyr Ala Asp Ser Val
                50                  55                  60
Lys Gly Arg Phe Thr Ile Ser Arg Asp Asn Ala Lys Lys Thr Leu Tyr
65                  70                  75                  80
Leu Gln Met Asn Ser Leu Lys Pro Glu Asp Thr Ala Val Tyr Tyr Cys
                85                  90                  95
Ala Ala Arg Arg Ile Asp Ala Ala Asp Phe Asp Ser Trp Gly Gln Gly
                100                 105                 110
Thr Gln Val Thr Val Ser Ser Gly Gly Gly Ser Ala Val Gln Leu
                115                 120                 125
Val Glu Ser Gly Gly Gly Leu Val Gln Ala Gly Asp Ser Leu Arg Leu
                130                 135                 140
Thr Cys Thr Ala Ser Gly Arg Ala Phe Ser Thr Tyr Phe Met Ala Trp
145                 150                 155                 160
Phe Arg Gln Ala Pro Gly Lys Glu Arg Glu Phe Val Ala Gly Ile Ala
                165                 170                 175
Trp Ser Gly Gly Ser Thr Ala Tyr Ala Asp Ser Val Lys Gly Arg Phe
                180                 185                 190
Thr Ile Ser Arg Asp Asn Ala Lys Asn Thr Val Tyr Leu Gln Met Asn
                195                 200                 205
Ser Leu Lys Ser Glu Asp Thr Ala Val Tyr Tyr Cys Ala Ser Arg Gly
                210                 215                 220
Ile Glu Val Glu Glu Phe Gly Ala Trp Gly Gln Gly Thr Gln Val Thr
225                 230                 235                 240
Val Ser Ser Gly Gly Gly Gly Ser Gly Gly Gly Ser Gly Gly Gly
                245                 250                 255
Gly Ser Asp Ile Lys Leu Gln Gln Ser Gly Ala Glu Leu Ala Arg Pro
                260                 265                 270
Gly Ala Ser Val Lys Met Ser Cys Lys Thr Ser Gly Tyr Thr Phe Thr
                275                 280                 285
Arg Tyr Thr Met His Trp Val Lys Gln Arg Pro Gly Gln Gly Leu Glu
                290                 295                 300
Trp Ile Gly Tyr Ile Asn Pro Ser Arg Gly Tyr Thr Asn Tyr Asn Gln
305                 310                 315                 320
Lys Phe Lys Asp Lys Ala Thr Leu Thr Thr Asp Lys Ser Ser Ser Thr
                325                 330                 335
Ala Tyr Met Gln Leu Ser Ser Leu Thr Ser Glu Asp Ser Ala Val Tyr
                340                 345                 350
Tyr Cys Ala Arg Tyr Tyr Asp Asp His Tyr Cys Leu Asp Tyr Trp Gly
                355                 360                 365
Gln Gly Thr Thr Leu Thr Val Ser Ser Val Glu Gly Gly Ser Gly Gly
                370                 375                 380
Ser Gly Gly Ser Gly Gly Ser Gly Gly Val Asp Asp Ile Gln Leu Thr
385                 390                 395                 400
Gln Ser Pro Ala Ile Met Ser Ala Ser Pro Gly Glu Lys Val Thr Met
                405                 410                 415
Thr Cys Arg Ala Ser Ser Ser Val Ser Tyr Met Asn Trp Tyr Gln Gln
                420                 425                 430
```

```
Lys Ser Gly Thr Ser Pro Lys Arg Trp Ile Tyr Asp Thr Ser Lys Val
            435                 440                 445

Ala Ser Gly Val Pro Tyr Arg Phe Ser Gly Ser Gly Ser Gly Thr Ser
    450                 455                 460

Tyr Ser Leu Thr Ile Ser Ser Met Glu Ala Glu Asp Ala Ala Thr Tyr
465                 470                 475                 480

Tyr Cys Gln Gln Trp Ser Ser Asn Pro Leu Thr Phe Gly Ala Gly Thr
                485                 490                 495

Lys Leu Glu Leu Lys
            500

<210> SEQ ID NO 203
<211> LENGTH: 430
<212> TYPE: PRT
<213> ORGANISM: Artificial Sequence
<220> FEATURE:
<223> OTHER INFORMATION: BCMA 269A37948VHH*269A37353 VHH-UCHT1 scFv

<400> SEQUENCE: 203

Gln Val Lys Leu Glu Glu Ser Gly Gly Gly Leu Val Gln Ala Gly Arg
1               5                   10                  15

Ser Leu Arg Leu Ser Cys Ala Ala Ser Glu His Thr Phe Ser Ser His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Trp Gly Gln Gly
            100                 105                 110

Thr Gln Val Thr Val Ser Ser Gly Gly Gly Gly Ser Ala Val Gln Leu
        115                 120                 125

Val Glu Ser Gly Gly Gly Leu Val Gln Ala Gly Asp Ser Leu Arg Leu
    130                 135                 140

Thr Cys Thr Ala Ser Gly Arg Ala Phe Ser Thr Tyr Phe Met Ala Trp
145                 150                 155                 160

Phe Arg Gln Ala Pro Gly Lys Glu Arg Glu Phe Val Ala Gly Ile Ala
                165                 170                 175

Trp Ser Gly Gly Ser Thr Ala Tyr Ala Asp Ser Val Lys Gly Arg Phe
            180                 185                 190

Thr Ile Ser Arg Asp Asn Ala Lys Asn Thr Val Tyr Leu Gln Met Asn
        195                 200                 205

Ser Leu Lys Ser Glu Asp Thr Ala Val Tyr Tyr Cys Ala Ser Arg Gly
    210                 215                 220

Ile Glu Val Glu Glu Phe Gly Ala Trp Gly Gln Gly Thr Gln Val Thr
225                 230                 235                 240

Val Ser Ser Gly Gly Gly Gly Ser Gly Gly Gly Gly Ser Gly Gly Gly
                245                 250                 255

Gly Ser Asp Lys Ser Ser Thr Ala Tyr Met Glu Leu Leu Ser Leu
            260                 265                 270

Thr Ser Glu Asp Ser Ala Val Tyr Tyr Cys Ala Arg Ser Gly Tyr Tyr
    275                 280                 285
```

Gly Asp Ser Asp Trp Tyr Phe Asp Val Trp Gly Gln Gly Thr Thr Leu
            290                 295                 300

Thr Val Phe Ser Gly Gly Gly Ser Gly Gly Gly Ser Gly Gly
305                 310                 315                 320

Gly Gly Ser Asp Ile Gln Met Thr Gln Thr Thr Ser Ser Leu Ser Ala
                325                 330                 335

Ser Leu Gly Asp Arg Val Thr Ile Ser Cys Arg Ala Ser Gln Asp Ile
                340                 345                 350

Arg Asn Tyr Leu Asn Trp Tyr Gln Gln Lys Pro Asp Gly Thr Val Lys
            355                 360                 365

Leu Leu Ile Tyr Tyr Thr Ser Arg Leu His Ser Gly Val Pro Ser Lys
        370                 375                 380

Phe Ser Gly Ser Gly Ser Gly Thr Asp Tyr Ser Leu Thr Ile Ser Asn
385                 390                 395                 400

Leu Glu Gln Glu Asp Ile Ala Thr Tyr Phe Cys Gln Gln Gly Asn Thr
                405                 410                 415

Leu Pro Trp Thr Phe Ala Gly Gly Thr Lys Leu Glu Ile Lys
            420                 425                 430

<210> SEQ ID NO 204
<211> LENGTH: 377
<212> TYPE: PRT
<213> ORGANISM: Artificial Sequence
<220> FEATURE:
<223> OTHER INFORMATION: J22.9-xi-CD3 VHH (60E11)

<400> SEQUENCE: 204

Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Tyr Ala Pro Ser Leu
50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Gly Asp Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Met Thr Gln Ser Gln Arg
    130                 135                 140

Phe Met Thr Thr Ser Val Gly Asp Arg Val Ser Val Thr Cys Lys Ala
145                 150                 155                 160

Ser Gln Ser Val Asp Ser Asn Val Ala Trp Tyr Gln Gln Lys Pro Arg
                165                 170                 175

Gln Ser Pro Lys Ala Leu Ile Phe Ser Ala Ser Leu Arg Phe Ser Gly
            180                 185                 190

Val Pro Ala Arg Phe Thr Gly Ser Gly Ser Gly Thr Asp Phe Thr Leu
        195                 200                 205

Thr Ile Ser Asn Leu Gln Ser Glu Asp Leu Ala Glu Tyr Phe Cys Gln
    210                 215                 220

```
Gln Tyr Asn Asn Tyr Pro Leu Thr Phe Gly Ala Gly Thr Lys Leu Glu
225                 230                 235                 240

Leu Lys Gly Gly Gly Gly Ser Gly Gly Gly Gly Ser Gly Gly Gly Gly
            245                 250                 255

Ser Glu Val Gln Leu Val Glu Ser Gly Gly Gly Leu Val Gln Pro Gly
        260                 265                 270

Gly Ser Leu Arg Leu Ser Cys Ala Ala Ser Gly Asp Ile Tyr Lys Ser
        275                 280                 285

Phe Asp Met Gly Trp Tyr Arg Gln Ala Pro Gly Lys Gln Arg Asp Leu
        290                 295                 300

Val Ala Val Ile Gly Ser Arg Gly Asn Asn Arg Gly Arg Thr Asn Tyr
305                 310                 315                 320

Ala Asp Ser Val Lys Gly Arg Phe Thr Ile Ser Arg Asp Gly Thr Gly
                325                 330                 335

Asn Thr Val Tyr Leu Leu Met Asn Lys Leu Arg Pro Glu Asp Thr Ala
            340                 345                 350

Ile Tyr Tyr Cys Asn Thr Ala Pro Leu Val Ala Gly Arg Pro Trp Gly
        355                 360                 365

Arg Gly Thr Leu Val Thr Val Ser Ser
    370                 375

<210> SEQ ID NO 205
<211> LENGTH: 381
<212> TYPE: PRT
<213> ORGANISM: Artificial Sequence
<220> FEATURE:
<223> OTHER INFORMATION: J22.9-xi-CD3 VHH (117G03)

<400> SEQUENCE: 205

Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Gly Asp Ala Met Asp Tyr Trp Gly Gln
            100                 105                 110

Gly Thr Ser Val Thr Val Ser Ser Gly Gly Gly Gly Ser Gly Gly Gly
        115                 120                 125

Gly Ser Gly Gly Gly Gly Ser Asp Ile Val Met Thr Gln Ser Gln Arg
    130                 135                 140

Phe Met Thr Thr Ser Val Gly Asp Arg Val Ser Val Thr Cys Lys Ala
145                 150                 155                 160

Ser Gln Ser Val Asp Ser Asn Val Ala Trp Tyr Gln Gln Lys Pro Arg
                165                 170                 175

Gln Ser Pro Lys Ala Leu Ile Phe Ser Ala Ser Leu Arg Phe Ser Gly
            180                 185                 190

Val Pro Ala Arg Phe Thr Gly Ser Gly Ser Gly Thr Asp Phe Thr Leu
        195                 200                 205
```

Thr Ile Ser Asn Leu Gln Ser Glu Asp Leu Ala Glu Tyr Phe Cys Gln
    210                 215                 220

Gln Tyr Asn Asn Tyr Pro Leu Thr Phe Gly Ala Gly Thr Lys Leu Glu
225                 230                 235                 240

Leu Lys Gly Gly Gly Gly Ser Gly Gly Gly Ser Gly Gly Gly Gly
                245                 250                 255

Ser Glu Val Gln Leu Val Glu Ser Gly Gly Pro Val Gln Ala Gly
                260                 265                 270

Gly Ser Leu Arg Leu Ser Cys Ala Ala Ser Gly Arg Thr Tyr Arg Gly
                275                 280                 285

Tyr Ser Met Gly Trp Phe Arg Gln Ala Pro Gly Lys Glu Arg Glu Phe
    290                 295                 300

Val Ala Ala Ile Val Trp Ser Gly Gly Asn Thr Tyr Tyr Glu Asp Ser
305                 310                 315                 320

Val Lys Gly Arg Phe Thr Ile Ser Arg Asp Asn Ala Lys Asn Thr Met
                325                 330                 335

Tyr Leu Gln Met Thr Ser Leu Lys Pro Glu Asp Ser Ala Thr Tyr Tyr
                340                 345                 350

Cys Ala Ala Lys Ile Arg Pro Tyr Ile Phe Lys Ile Ala Gly Gln Tyr
                355                 360                 365

Asp Tyr Trp Gly Gln Gly Thr Gln Val Thr Val Ser Ser
    370                 375                 380

<210> SEQ ID NO 206
<211> LENGTH: 378
<212> TYPE: PRT
<213> ORGANISM: Artificial Sequence
<220> FEATURE:
<223> OTHER INFORMATION: BCMA*CD38VHH-CD3 VHH (60E11)

<400> SEQUENCE: 206

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
    50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
                100                 105                 110

Thr Val Ser Ser Gly Gly Gly Ser Gln Val Gln Leu Val Glu Ser
            115                 120                 125

Gly Gly Gly Leu Val Gln Pro Gly Gly Ser Leu Arg Leu Ser Cys Glu
        130                 135                 140

Ala Ser Gly Phe Thr Leu Asp Tyr Tyr Ala Ile Gly Trp Phe Arg Gln
145                 150                 155                 160

Ala Pro Gly Lys Glu Arg Glu Gly Val Ile Cys Ile Ser Arg Ser Asp
                165                 170                 175

Gly Ser Thr Tyr Tyr Ala Asp Ser Val Lys Gly Arg Phe Thr Ile Ser
            180                 185                 190

```
Arg Asp Asn Ala Lys Lys Thr Val Tyr Leu Gln Met Ile Ser Leu Lys
        195                 200                 205

Pro Glu Asp Thr Ala Ala Tyr Tyr Cys Ala Ala Gly Ala Asp Cys Ser
210                 215                 220

Gly Tyr Leu Arg Asp Tyr Glu Phe Arg Gly Gln Gly Thr Gln Val Thr
225                 230                 235                 240

Val Ser Ser Gly Gly Gly Gly Ser Gly Gly Gly Ser Gly Gly Gly
            245                 250                 255

Gly Ser Glu Val Gln Leu Val Glu Ser Gly Gly Leu Val Gln Pro
        260                 265                 270

Gly Gly Ser Leu Arg Leu Ser Cys Ala Ala Ser Gly Asp Ile Tyr Lys
            275                 280                 285

Ser Phe Asp Met Gly Trp Tyr Arg Gln Ala Pro Gly Lys Gln Arg Asp
        290                 295                 300

Leu Val Ala Val Ile Gly Ser Arg Gly Asn Asn Arg Gly Arg Thr Asn
305                 310                 315                 320

Tyr Ala Asp Ser Val Lys Gly Arg Phe Thr Ile Ser Arg Asp Gly Thr
                325                 330                 335

Gly Asn Thr Val Tyr Leu Leu Met Asn Lys Leu Arg Pro Glu Asp Thr
            340                 345                 350

Ala Ile Tyr Tyr Cys Asn Thr Ala Pro Leu Val Ala Gly Arg Pro Trp
            355                 360                 365

Gly Arg Gly Thr Leu Val Thr Val Ser Ser
370                 375

<210> SEQ ID NO 207
<211> LENGTH: 382
<212> TYPE: PRT
<213> ORGANISM: Artificial Sequence
<220> FEATURE:
<223> OTHER INFORMATION: BCMA*CD38VHH-CD3 VHH (117G03)

<400> SEQUENCE: 207

Glu Val Gln Leu Val Glu Ser Gly Gly Gly Leu Val Gln Ala Gly Gly
1               5                   10                  15

Ser Leu Arg Leu Ser Cys Ile Ala Thr Gly Lys Val Phe Ser Ile Tyr
            20                  25                  30

Asp Met Gly Trp Tyr Arg Gln Ala Pro Gly Lys Gln Arg Glu Leu Val
        35                  40                  45

Ala Glu Ile Thr Ser Ser Gly Thr Thr His Tyr Asp Asp Phe Val Ser
50                  55                  60

Gly Arg Phe Thr Ile Ser Arg Asp Asn Ala Lys Asn Thr Val Tyr Leu
65                  70                  75                  80

Gln Met Asn Thr Leu Lys Ala Glu Asp Thr Ala Val Tyr Tyr Cys Arg
                85                  90                  95

Ala Asn His Val Phe Gly Gly Ser Tyr Trp Gly Gln Gly Thr Gln Val
            100                 105                 110

Thr Val Ser Ser Gly Gly Gly Gly Ser Gln Val Gln Leu Val Glu Ser
        115                 120                 125

Gly Gly Gly Leu Val Gln Pro Gly Gly Ser Leu Arg Leu Ser Cys Glu
130                 135                 140

Ala Ser Gly Phe Thr Leu Asp Tyr Tyr Ala Ile Gly Trp Phe Arg Gln
145                 150                 155                 160

Ala Pro Gly Lys Glu Arg Glu Gly Val Ile Cys Ile Ser Arg Ser Asp
                165                 170                 175
```

Gly Ser Thr Tyr Tyr Ala Asp Ser Val Lys Gly Arg Phe Thr Ile Ser
            180                 185                 190

Arg Asp Asn Ala Lys Lys Thr Val Tyr Leu Gln Met Ile Ser Leu Lys
            195                 200                 205

Pro Glu Asp Thr Ala Ala Tyr Tyr Cys Ala Ala Gly Ala Asp Cys Ser
        210                 215                 220

Gly Tyr Leu Arg Asp Tyr Glu Phe Arg Gly Gln Gly Thr Gln Val Thr
225                 230                 235                 240

Val Ser Ser Gly Gly Gly Gly Ser Gly Gly Gly Ser Gly Gly Gly Gly
            245                 250                 255

Gly Ser Glu Val Gln Leu Val Glu Ser Gly Gly Pro Val Gln Ala
        260                 265                 270

Gly Gly Ser Leu Arg Leu Ser Cys Ala Ala Ser Gly Arg Thr Tyr Arg
            275                 280                 285

Gly Tyr Ser Met Gly Trp Phe Arg Gln Ala Pro Gly Lys Glu Arg Glu
        290                 295                 300

Phe Val Ala Ala Ile Val Trp Ser Gly Gly Asn Thr Tyr Tyr Glu Asp
305                 310                 315                 320

Ser Val Lys Gly Arg Phe Thr Ile Ser Arg Asp Asn Ala Lys Asn Thr
            325                 330                 335

Met Tyr Leu Gln Met Thr Ser Leu Lys Pro Glu Asp Ser Ala Thr Tyr
            340                 345                 350

Tyr Cys Ala Ala Lys Ile Arg Pro Tyr Ile Phe Lys Ile Ala Gly Gln
        355                 360                 365

Tyr Asp Tyr Trp Gly Gln Gly Thr Gln Val Thr Val Ser Ser
        370                 375                 380

<210> SEQ ID NO 208
<211> LENGTH: 6
<212> TYPE: PRT
<213> ORGANISM: Artificial Sequence
<220> FEATURE:
<223> OTHER INFORMATION: His tag

<400> SEQUENCE: 208

His His His His His His
1               5

<210> SEQ ID NO 209
<211> LENGTH: 5
<212> TYPE: PRT
<213> ORGANISM: Artificial Sequence
<220> FEATURE:
<223> OTHER INFORMATION: 269B005 VHH CDR1

<400> SEQUENCE: 209

Ile Asn Val Met Ala
1               5

<210> SEQ ID NO 210
<211> LENGTH: 5
<212> TYPE: PRT
<213> ORGANISM: Artificial Sequence
<220> FEATURE:
<223> OTHER INFORMATION: 269B023 VHH CDR1

<400> SEQUENCE: 210

Thr Phe Thr Met Gly
1               5

```
<210> SEQ ID NO 211
<211> LENGTH: 5
<212> TYPE: PRT
<213> ORGANISM: Artificial Sequence
<220> FEATURE:
<223> OTHER INFORMATION: 269B024 VHH CDR1

<400> SEQUENCE: 211

Ile Asn Ala Met Gly
1               5

<210> SEQ ID NO 212
<211> LENGTH: 5
<212> TYPE: PRT
<213> ORGANISM: Artificial Sequence
<220> FEATURE:
<223> OTHER INFORMATION: 269B028 VHH CDR1

<400> SEQUENCE: 212

Lys Asn Thr Val Ala
1               5

<210> SEQ ID NO 213
<211> LENGTH: 5
<212> TYPE: PRT
<213> ORGANISM: Artificial Sequence
<220> FEATURE:
<223> OTHER INFORMATION: 269B030 VHH CDR1

<400> SEQUENCE: 213

Ser Ile Val Met Gly
1               5

<210> SEQ ID NO 214
<211> LENGTH: 5
<212> TYPE: PRT
<213> ORGANISM: Artificial Sequence
<220> FEATURE:
<223> OTHER INFORMATION: 269B038 VHH CDR1

<400> SEQUENCE: 214

Thr Phe Thr Met Gly
1               5

<210> SEQ ID NO 215
<211> LENGTH: 5
<212> TYPE: PRT
<213> ORGANISM: Artificial Sequence
<220> FEATURE:
<223> OTHER INFORMATION: 269B054 VHH CDR1

<400> SEQUENCE: 215

Lys Asn Thr Val Ala
1               5

<210> SEQ ID NO 216
<211> LENGTH: 5
<212> TYPE: PRT
<213> ORGANISM: Artificial Sequence
<220> FEATURE:
<223> OTHER INFORMATION: 269B059 VHH CDR1

<400> SEQUENCE: 216

Ile Asn Thr Met Asp
1               5
```

```
<210> SEQ ID NO 217
<211> LENGTH: 5
<212> TYPE: PRT
<213> ORGANISM: Artificial Sequence
<220> FEATURE:
<223> OTHER INFORMATION: 269B060 VHH CDR1

<400> SEQUENCE: 217

Lys Asn Thr Val Ala
1               5

<210> SEQ ID NO 218
<211> LENGTH: 5
<212> TYPE: PRT
<213> ORGANISM: Artificial Sequence
<220> FEATURE:
<223> OTHER INFORMATION: 269B069 VHH CDR1

<400> SEQUENCE: 218

Asp Tyr Trp Met His
1               5

<210> SEQ ID NO 219
<211> LENGTH: 5
<212> TYPE: PRT
<213> ORGANISM: Artificial Sequence
<220> FEATURE:
<223> OTHER INFORMATION: 269B074 VHH CDR1

<400> SEQUENCE: 219

Ser Asn Thr Met Ala
1               5

<210> SEQ ID NO 220
<211> LENGTH: 5
<212> TYPE: PRT
<213> ORGANISM: Artificial Sequence
<220> FEATURE:
<223> OTHER INFORMATION: 269B076 VHH CDR1

<400> SEQUENCE: 220

Thr Phe Thr Met Gly
1               5

<210> SEQ ID NO 221
<211> LENGTH: 6
<212> TYPE: PRT
<213> ORGANISM: Artificial Sequence
<220> FEATURE:
<223> OTHER INFORMATION: 269B079 VHH CDR1

<400> SEQUENCE: 221

Val Ala Ala Ile Ser Leu
1               5

<210> SEQ ID NO 222
<211> LENGTH: 5
<212> TYPE: PRT
<213> ORGANISM: Artificial Sequence
<220> FEATURE:
<223> OTHER INFORMATION: 269B083 VHH CDR1

<400> SEQUENCE: 222

Lys Asn Thr Val Ala
1               5

<210> SEQ ID NO 223
```

```
<211> LENGTH: 5
<212> TYPE: PRT
<213> ORGANISM: Artificial Sequence
<220> FEATURE:
<223> OTHER INFORMATION: 269B085 VHH CDR1

<400> SEQUENCE: 223

Thr Phe Thr Met Gly
1               5

<210> SEQ ID NO 224
<211> LENGTH: 5
<212> TYPE: PRT
<213> ORGANISM: Artificial Sequence
<220> FEATURE:
<223> OTHER INFORMATION: 269B093 VHH CDR1

<400> SEQUENCE: 224

Thr Phe Thr Met Gly
1               5

<210> SEQ ID NO 225
<211> LENGTH: 5
<212> TYPE: PRT
<213> ORGANISM: Artificial Sequence
<220> FEATURE:
<223> OTHER INFORMATION: 269B094 VHH CDR1

<400> SEQUENCE: 225

Ser Ile Val Met Gly
1               5

<210> SEQ ID NO 226
<211> LENGTH: 5
<212> TYPE: PRT
<213> ORGANISM: Artificial Sequence
<220> FEATURE:
<223> OTHER INFORMATION: 269B104 VHH CDR1

<400> SEQUENCE: 226

Thr Phe Thr Met Gly
1               5

<210> SEQ ID NO 227
<211> LENGTH: 5
<212> TYPE: PRT
<213> ORGANISM: Artificial Sequence
<220> FEATURE:
<223> OTHER INFORMATION: 269B109 VHH CDR1

<400> SEQUENCE: 227

Thr Phe Thr Met Gly
1               5

<210> SEQ ID NO 228
<211> LENGTH: 5
<212> TYPE: PRT
<213> ORGANISM: Artificial Sequence
<220> FEATURE:
<223> OTHER INFORMATION: 269B110 VHH CDR1

<400> SEQUENCE: 228

Thr Phe Thr Met Gly
1               5

<210> SEQ ID NO 229
<211> LENGTH: 5
```

```
<212> TYPE: PRT
<213> ORGANISM: Artificial Sequence
<220> FEATURE:
<223> OTHER INFORMATION: 269B113 VHH CDR1

<400> SEQUENCE: 229

Thr Phe Thr Met Gly
1               5

<210> SEQ ID NO 230
<211> LENGTH: 5
<212> TYPE: PRT
<213> ORGANISM: Artificial Sequence
<220> FEATURE:
<223> OTHER INFORMATION: 269B126 VHH CDR1

<400> SEQUENCE: 230

Thr Phe Thr Met Gly
1               5

<210> SEQ ID NO 231
<211> LENGTH: 5
<212> TYPE: PRT
<213> ORGANISM: Artificial Sequence
<220> FEATURE:
<223> OTHER INFORMATION: 269B129 VHH CDR1

<400> SEQUENCE: 231

Asn His Val Met Gly
1               5

<210> SEQ ID NO 232
<211> LENGTH: 5
<212> TYPE: PRT
<213> ORGANISM: Artificial Sequence
<220> FEATURE:
<223> OTHER INFORMATION: 269B131 VHH CDR1

<400> SEQUENCE: 232

Asn Tyr Ile Leu Ala
1               5

<210> SEQ ID NO 233
<211> LENGTH: 5
<212> TYPE: PRT
<213> ORGANISM: Artificial Sequence
<220> FEATURE:
<223> OTHER INFORMATION: 269B135 VHH CDR1

<400> SEQUENCE: 233

Thr Phe Thr Met Gly
1               5

<210> SEQ ID NO 234
<211> LENGTH: 5
<212> TYPE: PRT
<213> ORGANISM: Artificial Sequence
<220> FEATURE:
<223> OTHER INFORMATION: 269B136 VHH CDR1

<400> SEQUENCE: 234

Thr Phe Thr Met Gly
1               5

<210> SEQ ID NO 235
<211> LENGTH: 6
<212> TYPE: PRT
```

```
<213> ORGANISM: Artificial Sequence
<220> FEATURE:
<223> OTHER INFORMATION: 269B139 VHH CDR1

<400> SEQUENCE: 235

Asn Asn Phe Val Met Gly
1               5

<210> SEQ ID NO 236
<211> LENGTH: 16
<212> TYPE: PRT
<213> ORGANISM: Artificial Sequence
<220> FEATURE:
<223> OTHER INFORMATION: 269B005 VHH CDR2

<400> SEQUENCE: 236

Ala Val Thr Arg Asp Gly Arg Lys Ser Cys Gly Asp Ser Val Lys Gly
1               5                   10                  15

<210> SEQ ID NO 237
<211> LENGTH: 17
<212> TYPE: PRT
<213> ORGANISM: Artificial Sequence
<220> FEATURE:
<223> OTHER INFORMATION: 269B023 VHH CDR2

<400> SEQUENCE: 237

Ser Ile Thr Trp Asp Gly Arg Ser Ala Tyr Tyr Ala Glu Ser Val Lys
1               5                   10                  15

Gly

<210> SEQ ID NO 238
<211> LENGTH: 16
<212> TYPE: PRT
<213> ORGANISM: Artificial Sequence
<220> FEATURE:
<223> OTHER INFORMATION: 269B024 VHH CDR2

<400> SEQUENCE: 238

Thr Ile Thr Arg Gly Gly Ser Thr Asn Tyr Gly Pro Ser Val Lys Gly
1               5                   10                  15

<210> SEQ ID NO 239
<211> LENGTH: 17
<212> TYPE: PRT
<213> ORGANISM: Artificial Sequence
<220> FEATURE:
<223> OTHER INFORMATION: 269B028 VHH CDR2

<400> SEQUENCE: 239

Ser Ile Thr Cys Asp Gly Arg Thr Thr Tyr Tyr Ala Asn Ser Val Asn
1               5                   10                  15

Gly

<210> SEQ ID NO 240
<211> LENGTH: 17
<212> TYPE: PRT
<213> ORGANISM: Artificial Sequence
<220> FEATURE:
<223> OTHER INFORMATION: 269B030 VHH CDR2

<400> SEQUENCE: 240

Ala Ile Met Trp Asn Asp Gly Leu Thr Tyr Leu Gln Gly Ser Val Lys
1               5                   10                  15

Gly
```

```
<210> SEQ ID NO 241
<211> LENGTH: 17
<212> TYPE: PRT
<213> ORGANISM: Artificial Sequence
<220> FEATURE:
<223> OTHER INFORMATION: 269B038 VHH CDR2

<400> SEQUENCE: 241

Ala Ile Ser Leu Ser Pro Thr Leu Ala Tyr Tyr Ala Glu Ser Val Lys
1               5                   10                  15

Gly

<210> SEQ ID NO 242
<211> LENGTH: 17
<212> TYPE: PRT
<213> ORGANISM: Artificial Sequence
<220> FEATURE:
<223> OTHER INFORMATION: 269B054 VHH CDR2

<400> SEQUENCE: 242

Ser Ile Thr Trp Asp Gly Arg Thr Thr Tyr Tyr Ala Asp Ser Val Lys
1               5                   10                  15

Gly

<210> SEQ ID NO 243
<211> LENGTH: 17
<212> TYPE: PRT
<213> ORGANISM: Artificial Sequence
<220> FEATURE:
<223> OTHER INFORMATION: 269B059 VHH CDR2

<400> SEQUENCE: 243

Ala Ile Ser Leu Ser Pro Thr Leu Ala Tyr Tyr Ala Glu Ser Val Lys
1               5                   10                  15

Gly

<210> SEQ ID NO 244
<211> LENGTH: 17
<212> TYPE: PRT
<213> ORGANISM: Artificial Sequence
<220> FEATURE:
<223> OTHER INFORMATION: 269B060 VHH CDR2

<400> SEQUENCE: 244

Ser Ile Thr Cys Asp Gly Arg Thr Thr Tyr Tyr Ala Asn Ser Val Lys
1               5                   10                  15

Gly

<210> SEQ ID NO 245
<211> LENGTH: 17
<212> TYPE: PRT
<213> ORGANISM: Artificial Sequence
<220> FEATURE:
<223> OTHER INFORMATION: 269B069 VHH CDR2

<400> SEQUENCE: 245

Ser Ile Asp Thr Ser Gly Gln Thr Thr Tyr Tyr Ala Asp Ser Leu Lys
1               5                   10                  15

Gly

<210> SEQ ID NO 246
<211> LENGTH: 17
```

```
<212> TYPE: PRT
<213> ORGANISM: Artificial Sequence
<220> FEATURE:
<223> OTHER INFORMATION: 269B074 VHH CDR2

<400> SEQUENCE: 246

Ser Thr Thr Trp Asn Gly Arg Ser Thr Tyr Tyr Ala Asp Ser Val Lys
1               5                   10                  15

Gly

<210> SEQ ID NO 247
<211> LENGTH: 15
<212> TYPE: PRT
<213> ORGANISM: Artificial Sequence
<220> FEATURE:
<223> OTHER INFORMATION: 269B076 VHH CDR2

<400> SEQUENCE: 247

Asp Ile Ser Gly Gly Arg Thr Asn Tyr Ala Asp Ser Val Lys Gly
1               5                   10                  15

<210> SEQ ID NO 248
<211> LENGTH: 21
<212> TYPE: PRT
<213> ORGANISM: Artificial Sequence
<220> FEATURE:
<223> OTHER INFORMATION: 269B079 VHH CDR2

<400> SEQUENCE: 248

Phe Thr Ile Ser Arg Asp Asn Ala Lys Asn Thr Val Val Leu Gln Met
1               5                   10                  15

Asn Ser Leu Lys Pro
            20

<210> SEQ ID NO 249
<211> LENGTH: 17
<212> TYPE: PRT
<213> ORGANISM: Artificial Sequence
<220> FEATURE:
<223> OTHER INFORMATION: 269B083 VHH CDR2

<400> SEQUENCE: 249

Ser Ile Thr Trp Asp Gly Arg Thr Thr Tyr Tyr Ala Asp Ser Val Lys
1               5                   10                  15

Gly

<210> SEQ ID NO 250
<211> LENGTH: 17
<212> TYPE: PRT
<213> ORGANISM: Artificial Sequence
<220> FEATURE:
<223> OTHER INFORMATION: 269B085 VHH CDR2

<400> SEQUENCE: 250

Ala Ile Ser Leu Ser Pro Thr Leu Ala Tyr Tyr Ala Glu Ser Val Lys
1               5                   10                  15

Gly

<210> SEQ ID NO 251
<211> LENGTH: 19
<212> TYPE: PRT
<213> ORGANISM: Artificial Sequence
<220> FEATURE:
<223> OTHER INFORMATION: 269B093 VHH CDR2
```

```
<400> SEQUENCE: 251

Ala Ile Ser Leu Ser Pro Thr Leu Ala Tyr Tyr Ala Glu Ser Val Lys
1               5                   10                  15

Gly Lys Gly

<210> SEQ ID NO 252
<211> LENGTH: 17
<212> TYPE: PRT
<213> ORGANISM: Artificial Sequence
<220> FEATURE:
<223> OTHER INFORMATION: 269B094 VHH CDR2

<400> SEQUENCE: 252

Ala Ile Met Trp Asn Asp Gly Ile Thr Tyr Leu Gln Asp Ser Val Lys
1               5                   10                  15

Gly

<210> SEQ ID NO 253
<211> LENGTH: 17
<212> TYPE: PRT
<213> ORGANISM: Artificial Sequence
<220> FEATURE:
<223> OTHER INFORMATION: 269B104 VHH CDR2

<400> SEQUENCE: 253

Ala Ile Asn Leu Ser Pro Thr Leu Thr Tyr Tyr Ala Glu Ser Val Lys
1               5                   10                  15

Gly

<210> SEQ ID NO 254
<211> LENGTH: 17
<212> TYPE: PRT
<213> ORGANISM: Artificial Sequence
<220> FEATURE:
<223> OTHER INFORMATION: 269B109 VHH CDR2

<400> SEQUENCE: 254

Ser Ile Thr Leu Ile Pro Thr Phe Pro Tyr Tyr Ala Tyr Ser Val Lys
1               5                   10                  15

Gly

<210> SEQ ID NO 255
<211> LENGTH: 17
<212> TYPE: PRT
<213> ORGANISM: Artificial Sequence
<220> FEATURE:
<223> OTHER INFORMATION: 269B110 VHH CDR2

<400> SEQUENCE: 255

Ala Ile Ser Leu Ser Pro Thr Leu Ala Tyr Tyr Ala Glu Ser Val Lys
1               5                   10                  15

Gly

<210> SEQ ID NO 256
<211> LENGTH: 17
<212> TYPE: PRT
<213> ORGANISM: Artificial Sequence
<220> FEATURE:
<223> OTHER INFORMATION: 269B113 VHH CDR2

<400> SEQUENCE: 256

Ala Ile Ser Leu Ser Pro Thr Leu Ala Tyr Tyr Ala Glu Ser Val Lys
1               5                   10                  15
```

Gly

<210> SEQ ID NO 257
<211> LENGTH: 17
<212> TYPE: PRT
<213> ORGANISM: Artificial Sequence
<220> FEATURE:
<223> OTHER INFORMATION: 269B126 VHH CDR2

<400> SEQUENCE: 257

Val Ile Gly Trp Arg Asp Ile Asn Ala Ser Tyr Ala Asp Ser Val Lys
1               5                   10                  15
Gly

<210> SEQ ID NO 258
<211> LENGTH: 17
<212> TYPE: PRT
<213> ORGANISM: Artificial Sequence
<220> FEATURE:
<223> OTHER INFORMATION: 269B129 VHH CDR2

<400> SEQUENCE: 258

Val Ile Gly Trp Arg Asp Ile Ser Thr Ser Tyr Ala Asp Ser Val Lys
1               5                   10                  15
Gly

<210> SEQ ID NO 259
<211> LENGTH: 17
<212> TYPE: PRT
<213> ORGANISM: Artificial Sequence
<220> FEATURE:
<223> OTHER INFORMATION: 269B131 VHH CDR2

<400> SEQUENCE: 259

His Ile Ser Arg Ser Gly Gly Lys Ser Gly Tyr Gly Asp Ser Val Lys
1               5                   10                  15
Gly

<210> SEQ ID NO 260
<211> LENGTH: 17
<212> TYPE: PRT
<213> ORGANISM: Artificial Sequence
<220> FEATURE:
<223> OTHER INFORMATION: 269B135 VHH CDR2

<400> SEQUENCE: 260

Ala Ile Ser Leu Ser Pro Thr Leu Ala Tyr Tyr Ala Glu Ser Val Lys
1               5                   10                  15
Gly

<210> SEQ ID NO 261
<211> LENGTH: 17
<212> TYPE: PRT
<213> ORGANISM: Artificial Sequence
<220> FEATURE:
<223> OTHER INFORMATION: 269B136 VHH CDR2

<400> SEQUENCE: 261

Ala Ile Ser Leu Ser Pro Thr Leu Ala Tyr Tyr Ala Glu Pro Val Lys
1               5                   10                  15
Gly

```
<210> SEQ ID NO 262
<211> LENGTH: 17
<212> TYPE: PRT
<213> ORGANISM: Artificial Sequence
<220> FEATURE:
<223> OTHER INFORMATION: 269B139 VHH CDR2

<400> SEQUENCE: 262

Ala Ile Ser Leu Ser Pro Thr Leu Ala Tyr Tyr Val Glu Ser Val Lys
1               5                   10                  15
Gly

<210> SEQ ID NO 263
<211> LENGTH: 16
<212> TYPE: PRT
<213> ORGANISM: Artificial Sequence
<220> FEATURE:
<223> OTHER INFORMATION: 269B005 VHH CDR3

<400> SEQUENCE: 263

Asp Gly Trp Gly Ala Thr Thr Leu Asp Tyr Thr Tyr Gly Met Asp Tyr
1               5                   10                  15

<210> SEQ ID NO 264
<211> LENGTH: 12
<212> TYPE: PRT
<213> ORGANISM: Artificial Sequence
<220> FEATURE:
<223> OTHER INFORMATION: 269B023 VHH CDR3

<400> SEQUENCE: 264

Asp Arg Lys Ser Val Met Ser Ile Arg Pro Asp Tyr
1               5                   10

<210> SEQ ID NO 265
<211> LENGTH: 14
<212> TYPE: PRT
<213> ORGANISM: Artificial Sequence
<220> FEATURE:
<223> OTHER INFORMATION: 269B024 VHH CDR3

<400> SEQUENCE: 265

Glu Arg Leu Asp Gly Ser Gly Tyr Gly Tyr Glu Tyr Asp Tyr
1               5                   10

<210> SEQ ID NO 266
<211> LENGTH: 12
<212> TYPE: PRT
<213> ORGANISM: Artificial Sequence
<220> FEATURE:
<223> OTHER INFORMATION: 269B028 VHH CDR3

<400> SEQUENCE: 266

Tyr Arg Lys Ser Ile Met Ser Ile Gln Pro Asp Tyr
1               5                   10

<210> SEQ ID NO 267
<211> LENGTH: 12
<212> TYPE: PRT
<213> ORGANISM: Artificial Sequence
<220> FEATURE:
<223> OTHER INFORMATION: 269B030 VHH CDR3

<400> SEQUENCE: 267

Asp Arg Lys Ser Val Met Ser Ile Arg Pro Asp Tyr
1               5                   10
```

<210> SEQ ID NO 268
<211> LENGTH: 10
<212> TYPE: PRT
<213> ORGANISM: Artificial Sequence
<220> FEATURE:
<223> OTHER INFORMATION: 269B038 VHH CDR3

<400> SEQUENCE: 268

Arg Arg Ile Asp Ala Ala Asp Phe Asp Ser
1               5                   10

<210> SEQ ID NO 269
<211> LENGTH: 11
<212> TYPE: PRT
<213> ORGANISM: Artificial Sequence
<220> FEATURE:
<223> OTHER INFORMATION: 269B054 VHH CDR3

<400> SEQUENCE: 269

Leu Gly Lys Trp Pro Ala Gly Pro Ala Asp Tyr
1               5                   10

<210> SEQ ID NO 270
<211> LENGTH: 12
<212> TYPE: PRT
<213> ORGANISM: Artificial Sequence
<220> FEATURE:
<223> OTHER INFORMATION: 269B059 VHH CDR3

<400> SEQUENCE: 270

Asp Arg Lys Ser Val Met Ser Ile Arg Pro Asp Tyr
1               5                   10

<210> SEQ ID NO 271
<211> LENGTH: 11
<212> TYPE: PRT
<213> ORGANISM: Artificial Sequence
<220> FEATURE:
<223> OTHER INFORMATION: 269B060 VHH CDR3

<400> SEQUENCE: 271

Leu Gly Lys Trp Pro Ala Gly Ser Ala Asp Tyr
1               5                   10

<210> SEQ ID NO 272
<211> LENGTH: 12
<212> TYPE: PRT
<213> ORGANISM: Artificial Sequence
<220> FEATURE:
<223> OTHER INFORMATION: 269B069 VHH CDR3

<400> SEQUENCE: 272

Arg Tyr Arg Gly Gly Thr Trp Tyr Gly Met Ala Asn
1               5                   10

<210> SEQ ID NO 273
<211> LENGTH: 11
<212> TYPE: PRT
<213> ORGANISM: Artificial Sequence
<220> FEATURE:
<223> OTHER INFORMATION: 269B074 VHH CDR3

<400> SEQUENCE: 273

Leu Gly Lys Trp Pro Ala Gly Pro Ala Asp Tyr
1               5                   10

```
<210> SEQ ID NO 274
<211> LENGTH: 12
<212> TYPE: PRT
<213> ORGANISM: Artificial Sequence
<220> FEATURE:
<223> OTHER INFORMATION: 269B076 VHH CDR3

<400> SEQUENCE: 274

Asp Arg Lys Ser Val Met Ser Ile Arg Pro Asp Tyr
1               5                   10

<210> SEQ ID NO 275
<211> LENGTH: 12
<212> TYPE: PRT
<213> ORGANISM: Artificial Sequence
<220> FEATURE:
<223> OTHER INFORMATION: 269B079 VHH CDR3

<400> SEQUENCE: 275

Asp Arg Lys Ser Val Met Ser Ile Arg Pro Asp Tyr
1               5                   10

<210> SEQ ID NO 276
<211> LENGTH: 16
<212> TYPE: PRT
<213> ORGANISM: Artificial Sequence
<220> FEATURE:
<223> OTHER INFORMATION: 269B083 VHH CDR3

<400> SEQUENCE: 276

Thr Ala Ser Cys His Leu Phe Gly Leu Gly Ser Gly Ala Phe Val Ser
1               5                   10                  15

<210> SEQ ID NO 277
<211> LENGTH: 10
<212> TYPE: PRT
<213> ORGANISM: Artificial Sequence
<220> FEATURE:
<223> OTHER INFORMATION: 269B085 VHH CDR3

<400> SEQUENCE: 277

Ser Lys Asp Arg Tyr Ser Glu Tyr Glu Tyr
1               5                   10

<210> SEQ ID NO 278
<211> LENGTH: 8
<212> TYPE: PRT
<213> ORGANISM: Artificial Sequence
<220> FEATURE:
<223> OTHER INFORMATION: 269B093 VHH CDR3

<400> SEQUENCE: 278

Lys Asn Gly Gly Pro Val Asp Tyr
1               5

<210> SEQ ID NO 279
<211> LENGTH: 10
<212> TYPE: PRT
<213> ORGANISM: Artificial Sequence
<220> FEATURE:
<223> OTHER INFORMATION: 269B094 VHH CDR3

<400> SEQUENCE: 279

Ser Lys Gly Arg Tyr Ser Glu Tyr Glu Tyr
1               5                   10

<210> SEQ ID NO 280
```

```
<211> LENGTH: 12
<212> TYPE: PRT
<213> ORGANISM: Artificial Sequence
<220> FEATURE:
<223> OTHER INFORMATION: 269B104 VHH CDR3

<400> SEQUENCE: 280

Glu Arg Lys Ser Val Met Ala Ile Pro Pro Asp Tyr
1               5                   10

<210> SEQ ID NO 281
<211> LENGTH: 12
<212> TYPE: PRT
<213> ORGANISM: Artificial Sequence
<220> FEATURE:
<223> OTHER INFORMATION: 269B109 VHH CDR3

<400> SEQUENCE: 281

Tyr Arg Lys Tyr Leu Met Ser Ile Leu Pro Asp Tyr
1               5                   10

<210> SEQ ID NO 282
<211> LENGTH: 18
<212> TYPE: PRT
<213> ORGANISM: Artificial Sequence
<220> FEATURE:
<223> OTHER INFORMATION: 269B110 VHH CDR3

<400> SEQUENCE: 282

Asn Arg Asn Ser Gln Arg Val Ile Ala Ala Leu Ser Trp Ile Gly Met
1               5                   10                  15

Asn Tyr

<210> SEQ ID NO 283
<211> LENGTH: 10
<212> TYPE: PRT
<213> ORGANISM: Artificial Sequence
<220> FEATURE:
<223> OTHER INFORMATION: 269B113 VHH CDR3

<400> SEQUENCE: 283

Arg Arg Ile Asp Ala Ala Asp Phe Asp Ser
1               5                   10

<210> SEQ ID NO 284
<211> LENGTH: 10
<212> TYPE: PRT
<213> ORGANISM: Artificial Sequence
<220> FEATURE:
<223> OTHER INFORMATION: 269B126 VHH CDR3

<400> SEQUENCE: 284

Arg Arg Ile Asp Ala Thr Asp Phe Asp Ser
1               5                   10

<210> SEQ ID NO 285
<211> LENGTH: 10
<212> TYPE: PRT
<213> ORGANISM: Artificial Sequence
<220> FEATURE:
<223> OTHER INFORMATION: 269B129 VHH CDR3

<400> SEQUENCE: 285

Arg Arg Ile Asp Ala Ala Asp Phe Asp Ser
1               5                   10
```

```
<210> SEQ ID NO 286
<211> LENGTH: 12
<212> TYPE: PRT
<213> ORGANISM: Artificial Sequence
<220> FEATURE:
<223> OTHER INFORMATION: 269B131 VHH CDR3

<400> SEQUENCE: 286

Pro Leu Trp Tyr Gly Ser Pro Thr Leu Ile Asp Tyr
1               5                   10

<210> SEQ ID NO 287
<211> LENGTH: 12
<212> TYPE: PRT
<213> ORGANISM: Artificial Sequence
<220> FEATURE:
<223> OTHER INFORMATION: 269B135 VHH CDR3

<400> SEQUENCE: 287

Asp Arg Lys Ser Val Met Ser Ile Arg Pro Asp Tyr
1               5                   10

<210> SEQ ID NO 288
<211> LENGTH: 12
<212> TYPE: PRT
<213> ORGANISM: Artificial Sequence
<220> FEATURE:
<223> OTHER INFORMATION: 269B136 VHH CDR3

<400> SEQUENCE: 288

Asp Arg Lys Ser Val Met Ser Ile Arg Pro Asp Tyr
1               5                   10

<210> SEQ ID NO 289
<211> LENGTH: 12
<212> TYPE: PRT
<213> ORGANISM: Artificial Sequence
<220> FEATURE:
<223> OTHER INFORMATION: 269B139 VHH CDR3

<400> SEQUENCE: 289

Asp Arg Lys Ser Val Met Ser Ile Arg Pro Asp Tyr
1               5                   10

<210> SEQ ID NO 290
<211> LENGTH: 124
<212> TYPE: PRT
<213> ORGANISM: Artificial Sequence
<220> FEATURE:
<223> OTHER INFORMATION: 269B005 VHH AA

<400> SEQUENCE: 290

Glu Val Gln Leu Val Glu Ser Gly Gly Gly Leu Val Pro Pro Gly Gly
1               5                   10                  15

Ser Leu Arg Leu Ser Cys Thr Ala Ser Gly Ser Thr Val Ser Ile Asn
            20                  25                  30

Val Met Ala Trp Tyr Arg Gln Val Ser Gly Lys Gln Arg Glu Leu Val
        35                  40                  45

Ala Ala Val Thr Arg Asp Gly Arg Lys Ser Cys Gly Asp Ser Val Lys
    50                  55                  60

Gly Arg Phe Thr Ile Ser Arg Asp Gly Ala Lys Asn Ala Val Tyr Leu
65                  70                  75                  80

Gln Met Asn Ser Leu Lys Pro Glu Asp Thr Ala Val Tyr Leu Cys Gly
                85                  90                  95
```

Ala Asp Gly Trp Gly Ala Thr Thr Leu Asp Tyr Thr Tyr Gly Met Asp
            100                 105                 110

Tyr Trp Gly Lys Gly Thr Gln Val Thr Val Ser Ser
            115                 120

<210> SEQ ID NO 291
<211> LENGTH: 118
<212> TYPE: PRT
<213> ORGANISM: Artificial Sequence
<220> FEATURE:
<223> OTHER INFORMATION: 269B023 VHH AA

<400> SEQUENCE: 291

Ala Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Gly Phe Val Ala Ser Ile
        35                  40                  45

Thr Trp Asp Gly Arg Ser Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
            115

<210> SEQ ID NO 292
<211> LENGTH: 122
<212> TYPE: PRT
<213> ORGANISM: Artificial Sequence
<220> FEATURE:
<223> OTHER INFORMATION: 269B024 VHH AA

<400> SEQUENCE: 292

Gln Val Gln Leu Val Glu Ser Gly Gly Gly Leu Val Gln Pro Gly Gly
1               5                   10                  15

Ser Leu Arg Leu Ala Cys Glu Ala Pro Gly Ser Gly Asn Ser Ile Asn
            20                  25                  30

Ala Met Gly Trp Tyr Arg Gln Thr Pro Gly Lys Arg Arg Glu Leu Val
        35                  40                  45

Ala Thr Ile Thr Arg Gly Gly Ser Thr Asn Tyr Gly Pro Ser Val Lys
    50                  55                  60

Gly Arg Phe Thr Ile Thr Arg Asp Asn Val Lys Asn Thr Val His Leu
65                  70                  75                  80

Gln Met Asn Ser Leu Lys Pro Asp Asp Thr Ala Val Tyr Tyr Cys Asn
                85                  90                  95

Ala Glu Arg Leu Asp Gly Ser Gly Tyr Gly Tyr Glu Tyr Asp Tyr Trp
            100                 105                 110

Gly Gln Gly Thr Gln Val Thr Val Ser Ser
            115                 120

<210> SEQ ID NO 293
<211> LENGTH: 121
<212> TYPE: PRT
<213> ORGANISM: Artificial Sequence

<220> FEATURE:
<223> OTHER INFORMATION: 269B028 VHH AA

<400> SEQUENCE: 293

Gln Val Lys Leu Glu Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Val Arg Gln Ala Pro Gly Lys Glu Arg Gly Phe Val
        35                  40                  45

Thr Ser Ile Thr Cys Asp Gly Arg Thr Thr Tyr Tyr Ala Asn Ser Val
    50                  55                  60

Asn Gly Arg Phe Pro Ile Asn Arg Asn Asn Ala Glu Asn Leu Val Val
65                  70                  75                  80

Leu Gln Met Asn Ser Leu Lys Pro Asp Asp Thr Ala Leu Tyr Tyr Cys
                85                  90                  95

Ala Ala Tyr Arg Lys Ser Ile Met Ser Ile Gln Pro Asp Tyr Trp Gly
            100                 105                 110

Gln Gly Thr Gln Val Thr Val Ser Ser
        115                 120

<210> SEQ ID NO 294
<211> LENGTH: 121
<212> TYPE: PRT
<213> ORGANISM: Artificial Sequence
<220> FEATURE:
<223> OTHER INFORMATION: 269B030 VHH AA

<400> SEQUENCE: 294

Asp Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Leu Thr Tyr Leu Gln Gly Ser Val
    50                  55                  60

Lys Gly Arg Phe Thr Ile Ser Arg Asp Asn Ala Lys Asn Thr Val Val
65                  70                  75                  80

Leu Gln Met Asn Ser Leu Lys Pro Glu Asp Thr Ala Leu Tyr Tyr Cys
                85                  90                  95

Ala Ala Asp Arg Lys Ser Val Met Ser Ile Arg Pro Asp Tyr Trp Gly
            100                 105                 110

Gln Gly Thr Gln Val Thr Val Ser Ser
        115                 120

<210> SEQ ID NO 295
<211> LENGTH: 116
<212> TYPE: PRT
<213> ORGANISM: Artificial Sequence
<220> FEATURE:
<223> OTHER INFORMATION: 269B038 VHH AA

<400> SEQUENCE: 295

Gln Val Gln Leu Val Glu Ser Gly Gly Gly Leu Val Gln Ala Gly Gly
1               5                   10                  15

Ser Leu Arg Leu Ser Cys Ala Ser Gly Arg Thr Phe Thr Met Gly
            20                  25                  30

```
Trp Phe Arg Gln Ala Pro Gly Lys Glu Arg Glu Phe Val Ala Ala Ile
         35                  40                  45

Ser Leu Ser Pro Thr Leu Ala Tyr Tyr Ala Glu Ser Val Lys Gly Arg
 50                  55                  60

Phe Thr Ile Ser Arg Asp Asn Ala Lys Asn Thr Val Val Leu Gln Met
65                   70                  75                  80

Asn Ser Leu Lys Pro Glu Asp Thr Ala Val Tyr Tyr Cys Ala Ala Arg
             85                  90                  95

Arg Ile Asp Ala Ala Asp Phe Asp Ser Trp Gly Gln Gly Thr Gln Val
            100                 105                 110

Thr Val Ser Ser
        115

<210> SEQ ID NO 296
<211> LENGTH: 120
<212> TYPE: PRT
<213> ORGANISM: Artificial Sequence
<220> FEATURE:
<223> OTHER INFORMATION: 269B054 VHH AA

<400> SEQUENCE: 296

Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Phe Arg Gln Ala Pro Gly Lys Glu Arg Gly Phe Val
        35                  40                  45

Ala Ser Ile Thr Trp Asp Gly Arg Thr Thr Tyr Tyr Ala Asp Ser Val
 50                 55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Val Cys
            85                  90                  95

Ala Asp Leu Gly Lys Trp Pro Ala Gly Pro Ala Asp Tyr Trp Gly Gln
            100                 105                 110

Gly Thr Gln Val Thr Val Ser Ser
        115                 120

<210> SEQ ID NO 297
<211> LENGTH: 121
<212> TYPE: PRT
<213> ORGANISM: Artificial Sequence
<220> FEATURE:
<223> OTHER INFORMATION: 269B059 VHH AA

<400> SEQUENCE: 297

Gln Val Gln Leu Val Glu Ser Gly Gly Gly Leu Val Pro Gly Gly
1               5                   10                  15

Ser Leu Thr Leu Ser Cys Ala Ser Gly Ser Ile Asp Ser Ile Asn
            20                  25                  30

Thr Met Asp Trp Phe Arg Gln Ala Pro Gly Lys Glu Arg Glu Phe Val
        35                  40                  45

Ala Ala Ile Ser Leu Ser Pro Thr Leu Ala Tyr Tyr Ala Glu Ser Val
 50                 55                  60

Lys Gly Arg Phe Thr Ile Ser Arg Asp Asn Ala Lys Asn Thr Val Val
65                  70                  75                  80

Leu Gln Met Asn Ser Leu Lys Pro Glu Asp Thr Ala Leu Tyr Tyr Cys
            85                  90                  95
```

```
Ala Ala Asp Arg Lys Ser Val Met Ser Ile Arg Pro Asp Tyr Trp Gly
            100                 105                 110

Gln Gly Thr Gln Val Thr Val Ser Ser
        115                 120

<210> SEQ ID NO 298
<211> LENGTH: 120
<212> TYPE: PRT
<213> ORGANISM: Artificial Sequence
<220> FEATURE:
<223> OTHER INFORMATION: 269B060 VHH AA

<400> SEQUENCE: 298

Asp Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Leu Ser Lys Asn
            20                  25                  30

Thr Val Ala Trp Val Arg Gln Ala Pro Gly Lys Glu Arg Gly Phe Val
        35                  40                  45

Thr Ser Ile Thr Cys Asp Gly Arg Thr Thr Tyr Tyr Ala Asn Ser Val
    50                  55                  60

Lys Gly Arg Phe Pro Ile Ser Arg Asp Asn Ala Glu Asn Thr Val Tyr
65                  70                  75                  80

Leu Gln Met Asn Ser Leu Lys Pro Glu Asp Thr Ala Gly Tyr Val Cys
                85                  90                  95

Ala Asp Leu Gly Lys Trp Pro Ala Gly Ser Ala Asp Tyr Trp Gly Gln
            100                 105                 110

Gly Thr His Val Thr Val Ser Ser
        115                 120

<210> SEQ ID NO 299
<211> LENGTH: 121
<212> TYPE: PRT
<213> ORGANISM: Artificial Sequence
<220> FEATURE:
<223> OTHER INFORMATION: 269B069 VHH AA

<400> SEQUENCE: 299

Gln Val Lys Leu Glu Glu Ser Gly Gly Gly Leu Val Gln Pro Gly Gly
1               5                   10                  15

Ser Leu Arg Leu Ser Cys Thr Ala Ser Glu Phe Thr Phe Ser Asp Tyr
            20                  25                  30

Trp Met His Trp Val Arg Gln Ala Pro Gly Lys Gly Leu Glu Trp Val
        35                  40                  45

Ala Ser Ile Asp Thr Ser Gly Gln Thr Thr Tyr Tyr Ala Asp Ser Leu
    50                  55                  60

Lys Gly Arg Phe Thr Ile Ser Arg Asp Asn Ala Lys Ser Thr Leu Tyr
65                  70                  75                  80

Leu Gln Met Asn Ser Leu Lys Ser Glu Asp Thr Gly Val Tyr Phe Cys
                85                  90                  95

Ala Lys Arg Tyr Arg Gly Gly Thr Trp Tyr Gly Met Ala Asn Trp Gly
            100                 105                 110

Lys Gly Thr Gln Val Thr Val Ser Ser
        115                 120

<210> SEQ ID NO 300
<211> LENGTH: 120
<212> TYPE: PRT
```

<213> ORGANISM: Artificial Sequence
<220> FEATURE:
<223> OTHER INFORMATION: 269B074 VHH AA

<400> SEQUENCE: 300

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Leu Ser Ser Asn
            20                  25                  30

Thr Met Ala Trp Phe Arg Gln Ala Pro Gly Lys Glu Arg Glu Phe Val
        35                  40                  45

Ala Ser Thr Thr Trp Asn Gly Arg Ser Thr Tyr Tyr Ala Asp Ser Val
    50                  55                  60

Lys Gly Arg Phe Thr Ile Ser Arg Asp Asn Ala Lys Asn Thr Met Tyr
65                  70                  75                  80

Leu Gln Met Asn Ser Leu Lys Pro Glu Asp Thr Ala Val Tyr Val Cys
                85                  90                  95

Ala Asp Leu Gly Lys Trp Pro Gly Pro Ala Asp Tyr Trp Gly Gln
            100                 105                 110

Gly Thr Gln Val Thr Val Ser Ser
        115                 120

<210> SEQ ID NO 301
<211> LENGTH: 116
<212> TYPE: PRT
<213> ORGANISM: Artificial Sequence
<220> FEATURE:
<223> OTHER INFORMATION: 269B076 VHH AA

<400> SEQUENCE: 301

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Gln Arg Glu Leu Val Ala Asp Ile
        35                  40                  45

Ser Gly Gly Arg Thr Asn Tyr Ala Asp Ser Val Lys Gly Arg Phe Thr
    50                  55                  60

Ile Ser Arg Asp Asn Ala Lys Asn Thr Val Tyr Leu Gln Met Asn Ser
65                  70                  75                  80

Leu Lys Pro Glu Asp Thr Ala Val Tyr Tyr Cys Ala Ala Asp Arg Lys
                85                  90                  95

Ser Val Met Ser Ile Arg Pro Asp Tyr Trp Gly Gln Gly Thr Gln Val
            100                 105                 110

Thr Val Ser Ser
        115

<210> SEQ ID NO 302
<211> LENGTH: 104
<212> TYPE: PRT
<213> ORGANISM: Artificial Sequence
<220> FEATURE:
<223> OTHER INFORMATION: 269B079 VHH AA

<400> SEQUENCE: 302

Gln Val Gln Leu Val Glu Ser Gly Gly Gly Leu Val Gln Ala Gly Ala
1               5                   10                  15

Ser Leu Arg Leu Ser Cys Ala Ala Ser Gly Arg Thr Phe Thr Val Ala
            20                  25                  30

```
Ala Ile Ser Leu Ser Pro Thr Leu Ala Tyr Tyr Ala Glu Ser Val Lys
        35                  40                  45

Gly Arg Phe Thr Ile Ser Arg Asp Asn Ala Lys Asn Thr Val Val Leu
 50                  55                  60

Gln Met Asn Ser Leu Lys Pro Glu Asp Thr Ala Leu Tyr Tyr Cys Ala
 65                  70                  75                  80

Ala Asp Arg Lys Ser Val Met Ser Ile Arg Pro Asp Tyr Trp Gly Gln
                 85                  90                  95

Gly Thr Gln Val Thr Val Ser Ser
                100
```

<210> SEQ ID NO 303
<211> LENGTH: 125
<212> TYPE: PRT
<213> ORGANISM: Artificial Sequence
<220> FEATURE:
<223> OTHER INFORMATION: 269B083 VHH AA

<400> SEQUENCE: 303

```
Asp Val Gln Leu Val Glu Ser Gly Gly Gly Leu Glu Gln Ala Gly Gly
 1               5                  10                  15

Ser Leu Arg Leu Ser Cys Ala Ala Ser Gly Gly Thr Leu Ser Lys Asn
             20                  25                  30

Thr Val Ala Trp Phe Arg Gln Ala Pro Gly Lys Glu Arg Gly Phe Val
         35                  40                  45

Ala Ser Ile Thr Trp Asp Gly Arg Thr Thr Tyr Tyr Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Ser Thr Ala Ser Cys His Leu Phe Gly Leu Gly Ser Gly Ala Phe
            100                 105                 110

Val Ser Trp Gly Arg Gly Thr Gln Val Thr Val Ser Ser
        115                 120                 125
```

<210> SEQ ID NO 304
<211> LENGTH: 116
<212> TYPE: PRT
<213> ORGANISM: Artificial Sequence
<220> FEATURE:
<223> OTHER INFORMATION: 269B085 VHH AA

<400> SEQUENCE: 304

```
Ala Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Thr Met Gly
             20                  25                  30

Trp Phe His Gln Ala Pro Gly Lys Glu Arg Glu Phe Val Ala Ala Ile
         35                  40                  45

Ser Leu Ser Pro Thr Leu Ala Tyr Tyr Ala Glu Ser Val Lys Gly Arg
 50                  55                  60

Phe Thr Ile Ser Arg Asp Asn Ala Lys Asn Thr Val Val Leu Gln Met
 65                  70                  75                  80

Asn Ser Leu Lys Pro Glu Asp Thr Ala Leu Tyr Tyr Cys Ala Ala Ser
                 85                  90                  95

Lys Asp Arg Tyr Ser Glu Tyr Glu Tyr Trp Gly Gln Gly Thr Gln Val
```

```
                   100                 105                 110

Thr Val Ser Ser
        115

<210> SEQ ID NO 305
<211> LENGTH: 114
<212> TYPE: PRT
<213> ORGANISM: Artificial Sequence
<220> FEATURE:
<223> OTHER INFORMATION: 269B093 VHH AA

<400> SEQUENCE: 305

Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Lys Lys
                85                  90                  95

Asn Gly Gly Pro Val Asp Tyr Trp Gly Lys Gly Thr Gln Val Thr Val
            100                 105                 110

Ser Ser

<210> SEQ ID NO 306
<211> LENGTH: 119
<212> TYPE: PRT
<213> ORGANISM: Artificial Sequence
<220> FEATURE:
<223> OTHER INFORMATION: 269B094 VHH AA

<400> SEQUENCE: 306

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Val Met Gly Trp Phe Arg Gln Ala Pro Gly Lys Glu Arg Glu Phe Val
        35                  40                  45

Gly Ala Ile Met Trp Asn Asp Gly Ile Thr Tyr Leu Gln Asp Ser Val
    50                  55                  60

Lys Gly Arg Phe Thr Ile Phe Arg Asp Asn Ala Lys Asn Thr Val Tyr
65                  70                  75                  80

Leu Gln Met Asn Ser Leu Lys Leu Glu Asp Thr Ala Val Tyr Tyr Cys
                85                  90                  95

Ala Ala Ser Lys Gly Arg Tyr Ser Glu Tyr Tyr Trp Gly Gln Gly
            100                 105                 110

Thr Gln Val Thr Val Ser Ser
        115

<210> SEQ ID NO 307
<211> LENGTH: 118
<212> TYPE: PRT
<213> ORGANISM: Artificial Sequence
<220> FEATURE:
<223> OTHER INFORMATION: 269B104 VHH AA
```

<400> SEQUENCE: 307

```
Gln Val Lys Leu Glu Glu Ser Gly Gly Arg Leu Val Gln Ala Gly Gly
1               5                   10                  15

Ser Leu Lys Leu Ser Trp Ala Ala Ser Gly Arg Thr Phe Thr Met Gly
            20                  25                  30

Trp Phe Arg Gln Ala Pro Gly Lys Glu Arg Glu Phe Val Thr Ala Ile
        35                  40                  45

Asn Leu Ser Pro Thr Leu Thr Tyr Tyr Ala Glu Ser Val Lys Gly Arg
    50                  55                  60

Phe Pro Ile Ser Arg Asn Asn Ala Gln Asn Thr Val Val Leu Gln Met
65                  70                  75                  80

Asn Ser Leu Lys Pro Glu Asp Thr Ala Leu Tyr Tyr Cys Ala Ala Glu
                85                  90                  95

Arg Lys Ser Val Met Ala Ile Pro Pro Asp Tyr Trp Gly Gln Gly Thr
                100                 105                 110

Gln Val Thr Val Ser Ser
            115
```

<210> SEQ ID NO 308
<211> LENGTH: 118
<212> TYPE: PRT
<213> ORGANISM: Artificial Sequence
<220> FEATURE:
<223> OTHER INFORMATION: 269B109 VHH AA

<400> SEQUENCE: 308

```
Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Gly Phe Arg Arg Val Pro Arg Asp Glu Arg Glu Phe Val Ala Ser Ile
        35                  40                  45

Thr Leu Ile Pro Thr Phe Pro Tyr Tyr Ala Tyr Ser Val Lys Gly Arg
    50                  55                  60

Phe Ala Leu Phe Arg Asp Asn Pro Asn Thr Val Ile Leu Leu Met
65                  70                  75                  80

Ile Ser Leu Lys Pro Glu Asp Pro Asp Leu Tyr Tyr Cys Ala Ser Tyr
                85                  90                  95

Arg Lys Tyr Leu Met Ser Ile Leu Pro Asp Tyr Trp Gly Gln Gly Thr
                100                 105                 110

Gln Gly Thr Val Ser Ser
            115
```

<210> SEQ ID NO 309
<211> LENGTH: 124
<212> TYPE: PRT
<213> ORGANISM: Artificial Sequence
<220> FEATURE:
<223> OTHER INFORMATION: 269B110 VHH AA

<400> SEQUENCE: 309

```
Gln Val Lys Leu Glu Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45
```

```
Ser Leu Ser Pro Thr Leu Ala Tyr Tyr Ala Glu Ser Val Lys Gly Arg
        50                  55                  60

Phe Thr Ile Ser Arg Asp Asn Ala Lys Asn Thr Val Asp Leu Gln Met
 65                  70                  75                  80

Asn Ser Leu Lys Pro Glu Asp Thr Ala Val Tyr Phe Cys Ala Ala Asn
                 85                  90                  95

Arg Asn Ser Gln Arg Val Ile Ala Ala Leu Ser Trp Ile Gly Met Asn
            100                 105                 110

Tyr Trp Gly Glu Trp Thr Gln Val Thr Val Ser Ser
        115                 120
```

```
<210> SEQ ID NO 310
<211> LENGTH: 116
<212> TYPE: PRT
<213> ORGANISM: Artificial Sequence
<220> FEATURE:
<223> OTHER INFORMATION: 269B113 VHH AA

<400> SEQUENCE: 310

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
        50                  55                  60

Phe Thr Ile Ser Arg Asp Asn Ala Lys Lys Thr Leu Tyr Leu Arg Met
 65                  70                  75                  80

Asn Ser Leu Lys Pro Glu Asp Thr Ala Val Tyr Tyr Cys Ala Ala Arg
                 85                  90                  95

Arg Ile Asp Ala Ala Asp Phe Asp Ser Trp Gly Gln Gly Thr Gln Val
            100                 105                 110

Thr Val Ser Ser
        115
```

```
<210> SEQ ID NO 311
<211> LENGTH: 116
<212> TYPE: PRT
<213> ORGANISM: Artificial Sequence
<220> FEATURE:
<223> OTHER INFORMATION: 269B126 VHH AA

<400> SEQUENCE: 311

Gln Val Lys Leu Glu Glu Ser Gly Gly Gly Leu Val Gln Ala Gly Gly
 1               5                  10                  15

Ser Leu Arg Leu Ser Cys Ala Ala Ser Gly Arg Thr Phe Thr Met Gly
            20                  25                  30

Trp Phe Arg Arg Ala Pro Gly Lys Glu Arg Glu Ser Val Ala Val Ile
        35                  40                  45

Gly Trp Arg Asp Ile Asn Ala Ser Tyr Ala Asp Ser Val Lys Gly Arg
        50                  55                  60

Phe Ala Ile Ser Arg Asp Asn Ala Lys Lys Thr Leu Tyr Leu Gln Met
 65                  70                  75                  80

Asn Ser Leu Lys Pro Glu Asp Thr Ala Val Tyr Tyr Cys Ala Ala Arg
                 85                  90                  95

Arg Ile Asp Ala Thr Asp Phe Asp Ser Trp Gly Gln Gly Thr Gln Val
```

Thr Val Ser Ser
    115

<210> SEQ ID NO 312
<211> LENGTH: 119
<212> TYPE: PRT
<213> ORGANISM: Artificial Sequence
<220> FEATURE:
<223> OTHER INFORMATION: 269B129 VHH AA

<400> SEQUENCE: 312

Gln Val Lys Leu Glu Glu Ser Gly Gly Gly Leu Val Gln Thr Gly Gly
1               5                   10                  15

Ser Leu Arg Leu Ser Cys Ala Ala Ser Glu His Thr Phe Ser Asn His
            20                  25                  30

Val Met Gly Trp Phe Arg Gln Ala Pro Gly Lys Glu Arg Glu Ser Val
        35                  40                  45

Ala Val Ile Gly Trp Arg Asp Ile Ser Thr Ser Tyr Ala Asp Ser Val
    50                  55                  60

Lys Gly Arg Phe Thr Ile Ser Arg Asp Asn Ala Lys Lys Thr Leu Tyr
65                  70                  75                  80

Leu Gln Met Asn Ser Leu Lys Pro Glu Asp Thr Ala Val Tyr Tyr Cys
                85                  90                  95

Ala Ala Arg Arg Ile Asp Ala Ala Asp Phe Asp Ser Arg Gly Gln Gly
            100                 105                 110

Thr Gln Val Thr Val Ser Ser
        115

<210> SEQ ID NO 313
<211> LENGTH: 123
<212> TYPE: PRT
<213> ORGANISM: Artificial Sequence
<220> FEATURE:
<223> OTHER INFORMATION: 269B131 VHH AA

<400> SEQUENCE: 313

Ala Val Gln Leu Val Asp Ser Gly Gly Gly Leu Val Gln Ala Gly Gly
1               5                   10                  15

Ser Leu Arg Ile Ser Cys Ala Val Ser Gly Arg Thr Ser Ser Asn Tyr
            20                  25                  30

Ile Leu Ala Trp Phe Arg Gln Ala Pro Gly Lys Glu Arg Asp Phe Val
        35                  40                  45

Ala His Ile Ser Arg Ser Gly Gly Lys Ser Gly Tyr Gly Asp Ser Val
    50                  55                  60

Lys Gly Arg Phe Thr Ile Ser Arg Asp Asn Ala Glu Asn Thr Val Arg
65                  70                  75                  80

Val Tyr Leu Gln Met Asn Ser Leu Lys Pro Gly Asp Thr Ala Val Tyr
                85                  90                  95

Tyr Cys Asn Arg Pro Leu Trp Tyr Gly Ser Pro Thr Leu Ile Asp Tyr
            100                 105                 110

Trp Gly Gln Gly Thr Gln Val Thr Val Ser Ser
        115                 120

<210> SEQ ID NO 314
<211> LENGTH: 118
<212> TYPE: PRT
<213> ORGANISM: Artificial Sequence
<220> FEATURE:

<223> OTHER INFORMATION: 269B135 VHH AA

<400> SEQUENCE: 314

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Ser Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 315
<211> LENGTH: 118
<212> TYPE: PRT
<213> ORGANISM: Artificial Sequence
<220> FEATURE:
<223> OTHER INFORMATION: 269B136 VHH AA

<400> SEQUENCE: 315

Ala Val Gln Leu Val Asp Ser Gly Gly Gly Leu Val Gln Ala Gly Gly
1               5                   10                  15

Ser Leu Arg Leu Ser Cys Ala Ala Ser Gly Arg Thr Phe Thr Met Gly
            20                  25                  30

Trp Phe Arg Gln Ala Pro Gly Lys Glu Arg Glu Phe Val Ala Ala Ile
        35                  40                  45

Ser Leu Ser Pro Thr Leu Ala Tyr Tyr Ala Glu Pro Val Lys Gly Arg
    50                  55                  60

Phe Thr Ile Ser Arg Asp Asn Ala Lys Asn Thr Val Val Leu Gln Met
65                  70                  75                  80

Asn Ser Leu Lys Pro Glu Asp Thr Ala Leu Tyr Tyr Cys Ala Ala Asp
                85                  90                  95

Arg Lys Ser Val Met Ser Ile Arg Pro Asp Tyr Trp Gly Gln Gly Thr
            100                 105                 110

Gln Val Thr Val Ser Ser
        115

<210> SEQ ID NO 316
<211> LENGTH: 121
<212> TYPE: PRT
<213> ORGANISM: Artificial Sequence
<220> FEATURE:
<223> OTHER INFORMATION: 269B139 VHH AA

<400> SEQUENCE: 316

Asp Val Gln Leu Val Glu Ser Gly Gly Gly Ser Val Gln Thr Gly Gly
1               5                   10                  15

Ser Leu Arg Leu Ser Cys Thr Ala Ser Gly Arg Thr Leu Asn Asn Phe
            20                  25                  30

Val Met Gly Trp Phe Arg Gln Ala Pro Gly Lys Glu Arg Glu Phe Val

```
                 35                   40                  45
Ala Ala Ile Ser Leu Ser Pro Thr Leu Ala Tyr Tyr Val Glu Ser Val
         50                   55                  60
Lys Gly Arg Phe Thr Ile Ser Arg Asp Asn Ala Lys Asn Thr Val Val
 65                   70                  75                  80
Leu Gln Met Asn Ser Leu Lys Pro Glu Asp Thr Ala Leu Tyr Tyr Cys
                 85                   90                  95
Ala Ala Asp Arg Lys Ser Val Met Ser Ile Arg Pro Tyr Trp Gly
             100                 105                 110
Gln Gly Thr Gln Val Thr Val Ser Ser
        115                 120

<210> SEQ ID NO 317
<211> LENGTH: 5
<212> TYPE: PRT
<213> ORGANISM: Artificial Sequence
<220> FEATURE:
<223> OTHER INFORMATION: 60E11 VHH CDR1

<400> SEQUENCE: 317

Ser Phe Asp Met Gly
1               5

<210> SEQ ID NO 318
<211> LENGTH: 20
<212> TYPE: PRT
<213> ORGANISM: Artificial Sequence
<220> FEATURE:
<223> OTHER INFORMATION: 60E11 VHH CDR2

<400> SEQUENCE: 318

Val Ile Gly Ser Arg Gly Asn Asn Arg Gly Arg Thr Asn Tyr Ala Asp
1               5                   10                  15

Ser Val Lys Gly
            20

<210> SEQ ID NO 319
<211> LENGTH: 8
<212> TYPE: PRT
<213> ORGANISM: Artificial Sequence
<220> FEATURE:
<223> OTHER INFORMATION: 60E11 VHH CDR3

<400> SEQUENCE: 319

Ala Pro Leu Val Ala Gly Arg Pro
1               5

<210> SEQ ID NO 320
<211> LENGTH: 5
<212> TYPE: PRT
<213> ORGANISM: Artificial Sequence
<220> FEATURE:
<223> OTHER INFORMATION: 117G03 VHH CDR1

<400> SEQUENCE: 320

Gly Tyr Ser Met Gly
1               5

<210> SEQ ID NO 321
<211> LENGTH: 17
<212> TYPE: PRT
<213> ORGANISM: Artificial Sequence
<220> FEATURE:
<223> OTHER INFORMATION: 117G03 VHH CDR2
```

-continued

```
<400> SEQUENCE: 321

Ala Ile Val Trp Ser Gly Gly Asn Thr Tyr Tyr Glu Asp Ser Val Lys
1               5                   10                  15
Gly

<210> SEQ ID NO 322
<211> LENGTH: 15
<212> TYPE: PRT
<213> ORGANISM: Artificial Sequence
<220> FEATURE:
<223> OTHER INFORMATION: 117G03 VHH CDR3

<400> SEQUENCE: 322

Lys Ile Arg Pro Tyr Ile Phe Lys Ile Ala Gly Gln Tyr Asp Tyr
1               5                   10                  15

<210> SEQ ID NO 323
<211> LENGTH: 2
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (1)..(2)
<223> OTHER INFORMATION: Can be present in repeats of any integer

<400> SEQUENCE: 323

Gly Ser
1

<210> SEQ ID NO 324
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (1)..(5)
<223> OTHER INFORMATION: Can be present in repeats of any integer

<400> SEQUENCE: 324

Gly Ser Gly Gly Ser
1               5

<210> SEQ ID NO 325
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: VARIANT
<222> LOCATION: (1)..(4)
<223> OTHER INFORMATION: Can be present in repeats of any integer

<400> SEQUENCE: 325

Gly Gly Gly Ser
1

<210> SEQ ID NO 326
<211> LENGTH: 5
<212> TYPE: PRT
<213> ORGANISM: Artificial Sequence
<220> FEATURE:
<223> OTHER INFORMATION: Linker
```

```
<220> FEATURE:
<221> NAME/KEY: VARIANT
<222> LOCATION: (1)..(5)
<223> OTHER INFORMATION: Can be present in repeats of any integer

<400> SEQUENCE: 326

Gly Gly Gly Gly Ser
1               5
```